United States Patent
Kudo et al.

(10) Patent No.: US 9,701,637 B2
(45) Date of Patent: *Jul. 11, 2017

(54) TAU IMAGING PROBE

(71) Applicant: GE Healthcare Limited, Buckinghamshire (GB)

(72) Inventors: Yukitsuka Kudo, Sendai (JP); Shozo Furumoto, Sandai (JP); Nobuyuki Okamura, Sandai (JP)

(73) Assignee: GE Healthcare Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,604

(22) Filed: May 31, 2016

(65) Prior Publication Data

US 2016/0271278 A1    Sep. 22, 2016

Related U.S. Application Data

(63) Continuation of application No. 14/860,823, filed on Sep. 22, 2015, now Pat. No. 9,452,985, which is a continuation of application No. 13/881,872, filed as application No. PCT/JP2011/074930 on Oct. 28, 2011, now Pat. No. 9,249,101.

(30) Foreign Application Priority Data

Oct. 29, 2010 (JP) ................. 2010-243532
May 11, 2011 (JP) ................. 2011-106569

(51) Int. Cl.
| | |
|---|---|
| *A61K 31/535* | (2006.01) |
| *C07D 215/12* | (2006.01) |
| *A61K 9/00* | (2006.01) |
| *A61K 9/08* | (2006.01) |
| *A61K 51/04* | (2006.01) |
| *C07D 215/20* | (2006.01) |
| *C07D 215/233* | (2006.01) |
| *C07D 215/26* | (2006.01) |
| *C07D 215/38* | (2006.01) |
| *C07D 215/40* | (2006.01) |
| *C07D 401/04* | (2006.01) |
| *C07D 405/12* | (2006.01) |
| *C07D 405/14* | (2006.01) |
| *C07D 498/04* | (2006.01) |
| *C07D 215/14* | (2006.01) |
| *G01N 33/68* | (2006.01) |
| *C07B 59/00* | (2006.01) |

(52) U.S. Cl.
CPC .......... *C07D 215/12* (2013.01); *A61K 9/0019* (2013.01); *A61K 9/08* (2013.01); *A61K 51/0455* (2013.01); *A61K 51/0459* (2013.01); *A61K 51/0463* (2013.01); *C07B 59/002* (2013.01); *C07D 215/14* (2013.01); *C07D 215/20* (2013.01); *C07D 215/233* (2013.01); *C07D 215/26* (2013.01); *C07D 215/38* (2013.01); *C07D 215/40* (2013.01); *C07D 401/04* (2013.01); *C07D 405/12* (2013.01); *C07D 405/14* (2013.01); *C07D 498/04* (2013.01); *G01N 33/6893* (2013.01); *C07B 2200/05* (2013.01); *G01N 2800/2821* (2013.01)

(58) Field of Classification Search
CPC ............ A61K 51/0455; A61K 51/0463; A61K 9/0019; A61K 9/08; C07D 215/12; C07D 215/14; C07D 215/20; C07D 215/233; C07D 215/26; C07D 215/38; C07D 215/40; C07D 401/04; C07D 405/12; C07D 405/14
See application file for complete search history.

(56) References Cited

U.S. PATENT DOCUMENTS

| | | |
|---|---|---|
| 7,118,730 B2 | 10/2006 | Kudo et al. |
| 2005/0009865 A1 | 1/2005 | Kudo et al. |
| 2010/0239496 A1 | 9/2010 | Gangadharmath et al. |

FOREIGN PATENT DOCUMENTS

| | | |
|---|---|---|
| CN | 101857611 | 10/2010 |
| EP | 1574500 A1 | 9/2005 |
| JP | H07-33743 | 2/1995 |

(Continued)

OTHER PUBLICATIONS

Bonneau et al, Anticancer Research Oct. 2015, vol. 35, No. 10, pp. 5179-5184.*

Pinard et al., "4-Aminoquinolines as a Novel Class of NR I/2B Subtype Selective NMDA Receptor Antagonists", Bioorganic & Medicinal Chemistry Letters, vol. 12, No. 18, 2002, pp. 2615-2619.

(Continued)

Primary Examiner — Jean Cornet
(74) Attorney, Agent, or Firm — Wood IP LLC

(57) ABSTRACT

An object of the present invention is to provide a probe for imaging a β-sheet structure protein which can be used for the diagnosis of conformational diseases, particularly disease (tauopathy) having a cardinal symptom such as intracerebral accumulation of tau protein, for example, Alzheimer's disease. Another object of the present invention is to provide a compound which is highly specific to tau and can image tau with satisfactory sensitivity, and also has high brain transition, low or non-recognized bone-seeking properties and low or non-recognized toxicity.

According to the present invention, the above problems are solved by providing a compound of a formula I (wherein A, $R^1$, $R^2$, $R^3$, $R^4$, $R^5$, $R^6$, $R^a$ and $R^b$ are as defined in the present description) or a pharmaceutically acceptable salt or solvate thereof.

17 Claims, 17 Drawing Sheets

(56) References Cited

FOREIGN PATENT DOCUMENTS

| | | |
|---|---|---|
| KR | 2010-0112423 | 10/2010 |
| WO | 02/36567 A1 | 5/2002 |
| WO | 02/36569 A1 | 5/2002 |
| WO | 2004/054978 A1 | 7/2004 |
| WO | 2008/124703 A2 | 10/2008 |
| WO | 2010/111303 A2 | 9/2010 |
| WO | 2011/119565 A1 | 9/2011 |

OTHER PUBLICATIONS

Strekowski et al., "Synthesis of Bis(2-arylquinolin-4-yl)amines by Lithium Bis(trimethylsilyl)amide—Mediated Cyclization of Ketimines Derived from 2-(Trifluoromethyl)anilines and Aryl Methyl Ketones", Journal of Organic Chemistry, vol. 62, No. 12, 1997, pp. 4193-4196.

Giacalone, Gazzetta Chimica Italiana, vol. 65, 1935, pp. 124-128.

International Preliminary Report on Patentability, International Patent Application No. PCT/JP2011/074930, May 2, 2013.

Okamura et al., "Quinoline and Benzimidazole Derivatives: Candidate Proves for In Vivo Imaging of Tau Pathology in Alzheimer's Disease", The Journal of Neuroscience, vol. 25, No. 47, Nov. 23, 2005, pp. 10857-10862.

Shogi-Jadid et al., "Localization of Neurofibrillary Tangles and Beta-Amyloid Plaques in the Brains of Living Patients with Alzheimer Disease", Am. J. Geriatr. Psychiatry, vol. 10, No. 1, Jan.-Feb. 2002, pp. 24-35.

Klunk et al., "Imaging Brain Amyloid in Alzheimer's Disease with Pittsburgh Compound-B", Annals of Neurology, col. 55, No. 3, Mar. 2004, pp. 306-319.

Engler et al., "Two-year follow-up of amyloid deposition in patients with Alzheimer's disease", Brain, vol. 129, 2006, pp. 2856-2866.

Aizenstein et al., "Frequent Amyloid Deposition Without Significant Cognitive Impairment Among the Elderly", Arch Neurol., vol. 65, No. 11, Nov. 2008, pp. 1509-1517.

Holmes et al., "Long-term effects of AJ342 immunisation in Alzheimer's disease: follow-up of a randomized, placebo-controlled phase I trial", Lancet, vol. 372, 2008, pp. 216-223.

Arriagada et al., "Neurofibrillary tangles but not senile plaques parallel duration and severity of Alzheimer's disease", Neurology, vol. 42, Mar. 1992, pp. 631-639.

R.Schimnacher et al., "Alpha selective epoxide opening with 18F-: synthesis of 4-(3-[ 18F]fluoro-2-hydroxypropoxy ) benzaldehyde([ 18F]FPB) for peptide labeling", Tetrahedron Letters, Pergamon, GB, vol. 52, No. 16, Feb. 2011, pp. 1973-1976.

Extended European Search Report dated Apr. 15, 2014 issued in the European Patent Application No. 11836445.4.

Chinese Office Action (Patent Application No. 201180062845.8) mailed Jan. 27, 2015.

* cited by examiner

Fig.5
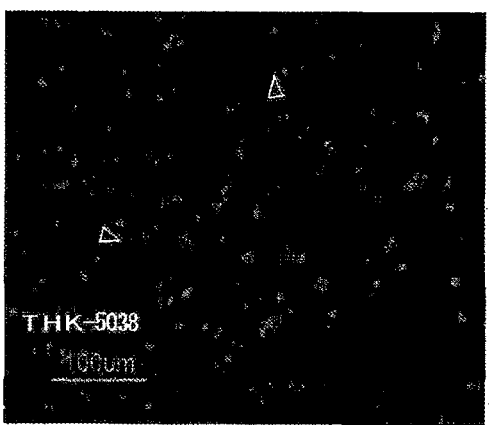
Fig.6
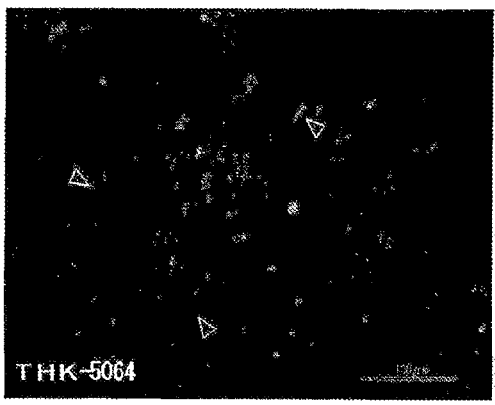

Fig. 7
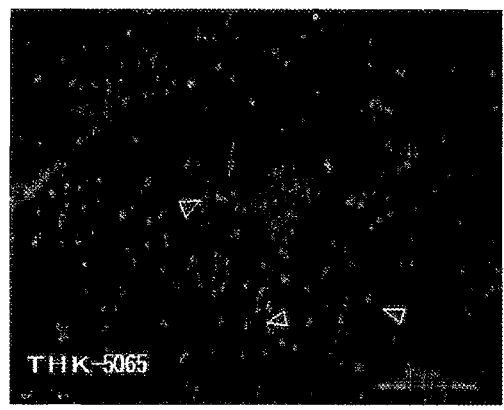
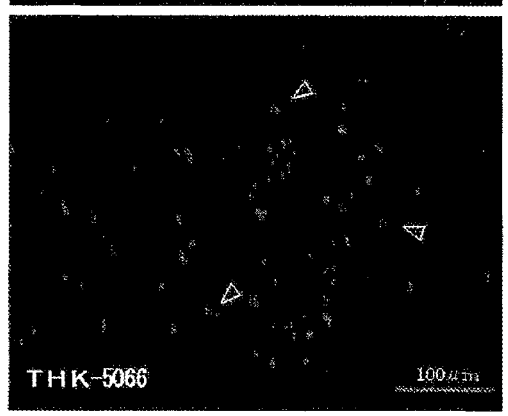
Fig. 8
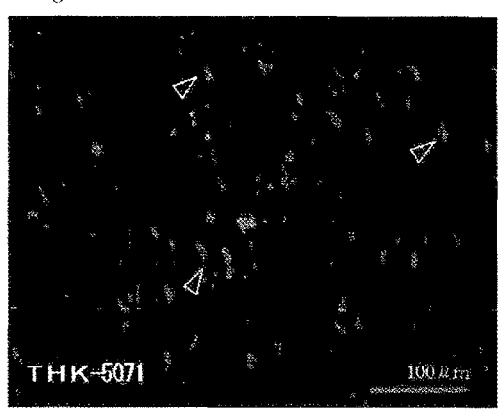
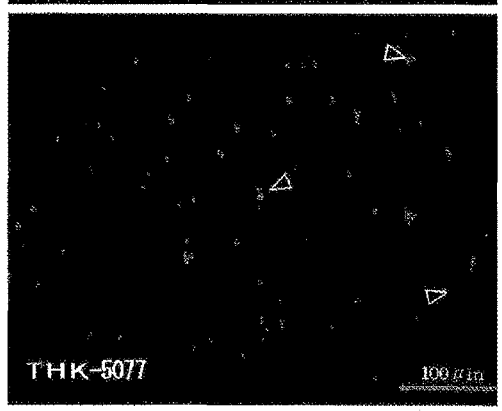

Fig. 11
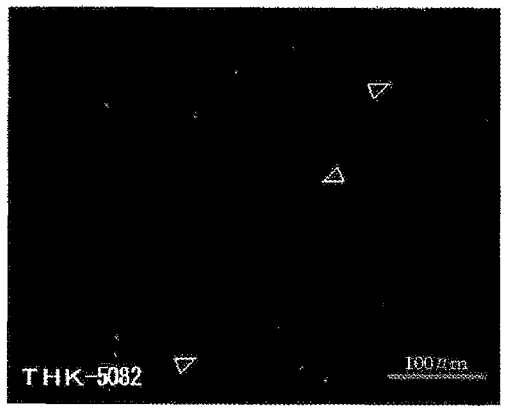
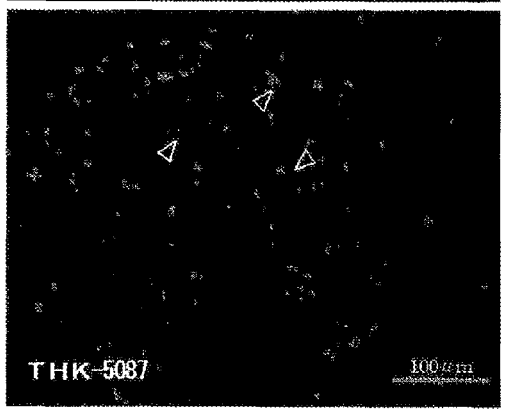
Fig. 12
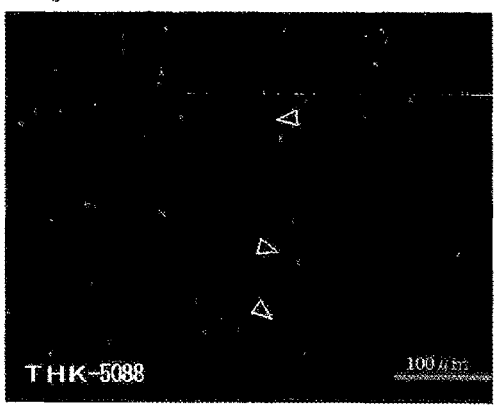
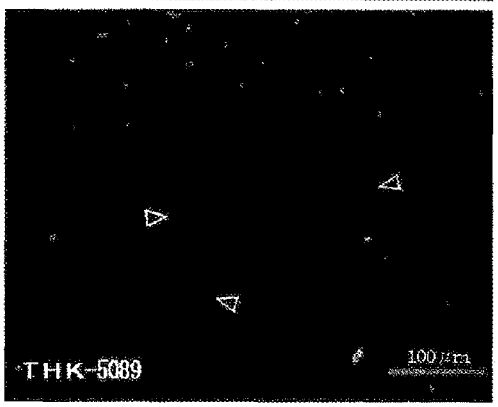

Fig. 13
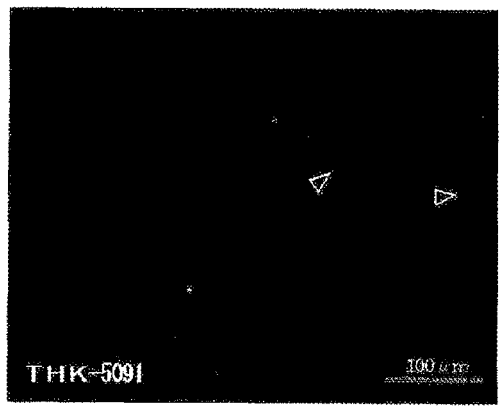
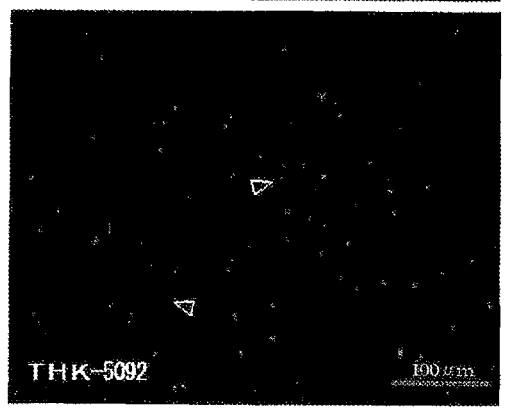
Fig. 14
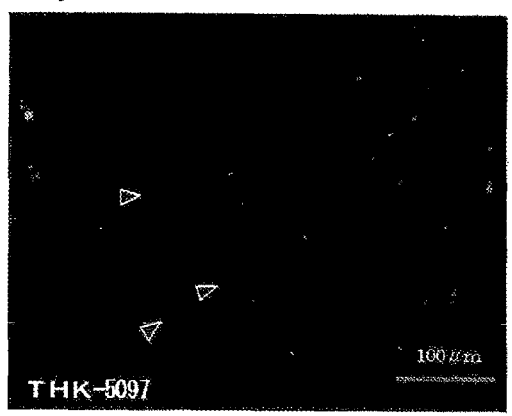
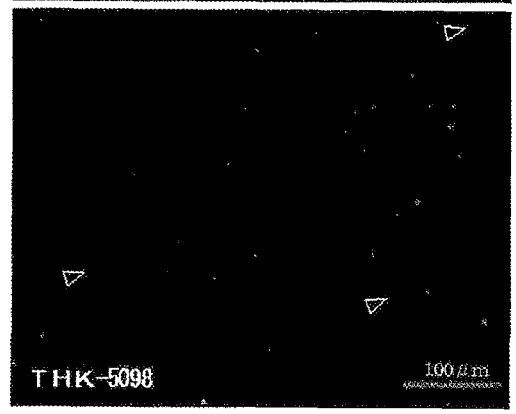

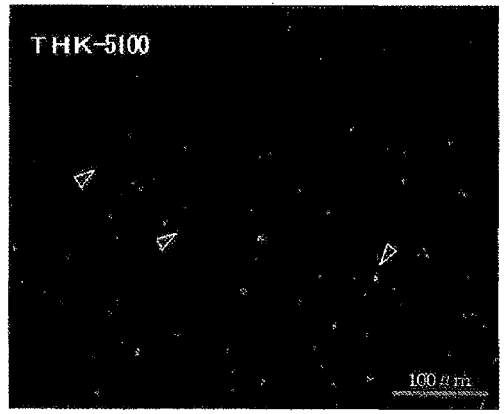
Fig. 17
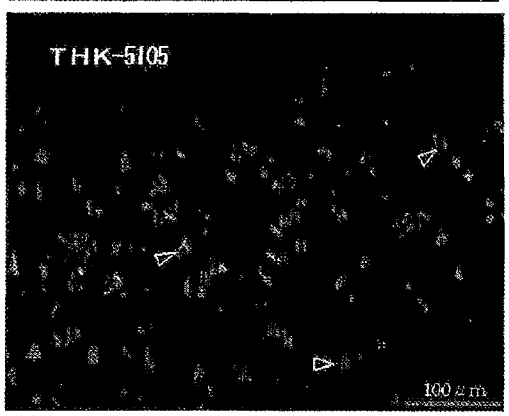
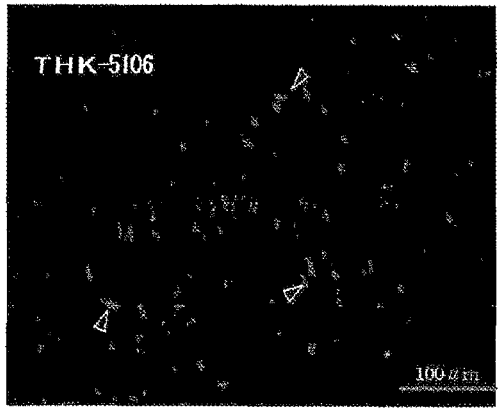
Fig. 18
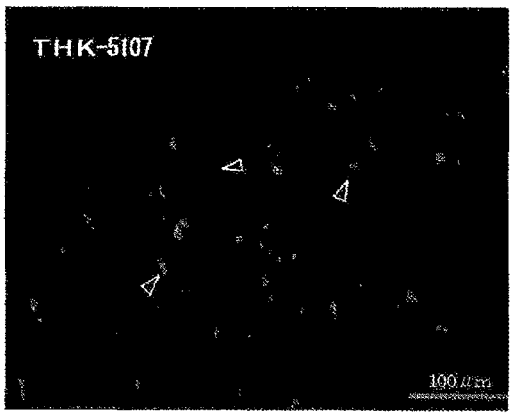

Fig.19
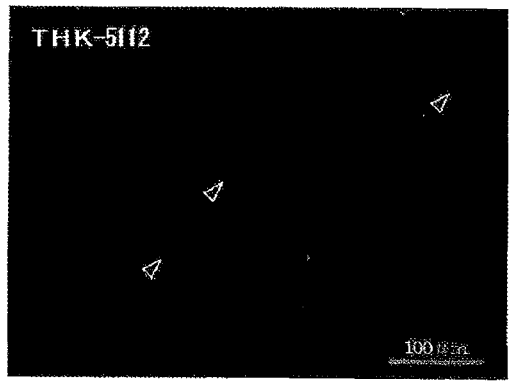
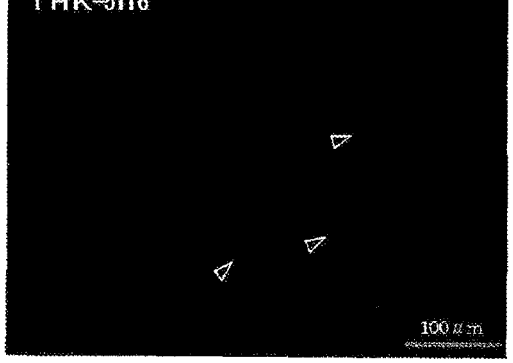
Fig.20
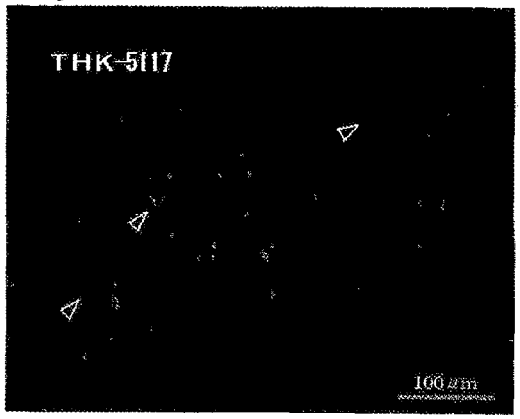
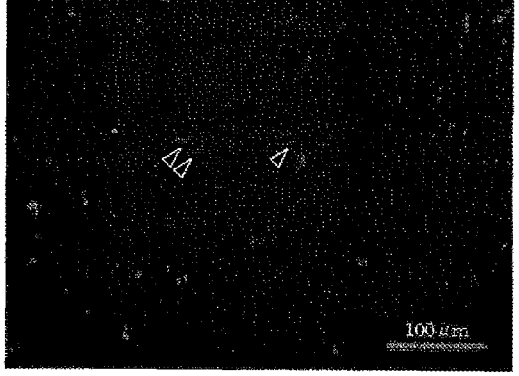

Fig. 25
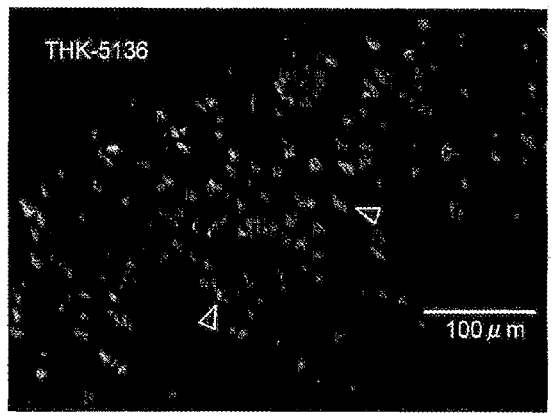
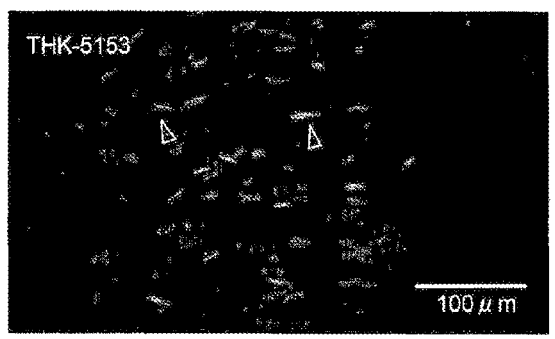
Fig. 26
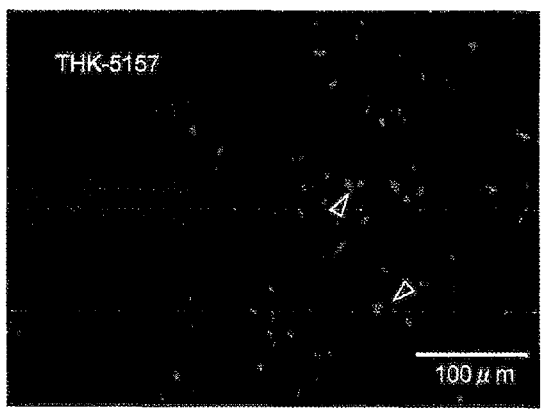
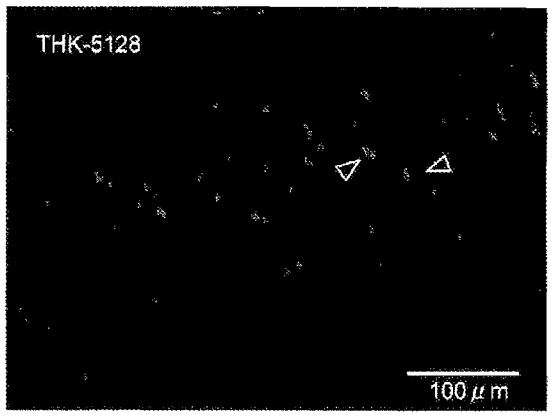

Fig. 27
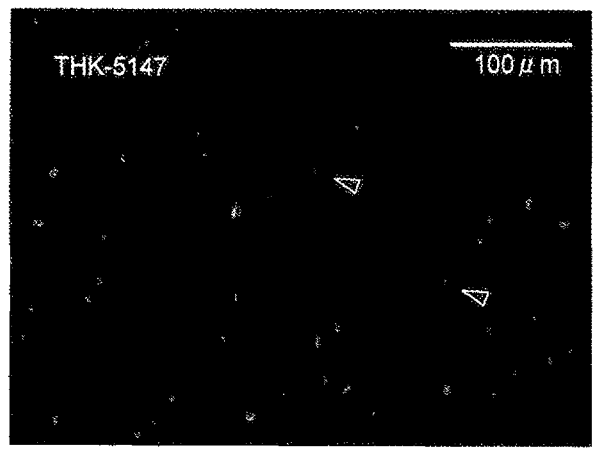
Fig. 28
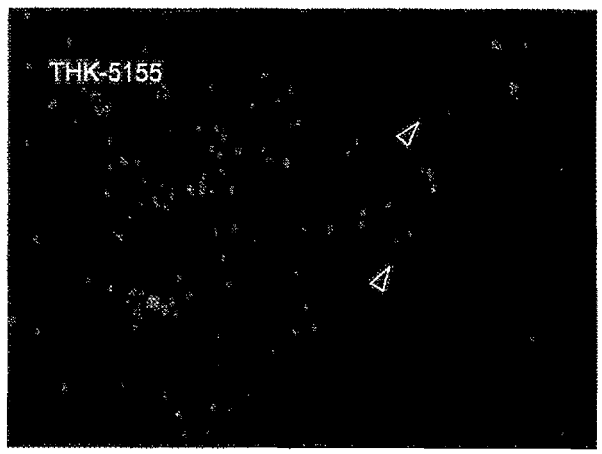
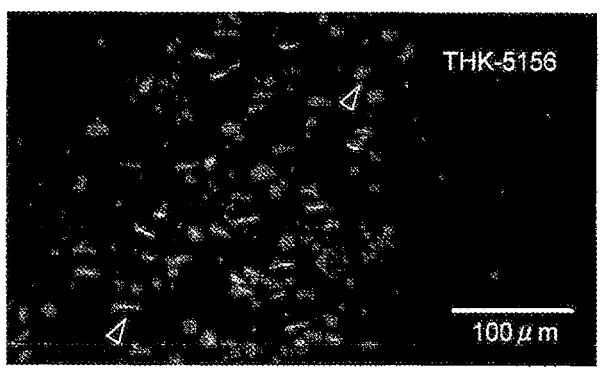

Fig.29
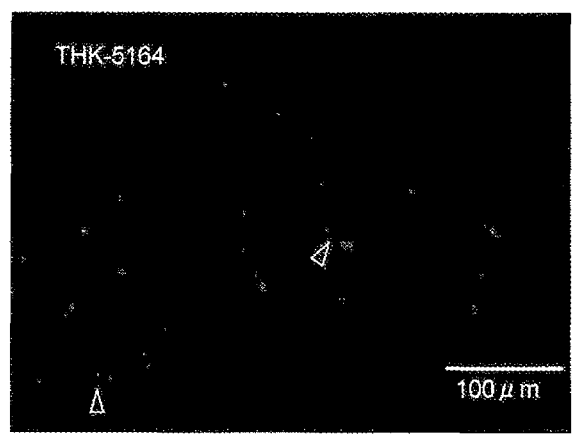
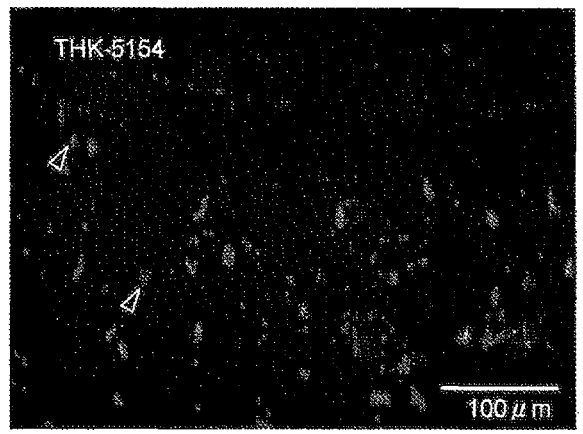

TAU IMAGING PROBE

CROSS-REFERENCE TO RELATED APPLICATIONS

This application is a continuation of U.S. patent application Ser. No. 14/860,823, filed Sep. 22, 2015, which is a continuation of U.S. patent application Ser. No. 13/881,872 filed Jun. 19, 2013, now U.S. Pat. No. 9,249,101 which is a filing under 35 U.S.C. § and claims priority to international patent Appl. No. PCT/JP2011/074930 filed Oct. 28, 2011, and claims priority to JP 2011-106569 filed May 11, 2011 and claims priority to JP 2010-243532 filed Oct. 29, 2010, the entire contents of which are hereby incorporated herein by reference.

TECHNICAL FIELD

The present invention relates to a probe for imaging a β-sheet structure protein which can be used for the diagnosis of conformational diseases, particularly disease (tauopathy) having a cardinal symptom such as intracerebral accumulation of tau protein, for example, Alzheimer's disease.

BACKGROUND ART

In Alzheimer's disease, it is known that the accumulation of senile plaque containing amyloid beta-protein (hereinafter referred collectively to as Aβ) as a main component and of neurofibrillary tangles containing hyperphosphorylated tau protein (hereinafter referred collectively to as tau) as a main component proceeds to the degree that it cannot be treated, when the people around the patient or the physician notice the specific clinical symptoms of the disease. In other words, if the current diagnosis of Alzheimer's disease is compared to that of cancer, it is detected only when it has reached the end stage.

Recently, it has been revealed that even in the case of the extremely early stage of very mild Alzheimer's disease that corresponds to mild cognitive impairment (MCI), which is considered as partly precursor state of Alzheimer's disease, autopsy samples show the accumulation of many Aβ and tau, and the state is pathologically almost Alzheimer's disease. Therefore, in Alzheimer's disease, the histopathology is manifested far before the symptom of memory loss appears. In other words, there is a quite large difference between the histopathology and clinical picture of Alzheimer's disease (so-called difference between pathological Alzheimer's disease and clinical Alzheimer's disease).

As illustrated in FIG. 1, the accumulation of Aβ is considered to start 10 or more years earlier than that of tau in the brain of Alzheimer's disease. As is apparent from FIG. 1, since the tracing of Aβ was considered most appropriate in order to diagnose Alzheimer's disease in the extremely early stage or before its' development, almost all PET probes for the diagnosis of Alzheimer's disease were so-called probes for amyloid imaging to trace Aβ from the 20th to 21st century. At first, [$^{11}$C] labeled probes were mainly used, but afterwards, the development of [$^{18}$F] labeled probes that have a long half-life and are easily used in the clinical setting has been attempted. FIG. 2 illustrates the examples of probes for amyloid imaging that have been developed until now.

In the beginning of 2002, images showing administration of PET probes for amyloid imaging to Alzheimer's disease patients were introduced for the first time in the world (refer to Non-Patent Document 1). The team of Barrio et al., UCLA got the honor of this, and the probes used were [$^{18}$F] FDDNP. Afterwards, however, [$^{11}$C] PIB developed by General Electric, University of Pittsburgh, which has probably now been used for more than 1,000 clinical cases, became the mainstream of probes for amyloid imaging (refer to Non-Patent Document 2).

Many researchers assumed that amyloid imaging in the diagnosis of Alzheimer's disease would be a so-called versatile diagnostic method that enables the diagnosis of the disease with high sensitivity and specificity, as well as early diagnosis, differential diagnosis, diagnosis of severity (or progress), and preclinical diagnosis (so-called detection of presymptomatic high-risk individuals).

However, as clinical research progresses, issues were appearing gradually in the amyloid imaging, which was considered as versatile diagnostic method. These issues are explained by taking [$^{11}$C] PIB as an example, as follows:

First, diagnosis of severity (or progress) is impossible. In other words, 2 years after a patient was diagnosed as Alzheimer's disease by [$^{11}$C] PIB, there was no change in the accumulation of the probe regardless of the progress of the clinical symptoms (refer to Non-Patent Document 3). The reason is considered that the accumulation of Aβ to which [$^{11}$C] PIB binds reaches a plateau far before MCI is seen prior to development of Alzheimer's disease. Therefore, the severity or progress of Alzheimer's disease cannot be diagnosed with [$^{11}$C] PIB.

Second, there is a problem that considerable false positives are seen. Surprisingly, the ADNI (Alzheimer's Disease Imaging Initiative) held ahead of the International Conference on Alzheimer's Disease in Chicago in July 2008 reported that 53% of healthy elderly were [$^{11}$C] PIB positive (refer to Non-Patent Document 4). Although the incidence rate of Alzheimer's disease is considered to be 4 to 6% of the population of 65 or more years old, the ADNI reported that 53% of the elderly except for Alzheimer's disease patients were [$^{11}$C] PIB positive. Although the present inventors think the figure of 53% is an overestimate, the developers of [$^{11}$C] PIB themselves recognize the possibility of considerable false positives (refer to Non-Patent Document 5).

The reason for these many false positives is believed to be that there is a considerable dispersion in the accumulation of Aβ in all of normal healthy subjects, MCI, and Alzheimer's disease.

Furthermore, in June to July 2008, it was successively reported that the effects of therapeutic drug (vaccines and secretase inhibitors) groups, which were expected to provide basic remedies based on the Alzheimer's disease/amyloid (or Aβ) hypothesis, were far below expectation. The most shocking was the report by Holmes et al. in Lancet that Aβ vaccines cannot stop the progress of the clinical symptoms at all although Aβ was removed from the brain of Alzheimer's disease patients (refer to Non-Patent Document 6).

However, another important information was provided in the report in Lancet; all accumulation of tau in the patients in Lancent progressed to the final stage. FIG. 3 illustrates the Braak stage of accumulation of Aβ and tau in Alzheimer's disease. For the Braak stage of post-mortem Case 7 and 8 of the report in Lancet, Aβ was considered not to be accumulated (or stage A), while the degree of tau accumulation was stage VI. This implies that in both cases the accumulation of Aβ was mild or less, while the accumulation of tau was the highest level of stage VI.

There were several reports that the histopathology correlated with the clinical symptoms of Alzheimer's disease was tau rather than Aβ in the early 1990s (Non-Patent Document 7). This was unexpectedly reaffirmed by the report by Holmes et al.

These findings strongly suggest that Aβ vaccines were less effective as therapeutic drugs after development of Alzheimer's disease and that the degree of Aβ accumulation does not always reflect the severity of Alzheimer's disease, as well as that it is more reasonable to trace tau rather than Aβ to diagnose the severity of Alzheimer's disease.

The present inventors think that by considering the clinical outcomes of vaccines, other therapeutic drugs, and probes for amyloid imaging, the relationship between amyloid (or Aβ) and tau in Alzheimer's disease should be revised to FIG. 4. As illustrated in FIG. 4, when there is low accumulation of amyloid, MCI and Alzheimer's disease develop when the tau accumulation reaches the threshold, and when the accumulation of amyloid is very high, MCI and Alzheimer's disease do not develop when the tau accumulation does not reach the threshold. That is to say, the amount of amyloid accumulation is not related to development of MCI and Alzheimer's disease, while tau accumulation defines this development. It is proposed to say "amyloid (or Aβ) has no threshold, but tau has one".

As described above, tau imaging is probably superior to amyloid imaging, in order to diagnose the severity (or progress) of Alzheimer's disease, or to detect presymptomatic high-risk individuals for Alzheimer's disease correctly.

The present inventors think that it is probable that "tau imaging will play the leading role in diagnosis of Alzheimer's disease, supplemented by amyloid imaging in the future".

The document in the relevant technical field includes, for example, (i) Okamura et al., J. Neurosci., 25 (4&), 10857-10862 (2005), (ii) EP 1574500 A1, (iii) Siemens US 2010/0239496 A1, and (iv) Korea KR 2010-0112423 A.

PRIOR ART DOCUMENT

Patent Document

Non-Patent Document 1: Shoghi-Jadid K, Small G W, Agdeppa E D, Kepe V, Ercoli L M, Siddarth P, Read S, Satyamurthy N, Petric A, Huang S C, Barrio J R: Localization of neurofibrillary tangles and beta-amyloid plaques in the brains of living patients with Alzheimer disease. Am. J. Geriatr. Psychiatry 10, 24-35. 2002.
Non-Patent Document 2: Klunk W E, Engler H, Nordberg A, Wang Y, Blomqvist G, Holt D P, Bergstrom M, Savitcheva I, Huang G F, Estrada S, Ausen B, Debnath M L, Barletta J, Price J C, Sandell J, Lopresti B J, Wall A, Koivisto P, Antoni G, Mathis C A and Langstrom B.: Imaging brain amyloid in Alzheimer's disease with Pittsburgh Compound-B. Ann. Neurol. 55. 306-319 (2004).
Non-Patent Document 3: Engler H, Forsberg A, Almkvist O, Blomquist G, Larsson E, Savitcheva I, Wall A, Ringheim A, Långström B, Nordberg A: Two-year follow-up of amyloid deposition in patients with Alzheimer's disease. Brain. 129. 2856-2866. 2006.
Non-Patent Document 4: Weiner: International Conference on Alzheimer's Disease (ICAD) meeting, Chicago, 2008, Jul. 19.
Non-Patent Document 5: Aizenstein H J, Aizenstein H J, Nebes R D, Saxton J A, Price J C, Mathis C A, Tsopelas N D, Ziolko S K, James J A, Snitz B E, Houck P R, Bi W, Cohen A D, Lopresti B J, DeKosky S T, Halligan E M, Klunk W E.: Frequent amyloid deposition without significant cognitive impairment among the elderly. Arch Neurol. 65. 1509-1517. 2008.
Non-Patent Document 6: Holmes C, Boche D, Wilkinson D, Yadegarfar G, Hopkins V, Bayer A, Jones R W, Bullock R, Love S, Neal J W, Zotova E, Nicoll J A: Long-term effects of Abeta42 immunisation in Alzheimer's disease: follow-up of a randomised, placebo-controlled phase I trial. Lancet. 372. 2132-2142. 2008.
Non-Patent Document 7: Arriagada P V, Growdon J H, Hedley-Whyte E T, Hyman B T: Neurofibrillary tangles but not senile plaques parallel duration and severity of Alzheimer's disease. Neurology. 42. 631-639. 1992.

DISCLOSURE OF THE INVENTION

Problems to be Solved by the Invention

An object of the present invention is to provide a compound which is highly specific to tau and can image tau with satisfactory sensitivity, and also has high brain transition, low or non-recognized bone-seeking properties and low or undetected toxicity.

Means for Solving the Problems

In light of the above problems, the present inventors have intensively studied and found that the compound of a formula (I), a salt thereof or a solvate thereof is a compound which is highly specific to tau and can image tau with satisfactory sensitivity, and also has high brain transition, low or non-recognized bone-seeking properties and low or non-recognized toxicity. They have also found that the compound of a formula (I') can be used as a precursor of the compound of a formula (I), a salt thereof or a solvate thereof. Thus, the present inventors have completed the present invention.

That is, the present invention provides the followings.
(1) A compound of the formula (I):

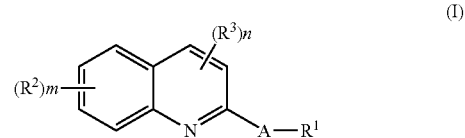

wherein
A is

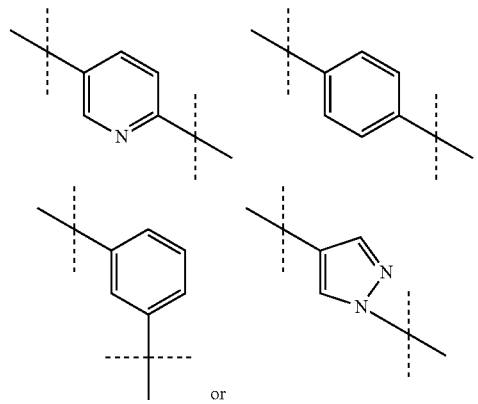

or $R^1$ is halogen, a —C(=O)-lower alkyl group (the alkyl group each independently may be substituted with one or more substituents selected from $NR^aR^b$, halogen and a hydroxy group), a lower alkyl group (the alkyl group each independently may be substituted with one or more substituents selected from halogen and a hydroxy group), a —O-lower alkyl group (the alkyl group each independently may be substituted with one or more substituents selected from halogen and a hydroxy group), or

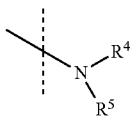

in which
$R^4$ and $R^5$ each independently represents hydrogen, a lower alkyl group or a cycloalkyl group, or $R^4$, $R^5$ and the nitrogen atom to which they are attached are taken together to form a 3- to 8-membered nitrogen-containing aliphatic ring (one or more carbon atoms constituting the nitrogen-containing aliphatic ring may be substituted with a nitrogen atom, a sulfur atom or an oxygen atom, and when a carbon atom is substituted with a nitrogen atom, the nitrogen atom may be substituted with a lower alkyl group),
or $R^4$ and the nitrogen atom to which it is attached are taken together with ring A to form a 8- to 16-membered nitrogen-containing fused bicyclic ring (one or more carbon atoms constituting the nitrogen-containing fused bicyclic ring may be substituted with a nitrogen atom, a sulfur atom or an oxygen atom, and when a carbon atom is substituted with a nitrogen atom, the nitrogen atom may be substituted with a lower alkyl group) and $R^5$ represents hydrogen, a lower alkyl group or a cycloalkyl group,
in which the line, that the dotted line intersects, means a bond of the above general formula to the other structural moiety,
$R^2$ or $R^3$ each independently represents halogen, OH, COOH, $SO_3H$, $NO_2$, SH, $NR^aR^b$, a lower alkyl group (the alkyl group each independently may be substituted with one or more substituents selected from halogen and a hydroxy group) or a —O-lower alkyl group (the alkyl group each independently may be substituted with one or more substituents selected from halogen, a hydroxy group and a —O-lower alkyl-O-lower alkyl group (the alkyl group each independently may be substituted with halogen)),
ring A is unsubstituted, or substituted with $R^6$ (in which $R^6$ is one or more substituents selected independently from halogen, OH, COOH, $SO_3H$, $NO_2$, SH, $NR^aR^b$, a lower alkyl group (the alkyl group each independently may be substituted with one or more substituents selected from halogen and a hydroxy group) and a —O-lower alkyl group (the alkyl group each independently may be substituted with one or more substituents selected from halogen and a hydroxy group),
$R^a$ and $R^b$ each independently represents hydrogen or a lower alkyl group (the alkyl group each independently may be substituted with one or more substituents selected from halogen and a hydroxy group),
m is an integer of 0 to 4, and
n is an integer of 0 to 4, or a pharmaceutically acceptable salt or solvate thereof.
(2) The compound according to (1), wherein $R^1$ is halogen, a —C(=O)-lower alkyl group (the alkyl group each independently may be substituted with $NH_2$), a lower alkyl group (the alkyl group each independently may be substituted with a hydroxy group), —O-lower alkyl group, or

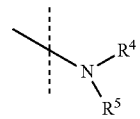

in which
$R^4$ and $R^5$ each independently represents hydrogen or a lower alkyl group, or a pharmaceutically acceptable salt or solvate thereof.
(3) The compound according to (1) or (2), wherein at least one of $R^2$, $R^3$ and $R^6$ is a —O-lower alkyl group substituted with one hydroxy group and one halogen, or a pharmaceutically acceptable salt or solvate thereof.
(4) The compound according to (3), wherein at least one of $R^2$, $R^3$ and $R^6$ is represented by:

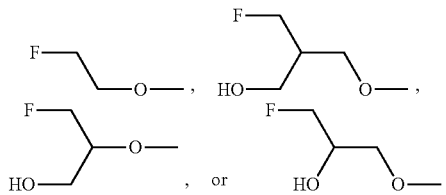

or a pharmaceutically acceptable salt or solvate thereof.
(5) The compound according to (1) or (2), wherein at least one of $R^2$, $R^3$ and $R^6$ is $NR^aR^b$, and $R^a$ and $R^b$ each independently represents hydrogen or an unsubstituted lower alkyl group, or a pharmaceutically acceptable salt or solvate thereof.
(6) The compound according to (1), wherein the compound of the formula (I) is a compound selected from the group consisting of:
2-(4-aminophenyl)-8-(1-fluoromethyl-2-hydroxyethoxy)quinoline,
2-(4-diethylaminophenyl)-6-(1-fluoromethyl-2-hydroxy)quinoline,
2-(4-diethylaminophenyl)-7-(2-fluoromethyl-2-hydroxyethoxy)quinoline,
2-(4-diethylaminophenyl)-8-(1-fluoromethyl-2-hydroxyethoxy)quinoline,
2-(4-diethylaminophenyl)-7-(1-fluoromethyl-2-hydroxyethoxy)quinoline,
2-(4-diethylaminophenyl)-4-(3-fluoro-2-hydroxypropoxy)quinoline,
2-(4-diethylaminophenyl)-5-(1-fluoromethyl-2-hydroxyethoxy)quinoline,
2-(4-diethylaminophenyl)-3-(1-fluoromethyl-2-hydroxyethoxy)quinoline,
2-(4-diethylaminophenyl)-8-[(3-fluoro-2-hydroxy)propoxy]quinoline,
2-(4-fluoromethyl-2-hydroxyethoxy)-2-(4-dimethylaminophenyl)quinoline,
7-(1-fluoromethyl-2-hydroxyethoxy)-2-(4-methylaminophenyl)quinoline,
2-(4-ethylmethylaminophenyl)-7-(1-fluoromethyl-2-hydroxyethoxy)-quinoline,
6-[((3-fluoro-2-hydroxy)propoxy]-2-(4-dimethylaminophenyl)quinoline, 7-[(3-fluoro-2-hydroxy)propoxy]-2-(4-methylaminophenyl)quinoline,
7-[(3-fluoro-2-hydroxy)propoxy]-2-(4-dimethylaminophenyl)quinoline,
2-(4-ethylmethylaminophenyl)-7-[(3-fluoro-2-hydroxy)propoxy]quinoline,
2-(4-aminophenyl)-6-[(3-fluoro-2-hydroxy)propoxy]quinoline,
6-[(3-fluoro-2-hydroxy)propoxy]-2-(4-methylaminophenyl)quinoline,
6-[(3-fluoro-2-hydroxy)propoxy]-2-(4-diethylaminophenyl)quinoline,
7-amino-2-(4-fluorophenyl)quinoline,
2-(4-fluorophenyl)-7-dimethylaminoquinoline,
5-amino-2-(4-fluorophenyl)quinoline,
2-(4-fluorophenyl)-5-dimethylaminoquinoline oxalate,
8-amino-2-(4-fluorophenyl)quinoline,
2-(4-fluorophenyl)-8-dimethylaminoquinoline,
6-amino-2-(4-fluorophenyl)quinoline,
2-(4-fluorophenyl)-6-dimethylaminoquinoline,
2-(2-aminopyrid-5-yl)-7-(1-fluoromethyl-2-hydroxyethoxy)quinoline,
6-ethylmethylamino-2-(4-fluorophenyl)quinoline,
6-diethylamino-2-(2-fluoropyrid-5-yl)quinoline,
8-ethylmethylamino-2-(2-fluoropyrid-5-yl)quinoline,
5-ethylamino-2-(2-fluoropyrid-5-yl)quinoline,
5-diethylamino-2-(2-fluoropyrid-5-yl)quinoline,
7-diethylamino-2-(2-fluoropyrid-5-yl)quinoline,
7-ethylmethylamino-2-(2-fluoropyrid-5-yl)quinoline,
2-(4-ethylaminophenyl)-6-[(3-fluoro-2-hydroxy)propoxy]quinoline,
2-(2-aminopyrid-5-yl)-6-[(3-fluoro-2-hydroxy)propoxy]quinoline,
2-(2-methylaminopyrid-5-yl)-6-[(3-fluoro-2-hydroxy)propoxy]quinoline,
6-[((3-fluoro-2-hydroxy)propoxy]-2-(2-dimethylaminopyrid-5-yl)quinoline,
2-(2-diethylaminopyrid-5-yl)-6-[(3-fluoro-2-hydroxy)propoxy]quinoline,
2-(2-ethylaminopyrid-5-yl)-6-[(3-fluoro-2-hydroxy)propoxy]quinoline,
1-fluoro-3-(2-[4-(4-methylpiperazin-1-yl)phenyl]quinolin-6-yloxy)propan-2-ol,
1-fluoro-3-{2-[6-(piperazin-1-yl)pyridin-3-yl]quinolin-6-yloxy}propan-2-ol,
1-fluoro-3-{2-[6-(4-methylpiperazin-1-yl)pyridin-3-yl]quinolin-6-yloxy}propan-2-ol,
6-[(3-fluoro-2-hydroxy)propoxy]-2-(4-methyl-3, 4-dihydro-2H-pyrido[3,2-b][1,4]oxazin-7-yl)quinoline,
6-[(3-fluoro-?-hydroxy) propoxy]-2-(1-methyl-1,2,3,4-tetrahydroquinolin-6-yl)quinoline,
6-[(3-fluoro-2-hydroxy-1, 1-dimethyl)propoxy]-2-(1-methyl-1,2,3,4-tetrahydroquinolin-6-yl)quinoline,
2-(4-amino-3-fluorophenyl)-6-dimethylaminoquinoline,
2-[4-(amino)-3-[(3-fluoro-2-hydroxy)propoxy]phenyl-6-methylaminoquinoline,
2-[3-(3-fluoro-2-hydroxy-1, 1-dimethyl)propoxy]-4-(dimethylamino)-phenyl]-6-dimethylaminoquinoline,
6-amino-2-[4-(amino)-3-[(3-fluoro-2-hydroxy) propoxy]phenyl]quinoline,
2-[3-[(3-fluoro-2-hydroxy)propoxy]-4-(dimethylamino)phenyl]-6-dimethylaminoquinoline,
2-[3-[(3-fluoro-2-hydroxy)propoxy]-4-(methylamino)phenyl]-6-methylaminoquinoline,
2-[4-(amino)-3-[(3-fluoro-2-hydroxy)propoxy]phenyl]-6-dimethylaminoquinoline,
6-amino-2-[3-[(3-fluoro-2-hydroxy)propoxy]-4-(dimethylamino)phenyl]-quinoline,
2-[3-[(3-fluoro-2-hydroxy)propoxy]-4-(dimethylamino)phenyl]-6-methylaminoquinoline,
2-[3-[2-[2-(2-fluoroethoxy)ethoxy]ethoxy-4-(methylamino)phenyl]-6-dimethylaminoquinoline,
2-[3-[(3-fluoro-2-hydroxy)propoxy]-4-(methylamino)phenyl]-6-dimethylaminoquinoline,
6-amino-2-[3-[(3-fluoro-2-hydroxy)propoxy]-4-(methylamino)phenyl]-quinoline,
2-[3-[(3-fluoro-2-hydroxy) propoxy]-2-(dimethylamino)pyrid-5-yl]-6-dimethylaminoquinoline,
2-[3-[(3-fluoro-2-hydroxy)propoxy]-2-(dimethylamino)pyrid-5-yl]quinoline,
6-[[2-(tetrahydro-2H-pyran-2-yloxy)-tosyloxy]propoxy]-2-(4-methyl-3,4-dihydro-2H-pyrido[3,2-b][1,4]oxazin-7-yl)quinoline,
6-[(3-fluoro-2-hydroxy)propoxy]-2-(6-fluoropyridin-3-yl)quinoline,
6-[(3-fluoro-2-hydroxy)propoxy]-2-(4-methoxyphenyl)quinoline,
6-[(3-fluoro-2-hydroxy)propoxy]-2-[4-(hydroxymethyl)phenyl]quinoline,
6-[(3-fluoro-2-hydroxy)propoxy]-2-(4-ethanonephenyl)quinoline,
6-[(3-fluoro-2-hydroxy)propoxy]-2-(6-methoxypyridin-3-yl)quinoline,
6-[(3-fluoro-2-hydroxy)propoxy]-2-(4-ethoxyphenyl)quinoline,
6-[(3-fluoro-2-hydroxy)propoxy]-2-(4-amino-3-methoxyphenyl)quinoline,
6-[(3-fluoro-2-hydroxy)propoxy]-2-(benzamido-4-yl)quinoline,
6-[(3-fluoro-2-hydroxy)propoxy]-2-(3-aminophenyl)quinoline, and
6-[(3-fluoro-2-hydroxy)propoxy]-2-(1-methyl-pyrazol-4-yl)quinoline, or a pharmaceutically acceptable salt or solvate thereof.

(7) The compound according to any one of (1) to (6), wherein the compound is labeled, or a pharmaceutically acceptable salt or solvate thereof.

(8) The compound according to (7), wherein the label is a radioactive nuclide, or a pharmaceutically acceptable salt or solvate thereof.

(9) The compound according to (8), wherein the radioactive nuclide is a γ-ray emitting nuclide, or a pharmaceutically acceptable salt or solvate thereof.

(10) The compound according to (7), wherein the label is a positron emitting nuclide, or a pharmaceutically acceptable salt or solvate thereof.

(11) The compound according to (10), wherein the positron emitting nuclide is selected from the group consisting of $^{11}$C, $^{13}$N, $^{15}$O, $^{18}$F, $^{35m}$Cl, $^{76}$Br, $^{45}$Ti, $^{48}$V, $^{60}$Cu, $^{61}$Cu, $^{62}$Cu, $^{64}$Cu, $^{66}$Ga, $^{89}$Zr, $^{94m}$Tc and $^{124}$I, or a pharmaceutically acceptable salt or solvate thereof.

(12) The compound according to (11), wherein the positron emitting nuclide is $^{11}$C or $^{18}$F, or a pharmaceutically acceptable salt or solvate thereof.

(13) A pharmaceutical composition comprising the compound according to any one of (1) to (12), or a pharmaceutically acceptable salt or solvate thereof.

(14) A pharmaceutical composition comprising the compound according to any one of (1) to (12), or a pharmaceutically acceptable salt or solvate thereof, and a solubilizing agent.

(15) The pharmaceutical composition according to (14), wherein the solubilizing agent is selected from the group consisting of Polysorbate 80, polyethylene glycol, ethanol, propylene glycol and a combination of two or more kinds thereof.

(16) The pharmaceutical composition according to any one of (13) to (15), which is an injection.

(17) A composition for the diagnosis of conformational disease, comprising the compound according to any one of (1) to (12) or a pharmaceutically acceptable salt or solvate thereof.

(18) A pharmaceutical composition for the treatment and/or prevention of conformational disease, comprising the compound according to any one of (1) to (12) or a pharmaceutically acceptable salt or solvate thereof.

(19) A kit for the diagnosis of conformational disease, comprising the compound according to any one of (1) to (12) or a pharmaceutically acceptable salt or solvate thereof as an essential ingredient.

(20) A composition or kit for the detection or staining of a β-sheet structure protein, comprising the compound according to any one of (1) to (12) or a pharmaceutically acceptable salt or solvate thereof as an essential ingredient.

(21) The kit according to (19) or (20) for imaging diagnosis.

(22) A method of treating and/or preventing conformational disease in a subject, which comprises administering the compound according to any one of (1) to (12) or a pharmaceutically acceptable salt or solvate thereof to the subject.

(23) A method of diagnosing conformational disease in a subject, which comprises administering the compound according to any one of (1) to (12) or a pharmaceutically acceptable salt or solvate thereof to the subject.

(24) Use of the compound according to any one of (1) to (12) or a pharmaceutically acceptable salt or solvate thereof for the production of a composition or kit for the diagnosis of conformational disease in a subject.

(25) Use of the compound according to any one of (1) to (12) or a pharmaceutically acceptable salt or solvate thereof for the production of a pharmaceutical composition for the treatment and/or prevention of conformational disease in a subject.

(26) A method of detecting or staining a β-sheet structure protein in a sample, which comprises staining the sample using the compound according to any one of (1) to (12) or a pharmaceutically acceptable salt or solvate thereof.

(27) Use of the compound according to any one of (1) to (12) or a pharmaceutically acceptable salt or solvate thereof for the production of a composition or kit for the detection or staining of a β-sheet structure protein.

(28) The composition, kit, method or use according to any one of (17) to (27), wherein the conformational disease is tauopathy, particularly Alzheimer's disease, and the β-sheet structure protein is tau protein.

(29) A method of producing the compound of the formula (I), which comprises the following steps of:
(i) reacting a compound of the formula (II):

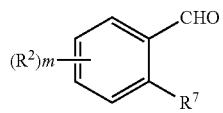
(II)

in which, $R^2$ and m are as defined in the formula (I), and $R^7$ represents $NH_2$ or $NO_2$, with a compound of the formula (III):

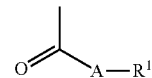
(III)

in which A and $R^1$ are as defined in the formula (I), to obtain a compound of the formula (IV):

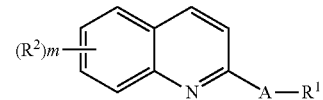
(IV)

and isolating this compound as the compound of the formula (I), or
(ii) optionally converting the compound of the formula (IV) into another compound of the formula (I) and isolating the compound.

(30) A method of producing the compound of the formula (I), which comprises the following steps of:
(i) reacting a compound of the formula (V):

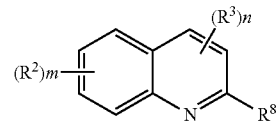
(V)

in which $R^2$, $R^3$, m and n are as defined in the formula (I), and $R^8$ is a hydroxyl group or halogen, provided that at least one of $R^2$ or $R^3$ is a hydroxy group, with a compound of the formula: OH-Ark (Ark each independently represents a lower alkyl group which may be substituted with one or more substituents selected from the group consisting of halogen and a hydroxy group, to obtain a compound of the formula (V'):

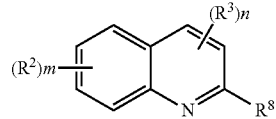
(V')

in which $R^2$, $R^3$, m and n are as defined in the formula (I), and $R^8$ is a hydroxyl group or halogen, provided that at least one of $R^2$ or $R^3$ is —O—Ark (Ark is as defined above), and
(ii) reacting the compound of the formula (V') with a compound of the formula (VI) or (VII):

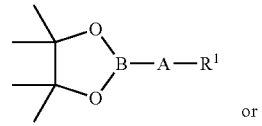
(VI)

or

-continued (VII)

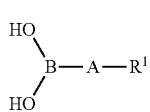

in which A and R$^1$ are as defined in the formula (I), to obtain the compound of the formula (I) in which at least one of R$^2$ and R$^3$ is a —O-lower alkyl group (the alkyl group each independently may be substituted with one or more substituents selected from the group consisting of halogen and a hydroxy group), or isolating the compound, or (iii) optionally converting the obtained compound of the formula (I) into another compound of the formula (I), and isolating the compound.

(31) A method of producing the compound of the formula (I) in which at least one of R$^2$ and R$^3$ is a —O-lower alkyl group (the alkyl group each independently may be substituted with one or more substituents selected from the group consisting of halogen and a hydroxy group), which comprises the following steps of:

(i) reacting a compound of the formula (V):

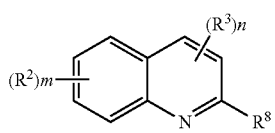

in which R$^2$, R$^3$, m and n are as defined in the formula (I), and R$^8$ is a hydroxyl group or halogen, provided that at least one of R$^2$ or R$^3$ is a hydroxy group, with a compound of the formula (VI) or (VII):

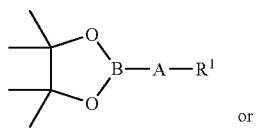

or

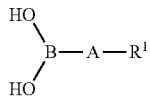

in which A and R$^1$ are as defined in the formula (I), to obtain a compound of the formula (V''):

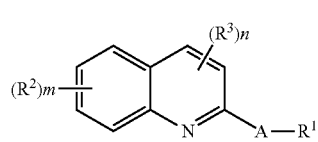

in which R$^1$, R$^2$, R$^3$, A, m and n are as defined in the formula (I), provided that at least one of R$^2$ or R$^3$ is a hydroxy group, and (ii) reacting the compound of the formula (V'') with a compound of the formula: OH-Ark (Ark each independently represents a lower alkyl group which may be substituted with one or more substituents selected from the group consisting of halogen and a hydroxy group) to obtain compound of the formula (I) in which at least one of R$^2$ and R$^3$ is a —O-lower alkyl group (the alkyl group each independently may be substituted with one or more substituents selected from the group consisting of halogen and a hydroxy group), and isolating the compound, or (iii) optionally converting the obtained compound of the formula (I) into another compound of the formula (I), and isolating the compound.

(32) The method according to (31), wherein the compound of the formula (I) is selected from:
6-[(3-fluoro-2-hydroxy)propoxy]-2-(4-dimethylaminophenyl)quinoline,
6-[(3-fluoro-2-hydroxy)propoxy]-2-(4-methylaminophenyl)quinoline, and
2-(4-ethylaminophenyl)-6-[(3-fluoro-2-hydroxy)propoxy]quinoline.

(33) A compound of the formula (I'):

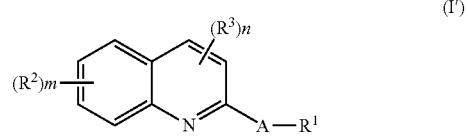

in which
A is

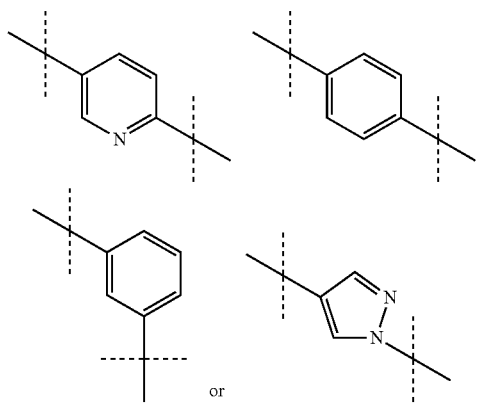

or

R$^1$ is halogen, a —C(═O)-lower alkyl group (the alkyl group each independently may be substituted with one or more substituents selected from NR$^a$R$^b$, halogen and a hydroxy group), a lower alkyl group (the alkyl group each independently may be substituted with one or more substituents selected from halogen and a hydroxy group), a —O-lower alkyl group (the alkyl group each independently may be substituted with one or more substituents selected from halogen and a hydroxy group), or

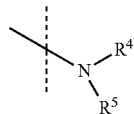

in which
R$^4$ and R$^5$ each independently represents hydrogen, a lower alkyl group or a cycloalkyl group, or R$^4$, R$^5$ and the nitrogen atom to which they are attached are taken together to form a 3- to 8-membered nitrogen-containing aliphatic ring (one or more carbon atoms constituting the nitrogen-containing aliphatic ring may be substituted with a nitrogen atom, a sulfur atom or an oxygen atom, and when a carbon atom is substituted with a nitrogen atom, the nitrogen atom may be substituted with a lower alkyl group), or $R^4$ and the nitrogen atom to which it is attached are taken together with ring A to form a 8- to 16-membered nitrogen-containing fused bicyclic ring (one or more carbon atoms constituting the nitrogen-containing fused bicyclic ring may be substituted with a nitrogen atom, a sulfur atom or an oxygen atom, and when a carbon atom is substituted with a nitrogen atom, the nitrogen atom may be substituted with a lower alkyl group), $R^5$ is hydrogen, a lower alkyl group or a cycloalkyl group, in which the line, that the dotted line intersects, means a bond of the above general formula to the other structural moiety, $R^2$ or $R^3$ each independently may be substituted with halogen, OH, COOH, $SO_3H$, $NO_2$, SH, $NR^aR^b$, a lower alkyl group (the lower alkyl group each independently may be substituted with one or more substituents selected from a p-toluenesulfonyloxy group (tosyloxy group, TsO), a methanesulfonyloxy group, a trifluoromethanesulfonyloxy group or a 2-tetrahydropyranyloxy (OTHP), halogen and a hydroxy group) or a —O-lower alkyl group (the lower alkyl group is substituted with a p-toluenesulfonyloxy group (tosyloxy group, TsO), a methanesulfonyloxy group, trifluoromethanesulfonyloxy group or a 2-tetrahydropyranyloxy (OTHP), and also may be substituted with a hydroxy group), ring A is unsubstituted or substituted with $R^6$ (in which $R^6$ is one or more substituents selected independently from halogen, OH, COOH, $SO_3H$, $NO_2$, SH, $NR^aR^b$, a lower alkyl group (the lower alkyl group each independently may be substituted with one or more substituents selected from the group consisting of a p-toluenesulfonyloxy group (tosyloxy group, TsO), a methanesulfonyloxy group, a trifluoromethanesulfonyloxy group or a 2-tetrahydropyranyloxy (OTHP), halogen and a hydroxy group) and an —O-lower alkyl group (the alkyl group each independently may be substituted with one or more substituents selected from a p-toluenesulfonyloxy group (tosyloxy group, TsO), a methanesulfonyloxy group, a trifluoromethanesulfonyloxy group or a 2-tetrahydropyranyloxy (OTHP), halogen, a hydroxy group and an —O-lower alkyl group-O-lower alkyl group (the alkyl group each independently may be substituted with halogen))), $R^a$ and $R^b$ independently represents hydrogen or a lower alkyl group (the alkyl group and the lower alkyl group each independently may be substituted with one or more substituents selected from a p-toluenesulfonyloxy group (tosyloxy group, TsO), a methanesulfonyloxy group, a trifluoromethanesulfonyloxy group or a 2-tetrahydropyranyloxy (OTHP), halogen and a hydroxy group), m is an integer of 0 to 4, and n is an integer of 0 to 4, provided that at least one of $R^2$, $R^3$ and $R^6$ represents an —O-lower alkyl group (the lower alkyl group is substituted with a p-toluenesulfonyloxy group (tosyloxy group, TsO), a methanesulfonyloxy group, a trifluoromethanesulfonyloxy group or a 2-tetrahydropyranyloxy (OTHP), and may also be substituted with one or more substituents selected from halogen and a hydroxy group), or a pharmaceutically acceptable salt or solvate thereof.

(34) The compound according to (33), wherein at least one of $R^2$, $R^3$ and $R^6$ is a group of the formula:

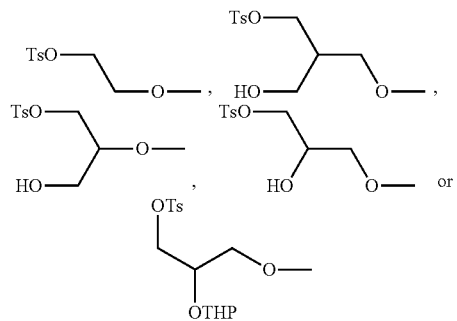

(35) The compound according to (33), wherein the compound of the formula (I') is a compound selected from the group consisting of:

2-(4-diethylaminophenyl)-6-[(2-hydroxy-1-tosyloxymethyl)ethoxy]quinoline, 2-(4-aminophenyl)-8-(2-hydroxy-1-tosyloxymethylethoxy)quinoline, 2-(4-diethylaminophenyl)-8-(2-hydroxy-1-tosyloxymethylethoxy)quinoline, 2-(4-diethylaminophenyl)-8-[[2-(tetrahydro-2H-pyran-2-yloxy)-3-tosyloxy]propoxy]quinoline, 2-(4-diethylaminophenyl)-7-(2-hydroxy-1-tosyloxymethylethoxy)quinoline, 2-(4-diethylaminophenyl)-7-[[(2-tetrahydro-2H-pyran-2-yloxy)-3-tosyloxy]propoxy]quinoline, 7-(2-hydroxy-1-tosyloxymethylethoxy)-2-(4-dimethylaminophenyl)quinoline, 7-(2-hydroxy-1-tosyloxymethylethoxy)-2-(4-methylaminophenyl)quinoline, 2-(4-ethylmethyl aminophenyl)-7-(2-hydroxy-1-tosyloxymethylethoxy)quinoline, 2-(4-diethylaminophenyl)-5-(2-hydroxy-1-tosyloxymethylethoxy)quinoline, 2-(4-ethylmethylaminophenyl)-7-[[2-(tetrahydro-2H-pyran-2-yloxy)-3-tosyloxy]propoxy]quinoline, 2-(4-methylaminophenyl)-7-[[2-(tetrahydro-2H-pyran-2-yloxy)-3-tosyloxy]propoxy]quinoline, 2-(4-dimethylaminophenyl)-7-[[2-(tetrahydro-2H-pyran-2-yloxy)-3-tosyloxy]propoxy]quinoline, 2-(4-methylaminophenyl)-6-[[2-(tetrahydro-2H-pyran-2-yloxy)-3-tosyloxy]propoxy]quinoline, 2-(4-diethylaminophenyl)-6-[[2-(tetrahydro-2H-pyran-2-yloxy)-3-tosyloxy]propoxy]quinoline, 2-(4-dimethylaminophenyl)-6-[[2-(tetrahydro-2H-pyran-2-yloxy)-3-tosyloxy]propoxy]quinoline, 2-(4-aminophenyl)-6-[[2-(tetrahydro-2H-pyran-2-yloxy)-3-tosyloxy]propoxy]quinoline, 2-(4-ethylaminophenyl)-6-[[2-(tetrahydro-2H-pyran-2-yloxy)-3-tosyloxy]propoxy]quinoline, 2-(2-aminopyrid-5-yl)-6-[[2-(tetrahydro-2H-pyran-2-yloxy)-3-tosyloxy]propoxy]quinoline, 2-(2-methylaminopyrid-5-yl)-6-[[2-(tetrahydro-2H-pyran-2-yloxy)-3-tosyloxy]propoxy]quinoline, 2-(2-dimethylaminopyrid-5-yl)-6-[[2-(tetrahydro-2H-pyran-2-yloxy)-3-tosyl oxy]propoxy]quinoline, 2-(2-diethylaminopyrid-5-yl)-6-[[2-(tetrahydro-2H-pyran-2-yloxy)-3-tosyloxy]propoxy]quinoline, 2-(2-ethylaminopyrid-5-yl)-6-[[2-(tetrahydro-2H-pyran-2-yloxy)-3-tosyloxy]propoxy]quinoline, 2-[4-(methylamino)-3-[[2-(tetrahydro-2H-pyran-2-yloxy)-3-tosyloxy]propoxy]phenyl]-6-dimethylaminoquinoline, and 2-[4-(dimethylamino)-3-[[2-(tetrahydro-2H-pyran-2-yloxy)-3-tosyloxy]propoxy]phenyl]-6-dimethylaminoquinoline.

(36) A kit for producing the labeled compound according to any one of (33) to (35), or a pharmaceutically acceptable salt or solvate thereof, comprising: the compound according to any one of (33) to (35), or a pharmaceutically acceptable salt or solvate thereof,
a labeling agent, and
optionally, instructions for carrying out labeling.

(37) The kit according to (36), wherein the labeling agent is a radioactive nuclide.

(38) The kit according to (37), wherein the radioactive nuclide is a γ-ray emitting nuclide.

(39) The kit according to (36), wherein the labeling agent is a positron emitting nuclide.

(40) The kit according to (39), wherein the positron emitting nuclide is selected from the group consisting of $^{11}$C, $^{13}$N, $^{15}$O, $^{18}$F, $^{35}$mCl, $^{76}$Br, $^{45}$Ti, $^{48}$V, $^{60}$Cu, $^{61}$Cu, $^{62}$Cu, $^{64}$Cu, $^{66}$Ga, $^{89}$Zr, $^{94m}$Tc and $^{124}$I.

(41) The kit according to (40), wherein the positron emitting nuclide is $^{11}$C or $^{18}$F.

(42) A method for producing the compound according to (7), which comprises the step of reacting the compound according to (34) with a labeling agent.

(43) The method according to (42), wherein the labeling agent is a radioactive nuclide.

Effects of the Invention

According to the present invention, there is provided a compound having very high safety, which is highly specific to tau and can image tau with satisfactory sensitivity, and also has high brain transition, low or undetected bone-seeking properties and low or undetected toxicity, and a precursor thereof. Accordingly, the diagnosis, the treatment and/or prevention of tauopathy can be carried out using the compound of the present invention. Also, according to the present invention, it becomes possible to carry out imaging diagnosis of tauopathy, particularly imaging diagnosis using PET. Accordingly, according to the present invention, it becomes possible to carry out accurate diagnosis, effective treatment and prevention in the early stages of tauopathy, particularly Alzheimer's disease.

The upper panel of FIG. 5 is a THK-5035 stained image in a brain section of Alzheimer's disease patients. The outline arrowhead denotes neurofibrillary tangles. The lower panel of FIG. 5 is a THK-5038 stained image in a brain section of Alzheimer's disease patients. The outline arrowhead denotes neurofibrillary tangles.

The upper panel of FIG. 6 is a THK-5058 stained image in a brain section of Alzheimer's disease patients. The outline arrowhead denotes neurofibrillary tangles. The lower panel of FIG. 6 is a THK-5064 stained image in a brain section of Alzheimer's disease patients. The outline arrowhead denotes neurofibrillary tangles.

The upper panel of FIG. 7 is a THK-5065 stained image in a brain section of Alzheimer's disease patients. The outline arrowhead denotes neurofibrillary tangles. The lower panel of FIG. 7 is a THK-5066 stained image in a brain section of Alzheimer's disease patients. The outline arrowhead denotes neurofibrillary tangles.

The upper panel of FIG. 8 is a THK-5071 stained image in a brain section of Alzheimer's disease patients. The outline arrowhead denotes neurofibrillary tangles. The lower panel of FIG. 8 is a THK-5077 stained image in a brain section of Alzheimer's disease patients. The outline arrowhead denotes neurofibrillary tangles.

Figure 1:
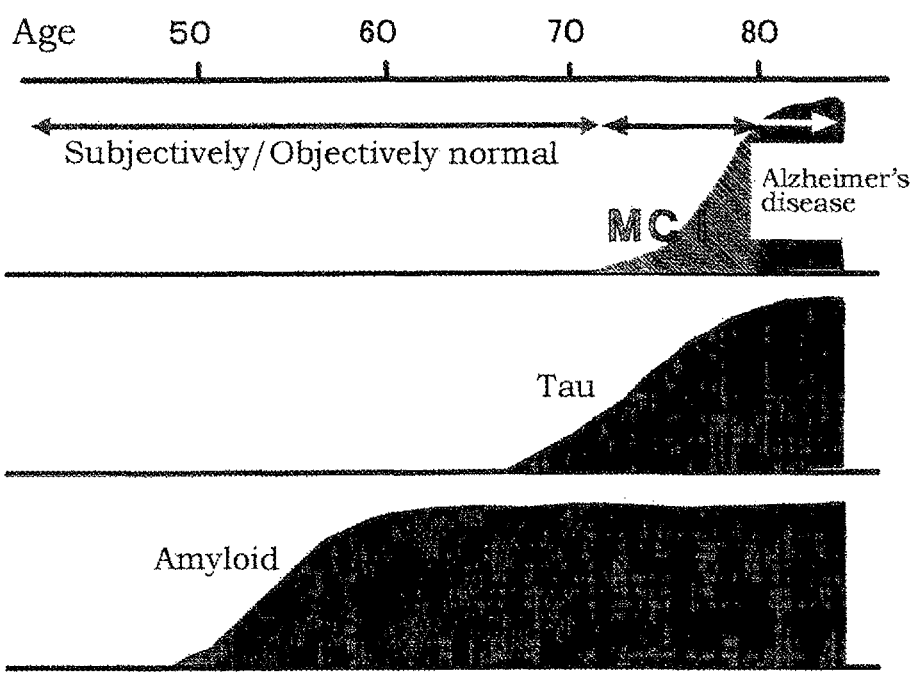
FIG. 1 is a diagram showing deviation between a clinical picture and a histological picture in Alzheimer's disease. Cited from Alzheimer's Disease (written by Yasuo IHARA, Hiroyuki ARAKI), Asahi Shimbun Company, 2007, Tokyo, partly revised. In the onset of Alzheimer's disease of patients aged 80 years, accumulation of Aβ starts at the age of 50 years and has already reach a plateau at the age of 60 years. On the other hand, tau accumulation proceeds age-dependently at the age of 70 years.
Figure 2:
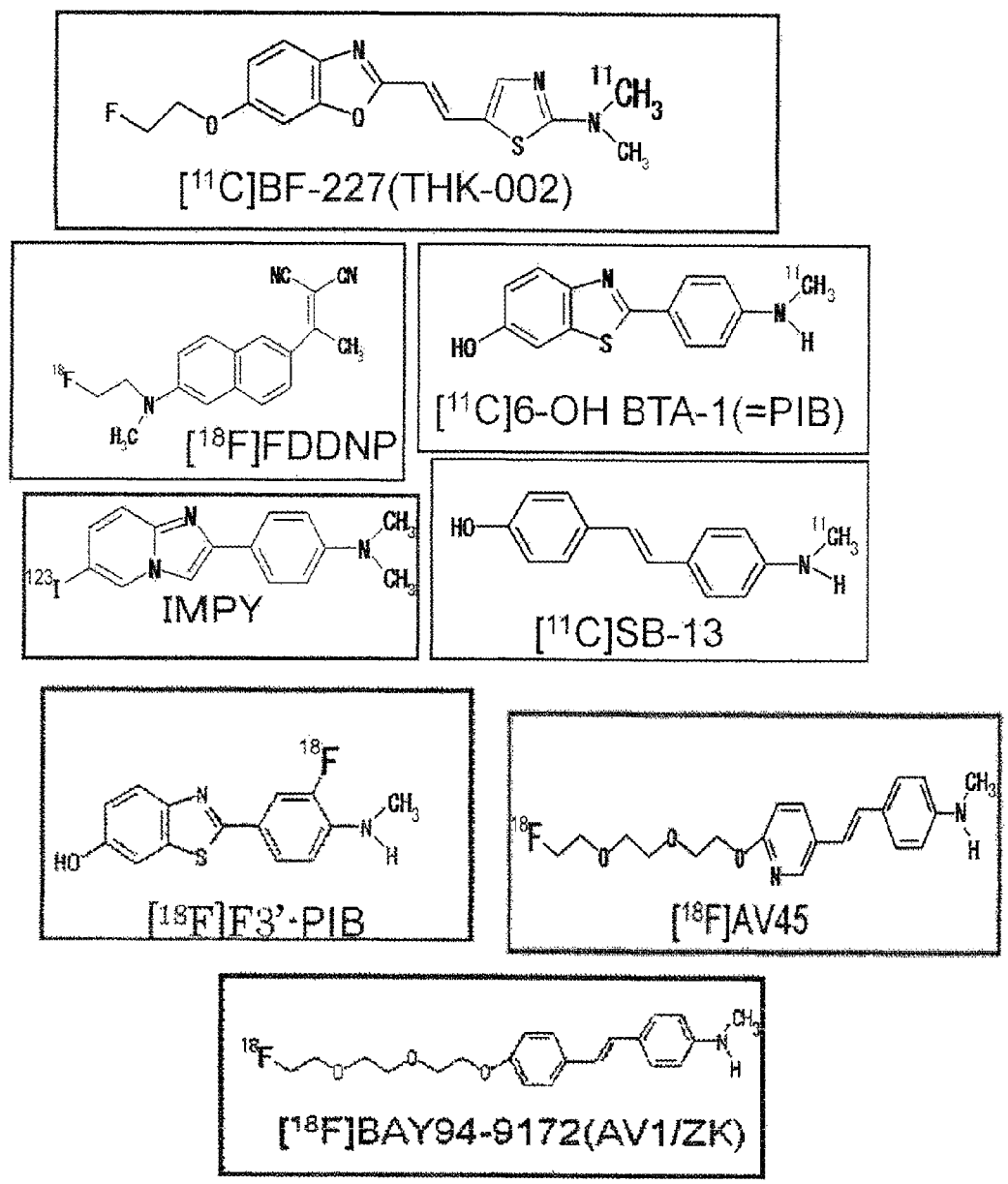
FIG. 2 illustrates PET probes for amyloid imaging, which have been developed so far.
Figure 3:
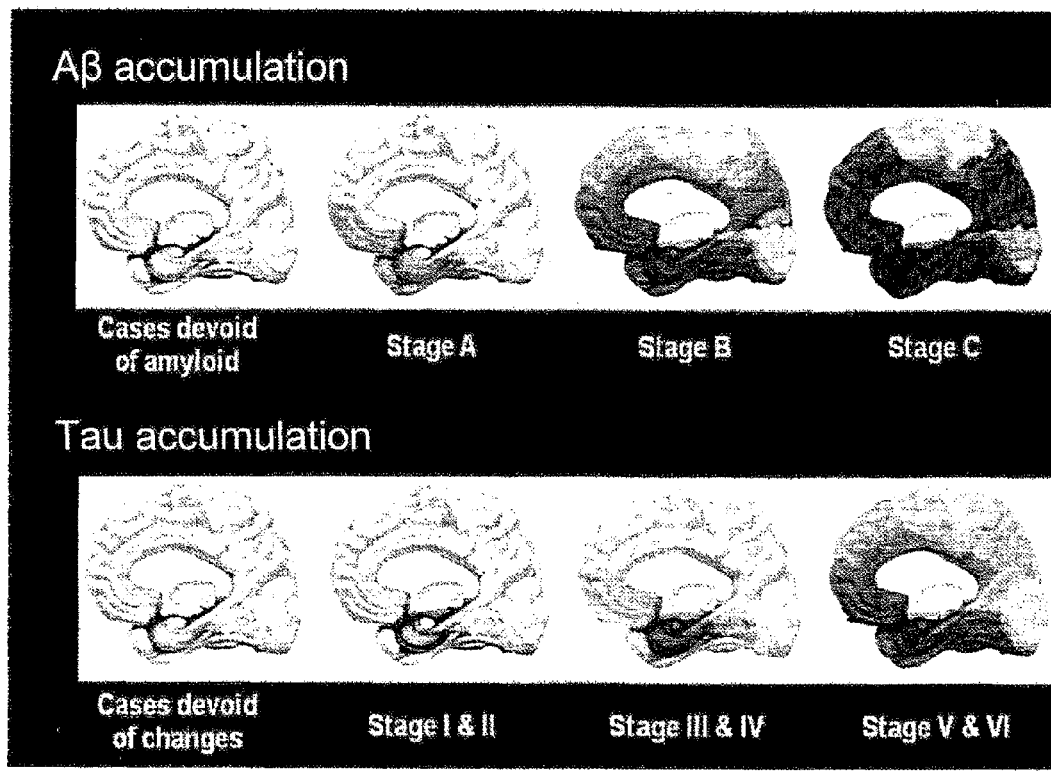
FIG. 3 is a diagram showing stages of Aβ accumulation and tau accumulation in Alzheimer's disease. Cited from Braak & Braak: Neurobiol aging. 18. 351-357. 1997, partly revised. Referring to stages of Braak after death of cases 7 and 8 in Non-Patent Document 6, Aβ accumulation was considered as Cases devoid of amyloid (or stage A), while tau accumulation was in stage VI. That is, this means that although Aβ accumulation is mild or globally mild in both cases, tau accumulation was in stage VI in which an accumulation level is the highest.
Figure 4:
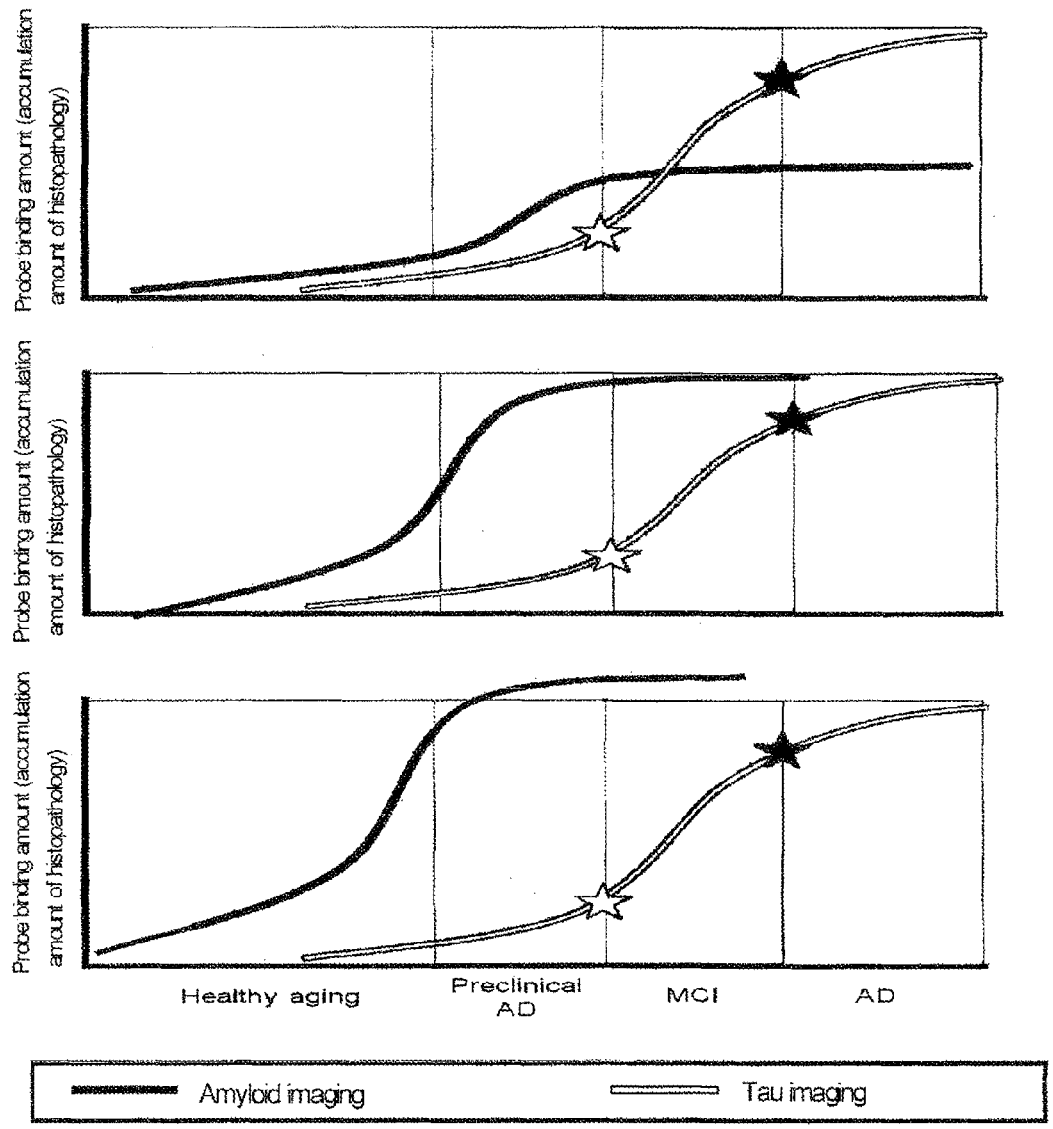
FIG. 4 is a graph showing a relation between amyloid (or Aβ) and tau in Alzheimer's disease (proposed by the present inventors). As shown in upper, middle and lower columns, when amyloid is not much accumulated, MCI and Alzheimer's disease develop when the tau accumulation reaches the threshold, and when amyloid is strongly accumulated, MCI and Alzheimer's disease do not develop when the tau accumulation does not reach the threshold. That is to say, the amount of amyloid accumulation is not related to development of MCI and Alzheimer's disease, while tau accumulation defines this development. In other words, "amyloid (or Aβ) has no threshold, but tau has one.
Figure 9:
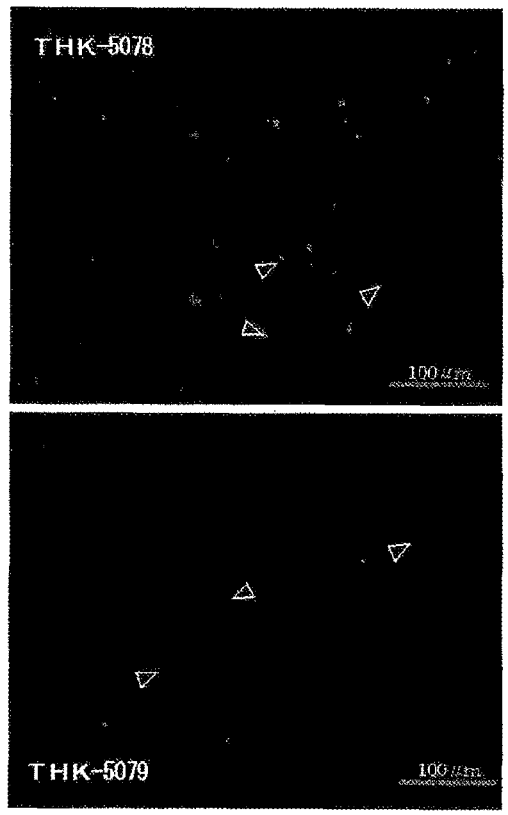

The upper panel of FIG. 9 is a THK-5078 stained image in a brain section of Alzheimer's disease patients. The outline arrowhead denotes neurofibrillary tangles. The lower panel of FIG. 9 is a THK-5079 stained image in a brain section of Alzheimer's disease patients. The outline arrowhead denotes neurofibrillary tangles.

Figure 10:
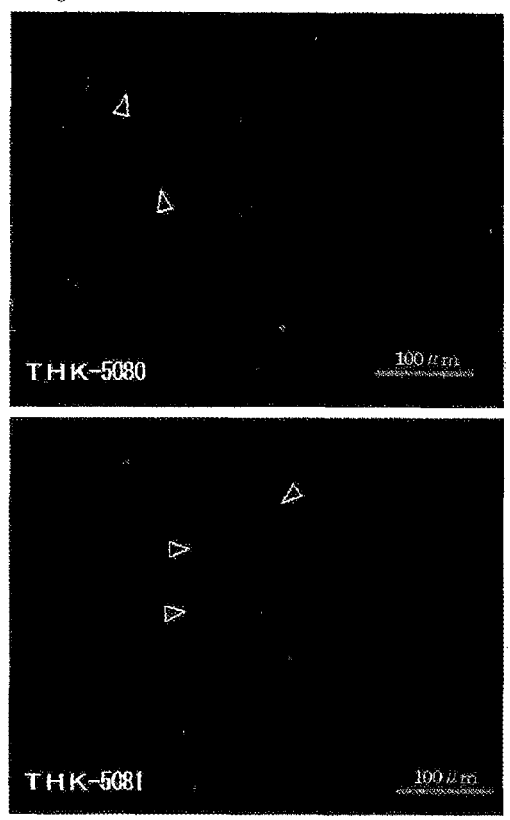

The upper panel of FIG. 10 is a THK-5080 stained image in a brain section of Alzheimer's disease patients. The outline arrowhead denotes neurofibrillary tangles. The lower panel of FIG. 10 is lower panel is a THK-5081 stained image in a brain section of Alzheimer's disease patients. The outline arrowhead denotes neurofibrillary tangles.

The upper panel of FIG. 11 is a THK-5082 stained image in a brain section of Alzheimer's disease patients. The outline arrowhead denotes neurofibrillary tangles. The lower panel of FIG. 11 is a THK-5087 stained image in a brain section of Alzheimer's disease patients. The outline arrowhead denotes neurofibrillary tangles.

The upper panel of FIG. 12 is a THK-5088 stained image in a brain section of Alzheimer's disease patients. The outline arrowhead denotes neurofibrillary tangles. The lower panel of FIG. 12 is a THK-5089 stained image in a brain section of Alzheimer's disease patients. The outline arrowhead denotes neurofibrillary tangles.

The upper panel of FIG. 13 is a THK-5091 stained image in a brain section of Alzheimer's disease patients. The outline arrowhead denotes neurofibrillary tangles. The lower panel of FIG. 13 is a THK-5092 stained image in a brain section of Alzheimer's disease patients. The outline arrowhead denotes neurofibrillary tangles.

The upper panel of FIG. 14 is a THK-5097 stained image in a brain section of Alzheimer's disease patients. The outline arrowhead denotes neurofibrillary tangles. The lower panel of FIG. 10 is a THK-5098 stained image in a brain section of Alzheimer's disease patients. The outline arrowhead denotes neurofibrillary tangles.

Figure 15:
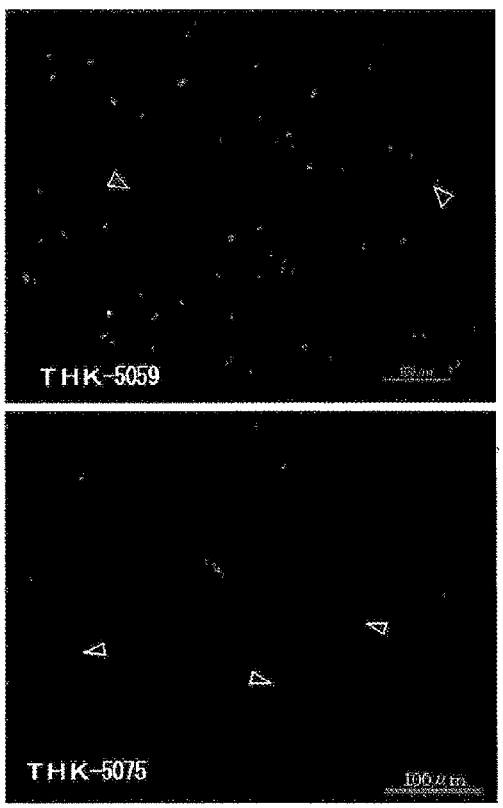

The upper panel of FIG. 15 is a THK-5059 stained image in a brain section of Alzheimer's disease patients. The outline arrowhead denotes neurofibrillary tangles. The lower panel of FIG. 15 is a THK-5075 stained image in a brain section of Alzheimer's disease patients. The outline arrowhead denotes neurofibrillary tangles.

Figure 16:
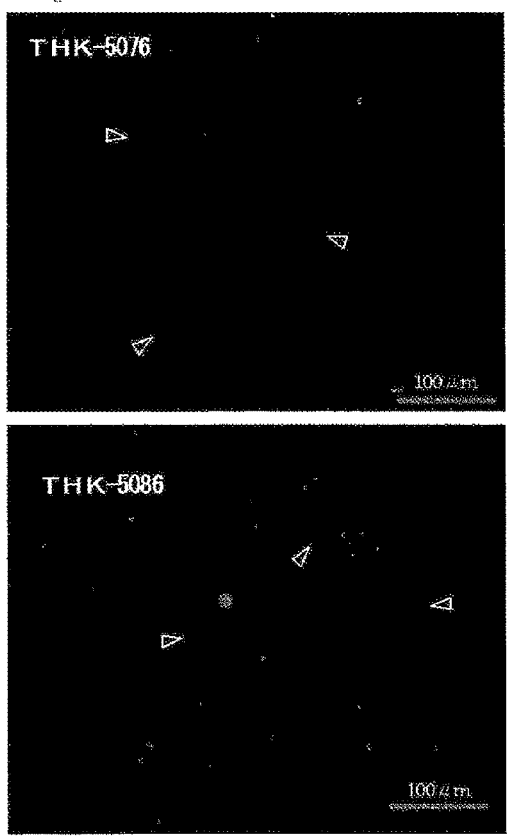

The upper panel of FIG. 16 is a THK-5076 stained image in a brain section of Alzheimer's disease patients. The outline arrowhead denotes neurofibrillary tangles. The lower panel of FIG. 15 is a THK-5086 stained image in a brain section of Alzheimer's disease patients. The outline arrowhead denotes neurofibrillary tangles.

The upper panel of FIG. 17 is a THK-5100 stained image in a brain section of Alzheimer's disease patients. The outline arrowhead denotes neurofibrillary tangles. The lower panel of FIG. 17 is a THK-5105 stained image in a brain section of Alzheimer's disease patients. The outline arrowhead denotes neurofibrillary tangles.

The upper panel of FIG. 18 is a THK-5106 stained image in a brain section of Alzheimer's disease patients. The outline arrowhead denotes neurofibrillary tangles. The lower panel of FIG. 18 is a THK-5107 stained image in a brain section of Alzheimer's disease patients. The outline arrowhead denotes neurofibrillary tangles.

The upper panel of FIG. 19 is a THK-5112 stained image in a brain section of Alzheimer's disease patients. The outline arrowhead denotes neurofibrillary tangles. The lower panel of FIG. 19 is a THK-5116 stained image in a brain section of Alzheimer's disease patients. The outline arrowhead denotes neurofibrillary tangles.

The upper panel of FIG. 20 is a THK-5117 stained image in a brain section of Alzheimer's disease patients. The outline arrowhead denotes neurofibrillary tangles. The lower panel of FIG. 20 is a THK-932 stained image in a brain section of Alzheimer's disease patients. The outline arrowhead denotes neurofibrillary tangles.

Figure 21:
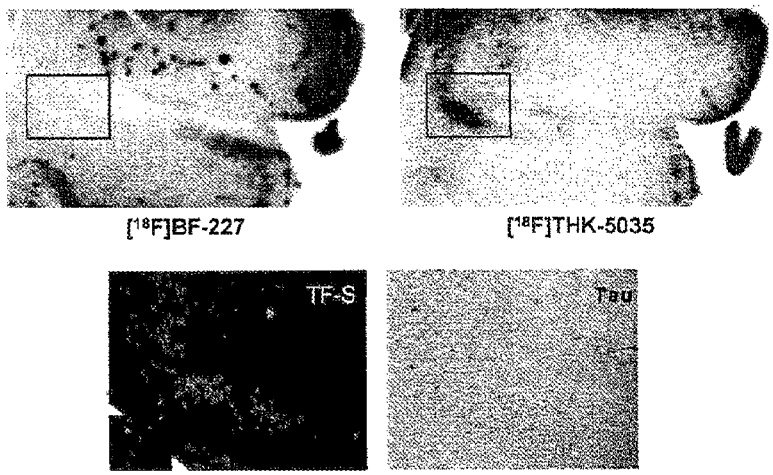

FIG. 21 shows an autoradiography image (upper left-hand and upper right-hand, respectively) of [$^{18}$F] BF-227 and [$^{18}$F] THK-5035, a thioflavin S (TF-S) stained image (lower left-hand) in a serial section, and an anti-Tau antibody (Tau) stained image (lower right-hand).

Figure 22:
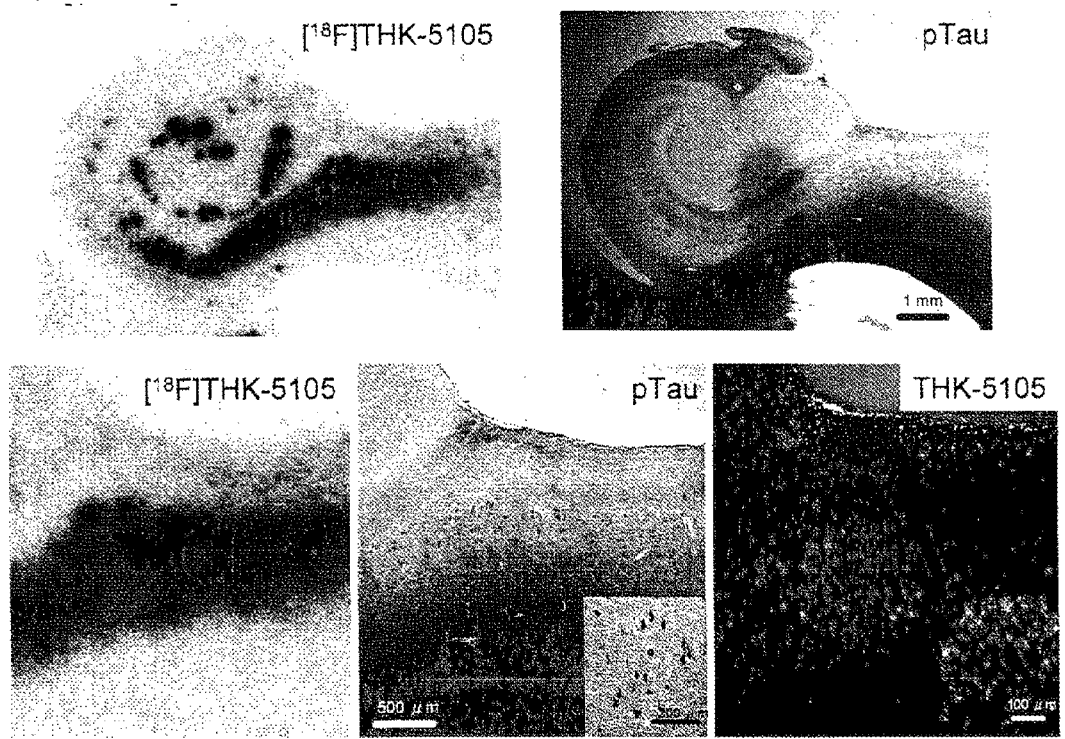

FIG. 22 shows an image of [$^{18}$F] THK-5105 autoradiography (upper left) and an image of anti-phosphorylated tau antibody (pTau) staining, of sections of the hippocampus from an Alzheimer's disease patient (a female of 83 years old and with a brain weight of 900 g). The lower panels show, from left to right, higher magnification images of [$^{18}$F] THK-5105 autoradiography, of anti-phosphorylated tau antibody (pTau) staining, and of unlabeled THK-5105 staining, with insets representing a much higher magnification of the anti-phosphorylated tau antibody (pTau) staining and of the unlabeled THK-5105 staining.

Figure 23:
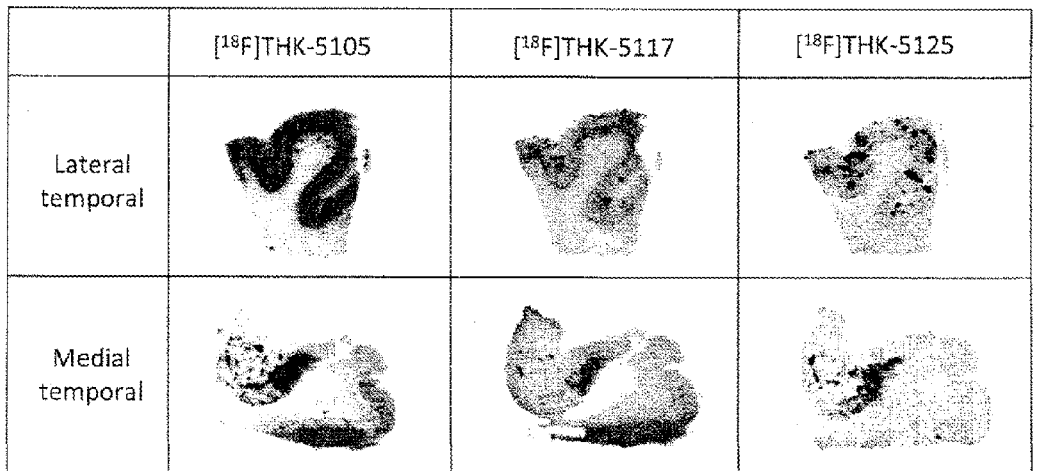

FIG. 23 shows images of [$^{18}$F] THK-5105, [$^{18}$F] THK-5117, and [$^{18}$F] THK-5125 autoradiography of sections of the lateral temporal cortex and of the medial temporal cortex from an Alzheimer's disease patient (a female of 77 years old and with a brain weight of 1,100 g).

Figure 24:
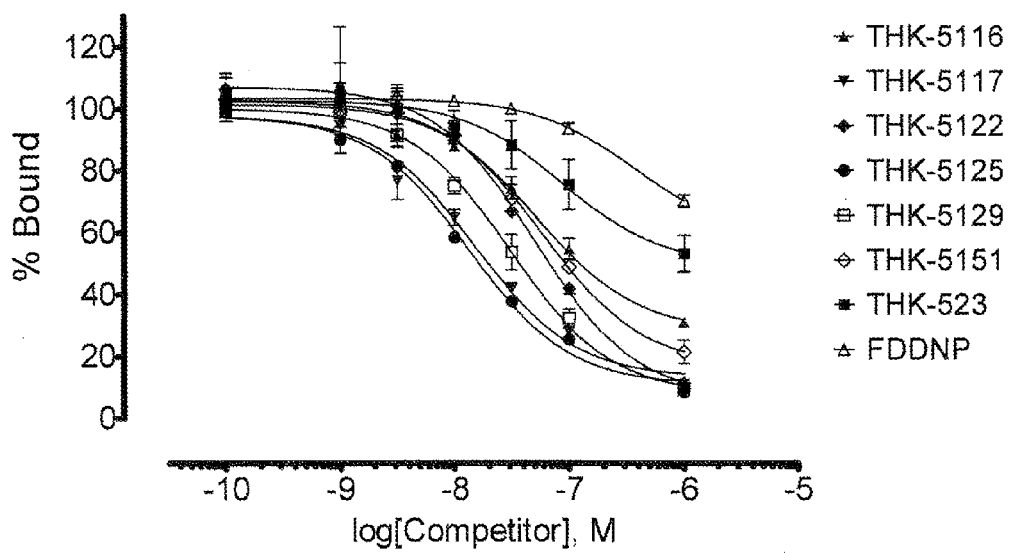

FIG. 24 shows binding affinities (Kis) of various probes to a tau. The tau used was aggregates of mutated tau (K18-ΔK280) and the radioactive ligand used was [$^{18}$F] THK-5105.

The upper panel of FIG. 25 is a THK-5136 stained image in a brain section of Alzheimer's disease patients. The outline arrowhead denotes neurofibrillary tangles. The lower panel of FIG. 25 is a THK-5153 stained image in a brain section of Alzheimer's disease patients. The outline arrowhead denotes neurofibrillary tangles.

The upper panel of FIG. 26 is a THK-5157 stained image in a brain section of Alzheimer's disease patients. The outline arrowhead denotes neurofibrillary tangles. The lower panel of FIG. 26 is a THK-5128 stained image in a brain section of Alzheimer's disease patients. The outline arrowhead denotes neurofibrillary tangles.

The upper panel of FIG. 27 is a THK-5147 stained image in a brain section of Alzheimer's disease patients. The outline arrowhead denotes neurofibrillary tangles.

The upper panel of FIG. 28 is a THK-5155 stained image in a brain section of Alzheimer's disease patients. The outline arrowhead denotes neurofibrillary tangles. The lower panel of FIG. 28 is a THK-5156 stained image in a brain section of Alzheimer's disease patients. The outline arrowhead denotes neurofibrillary tangles.

The upper panel of FIG. 29 is a THK-5164 stained image in a brain section of Alzheimer's disease patients. The outline arrowhead denotes neurofibrillary tangles. The lower panel of FIG. 29 is a THK-5154 stained image in a brain section of Alzheimer's disease patients. The outline arrowhead denotes neurofibrillary tangles.

MODE FOR CARRYING OUT THE INVENTION

The compounds of the present invention are compounds of formulae (I) and (I') described below, or salts or solvates thereof. As used herein, "compound of the present invention" and "compound according to the present invention" include the compounds of formulae (I) and (I') described below, and salts and solvates thereof, unless otherwise specified.

As used herein, "lower alkyl group" means a linear or branched alkyl group having 1 to 6 carbon atoms, and specific examples thereof include a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group and the like. The term "lower alkoxy" means —O-lower alkyl.

As used herein, "cycloalkyl group" means a cycloalkyl group having 3 to 7 carbon atoms, and specific examples thereof include a cyclopropyl group, a cyclobutyl group, a cyclopentyl group, a cyclohexyl group and a cycloheptyl group.

As used herein, "halogen" means fluorine, chlorine, bromine or iodine.

As used herein, "tau protein" and "tau" have the same meanings. As used herein, "amyloidbeta protein", "amyloid β protein", "Aβ protein", "amyloidbeta", "amyloid β" and "Aβ" have the same meanings.

In case an asymmetric carbon atom exists in the compound of the present invention, a mixture of isomers, and individual isomer are also included in the compound of the present invention.

For example, in case one asymmetric carbon exists in the compound of the present invention, each optically active compound can be separately synthesized, or individual optical isomer can be separated by column chromatography. For example, in case the optical isomer is separated by column chromatography, a column to be used includes, for example, CHIRALPAK AD (manufactured by DAICEL CHEMICAL INDUSTRIES, LTD.) or the like. Also, a solvent used in column chromatography may be a solvent which is usually used to separate the isomer. For example, chloroform, acetonitrile, ethyl acetate, methanol, ethanol, acetone, hexane, water and the like are used alone, or two or more kinds of these solvents can also be used in combination.

In order to disclose the compound of the formula (I):

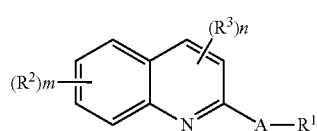
(I)

[wherein the respective symbols are as defined above] according to the present invention in more specifically, various symbols used in the formula (I) will be described by way of specific examples.

Ring A Means

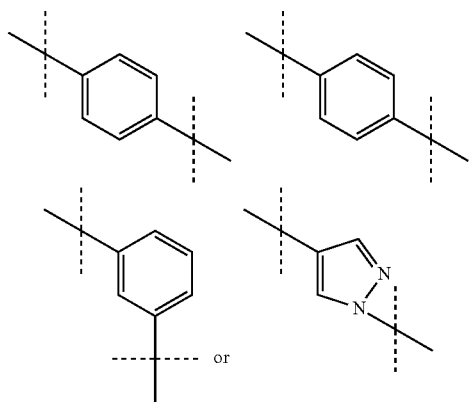

in which the line, that the dotted line intersects, means a bond of the above general formula to the other structural moiety. That is, bonds existing at 2- and 5-positions of pyridine ring are respectively attached to $R^1$ and quinoline ring of the general formula (I). The ring A is unsubstituted or substituted with one to four substituents, and preferably unsubstituted or substituted with one substituent selected from fluorine, (3-fluoro-2-hydroxy)propoxy, (3-fluoro-2-hydroxy-1,1-dimethyl)propoxy, 2-[2-(2-fluoroethoxy) ethoxy] ethoxy and methoxy.

$R^1$ is halogen, a —C(=O)-lower alkyl group (the alkyl group each independently may be substituted with one or more substituents selected from $NR^aR^b$, halogen and a hydroxy group), a lower alkyl group (the alkyl group each independently may be substituted with one or more substituents selected from halogen and a hydroxy group), a —O-lower alkyl group (the alkyl group each independently may be substituted with one or more substituents selected from halogen and a hydroxy group), or

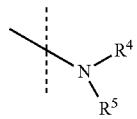

in which $R^4$ and $R^5$ each independently represents hydrogen, a lower alkyl group or a cycloalkyl group, or $R^4$, $R^5$ and the nitrogen atom to which they are attached are taken together to form a 3- to 8-membered nitrogen-containing aliphatic ring (one or more carbon atoms constituting the nitrogen-containing aliphatic ring may be substituted with a nitrogen atom, a sulfur atom or an oxygen atom, and when a carbon atom is substituted with a nitrogen atom, the nitrogen atom may be substituted with a lower alkyl group), or $R^4$ and the nitrogen atom to which it is attached are taken together with ring A to form a 8- to 16-membered nitrogen-containing fused bicyclic ring (one or more carbon atoms constituting the nitrogen-containing fused bicyclic ring may be substituted with a nitrogen atom, a sulfur atom or an oxygen atom, and when a carbon atom is nitrogen atom a carbon atom is substituted with a nitrogen atom, the nitrogen atom may be substituted with a lower alkyl group), $R^5$ is hydrogen, a lower alkyl group or a cycloalkyl group.

The "lower alkyl group" represented by $R^4$ and $R^5$ means the same groups as those in the lower alkyl group defined above. Among these groups, a methyl group, an ethyl group and a propyl group are preferable, and a methyl group is more preferable.

The "cycloalkyl group" represented by $R^4$ and $R^5$ means the same groups as those in the cycloalkyl group defined above.

Specific examples of the 3- to 8-membered nitrogen-containing aliphatic ring formed by taking $R^4$, $R^5$ and the nitrogen atom to which they are attached together (carbon atoms constituting the nitrogen-containing aliphatic ring may be substituted with a nitrogen atom, a sulfur atom or an oxygen atom and, in case carbon atoms are substituted with a nitrogen atom, the nitrogen atom may be substituted with a lower alkyl group) include groups of formula:

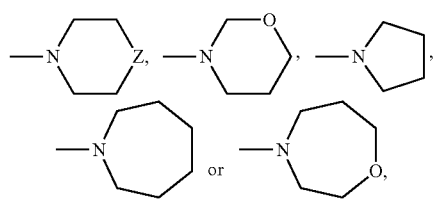

wherein Z is O, S, $CH_2$ or $NR^e$, and $R^e$ represents hydrogen or a $C_{1-4}$ alkyl group. Among these groups, a morpholino group, a piperazine group and a 4-methyl-piperazine group are preferable.

Specific examples of the 8- to 16-membered nitrogen-containing fused bicyclic ring formed by taking $R^4$ and the nitrogen atom to which it is attached together with ring A (one or more carbon atoms constituting the nitrogen-containing fused bicyclic ring may be substituted with a nitrogen atom, a sulfur atom or an oxygen atom and, in case carbon atoms are substituted with a nitrogen atom, the nitrogen atom may be substituted with a lower alkyl group) include groups of formula:

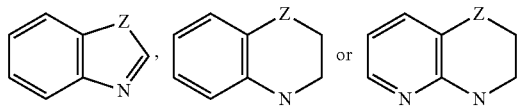

wherein Z is O, S, $CH_2$ or $NR^e$, and $R^e$ represents hydrogen or a $C_{1-4}$ alkyl group. Among these groups,

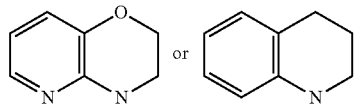

is particularly preferable.

$R^2$, $R^3$ and $R^6$ each independently represents halogen, OH, COOH, $SO_3H$, $NO_2$, SH, $NR^aR^b$ or a lower alkyl group (the alkyl group is substituted with a halogen atom, and also may be substituted with a hydroxy group) or a —O-lower alkyl group (the alkyl group each independently may be substituted with one or more substituents selected from the group consisting of halogen, a hydroxy group and an —O-lower alkyl group-O-lower alkyl group (the alkyl group each independently may be substituted with halogen)).

At least one of $R^2$, $R^3$ and $R^6$ is preferably a —O-lower alkyl group (the alkyl group is substituted with a halogen atom, and also may be substituted with a hydroxy group). Among these groups, a —O-lower alkyl group substituted with a halogen atom or a —O-lower alkyl group substituted with a halogen atom and a hydroxy group is preferable, and a group of a formula:

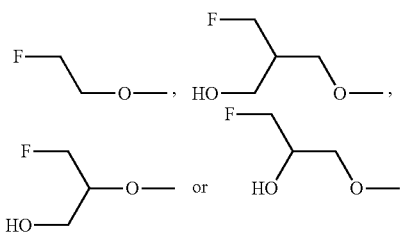

is more preferable.

$R^a$ and $R^b$ independently represents hydrogen or a lower alkyl group (the alkyl group is substituted with a halogen atom, and also may be substituted with a hydroxy group). Preferred $R^a$ and $R^b$ are hydrogens.

m is an integer of 0 to 4, and preferably 1.

n is an integer of 0 to 4. Preferably, all $R^4$(s) are hydrogens.

Examples of preferred compounds of formula (I) include:
2-(4-aminophenyl)-8-(1-fluoromethyl-2-hydroxyethoxy)quinoline (THK-5004),
2-(4-diethylaminophenyl)-6-(1-fluoromethyl-2-hydroxy)quinoline (THK-5035),
2-(4-diethylaminophenyl)-7-(2-fluoromethyl-2-hydroxyethoxy)quinoline (THK-5038),
2-(4-diethylaminophenyl)-8-(1-fluoromethyl-2-hydroxyethoxy)quinoline (THK-5051),
2-(4-diethylaminophenyl)-7-(1-fluoromethyl-2-hydroxyethoxy)quinoline (THK-5058),
2-(4-diethylaminophenyl)-4-(3-fluoro-2-hydroxypropoxy)quinoline (THK-5059),
2-(4-diethylaminophenyl)-5-(1-fluoromethyl-2-hydroxyethoxy)quinoline (THK-5064),
2-(4-diethylaminophenyl)-3-(1-fluoromethyl-2-hydroxyethoxy)quinoline (THK-5065),
2-(4-diethylaminophenyl)-8-[(3-fluoro-2-hydroxy)propoxy]quinoline (THK-5066),
2-(4-fluoromethyl-2-hydroxyethoxy)-2-(4-dimethylaminophenyl)quinoline (THK-5071),
7-(1-fluoromethyl-2-hydroxyethoxy)-2-(4-methylaminophenyl)quinoline (THK-5077),
2-(4-ethylmethylaminophenyl)-7-(1-fluoromethyl-2-hydroxyethoxy)-quinoline (THK-5078),
6-[(3-fluoro-?-hydroxy)propoxy]-2-(4-dimethylaminophenyl)quinoline (THK-5105),
7-[(3-fluoro-2-hydroxy)propoxy]-2-(4-methylaminophenyl)quinoline (THK-5106),
7-[(3-fluoro-2-hydroxy)propoxy]-2-(4-dimethylaminophenyl)quinoline (THK-5107),
2-(4-ethylmethylaminophenyl)-7-[(3-fluoro-2-hydroxy)propoxy]quinoline (THK-5112),
2-(4-aminophenyl)-6-[(3-fluoro-2-hydroxy)propoxy]quinoline (THK-5116),
6-[(3-fluoro-2-hydroxy)propoxy]-2-(4-methylaminophenyl)quinoline (THK-5117),
6-[(3-fluoro-2-hydroxy)propoxy]-2-(4-diethylaminophenyl)quinoline (THK-5122),
7-amino-2-(4-fluorophenyl)quinoline (THK-5075),
2-(4-fluorophenyl)-7-dimethylaminoquinoline (THK-5076),
5-amino-2-(4-fluorophenyl)quinoline (THK-5079),
2-(4-fluorophenyl)-5-dimethylaminoquinoline oxalate (THK-5080),
8-amino-2-(4-fluorophenyl)quinoline (THK-5081),
2-(4-fluorophenyl)-8-dimethylaminoquinoline (THK-5082),
6-amino-2-(4-fluorophenyl)quinoline (THK-5086),
2-(4-fluorophenyl)-6-dimethylaminoquinoline (THK-5087),
2-(2-aminopyrid-5-yl)-7-(1-fluoromethyl-2-hydroxyethoxy)quinoline (THK-932),
6-ethylmethylamino-2-(4-fluorophenyl)quinoline (THK-5100),
6-diethylamino-2-(2-fluoropyrid-5-yl)quinoline (THK-5088),
8-ethylmethylamino-2-(2-fluoropyrid-5-yl)quinoline (THK-5089),
5-ethylamino-2-(2-fluoropyrid-5-yl)quinoline (THK-5091),
5-diethylamino-2-(2-fluoropyrid-5-yl)quinoline (THK-5092),
7-diethylamino-2-(2-fluoropyrid-5-yl)quinoline (THK-5097),
7-ethylmethylamino-2-(2-fluoropyrid-5-yl)quinoline (THK-5098),
2-(4-ethylaminophenyl)-6-[(3-fluoro-2-hydroxy)propoxy]quinoline (THK-5125),
2-(2-aminopyrid-5-yl)-6-[(3-fluoro-2-hydroxy)propoxy]quinoline (THK-5127),
6-[(3-fluoro-2-hydroxy)propoxy]-2-(2-dimethylaminopyrid-5-yl)quinoline (THK-5129),
2-(2-diethylaminopyrid-5-yl)-6-[(3-fluoro-2-hydroxy)propoxy]quinoline (THK-5130),
2-(2-ethylaminopyrid-5-yl)-6-[(3-fluoro-2-hydroxy)propoxy]quinoline (THK-5142), 2-(2-methylaminopyrid-5-yl)-6-[(3-fluoro-2-hydroxy) propoxy]quinoline (THK-5151),
1-fluoro-3-{2-[4-(4-methylpiperazin-1-yl)phenyl]quinolin-6-yloxy}propan-2-ol (THK-5177),
1-fluoro-3-{2-[6-(piperazin-1-yl)pyridin-3-yl]quinolin-6-yloxy}propan-2-ol (THK-5178),
1-fluoro-3-{2-[6-(4-methylpiperazin-1-yl)pyridin-3-yl]quinolin-6-yloxy}propan-2-ol (THK-5180),
6-[(3-fluoro-2-hydroxy)propoxy]-2-(4-methyl-3,4-dihydro-2H-pyrido[3, 2-b][1,4]oxazin-7-yl)quinoline (THK-5136),
6-[(3-fluoro-2-hydroxy)propoxy]-2-(1-methyl-1,2,3,4-tetrahydroquinolin-6-yl)quinoline (THK-5153),
6-[(3-fluoro-?-hydroxy-1,1-dimethyl)propoxy]-2-(1-methyl-1,2,3,4-tetrahydroquinolin-6-yl)quinoline (THK-5157),
2-(4-amino-3-fluorophenyl)-6-dimethylaminoquinoline (THK-5128),
2-[4-(amino)-3-[(3-fluoro-2-hydroxy)propoxy]phenyl)-6-methylaminoquinoline (THK-5147),
2-[3-(3-fluoro-2-hydroxy-1,1-dimethyl)propoxy]-4-(dimethylamino)-phenyl]-6-dimethylaminoquinoline (THK-5148),
6-amino-2-[4-(amino)-3-[(3-fluoro-2-hydroxy)propoxy]phenyl]quinoline (THK-5155),
2-[3-[(3-fluoro-2-hydroxy)propoxy]-4-(dimethylamino)phenyl]-6-dimethylaminoquinoline (THK-5156),
2-[3-[(3-fluoro-2-hydroxy)propoxy]-4-(methylamino)phenyl]-6-methylaminoquinoline (THK-5158),
2-[4-(amino)-3-[(3-fluoro-2-hydroxy)propoxy]phenyl]-6-dimethylaminoquinoline (THK-5159),
6-amino-2-[3-[(3-fluoro-2-hydroxy)propoxy]-4-(dimethylamino)phenyl]-quino line (THK-5160),
2-[3-[(3-fluoro-2-hydroxy)propoxy]-4-(dimethylamino)phenyl]-6-methylamino quinoline (THK-5161),
2-[3-[2-[2-(2-fluoroethoxy)ethoxy]ethoxy-4-(methylamino)phenyl]-6-dimethylaminoquinoline (THK-5162),
2-[3-[(3-fluoro-2-hydroxy)propoxy]-4-(methylamino)phenyl]-6-dimethylamino quinoline (THK-5164),
6-amino-2-[3-[(3-fluoro-2-hydroxy)propoxy]-4-(methylamino)phenyl]-quinoline (THK-5165),
2-[3-[(3-fluoro-2-hydroxy)propoxy]-2-(dimethylamino)pyrid-5-yl]-6-dimethylaminoquinoline (THK-5154),
2-[3-[(3-fluoro-2-hydroxy)propoxy]-2-(dimethylamino)pyrid-5-yl]quinoline (THK-5166),
6-[(3-fluoro-2-hydroxy)propoxy]-2-(6-fluoropyridin-3-yl)quinoline (THK-5170),
6-[(3-fluoro-2-hydroxy)propoxy]-2-(4-methoxyphenyl)quinoline (THK-5171),
6-[(3-fluoro-2-hydroxy)propoxy]-2-[4-(hydroxymethyl)phenyl]quinoline (THK-5172),
6-[(3-fluoro-2-hydroxy)propoxy]-2-(4-ethanonephenyl)quinoline (THK-5173),
6-[(3-fluoro-2-hydroxy)propoxy]-2-(6-methoxypyridin-3-yl)quinoline (THK-5174),
6-[(3-fluoro-2-hydroxy)propoxy]-2-(4-ethoxyphenyl)quinoline (THK-5175),
6-[(3-fluoro-2-hydroxy)propoxy]-2-(4-amino-3-methoxyphenyl)quinoline (THK-5176),
6-[(3-fluoro-2-hydroxy)propoxy]-2-(benzamido-4-yl)quinoline (THK-5179),
6-[(3-fluoro-2-hydroxy)propoxy]-2-(3-aminophenyl)quinoline (THK-5181), and
6-[(3-fluoro-2-hydroxy)propoxy]-2-(1-methyl-pyrazol-4-yl)quinoline (THK-5182).
Examples of more preferred compound of the formula (I) include:

6-[(3-fluoro-2-hydroxy)propoxy]-2-(4-dimethylaminophenyl)quinoline (THK-5105),
6-[(3-fluoro-2-hydroxy)propoxy]-2-(4-methylaminophenyl)quinoline (THK-5117), and
2-(4-ethylaminophenyl)-6-[(3-fluoro-2-hydroxy)propoxy]quinoline (THK-5125).

As shown in Examples, the compound of the formula (I) is highly specific to tau, and also has high brain uptake. Also, the compound of the formula (I) is a compound having very high safety, which has low or non-recognized bone-seeking properties and low or non-recognized toxicity. Accordingly, the diagnosis of tauopathy can be carried out using the compound of formula (I) as a probe against tau, and also the treatment and/or prevention of tauopathy can be carried out by using the compound of the formula (I). Particularly, the compound of formula (I) is suited for imaging diagnosis of tauopathy, particularly imaging diagnosis using PET. Accordingly, it becomes possible to carry out accurate diagnosis, effective treatment and prevention in the early stages of tauopathy, particularly Alzheimer's disease, using the compound of formula (I).

The conformational disease is the disease in which a protein having a specific n-sheet structure accumulates, and there are various diseases characterized by deposition of an insoluble fibrillar protein to various internal organs and tissues. These diseases include Alzheimer's disease, prion disease, dementia with Lewy bodies, Parkinson's disease, Huntington's disease, spinal and bulbar atrophy, dentate-rubro-pallido-luysian atrophy, Spinocerebellar Degeneration, Machado-Joseph Disease, Amyophic Lateral Sclerosis (ALS), Down's syndrome, Pick's disease, FTDP-17 (Frontotemporal Dementia and Parkinsonism linked to Chromosome 17), LNTD (Limbic Neurofibrillary tangles Dementia), Sudanophiloc Leukodystrophy, amyloidosis and the like.

In the present invention, the conformational disease preferably means disease (tauopathy) having a cardinal symptom such as intracerebral accumulation of tau protein. Tauopathy includes Alzheimer's disease, Pick's disease, progressive supranuclear palsy (PSP) and the like.

In order to disclose the compound of a formula (I'):

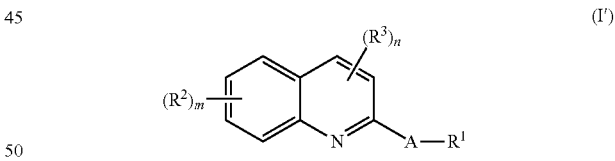

[wherein the respective symbols are as defined above] which is a precursor of the compound of the formula (I) according to the present invention in more specifically, various symbols used in the formula (I') will be described by way of specific examples.

A and $R^1$ are the same as defined in the formula (I), as described above. $R^a$ and $R^b$ are also the same as defined in the formula (I), as described above.

$R^2$, $R^3$ and $R^6$ each independently represents halogen, —OH, —COOH, —$SO_3H$, —$NO_2$, —SH, —$NR^aR^b$ ($R^a$ and $R^b$ independently represents hydrogen or a lower alkyl group (the alkyl group each independently may be substituted with one or more substituents selected from halogen and a hydroxy group)), a lower alkyl group (the lower alkyl group each independently may be substituted with one or more substituents selected from a p-toluenesulfonyloxy group (tosyloxy group, TsO), a methanesulfonyloxy group, a trifluoromethanesulfonyloxy group or a 2-tetrahydropyranyloxy (OTHP), halogen and a hydroxy group), a —O-lower alkyl group (the lower alkyl group each independently maybe substituted with one or more substituents selected from a p-toluenesulfonyloxy group (tosyloxy group, TsO), a methanesulfonyloxy group, a trifluoromethanesulfonyloxy group or a 2-tetrahydropyranyloxy (OTHP), halogen, a hydroxy group and a —O-lower alkyl group-O-lower alkyl group (the alkyl group each independently may be substituted with halogen)), in which at least one of $R^2$, $R^3$ and $R^6$ is a —O-lower alkyl group (the lower alkyl group is substituted with a p-toluenesulfonyloxy group (tosyloxy group, TsO), a methanesulfonyloxy group, a trifluoromethanesulfonyloxy group or a 2-tetrahydropyranyloxy (OTHP), and also may be substituted with one or more substituents selected from halogen, hydroxy group and a —O-lower alkyl group-O-lower alkyl group (the alkyl group each independently may be substituted with halogen)).

At least one of $R^2$, $R^3$ and $R^6$ is preferably a group of a formula:

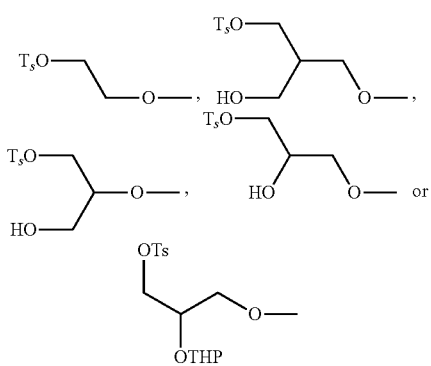

m is an integer of 0 to 4. Preferably, m is 0.
n is an integer of 0 to 4. Preferably, n is 0.

Examples of preferred compound of the formula (I') include:
2-(4-diethylaminophenyl)-6-[(2-hydroxy-1-tosyloxymethyl)ethoxy]quinolin (THK-5039),
2-(4-aminophenyl)-8-(2-hydroxy-1-tosyloxymethylethoxy) quinoline (THK-5041),
2-(4-diethylaminophenyl)-8-(2-hydroxy-1-tosyloxymethylethoxy)quinoline (THK-5050),
2-(4-diethylaminophenyl)-8-[[2-(tetrahydro-2H-pyran-2-yloxy)-3-tosyloxy]propoxy]quinoline (THK-5070),
2-(4-diethylaminophenyl)-7-(2-hydroxy-1-tosyloxymethylethoxy)quinoline (THK-5072),
2-(4-diethylaminophenyl)-7-[[(2-tetrahydro-2H-pyran-2-yloxy)-3-tosyloxy]propoxy]quinoline (THK-5073),
7-(2-hydroxy-1-tosyloxymethylethoxy)-2-(4-dimethylaminophenyl)quinoline (THK-5090),
7-(2-hydroxy-1-tosyloxymethylethoxy)-2-(4-methylaminophenyl)quinoline (THK-5095),
2-(4-ethylmethylaminophenyl)-7-(2-hydroxy-1-tosyloxymethylethoxy)quinoline (THK-5096),
2-(4-diethylaminophenyl)-5-(2-hydroxy-1-tosyloxymethylethoxy)quinoline (THK-5099),
2-(4-ethylmethylaminophenyl)-7-[[2-(tetrahydro-2H-pyran-2-yloxy)-3-tosyloxy]propoxy]quinoline (THK-5111),
2-(4-methylaminophenyl)-7-[[2-(tetrahydro-2H-pyran-2-yloxy)-3-tosyloxy]propoxy]quinoline (THK-5113),
2-(4-dimethylaminophenyl)-7-[[2-(tetrahydro-2H-pyran-2-yloxy)-3-tosyloxy]propoxy]quinoline (THK-5115),
2-(4-methylaminophenyl)-6-[[2-(tetrahydro-2H-pyran-2-yloxy)-3-tosyloxy]propoxy]quinoline (THK-5119),
2-(4-diethylaminophenyl)-6-[[2-(tetrahydro-2H-pyran-2-yloxy)-3-tosyloxy]propoxy]quinoline (THK-5120),
2-(4-dimethylaminophenyl)-6-[[2-(tetrahydro-2H-pyran-2-yloxy)-3-tosyloxy]propoxy]quinoline (THK-5121),
2-(4-aminophenyl)-6-[[2-(tetrahydro-2H-pyran-2-yloxy)-3-tosyloxy]-propoxy]quinoline (THK-5123),
2-(4-ethylaminophenyl)-6-[[2-(tetrahydro-2H-pyran-2-yloxy)-3-tosyloxy]propoxy]quinoline (THK-5131),
2-(2-aminopyrid-5-yl)-6-[[2-(tetrahydro-2H-pyran-2-yloxy)-3-tosyloxy]propoxy]quinoline (THK-5150),
2-(2-methylaminopyrid-5-yl)-6-[[2-(tetrahydro-2H-pyran-2-yloxy)-3-tosyloxy]propoxy]quinoline (THK-5152),
2-(2-dimethylaminopyrid-5-yl)-6-[[2-(tetrahydro-2H-pyran-2-yloxy)-3-tosyl oxy]propoxy]quinoline (THK-5135),
2-(2-diethylaminopyrid-5-yl)-6-[[2-(tetrahydro-2H-pyran-2-yloxy)-3-tosyloxy]propoxy]quinoline (THK-5138),
2-(2-ethylaminopyrid-5-yl)-6-[[2-(tetrahydro-2H-pyran-2-yloxy)-3-tosyloxy]propoxy]quinoline (THK-5143),
2-[4-(methylamino)-3-[[2-(tetrahydro-2H-pyran-2-yloxy)-3-tosyloxy]propoxy]phenyl]-6-dimethylaminoquinoline (THK-5163),
6-[[2-(tetrahydro-2H-pyran-2-yloxy)-tosyloxy]propoxy]-2-(4-methyl-3,4-dihydro-2H-pyrido[3,2-b][1,4]oxazin-7-yl)quinoline (THK-5167), and
2-[4-(dimethylamino)-3-[[2-(tetrahydro-2H-pyran-2-yloxy)-3-tosyloxy]propoxy]phenyl]-6-dimethylaminoquinoline (THK-5168).

The compound of the formula (I') can be used as a synthetic precursor of the compound of the formula (I). The method of converting into the compound of the formula (I) from the compound of the formula (I') is well known to a person with an ordinary skill in the art, and the compound of the formula (I) can be easily obtained.

Salts of the compound of the present invention are also included in the present invention. The salt can be produced in accordance with a conventional method using the compound of a formula (I) or (I') provided by the present invention.

Specifically, when the compound of the formula (I) or (I') has, for example, a basic group derived from an amino group, a pyridyl group and the like in the molecule, the compound can be converted into a corresponding salt by treating with an acid.

Examples of the acid addition salt include hydrohalide salts such as hydrochloride, hydrofluoride, hydrobromide and hydroiodide; inorganic acid salts such as nitrate, perchlorate, sulfate, phosphate and carbonate; lower alkyl sulfonic acid salts such as methanesulfonate, trifluoromethanesulfonate and ethanesulfonate; aryl sulfonic acid salts such as benzenesulfonate and p-toluenesulfonate; organic acid salts such as fumarate, succinate, citrate, tartrate, oxalate and maleate; and acid addition salts of amino acids, such as glutamate and aspartate.

Also, when the compound of the present invention has an acidic group such as a carboxyl group in the molecule, the compound can also be converted into a corresponding pharmaceutically acceptable salt by treating with a base. Examples of the base addition salt include alkali metal salts such as sodium and potassium; alkali earth metal salts such as calcium and magnesium; and salts of organic bases, such as ammonium salts, guanidine, triethylamine and dicyclohexylamine.

Furthermore, the compound of the present invention may be present as a free compound, or arbitrary hydrate or solvate of a salt thereof.

Depending on selection of starting materials and methods, the compounds of the present invention may exist as one form in possible isomers or mixtures thereof, for example, substantially pure geometrical (cis- or trans-) isomers, optical isomers (enantiomers, antipodes), racemic forms, or mixtures thereof. The above-mentioned possible isomers or mixtures thereof fall within the scope of the present invention.

All obtainable isomer mixtures can be separated into pure geometrical or optical isomers, diastereomers or racemic forms based on a physicochemical difference of component by, for example, chromatography and/or fractional crystallization.

All of the obtained racemic forms of the final product or intermediate can be optically resolved into optical antipodes by a known method, for example, a diastero isomer salt obtained from an optically active acid or base compound is separated and each optically active acid or base compound is isolated. The products from the racemic forms can also be resolved by chiral chromatography, for example, high performance liquid chromatography using a chiral adsorbent.

In starting compounds and precursors which are converted into the compounds of the present invention by the method in the present description, existing functional groups such as amino, thiol, carboxyl and hydroxy groups may be optionally protected with a common conventional protecting group in preparative organic chemistry. The thus protected amino, thiol, carboxyl and hydroxy groups can be converted into free amino, thiol, carboxyl and hydroxy groups under mild conditions without causing breakage of a molecular framework or the other undesirable minor reaction.

The protecting group is inserted so as to protect the functional group from an undesirable reaction with a reaction component under the conditions used to perform a desired chemical conversion. Necessity and selection of the protecting group for a specific reaction are known to those skilled in the art, and depend on properties of the functional group to be protected (hydroxy group, amino group, etc.), structure and stability of the molecule with the substituent constituting a part thereof, and reaction conditions. Examples of the protecting group include OTs, OTHP, methoxymethyl and OAc. The protecting group is preferably a protecting group which is eliminated under acidic conditions.

In the diagnosis of tauopathy, the compound of the present invention can be used as a probe without labeling. For example, the presence or absence of the portion to be stained may be examined by bringing the compound of the present invention into contact with a biopsy tissue sample. However, it is common to use the labeled compound of the present invention as a probe for the diagnosis of tauopathy. Examples of label include a fluorescent substance, an affinity substance, an enzyme substrate, a radioactive nuclide and the like. A probe labeled with a radioactive nuclide is usually used in image diagnosis of tauopathy. It is possible to label the compound of the present invention with various radioactive nuclides by the methods which are well known in the art. For example, $^3H$, $^{14}C$, $^{35}S$, $^{131}I$ and the like are radioactive nuclides which have been used for a long time, and is often utilized in vivo. General requirements for imaging diagnosis probes and means for their detection are to allow making an in vivo diagnosis, to cause less harm to patients (particularly, to be non-invasive), to have a high sensitivity of detection, to have an appropriate half-life (to have an appropriate period of time for preparing the labeled probes and for diagnosis) and the like. Accordingly, it has recently tended to employ positron emission tomography (PET) utilizing γ-ray displaying a high sensitivity and permeability of materials or computed tomography (SPECT) with γ-ray emitting nuclides. Among them, PET, which detects two γ-rays emitting in opposite directions from a positron emitting nuclide by means of simultaneous counting with a pair of detectors, provides information which is excellent in resolution and quantification and thus is preferable. For SPECT, the compound of the present invention can be labeled with a γ-ray emitting nuclide such as $^{99m}Tc$, $^{111}In$, $^{67}Ga$, $^{201}Tl$, $^{123}I$, $^{133}Xe$ and the like. $^{99m}Tc$ and $^{123}I$ are often used for SPECT. For PET, the compound of the present invention can be labeled with a positron emitting nuclide such as $^{11}C$, $^{13}N$, $^{15}O$, $^{18}F$, $^{62}Cu$, $^{64}Cu$, $^{68}Ga$, $^{76}Br$ and the like. Among positron emitting nuclides, $^{11}C$, $^{13}N$, $^{15}O$ and $^{18}F$ are preferable, $^{18}F$ and $^{11}C$ are more preferable, $^{18}F$ is particularly preferable, from the viewpoint of having an appropriate half-life, the ease of labeling and the like. Although the position of labeling the compound of the present invention with a radiation emitting nuclide such as a positron emitting nuclides or γ-ray emitting nuclide can be any position, labeling may preferably be carried out at an alkyl group and on phenyl ring in the compound. Such labeled compounds of the present invention are also included in the present invention. For example, when the compound of the present invention is labeled with $^{18}F$, any position of the side chain may be labeled with $^{18}F$, or hydrogen on the ring may be substituted with $^{18}F$. For example, hydrogen contained in any one of alkyl substituents may be substituted with $^{18}F$. Also, when the compound of the present invention is labeled with $^{11}C$, carbon contained in any one of alkyl substituents in the side chain may be substituted with $^{11}C$. Although it is obvious to a person with an ordinary skill in the art, m of $^{99m}Tc$ denotes a nuclear isomer in a quasi-stable state.

Radionuclides used in the compounds according to the present invention are generated on an instrument termed cyclotron or generator. A person with an ordinary skill in the art can select methods and instruments for production depending upon nuclides to be produced. Nuclides thus produced can be used to label the compounds of the present invention.

Methods of producing labeled compounds, which have been labeled with these radionuclides, are well known in the art. Typical methods include chemical synthesis, isotope exchange, and biosynthesis processes. Chemical synthesis processes have been traditionally and widely employed, and are essentially the same as usual chemical synthesis processes, except that radioactive starting materials are used. Various nuclides are introduced into compounds by these chemical processes. Isotope exchanging processes are processes by which $^3H$, $^{35}S$, $^{125}I$ or the like contained in a compound of a simple structure is transferred into compound having a complex structure, thereby obtaining a compound having a complex structure that has been labeled with these nuclide. Biosynthesis processes are processes by which a compound labeled with $^{14}C$, $^{35}S$ or the like is given to cells such as microorganisms to obtain its metabolites having these nuclide introduced therein.

With respect to the labeling position, similarly to usual synthesis, synthetic schemes can be designed, depending upon the purpose, so that a label can be introduced at a desired position. Such design is well known to a person with ordinary skill in the art.

When utilizing positron emitting nuclides such as $^{11}$C, $^{13}$N, $^{15}$O and $^{18}$F, which have relatively short half-lives, for example, it is also possible to generate a desired nuclide from a (highly) small-sized cyclotron placed in a facility such as hospital, which in turn is used to label a desired compound at its desired position by any of the above-described methods, followed by carrying out immediately diagnosis, examination, treatment or the like.

These methods well known to a person with ordinary skill in art, and enable one to carry out labeling by introducing a desired nuclide into the compound of the present invention at its desired position.

The compound of the present invention, which has been labeled, may be administered to subjects locally or systemically. Routes for administration include intradermal, intraperitoneal, intravenous, intra-arterial injections or infusions into the spinal fluid and the like, and can be selected depending on factors such as the disease type, nuclide used, compound used, the condition of the subject, the site to be examined. The site to be examined can be investigated with means such as PET, SPECT by administering the probe of the present invention, followed by the elapse of a sufficient time to allow its binding to tau protein and decay. These procedures can be selected as appropriate depending on factors such as the disease type, nuclide used, compound used, the condition of the subject, the site to be examined.

The dose of the compound of the present invention, which has been labeled with a radionuclide, varies depending on the disease type, nuclide used, compound used, the age, physical condition, and gender of the subject, the degree of the disease, the site to be examined and the like. In particular, sufficient care has to be taken about exposure doses to the subject. For example, the amount of radioactivity of the compound labeled with a positron emitting nuclide such as $^{11}$C, $^{13}$N, $^{15}$O and $^{18}$F of the present invention, is usually within a range from 3.7 megabecquerels to 3.7 gigabecquerels, and preferably from 18 megabecquerels to 740 megabecquerels.

The compound of the present invention or a salt or solvate thereof is suited for use in a treatment method of tauopathy, a diagnosis method, a composition for treatment, a composition for diagnosis, a kit for diagnosis, use for the production of these compositions and kits, and other uses, which will be described below. The compounds or salts or solvates thereof exemplified in the above description about the compounds of formulae (I) to (VI) are preferable, and those included in the compound of formula (I) or a salt or solvate thereof are particularly preferable. Among the compounds of the present invention, compounds having, as $R^2$, $R^3$ or $R^6$ in formula (I),

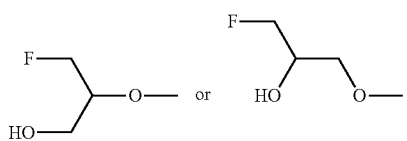

are suited for administration to the human body because of considerably less or scarce accumulation in bone.

The present invention provides a composition for image diagnosis of tauopathy, containing the compound of the present invention. The composition of the present invention contains the compound of the present invention and a pharmaceutically acceptable carrier. It is preferred that the compound of the present invention in the composition is labeled. Although various labeling methods are possible as described above, labeling with radionuclides (in particular, positron emitting nuclides such as $^{11}$C, $^{13}$N, $^{15}$O and $^{18}$F for PET) is desirable for in vivo image diagnosis applications. It is preferable from their purposes that the form of the composition of the present invention is one allowing injection or infusion. Accordingly, a pharmaceutically acceptable carrier is preferably liquid and examples thereof include, but are not limited to, aqueous solvents such as potassium phosphate buffer, physiological saline, ringer solution and distilled water; and non-aqueous solvents such as polyethylene glycol, vegetable oil, ethanol, glycerin, dimethylsulfoxide and propylene glycol. A mixing ratio of the carrier to the compound of the present invention can be appropriately selected depending on the site of application, detection means and the like, and is usually from 100,000:1 to 2:1, and preferably from 10,000:1 to 10:1. The composition of the present invention may further contain known antimicrobials (for example, antimicrobial drug, etc.), local anesthetics (for example, procaine hydrochloride, etc.), buffers (for example, Tris-hydrochloride buffer, HEPES buffer, etc.), osmolytes (for example, glucose, sorbitol, sodium chloride, etc.) and the like.

Furthermore, the present invention provides a kit for image diagnosis of tauopathy, containing the compound of the present invention as the essential ingredient. Usually, the kit is a package in which each of the components such as the compound of the present invention, a solvent for dissolving the compound, a buffer, an osmoregulatory agent, an antimicrobial, a local anesthetic are packaged separately into respective containers, or some of the components are packaged together into respective containers. The compound of the present invention may be unlabeled or labeled. When not labeled, the compound of the present invention can be labeled, prior to use, by usual methods as described above. In addition, the compound of the present invention may be presented as a solid, such as a lyophilized powder, or in solution in appropriate solvents. Solvents may be similar to carriers used in the above composition of the present invention. Each of the components such as a buffer, an osmoregulatory agent, an antimicrobial, a local anesthetic, also may be similar to those used in the above composition of the present invention. While various containers can be selected as appropriate, they may be of shapes suitable for carrying out the introduction of a label into the compound of the present invention, or of light-shielding materials, depending on the nature of compounds, or take forms such as vials or syringes, so as to be convenient for administration to patients. The kit may also contains, as appropriate, tools necessary for diagnosis, for example, syringes, an infusion set, or device for use in a PET or SPECT apparatus. The kit usually has its instructions attached thereto.

Furthermore, the compounds of the present invention are specifically bound to tau protein, and thus the compounds of the present invention can be also used, for example, for detecting and quantifying tau protein with or without labeling by contacting with sample specimens in vitro. For example, the compounds of the present invention can be used for staining tau protein in microscopic specimens, for colorimetric determination of tau protein in samples, or for quantifying tau protein using a scintillation counter. Preparation of a microscope specimen and staining using the compound of the present invention can be carried out by a conventional method known to a person with an ordinary skill in the art.

As described above, the compounds of the present invention are highly specific to tau protein. Therefore, the compounds of the present invention are useful, for example, for studies of disease with tau protein accumulation or in their diagnosis before and after death, and could be useful, for example, as agents for staining neurofibrillary tangles in brain sections of Alzheimer's disease patients. Staining of specimens, for example, brain sections using the compounds of the present invention can be carried out in a conventional method known to a person of ordinary skill in the art.

As described above, among the compounds of the present invention, compounds having, as $R^2$, $R^3$ or $R^6$ in formula (I):

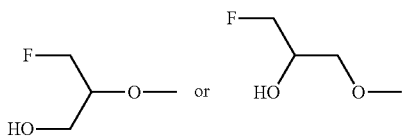

may cause considerably less or scarce accumulation in bone. Accordingly, these compounds of the present invention are not only considerably safe probes for the diagnosis of tauopathy, but also exhibit high safety even when used as remedies or preventives described hereinafter.

Accordingly, the present invention is directed to a composition for staining of amyloid β protein, particularly tau in a sample, containing the compound of the present invention or a pharmaceutically acceptable salt or solvate thereof, and a kit for staining of amyloid β protein, particularly tau in a sample, containing the compound of the present invention or a pharmaceutically acceptable salt or solvate thereof as essential ingredients. Furthermore, the present invention is directed to a method of staining amyloid β protein, particularly tau in a sample, the method comprising using the compound of the present invention or a pharmaceutically acceptable salt or solvate thereof. Samples suited for above staining are brain sections.

As described above, it has been found that neurotoxicity is present in amyloid β protein or tau of a β-sheet structure. It is considered that the compound of the present invention is specifically bound to amyloid β protein of a R-sheet structure, particularly tau, and thus neurotoxicity is inhibited. Accordingly, it is considered that the compound of the present invention serves as remedies or preventives for causes of a disease, particularly tauopathy, for example, Alzheimer's disease since protein itself has a β-sheet structure.

Accordingly, the present invention provides:

a method of treating and/or preventing diseases with amyloid β protein accumulation, particularly tauopathy, the method comprising administering a compound of the formula (I) or a salt or solvate thereof;

a method of diagnosing diseases with amyloid β protein accumulation, particularly tauopathy, the method comprising using a compound of the formula (I) or a salt or solvate thereof; and use of a compound of the formula (I) or a salt or solvate thereof for the production of a composition or kit for the treatment, prevention or diagnosis of diseases with amyloid β protein accumulation, particularly tauopathy.

Forms of such pharmaceutical compositions are not limited in particular, but liquid formulations, particularly formulations for injection, are preferable. Such formulations for injection can be infused directly into the brain, or alternatively the above pharmaceutical compositions can be formulated for intravenous injection or drip and administered, since the compounds of the present invention have high permeability through the blood-brain barrier, as shown in the Examples. Such liquid formulations can be prepared by methods well known in the art. Solutions can be prepared, for example, by dissolving the compound of the present invention in an appropriate carrier, water for injection, phisilogical saline, Ringer's solution or the like, sterilizing the solution through a filter or the like, and then filling the sterilized solution into appropriate containers, for example, vials or ampules. Solutions also can be lyophilized and when used, reconstituted with an appropriate carrier. Suspensions can be prepared, for example, by sterilizing the compound of the present invention, for example, by exposure to ethylene oxide, and then suspending it in a sterilized liquid carrier.

When such a pharmaceutical composition is used in a liquid formulation, particularly a formulation for injection, an injection can be prepared by adding a solubilizing agent to a quinoline derivative according to the present invention.

It is possible to use, as the solubilizing agent, nonionic surfactants, cationic surfactants, amphoteric surfactants and the like used in the art. Among these solubilizing agents, Polysorbate 80, polyethylene glycol, ethanol or propylene glycol is preferable, and Polysorbate 80 is more preferable.

The amount of the compounds of the present invention to be administered to a human subject in the above treatment method, prevention method and use varies depending on the condition, gender, age, weight of the patient and the like, and is generally within a range from 0.1 mg to 1 g, preferably from 1 mg to 100 mg, and more preferably from 5 mg to 50 mg, per day for adult humans weighing 70 kg. It is possible to conduct a treatment with such a dose for a specified period of time, followed by increasing or reducing the dose according to the outcome.

Furthermore, the compound of the present invention or a pharmaceutically acceptable salt or solvate thereof can also be used as a probe for the diagnosis of conformational disease, particularly tauopathy, preferably an image diagnosis probe labeled with a radiation nuclide. Furthermore, the compounds of the present invention have the effect for the treatment and/or prevention of conformational disease, particularly tauopathy.

Accordingly, the present invention is also directed to:

a compound of the present invention used as an image diagnosis probe of conformational disease, particularly tauopathy, or a salt or solvate thereof;

a composition or kit for image diagnosis of conformational disease, particularly tauopathy, comprising the compound of the present invention or a salt or solvate thereof;

a pharmaceutical composition for the prevention and/or treatment of conformational disease, particularly tauopathy, comprising a compound of the present invention or a pharmaceutically acceptable salt or solvate thereof, and a pharmaceutically acceptable carrier;

a method of diagnosing conformational disease, particularly tauopathy, the method comprising using a compound of the present invention or a pharmaceutically acceptable salt or solvate thereof;

use of a compound of the present invention or a pharmaceutically acceptable salt or solvate thereof for the diagnosis of conformational disease, particularly tauopathy:

a method of preventing and/or treating conformational disease, particularly tauopathy, the method comprising administering a compound of the present invention or a pharmaceutically acceptable salt or solvate thereof to the subject;

use of a compound of the present invention or a pharmaceutically acceptable salt or solvate thereof for the prevention and/or treatment of conformational disease, particularly tauopathy; and use of a compound of the present invention in the production of a pharmaceutical composition for the prevention and/or treatment of conformational disease, particularly tauopathy.

The dose of the compounds of the present invention to be administered to a human subject in the above treatment methods and prevention methods is as described above.

The compounds of the present invention recognize neurofibrillary tangles containing excessively phosphorylated tau protein as a constituent ingredient, and thus the compounds can be used as a probe for the detection of neurofibrillary tangles, or as an agent for staining neurofibrillary tangles. Accordingly, the present invention also relates to use of the compound of the present invention or a salt or solvate thereof as a probe for detecting neurofibrillary tangles, particularly a probe for the diagnoses of images. Examples of compounds of the present invention which are preferable for staining of neurofibrillary tangles include THK-5004, THK-5035, THK-5038, THK-5051, THK-5058, THK-5064, THK-5065, THK-5066, THK-5071, THK-5077, THK-5078, THK-5105, THK-5106, THK-5107, THK-5112, THK-5116, THK-5117, THK-5122 and the like.

Accordingly, the present invention provides a composition for detecting or staining neurofibrillary tangles, containing the compound of the present invention or a salt or solvate thereof;

a kit for detecting or staining neurofibrillary tangles, containing the compound of the present invention or a salt or solvate thereof;

a method of detecting or staining neurofibrillary tangles, which comprises using the compound of the present invention or a salt or solvate thereof; and use of the compound of the present invention or a salt or solvate thereof for the production of a composition for detecting or staining neurofibrillary tangles.

Methods known in a person with an ordinary skill in the art can be applied to methods of preparing and staining a sample specimen in the detection or staining of the above neurofibrillary tangles.

Further, the present invention provides a kit for preparing a compound of the present invention or a pharmaceutically acceptable salt or solvate thereof, the kit comprising a compound of the present invention or a pharmaceutically acceptable salt or solvate thereof, a labeling agent, and optionally instructions for labeling the compound. The labeling agent is, for example, a radioactive nuclide or a positron emitting nuclide. The radioactive nuclide is, for example, a γ-ray emitting nuclide. The positron emitting nuclide is selected from, for example, the group consisting of $^{11}C$, $^{13}N$, $^{15}O$, $^{18}F$, $^{35}mCl$, $^{76}Br$, $^{45}Ti$, $^{48}V$, $^{60}Cu$, $^{61}Cu$, $^{62}Cu$, $^{64}Cu$, $^{66}Ga$, $^{89}Zr$, $^{94m}Tc$ and $^{124}I$. Preferably, the positron emitting nuclide is $^{11}C$ or $^{18}F$. The labeling agent is an agent that is suitable for labeling the compound, and is known to those skilled in the art.

Typical examples of the compound of the formula (I) used preferably in the present invention are shown below.

TABLE 1-1

THK-5004 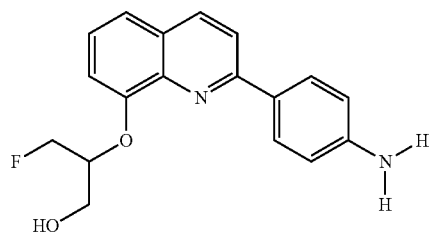 [SMILES: Nc1ccc(-c2ccc3cccc(OC(CO)CF)c3n2)cc1] 2-(4-aminophenyl)-8-(1-fluoromethyl-2-hydroxyethoxy)quinoline THK-5035 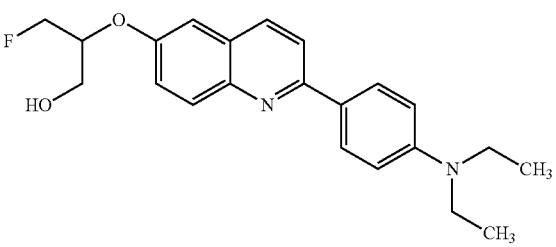 [SMILES: CCN(CC)c1ccc(-c2ccc3cc(OC(CO)CF)ccc3n2)cc1] 2-(4-diethylaminophenyl)-6-(1-fluoromethyl-2-hydroxy)quinoline THK-5038 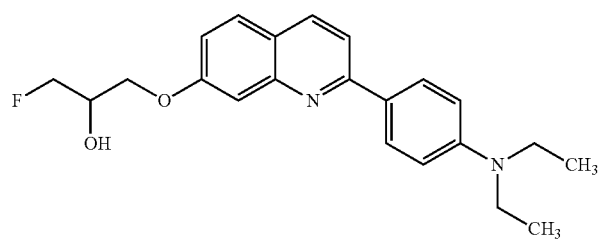 [SMILES: CCN(CC)c1ccc(-c2ccc3ccc(OCC(O)CF)cc3n2)cc1] 2-(4-diethylaminophenyl)-7-(2-fluoromethyl-2-hydroxyethoxy)quinoline

TABLE 1-1-continued
| THK-5051 | 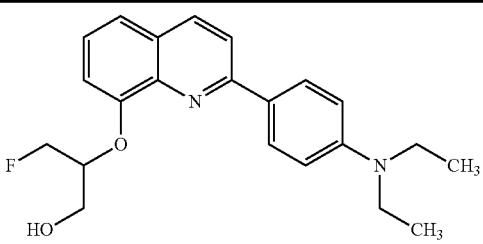 | 2-(4-diethylaminophenyl)-8-(1-fluoromethyl-2-hydroxyethoxy)quinoline |
TABLE 1-2
| THK-5058 | 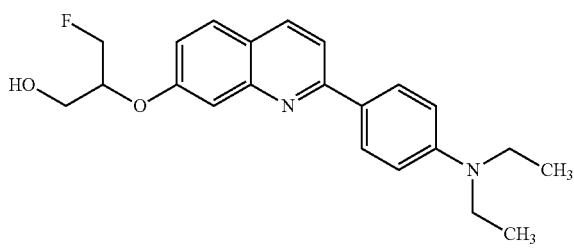 [SMILES: CCN(CC)c1ccc(-c2ccc3ccc(OC(CO)CF)cc3n2)cc1] | 2-(4-diethylaminophenyl)-7-(1-fluoromethyl-2-hydroxyethoxy)quinoline |
| THK-5059 | 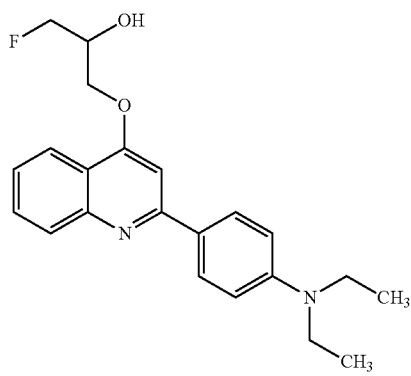 [SMILES: CCN(CC)c1ccc(-c2cc(OCC(O)CF)c3ccccc3n2)cc1] | 2-(4-diethylaminophenyl)-4-(3-fluoro-2-hydroxy-propoxy)quinoline |
| THK-5064 | 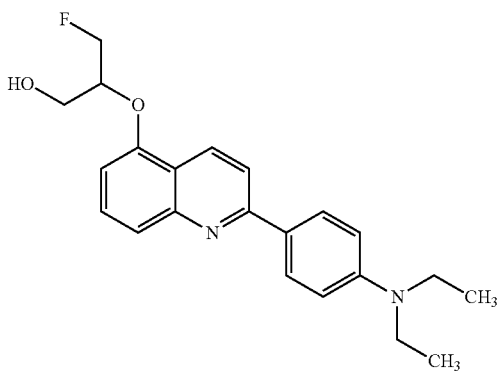 [SMILES: CCN(CC)c1ccc(-c2ccc3c(OC(CO)CF)cccc3n2)cc1] | 2-(4-diethylaminophenyl)-5-(1-fluoromethyl-2-hydroxyethoxy)quinoline |

TABLE 1-2-continued
| | | |
|---|---|---|
| THK-5065 | 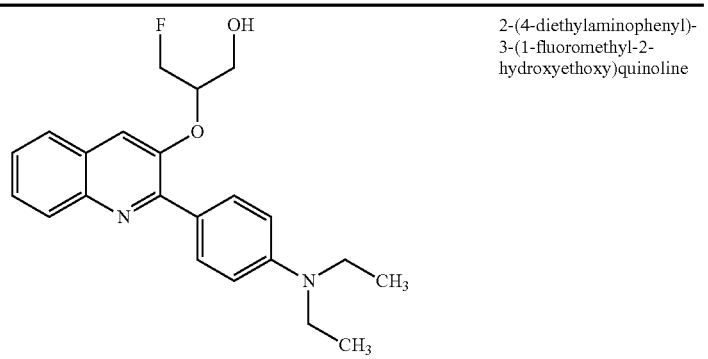 | 2-(4-diethylaminophenyl)-3-(1-fluoromethyl-2-hydroxyethoxy)quinoline |
TABLE 1-3
| | | |
|---|---|---|
| THK-5066 | 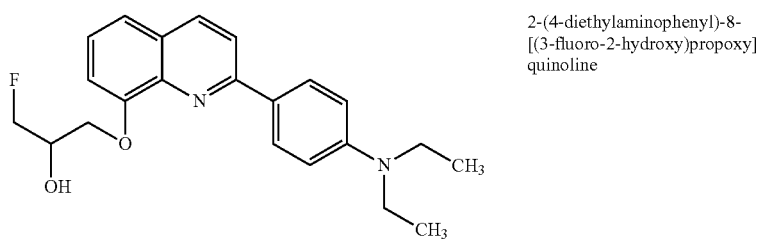 | 2-(4-diethylaminophenyl)-8-[(3-fluoro-2-hydroxy)propoxy]quinoline |
| THK-5071 | 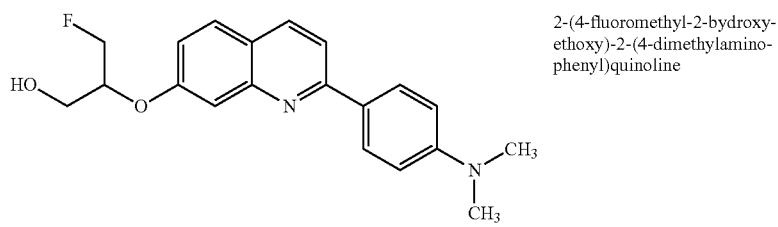 | 2-(4-fluoromethyl-2-bydroxy-ethoxy)-2-(4-dimethylamino-phenyl)quinoline |
| THK-5077 | 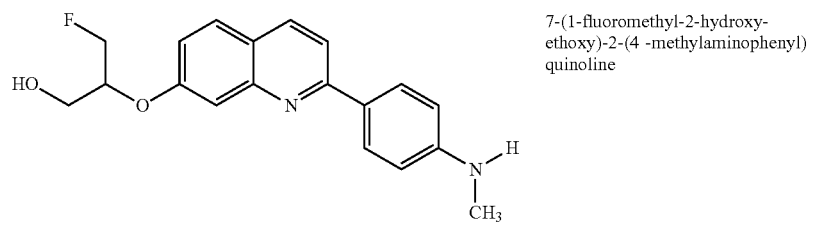 | 7-(1-fluoromethyl-2-hydroxy-ethoxy)-2-(4-methylaminophenyl)quinoline |
| THK-5078 | 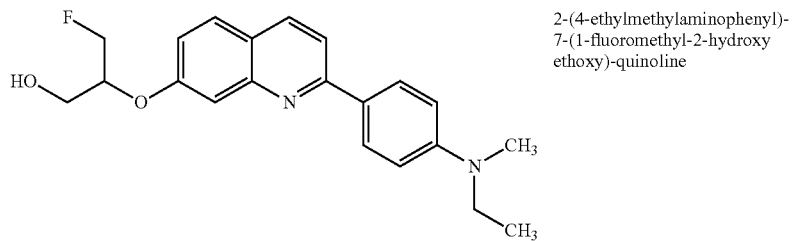 | 2-(4-ethylmethylaminophenyl)-7-(1-fluoromethyl-2-hydroxy ethoxy)-quinoline |

TABLE 1-3-continued

| | | |
|---|---|---|
| THK-5105 | [structure] | 6-[(3-fluoro-2-hydroxy)propoxy]-2-(4-dimethylaminophenyl)quinoline |

TABLE 1-4

| | | |
|---|---|---|
| THK-5106 | [structure] | 7-[(3-fluoro-2-hydroxy)propoxy]-2-(4-methylaminophenyl)quinoline |
| THK5107 | [structure] | 7-[(3-fluoro-2-hydroxy)propoxy]-2-(4-dimethylaminophenyl)quinoline |
| THK-5112 | [structure] | 2-(4-ethylmethylaminophenyl)-7-[(3-fluoro-2-hydroxy)propoxy]quinoline |
| THK-5116 | [structure] | 2-(4-aminophenyl)-6-[(3-fluoro-2-hydroxy)propoxy]quinoline |
| THK-5117 | [structure] | 6-[(3-fluoro-2-hydroxy)propoxy]-2-(4-methylaminophenyl)quinoline |

TABLE 1-5

| | | |
|---|---|---|
| THK-5122 | (structure) | 6-[(3-fluoro-2-hydroxy)propoxy]-2-(4-diethylaminophenyl)quinoline |
| THK-5075 | (structure) | 7-amino-2-(4-fluorophenyl)quinoline |
| THK-5076 | (structure) | 2-(4-fluorophenyl)-7-dimethylaminoquinoline |
| THK-5079 | (structure) | 5-amino-2-(4-fluorophenyl)quinoline |
| THK-5080 | (structure) | 2-(4-fluorophenyl-5-dimethylaminoquinoline oxalate |

TABLE 1-6

| | | |
|---|---|---|
| THK-5081 | (structure) | 8-amino-2-(4-fluorophenyl)quinoline |
| THK-5082 | (structure) | 2-(4-fluorophenyl)-8-dimethylaminoquinoline |

TABLE 1-6-continued
| | | |
|---|---|---|
| THK-5086 | 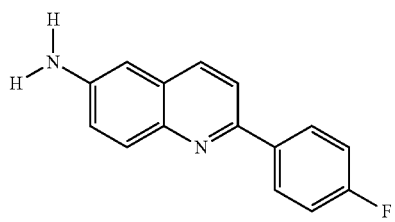 [SMILES: Nc1ccc2nc(-c3ccc(F)cc3)ccc2c1] | 6-amino-2-(4-fluorophenyl)quinoline |
| THK-5087 | 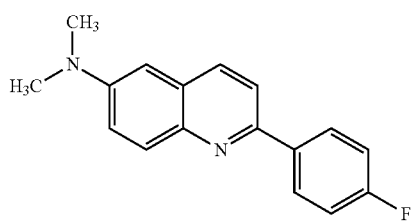 [SMILES: CN(C)c1ccc2nc(-c3ccc(F)cc3)ccc2c1] | 2-(4-fluorophenyl)-6-dimethylaminoquinoline |
| THK-932 | 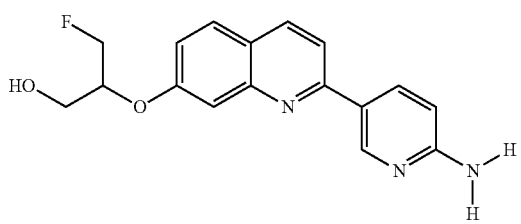 [SMILES: Nc1ccc(-c2ccc3ccc(OC(CO)CF)cc3n2)cn1] | 2-(2-aminopyrid-5-yl)-7-(1-fluoromethyl-2-hydroxy-ethoxy)quinoline |
TABLE 1-7
| | | |
|---|---|---|
| THK-5100 | 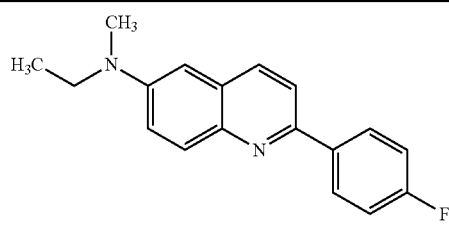 | 6-ethylmethylamino-2-(4-fluorophenyl)quinoline |
| THK-5088 | 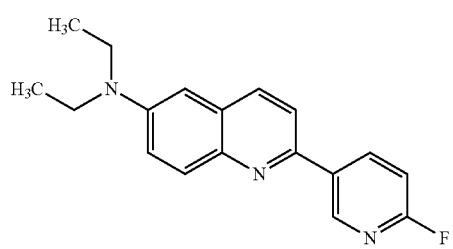 [SMILES: CCN(CC)c1ccc2nc(-c3ccc(F)nc3)ccc2c1] | 6-diethylamino-2-(2-fluoropyrid-5-yl)quinoline |
| THK-5089 | 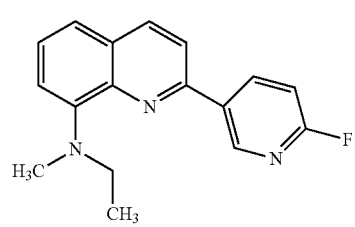 [SMILES: CCN(C)c1cccc2ccc(-c3ccc(F)nc3)nc12] | 8-ethylmethylamino-2-(2-fluoropyrid-5-yl)quinoline |

TABLE 1-7-continued
| | | |
|---|---|---|
| THK-5091 | 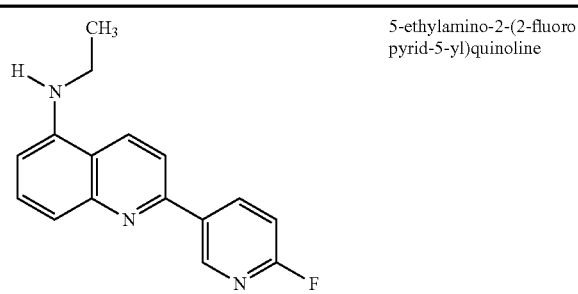 | 5-ethylamino-2-(2-fluoro pyrid-5-yl)quinoline |
TABLE 1-8
| | | |
|---|---|---|
| THK-5092 | 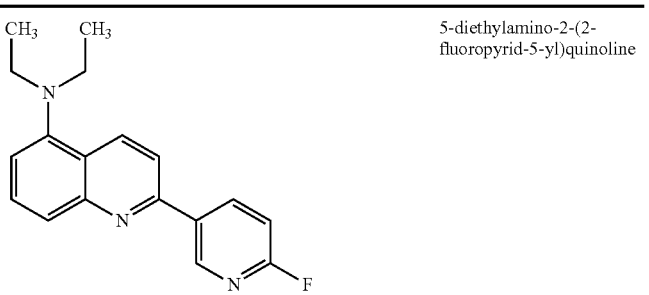 | 5-diethylamino-2-(2-fluoropyrid-5-yl)quinoline |
| THK-5097 | 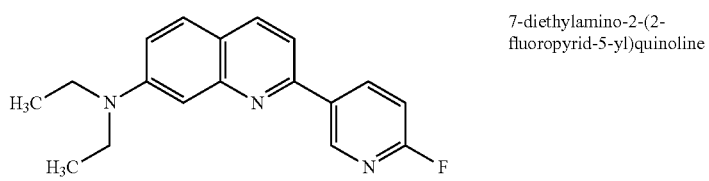 | 7-diethylamino-2-(2-fluoropyrid-5-yl)quinoline |
| THK-5098 | 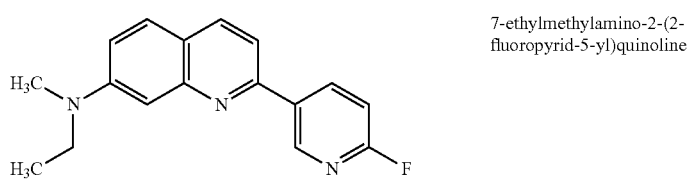 | 7-ethylmethylamino-2-(2-fluoropyrid-5-yl)quinoline |
| THK-5125 | 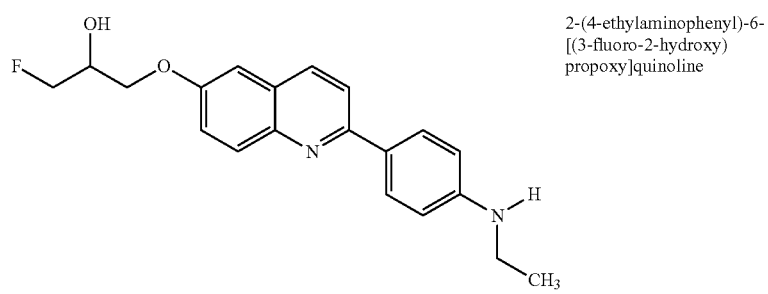 | 2-(4-ethylaminophenyl)-6-[(3-fluoro-2-hydroxy)propoxy]quinoline |

TABLE 1-9
| | | |
|---|---|---|
| THK-5127 | 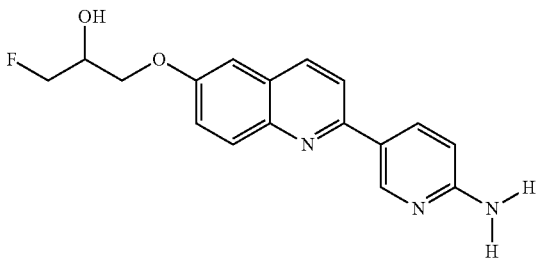 | 2-(2-aminopyrid-5-yl)-6-[(3-fluoro-2-hydroxy)propoxy]quinoline |
| THK-5151 | 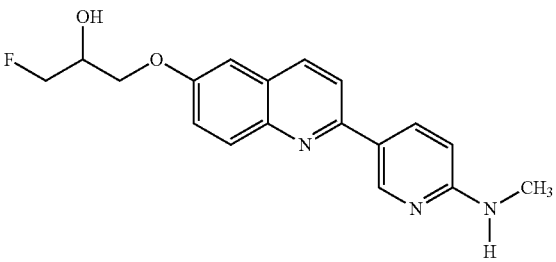 | 2-(2-methylaminopyrid-5-yl)-6-[(3-fluoro-2-hydroxy)propoxy]quinoline |
| THK-5129 | 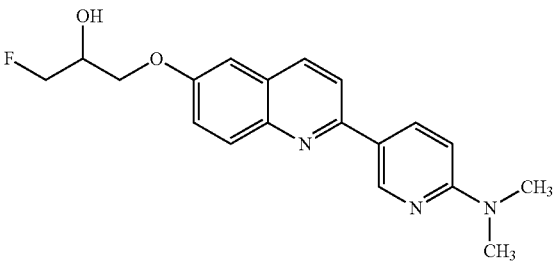 [SMILES: CN(C)c1ccc(-c2ccc3cc(OCC(O)CF)ccc3n2)cn1] | 6-[(3-fluoro-2-hydroxy)propoxy]-2-(2-dimethylaminopyrid-5-yl)quinoline |
| THK-5130 | 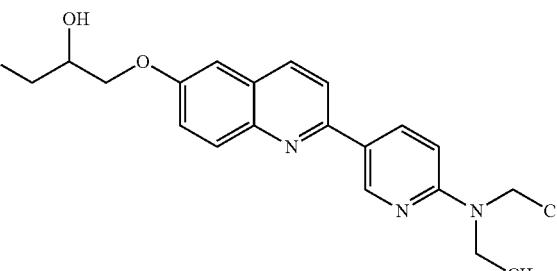 | 2-(2-diethylaminopyrid-5-yl)-6-[(3-fluoro-2-hydroxy)propoxy]quinoline |
| THK-5142 | 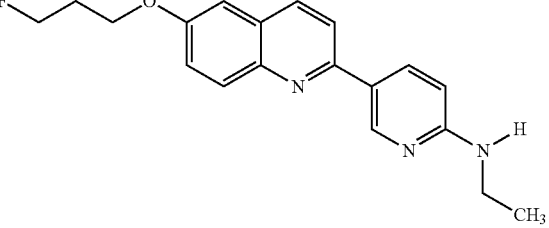 | 2-(2-ethylaminopyrid-5-yl)-6-[(3-fluoro-2-hydroxy)propoxy]quinoline |

TABLE 1-10

| THK-5177 | 1-fluoro-3-{2-[4-(4-methyl piperazin-1-yl)phenyl] quinolin-6-yloxy)propan-2-ol |
| THK-5178 | 1-fluoro-3-{2-[6-(piperazin-1-yl)pyridin-3-yl]quinolin-6-yloxy}propan-2-ol |
| THK-5180 | 1-fluoro-3-{2-[6-(4-methyl piperazin-1-yl)pyridin-3-yl] quinolin-6-yloxyl}propan-2-ol |

TABLE 1-11

| THK-5136 | 6-[(3-fluoro-2-hydroxy)propoxy]-2-(4-methyl-3,4-dihydro-2H-pyrido[3,2-b][1,4]oxazin-7-yl)quinoline |
| THK-5153 | 6-[(3-fluoro-2-hydroxy)propoxy]-2-(1-methyl-1,2,3,4-tetrahydroquinolin-6-yl)quinoline |

TABLE 1-11-continued

| | | |
|---|---|---|
| THK-5157 | [structure] | 6-[(3-fluoro-2-hydroxy-1,1-dimethyl)propoxy]-2-(1-methyl-1,2,3,4-tetrahydroquinolin-6-yl)quinoline |

TABLE 1-12

| | | |
|---|---|---|
| THK-5128 | [structure] | 2-(4-amino-3-fluorophenyl) 6-dimethylaminoquinoline |
| THK-5147 | [structure] | 2-[4-(amino)-3-[(3-fluoro 2-hydroxy)propoxy]phenyl] 6-methylaminoquinoline |
| THK-5148 | [structure] | 2-[3-(3-fluoro-2-hydroxy-1,1-dimethyl)propoxy]-4-(dimethylamino)-phenyl]-6-dimethylaminoquinoline |
| THK-5155 | [structure] | 6-amino-2-[4-(amino)-3-[(3-fluoro-2-hydroxy)propoxy]phenyl]quinoline |

TABLE 1-13

| | | |
|---|---|---|
| THK-5156 | 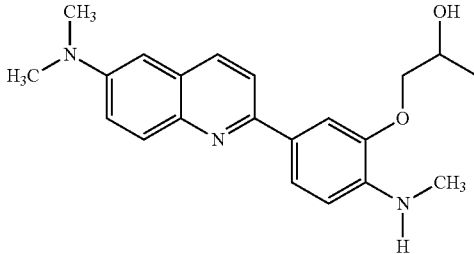 | 2-[3-[(3-fluoro-2-hydroxy)propoxy]-4-(dimethylamino)phenyl]-6-dimethylaminoquinoline |
| THK-5158 | 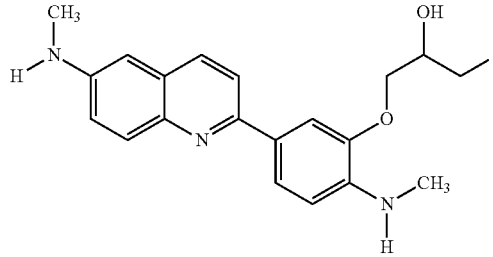 | 2-[3-[(3-fluoro-2-hydroxy)propoxy]-4-(methylamino)phenyl]-6-methylaminoquinoline |
| THK-5159 | 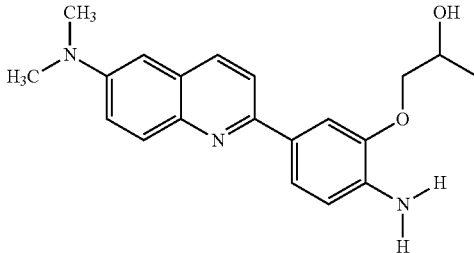 | 2-[4-(amino)-3-[(3-fluoro-2-hydroxy)propoxy]phenyl]-6-dimethylaminoquinoline |
| THK-5160 | 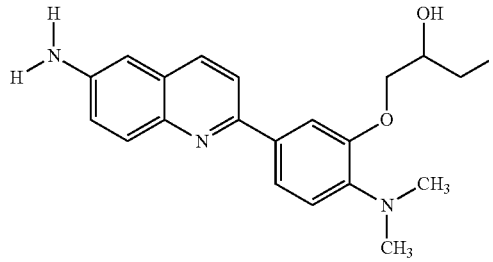 | 6-amino-2-[3-[(3-fluoro-2-hydroxy)propoxy]-4-(dimethylamino)phenyl]-quinoline |
| THK-5161 | 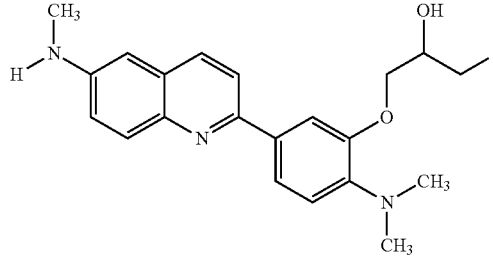 | 2-[3-[(3-fluoro-2-hydroxy)propoxy]-4-(dimethylamino)phenyl]-6-methylaminoquinoline |

TABLE 1-14

| | | |
|---|---|---|
| THK-5162 | [structure] | 2-[3-[2-[2-(2-fluoro ethoxy)ethoxy]ethoxy-4-(methylamino)phenyl]-6-dimethylaminoquinoline |
| THK-5164 | [structure] | 2-[3-[(3-fluoro-2-hydroxy)propoxy]-4-(methylamino)phenyl]-6-dimethylaminoquinoline |
| THK-5165 | [structure] | 6-amino-2-[3-[(3-fluoro-2-hydroxy)propoxy]-4-(methylamino)phenyl]-quinoline |

TABLE 1-15

| | | |
|---|---|---|
| THK-5154 | [structure] | 2-[3-[(3-fluoro-2-hydroxy)propoxy]-2-(dimethylamino)pyrid-5-yl]-6-dimethyl-aminoquinoline |
| THK-5166 | [structure] | 2-[3-[(3-fluoro-2-hydroxy)propoxy]-2-(dimethylamino) pyrid-5-yl]quinoline |

TABLE 1-16

| | | |
|---|---|---|
| THK-5170 | | 6-[(3-fluoro-2-hydroxy)propoxy]-2-(6-fluoro-pyridin-3-yl)quinoline |
| THK-5171 | | 6-[(3-fluoro-2-hydroxy)propoxy]-2-(4-methoxy-phenyl)quinoline |
| THK-5172 | | 6-[(3-fluoro-2-hydroxy)propoxy]-2-[4-(hydroxy-methyl)phenyl]quinoline |
| THK-5173 | | 6-[(3-fluoro-2-hydroxy)propoxy]-2-(4-ethanone-phenyl)quinoline |
| THK-5174 | | 6-[(3-fluoro-2-hydroxy)propoxy]-2-(6-methoxy-pyridin-3-yl)quinoline |

TABLE 1-17

| | | |
|---|---|---|
| THK-5175 | | 6-[(3-fluoro-2-hydroxy)propoxy]-2-(4-ethoxy-phenyl)quinoline |

TABLE 1-17-continued

| THK-5176 | 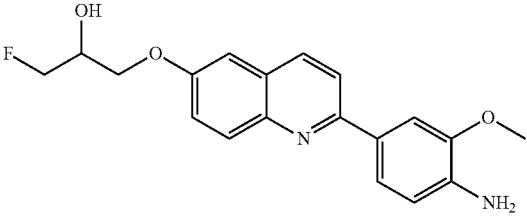 [SMILES: COc1cc(-c2ccc3cc(OCC(O)CF)ccc3n2)ccc1N] | 6-[(3-fluoro-2-hydroxy)propoxy]-2-(4-amino-3-methoxyphenyl)quinoline |
| THK-5179 | 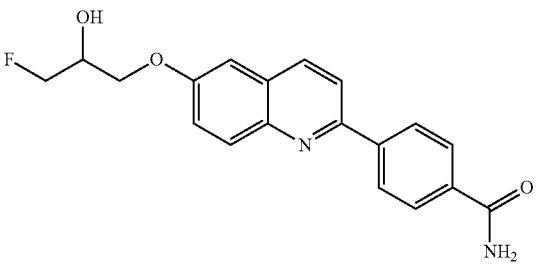 [SMILES: NC(=O)c1ccc(-c2ccc3cc(OCC(O)CF)ccc3n2)cc1] | 6-[(3-fluoro-2-hydroxy)propoxy]-2-(benzamido-4-yl)quinoline |
| THK-5181 | 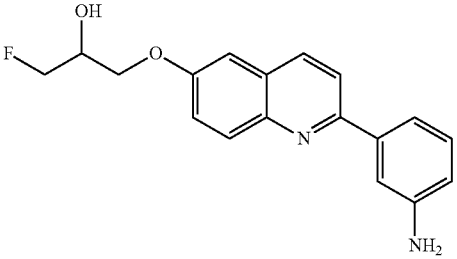 [SMILES: Nc1cccc(-c2ccc3cc(OCC(O)CF)ccc3n2)c1] | 6-[(3-fluoro-2-hydroxy)propoxy]-2-(3-aminophenyl)quinoline |
| THK-5182 | 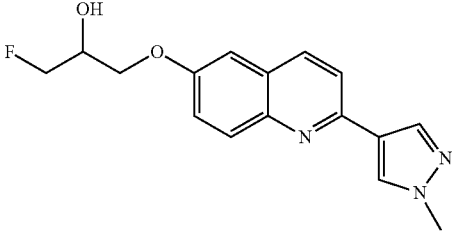 [SMILES: Cn1cc(-c2ccc3cc(OCC(O)CF)ccc3n2)cn1] | 6-[(3-fluoro-2-hydroxy)propoxy]-2-(1-methyl-pyrazol-4-yl)quinoline |

Typical examples of the compound of formula (I') used preferably in the present invention are shown below. Among these compounds, THK-5039 can be used as a synthetic precursor of THK-5035, THK-5041 can be used as a synthetic precursor of THK-5004, THK-5050 can be used as a synthetic precursor of THK-5051, THK-5070 can be used as a synthetic precursor of THK-5066, THK-5072 can be used as a synthetic precursor of THK-5058, THK-5073 can be used as a synthetic precursor of THK-5038, THK-5090 can be used as a synthetic precursor of THK-5071, THK-5095 can be used as a synthetic precursor of THK-5077, THK-5096 can be used as a synthetic precursor of THK-5078, THK-5099 can be used as a synthetic precursor of THK-5064, THK-5111 can be used as a synthetic precursor of THK-5112, THK-5113 can be used as a synthetic precursor of THK-5106, THK-5115 can be used as a synthetic precursor of THK-5107, THK-5119 can be used as a synthetic precursor of THK-5117, THK-5120 can be used as a synthetic precursor of THK-5122, THK-5121 can be used as a synthetic precursor of THK-5105, THK-5123 can be used as a synthetic precursor of THK-5116, THK-5131 can be used as a synthetic precursor of THK-5125, THK-5150 can be used as a synthetic precursor of THK-5127, THK-5152 can be used as a synthetic precursor of THK-5151, THK-5135 can be used as a synthetic precursor of THK-5129, THK-5138 can be used as a synthetic precursor of THK-5130, THK-5143 can be used as a synthetic precursor of THK-5142, THK-5163 can be used as a synthetic precursor of THK-5164, THK-5167 can be used as a synthetic precursor of THK-5136, and THK-5168 can be used as a synthetic precursor of THK-5156.

TABLE 2-1

| | | |
|---|---|---|
| THK-5039 | [structure] | 2-(4-diethylaminophenyl)-6-[(2-hydroxy-1-tosyloxy-methyl)ethoxy]quinoline |
| THK-5041 | [structure] | 2-(4-aminophenyl)-8-(2-hydroxy-1-tosyloxymethyl-ethoxy)quinoline |

TABLE 2-2

| | | |
|---|---|---|
| THK-5050 | [structure] | 2-(4-diethylaminophenyl)-8-(2-hydroxy-1-tosyloxy methylethoxy)quinoline |
| THK-5070 | [structure] | 2-(4-diethylaminophenyl)-8-[[2-(tetrahydro-2H-pyran-2-yloxy)-3-tosyloxy]propoxy]quinoline |
| THK-5072 | [structure] | 2-(4-diethylaminophenyl)-7-(2-hydroxy-1-tosyloxy methylethoxy)quinoline |
| THK-5073 | [structure] | 2-(4-diethylaminophenyl)-8-[[2-tetrahydro-2H-pyran-2-yloxy)-3-tosyloxy]propoxy]quinoline |

TABLE 2-2-continued

| THK-5090 | [structure] | 7-(2-hydroxy-1-tosyloxy-methylethoxy)-2-(4-dimethylaminophenyl)quinoline |
| THK-5095 | [structure] | 7-(2-hydroxy-1-tosyloxy-methylethoxy)-2-(4-methylaminophenyl)quinoline |
| THK-5096 | [structure] | 2-(4-ethylmethylamino-phenyl)-7-(2-hydroxy-1-tosyloxymethylethoxy)quinoline |

TABLE 2-3

| THK-5099 | [structure] | 2-(4-diethylaminophenyl)-5-(2-hydroxy-1-tosyloxy methylethoxy)quinoline |
| THK-5111 | [structure] | 2-(4-ethylmethylamino-phenyl)-7-[[2-(tetrahydro-2H-pyran-2-yloxy)-3-tosyloxy]propoxy]quinoline |
| THK-5113 | [structure] | 2-(4-ethylmethylamino-phenyl)-7-[[2-(tetrahydro-2H-pyran-2-yloxy)-3-tosyloxy]propoxy]quinoline |

TABLE 2-3-continued

| THK-5115 | 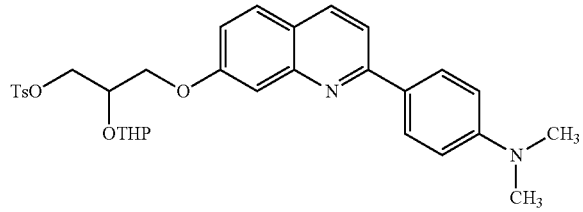 | 2-(4-dimethylaminophenyl)-7-[[2-(tetrahydro-2H-pyran-2-yloxy)-3-tosyloxy]propoxy]quinoline |
| THK-5119 | 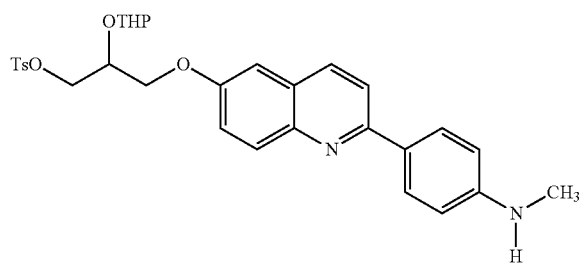 | 2-(4-methylaminophenyl)-6-[[2-(tetrahydro-2H-pyran-2-yloxy)-3-tosyloxy]propoxy]quinoline |
| THK-5120 | 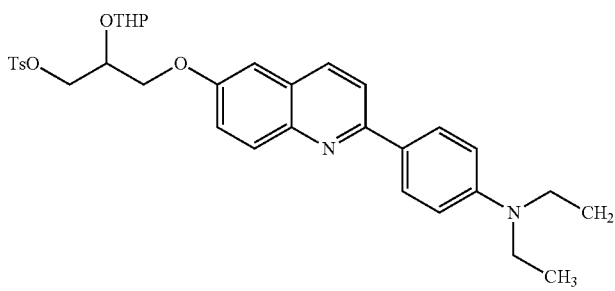 | 2-(4-diethylaminophenyl)-6-[[2-(tetrahydro-2H-pyran-2-yloxy)-3-tosyloxy]propoxy]quinoline |

TABLE 2-4

| THK-5121 | 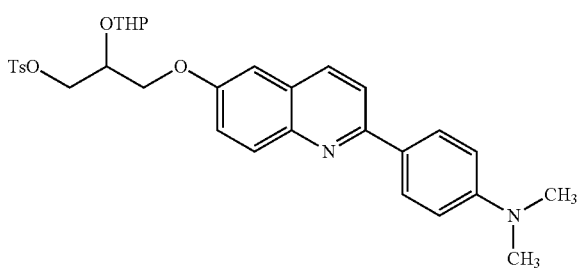 | 2-(4-dimethylaminophenyl)-6-[[2-(tetrahydro-2H-pyran-2-yloxy)-3-tosyloxy]propoxy]quinoline |
| THK-5123 | 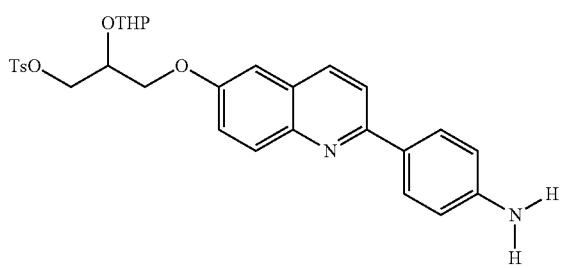 | 2-(4-aminophenyl)-6-[[2-(tetrahydro-2H-pyran-2-yloxy)-3-tosyloxy]propoxy]quinoline |

TABLE 2-5

| | | |
|---|---|---|
| THK-5131 | 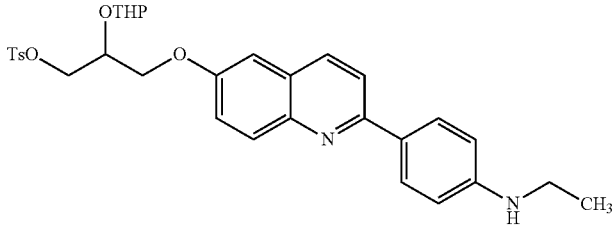 | 2-(4-ethylaminophenyl)-6-[[2-(tetrahydro-2H-pyran-2-yloxy)-3-tosyloxy]propoxy]quinoline |
| THK-5150 | 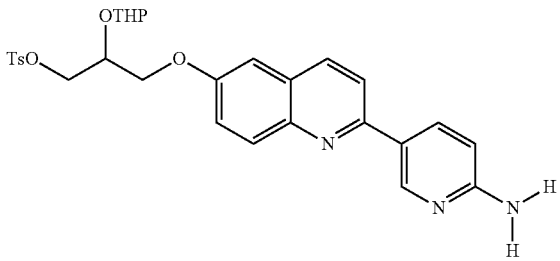 | 2-(2-aminopyrld-5-yl)-6-[[2-(tetrahydro-2H-pyran-2-yloxy)-3-tosyloxy]propoxy]quinoline |
| THK-5152 | 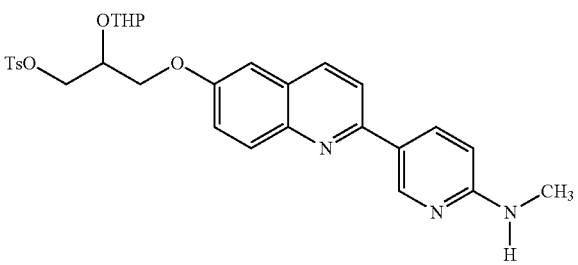 | 2-(2-methylaminopyrid-5-yl)-6-[[2-(tetrahydro-2H-pyran-2-yloxy)-3-tosyloxy]propoxy]quinoline |
| THK-5135 | 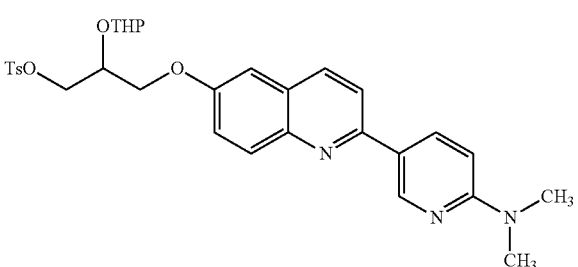 | 2-(2-dimethylaminopyrid-5-yl)-6-[[2-(tetrahydro-2H-pyran-2-yloxy)-3-tosyloxy]propoxy]quinoline |
| THK-5138 | 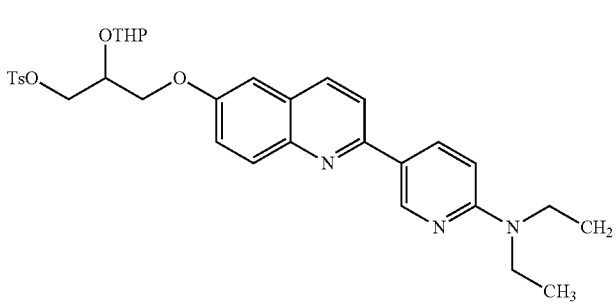 | 2-(2-diethylaminopyrid-5-yl)-5-[[2-(tetrahydro-2H-pyran-2-yloxy-3-tosyloxy]propoxy]quinoline |
| THK-5143 | 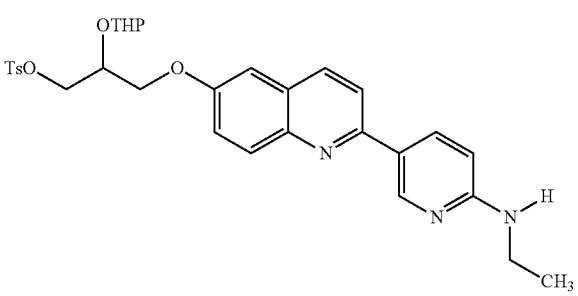 | 2-(2-ethylaminopyrid-5-yl)-6-[[2-(tetrahydro-2H-pyran-2-yloxy)-3-tosyloxy]propoxy]quinoline |

TABLE 2-6

| | | |
|---|---|---|
| THK-5163 | (structure) | 2-[4-(methylamino)-3-[[2-(tetrahydro-2H-pyran-2-yloxy)-3-tosyloxy]propoxy]phenyl]-6-dimethyl-aminoquinoline |
| THK-5167 | (structure) | 6-[[2-(tetrahydro-2H-pyran-2-yloxy)-tosyloxy]propoxy]-2-(4-methyl-3,4-dihydro-2H-pyrido[3,2-b][1,4]oxazin-7-yl)quinoline |
| THK-5168 | (structure) | 2-[4-(dimethylamino)-3-[[2-(tetrahydro-2H-pyran-2-yloxy)-3-tosyloxy]propoxy]phenyl]-6-dimethyl-aminoquinoline |

The present invention will be descried in more detail and specifically below by way of Examples, but the present invention is not limited to the Examples.

Example 1

Synthesis of the Compounds of the Present Invention

Silica gel BW300 manufactured by Fuji Silysia Chemical Ltd. was used in silica gel column chromatography of Examples. Chromatorex NH-DM1020 manufactured by Fuji Silysia Chemical Ltd. was used in basic silica gel column chromatography using an amino group-bonded type silica gel.

$^1$H-NMR was measured using UNITY INOVA500 (500 MHz) manufactured by VARIAN, JNM-LA400 (400 MHz) manufactured by JEOL, Ltd. and Gemini 2000 (300 MHz) tetramethylsilane manufactured by VARIAN as standard substances, and all δ values were measured by ppm.

Mass spectrum was measured by atmospheric pressure chemical ionization (APCI) using LCQ-Advantage manufactured by ThermoQuest or SSQ-7000C manufactured by FinniganMAT.

Infrared spectra were measured using a Paragon1000 FT-IR manufactured by Perkin-Elmer, and B-545 manufactured by BUCHI was used for the measurement of a melting point.

Meanings of abbreviations in the measurement of NMR are shown below.
s: singlet
d: doublet
dd: double doublet
ddd: double double doublet
t: triplet
dt: double triplet
q: quartet
m: multiplet
br: broad
J: coupling constant
Hz: hertz
CDCl$_3$: deuterated chloroform
DMSO-d$_6$: deuterated dimethylsulfoxide Synthesis Examples and Label Example of the compounds of the present invention are shown below.

Synthesis Method of THK-5004

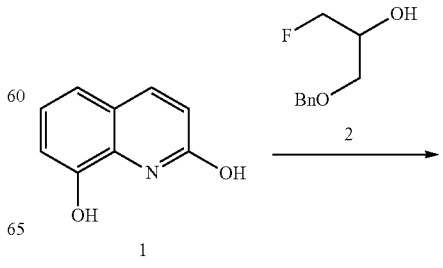

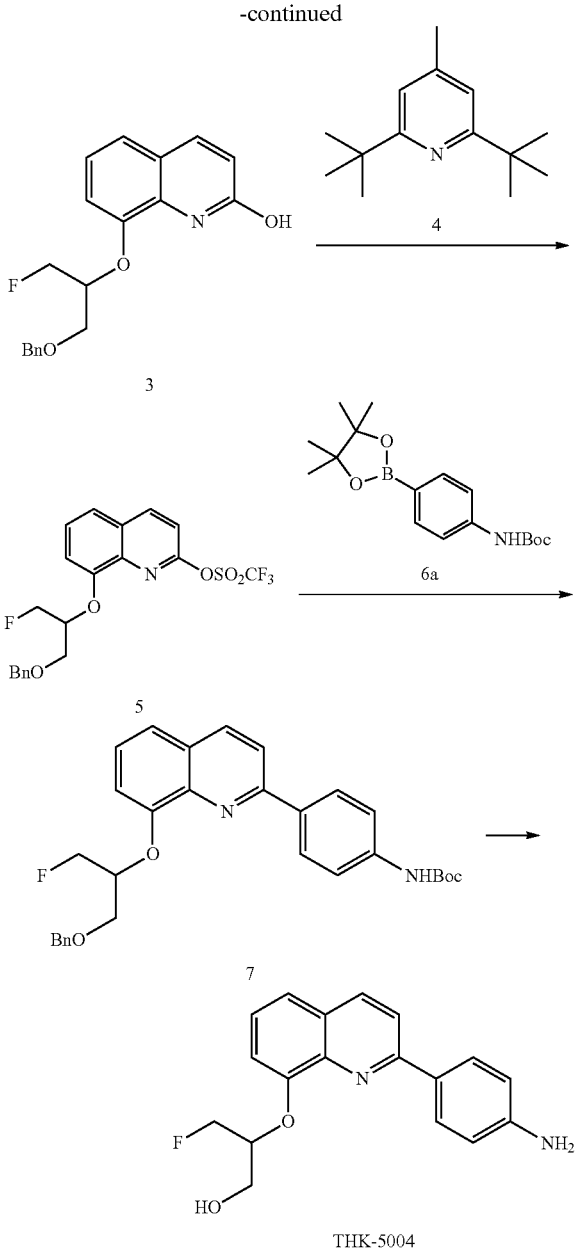

Synthesis of 3

To a mixture of 1 (1.29 g, 8.0 mmol), 2 (1.66 g, 9.0 mmol), triphenylphosphine (2.36 g, 9.0 mmol) and tetrahydrofuran (20 ml), a tetrahydrofuran (10 ml) solution of diisopropyl azodicarboxylate (1.82 g, 9.0 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: ethyl acetate/n-hexane=2/3) to obtain 3 (2.62 g, 100%) as a pale yellow oily substance.

Synthesis of 5

To a methylene chloride (20 ml) solution of 3 (2.62 g, 8.0 mmol) and 4 (2.2 g, 10.4 mmol), a methylene chloride (10 ml) solution of trifluoromethanesulfonic anhydride (2.7 g, 9.6 mmol) was added dropwise under ice cooling and stirring, and the mixed solution was stirred at room temperature for 16 hours. 4 (2.2 g, 10.4 mmol) and trifluoromethanesulfonic anhydride (2.7 g, 9.6 mmol) were added, followed by further stirring at room temperature for 16 hours. To the reaction solution, ice water was added and the solution was extracted with chloroform. The extraction liquid was dried and the solvent was distilled off under reduced pressure, and then the residue was purified by silica gel column chromatography (eluting solvent: n-hexane/ethyl acetate=20/1) to obtain 5 (1.47 g, 40%) as a colorless oily substance.

APCI-MS m/z 460[M+H]$^+$

Synthesis of 7

To a mixture of 5 (1.45 g, 3.15 mmol), 6a (1.00 g, 3.15 mmol) and 1,2-dimethoxyethane (20 ml), an aqueous 2M sodium carbonate solution (3.5 ml, 7.0 mmol) and tetrakis-triphenylphosphine palladium (146 mg, 0.126 mmol) were added and the mixture was heated at reflux for 16 hours under an argon atmosphere. The reaction solution was allowed to return to room temperature and the solvent was distilled off under reduced pressure, and then water was added to the residue and the solution was extracted with chloroform. The extraction liquid was dried and the solvent was distilled off under reduced pressure, and then the residue was purified by silica gel column chromatography (eluting solvent: n-hexane/ethyl acetate=9/1) to obtain 7 (1.55 g, 98%) as a pale yellow foam-like substance.

APCI-MS m/z 503[M+H]$^+$

Synthesis of THK-5004

To a mixture of 7 (1.54 g, 3.0 mmol) and anisole (0.98 ml), methanesulfonic acid (4.9 ml) was added and the mixture was stirred at room temperature for 16 hours. To the reaction solution, ice water was added and the solution was made basic with an aqueous potassium carbonate solution and then extracted with chloroform. The extraction liquid was dried and the solvent was distilled off under reduced pressure, the residue was purified by silica gel column chromatography (eluting solvent: n-hexane/ethyl acetate=2/1→3/2→1/4) and then washed with diisopropylether to obtain THK-5004 (593 mg, 62%) as a yellow solid.

mp 97-100° C., $^1$H NMR (400 MHz, CDCl$_3$) δ 3.70-3.80 (2H, m), 3.80-3.90 (2H, brs), 4.40-4.50 (1H, m), 4.70 to 5.00 (2H, m), 6.29 (1H, t, J=6.4 Hz), 6.75-6.85 (2H, m), 7.49 (1H, t, J=7.6 Hz), 7.59 (1H, d, J=7.6 Hz), 7.82 (1H, d, J=8.8 Hz), 7.92 (2H, d, J=8.8 Hz), 8.19 (1H, d, J=8.8 Hz)

IR (Nujol) 1600 cm$^{-1}$

APCI-MS m/z 313[M+H]$^+$

Synthesis Method of THK-5035

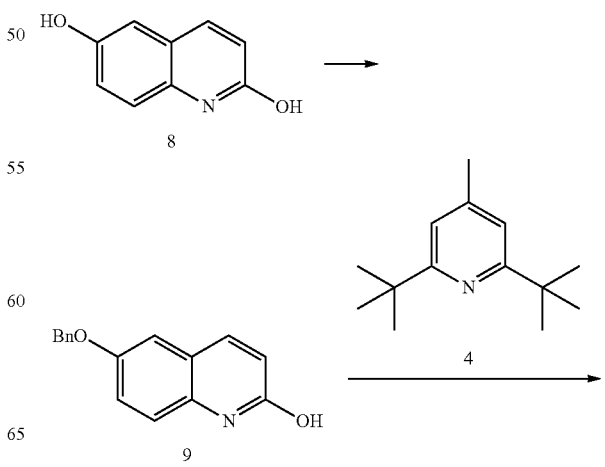

Synthesis of 9

To an N,N-dimethylformamide (50 ml) suspension of 8 (3.00 g, 18.6 mmol), potassium carbonate (2.83 g, 20.5 mmol) and benzyl chloride (2.25 ml, 19.6 mmol) were added and the mixture was stirred at 105° C. for 1 hour. The reaction solution was allowed to return to room temperature and water was added, and then the solution was extracted with warm ethyl acetate. The extraction liquid was washed with water and dried, and then solvent was concentrated to about 100 ml under reduced pressure. After being allowed to cool, the precipitated crystal was collected by filtration and then dried to obtain 9 (2.66 g, 57%) as colorless crystals.

mp 220-221° C., IR (Nujol) 1661, 1623 cm$^{-1}$
APCI-MS m/z 252[M+H]$^+$

Synthesis of 10

To a methylene chloride (70 ml) suspension of 9 (2.66 g, 10.6 mmol) and 4 (3.04 g, 14.8 mmol), trifluoromethanesulfonic anhydride (2.14 ml, 12.7 mmol) was added dropwise under ice cooling and stirring, and the mixture was stirred at room temperature for 2 hours. 4 (1.52 g, 7.41 mmol) and trifluoromethanesulfonic anhydride (1.07 ml, 6.35 mmol) were added, followed by further stirring at room temperature for 3 days. Water was added to the reaction solution and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=20/1, 9/1) and then recrystallized from ethyl acetate-n-hexane to obtain 10 (3.75 g, 92%) as a colorless crystal.

mp 109.5-110° C., APCI-MS m/z 384[M+H]$^+$

Synthesis of 11

To a mixture of 10 (2.19 g, 5.7 mmol), 6 (1.65 g, 6.0 mmol) and 1,2-dimethoxyethane (20 ml), an aqueous 2M sodium carbonate solution (5.5 ml, 11 mmol) and tetrakistriphenylphosphine palladium (277 mg, 0.240 mmol) were added and the mixture was stirred under an argon atmosphere at 90° C. for 16 hours. The reaction solution was allowed to return to room temperature and insolubles were removed by filtration and then washed with chloroform. The filtrate and the wash were combined and the mixture was extracted with chloroform. The extraction liquid was washed with saturated saline and then dried, and the solvent was distilled off under reduced pressure. The residue was purified by silica gel column chromatography (eluting solvent: chloroform) to obtain 11 (1.86 g, 85%) as an orange solid.

APCI-MS m/z 383[M+H]$^+$

Synthesis of 12

To a mixture of 11 (1.85 g, 4.84 mmol) and anisole (1 ml), methanesulfonic acid (5 ml) was added and the mixture was stirred at room temperature for 30 minutes. To the reaction solution, ice water was added and the solution was washed with ethyl acetate. The aqueous layer was made basic with sodium hydrogen carbonate and extracted with chloroform-tetrahydrofuran. The extraction liquid was dried and the solvent was distilled off under reduced pressure, and then the residue was washed with n-hexane to obtain 12 (1.25 g, 88%) as an orange solid.

APCI-MS m/z 293[M+H]$^+$

Synthesis of 13

To a mixture of 12 (468 mg, 1.6 mmol), 2 (354 mg, 1.9 mmol), triphenylphosphine (504 mg, 1.9 mmol) and tetrahydrofuran (20 ml), a tetrahydrofuran (10 ml) solution of diisopropyl azodicarboxylate (388 mg, 1.9 mmol) was added dropwise under ice cooling and stirring, and the mixture was stirred at room temperature for 16 hours. Triphenylphosphine (150 mg, 0.57 mmol) and diisopropyl azodicarboxylate (120 mg, 0.59 mmol) were added, followed by further stirring at room temperature for 2 hours. The solvent of the reaction solution was distilled off under reduced pressure and the residue was purified by silica gel column chromatography (eluting solvent: chloroform) to obtain 13 (733 mg, 100) as an orange solid.

Synthesis of 14

To a mixture of 13 (733 mg, 1.6 mmol) and anisole (1 ml), methanesulfonic acid (5 ml) was added under ice cooling and stirring, and the mixture was stirred at room temperature for 50 minutes. To the reaction solution, ice water (40 ml) was added and the solution was washed with ethyl acetate. The aqueous layer was made basic with potassium carbonate and extracted with chloroform. The extraction liquid was dried and the solvent was distilled off under reduced pressure. The residue was purified by silica gel column chromatography (eluting solvent: chloroform/methanol=99/1) and then washed with diisopropylether to obtain 14 (400 mg, 68%) as a yellow solid.

APCI-MS m/z 369[M+H]$^+$

Synthesis of THK-5035

To an ethanol (10 ml) solution of 14 (400 mg, 1.09 mmol), 4M HCl/ethyl acetate (1 ml, 4 mmol) was added and the solvent was distilled off under reduced pressure. The residue was washed with diethyl ether and then recrystallized from isopropanol-acetone to obtain THK-5035 (368 mg, 84%) as orange crystals.

mp 207-209° C., $^1$H NMR (400 MHz, DMSO-d$_6$+D$_2$O) δ 2.53 (6H, t, J=7.0 Hz), 3.52 (4H, q, J=7.0 Hz), 4.6-4.9 (3H, m), 6.99 (2H, d, J=8.5 Hz), 7.7-7.8 (2H, m), 8.13 (2H, d, J=9.1 Hz), 8.27 (2H, d, J=9.1 Hz), 8.71 (1H, d, J=9.1 Hz)

IR (Nujol) 1595, 1460, 1216 cm$^{-1}$

APCI-MS m/z 369[M+H]$^+$

Synthesis Method of THK-5038

7.45 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: ethyl acetate/n-hexane=1/2) to obtain 17 (1.80 g, 82%) as a pale pink solid.

mp 132-135° C., APCI-MS m/z 352[M+H]$^+$

Synthesis of 18

To a methylene chloride (25 ml) solution of 17 (1.80 g, 5.12 mmol) and 4 (1.47 g, 7.17 mmol), trifluoromethanesulfonic anhydride (1.03 ml, 6.14 mmol) was added dropwise under ice cooling and stirring, and the mixture was stirred at room temperature for 70 minutes. Water was added to the reaction solution and the solution was extracted with ethyl acetate. The extraction liquid was washed with water and dried, and then the solvent was distilled off under reduced pressure. The residue was purified by silica gel column chromatography (eluting solvent: n-hexane→n-hexane/ethyl acetate=50/1→30/1) to obtain 18 (2.09 g, 84%) as a pale pink oily substance.

APCI-MS m/z 484[M+H]$^+$

Synthesis of 19

To a mixture of 18 (1.20 g, 2.48 mmol), 6 (680 mg, 2.48 mmol) and 1, 2-dimethoxyethane (30 ml), potassium car-

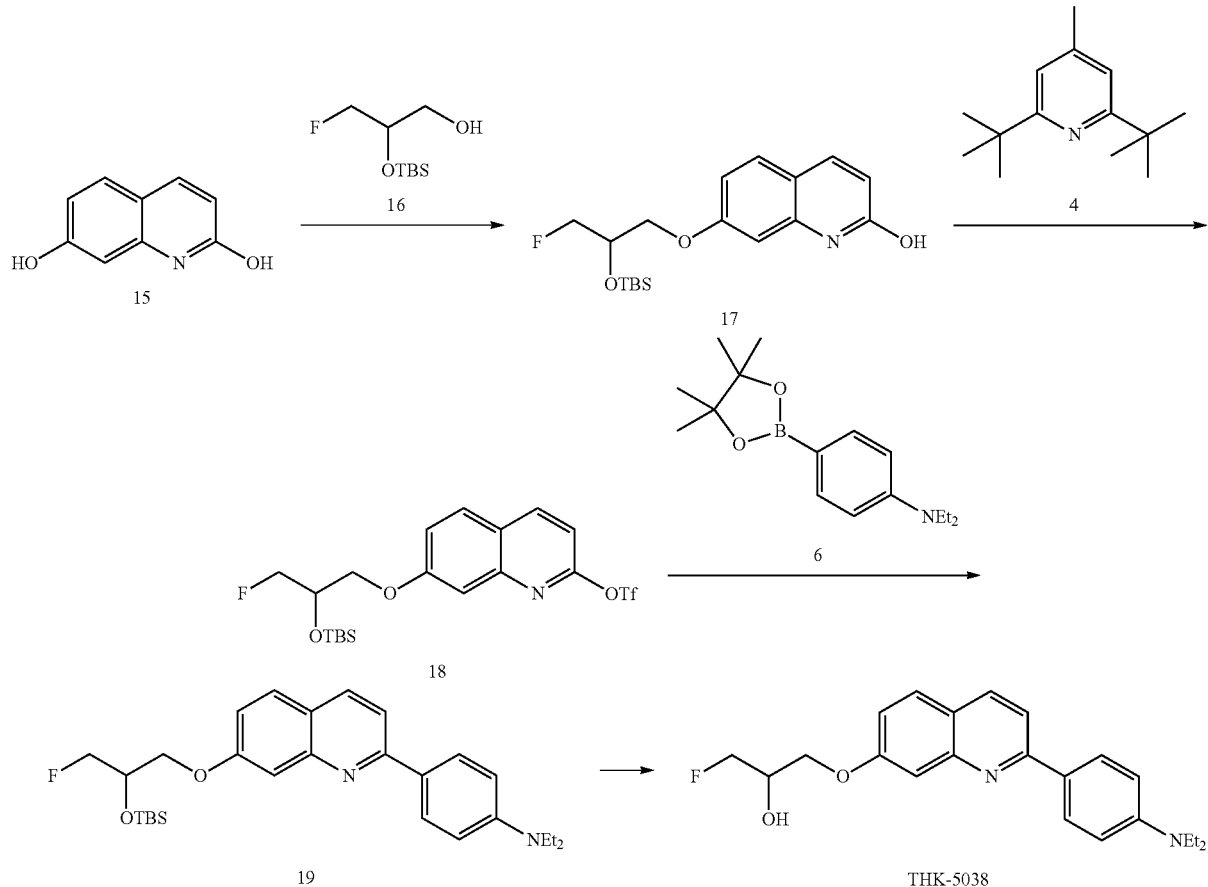

Synthesis of 17

To a mixture of 15 (1.00 g, 6.21 mmol), 16 (1.55 g, 7.45 mmol), triphenylphosphine (1.95 g, 7.45 mmol) and tetrahydrofuran (80 ml), diisopropyl azodicarboxylate (1.48 ml, bonate (1.03 g, 7.44 mmol) and water (0.62 ml) were added, and tetrakistriphenylphosphine palladium (124 mg, 0.124 mmol) was added under an argon atmosphere, followed by stirring at 80° C. for 2.5 hours. The reaction solution was allowed to return to room temperature, water was added and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=20/1) and then recrystallized from n-hexane to obtain 19 (700 mg, 59%) as pale yellow crystals.

mp 102-102.5° C., APCI-MS m/z 483[M+H]$^+$

Synthesis of THK-5038

To a tetrahydrofuran (10 ml) solution of 19 (700 mg, 1.45 mmol), 1M tetra-n-butylammonium fluoride/tetrahydrofuran (1.45 ml, 1.45 mmol) was added and the mixture was stirred at room temperature for 1 hour. Water was added to the reaction solution and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=2/1) and then recrystallized from ethyl acetate-n-hexane to obtain THK-5038 (482 mg, 90%).

mp 110-110.5° C., $^1$H NMR (500 MHz, DMSO-d$_6$) δ 1.14 (6H, t, J=7.0 Hz), 3.42 (4H, q, J=7.0 Hz), 4.10-4.19 (3H, m), 4.45 to 4.64 (2H, m), 5.55 (1H, d, J=4.8 Hz), 6.78 (2H, d, J=9.0 Hz), 7.12 (1H, dd, J=8.7, 2.6 Hz), 7.35 (1H, d, J=2.6 Hz), 7.81 (1H, d, J=9.0 Hz), 7.85 (1H, d, J=9.0 Hz), 8.10 (2H, d, J=9.0 Hz), 8.21 (1H, d, J=9.0 Hz)

IR (Nujol) 1622, 1596 cm$^{-1}$

APCI-MS m/z 369[M+H]$^+$

Synthesis Method of THK-5039

Synthesis of 21

To a mixture of 12 (400 mg, 1.37 mmol), 20 (592 mg, 1.64 mmol), triphenylphosphine (431 mg, 1.64 mmol) and tetrahydrofuran (20 ml), diisopropyl azodicarboxylate (0.325 ml, 1.64 mmol) was added dropwise under ice cooling and stirring, and the mixture was stirred at room temperature for 16 hours. 20 (592 mg, 1.64 mmol), triphenylphosphine (431 mg, 1.64 mmol) and tetrahydrofuran (10 ml) were added, followed by further stirring at room temperature for 24 hours. The solvent of the reaction solution was distilled off under reduced pressure and the residue was purified by silica gel column chromatography (eluting solvent: ethyl acetate/n-hexane=1/9) to obtain 21 (870 mg, 100%) as a yellow oily substance.

APCI-MS m/z 635[M+H]$^+$

Synthesis of THK-5039

To a chloroform (12 ml) solution of 21 (870 mg, 1.37 mmol), trifluoroacetic acid (8 ml) and then water (2 ml) were added dropwise under ice cooling and stirring, and the mixture was stirred at room temperature for 1.5 hours. To the reaction solution, ice water and ethyl acetate were added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=4/1, 2/1) and then recrystallized from ethyl acetate-n-hexane to obtain THK-5039 (219 mg, 31).

mp 119-120° C., 1H NMR (500 MHz, DMSO-d$_6$) δ 1.14 (6H, t, J=7.0 Hz), 2.33 (3H, s), 3.42 (4H, q, J=7.0 Hz), 4.07 (5H, m), 5.62 (1H, d, J=4.8 Hz), 6.78 (2H, d, J=9.0 Hz), 7.21 (2H, m), 7.40 (2H, d, J=8.0 Hz), 7.78 (2H, d, J=8.0 Hz), 7.86 (1H, d, J=8.0 Hz), 7.97 (1H, d, J=8.7 Hz), 8.07 (2H, d, J=8.7 Hz), 8.20 (1H, d, J=8.7 Hz)

APCI-MS m/z 521[M+H]$^+$

Synthesis Method of THK-5050

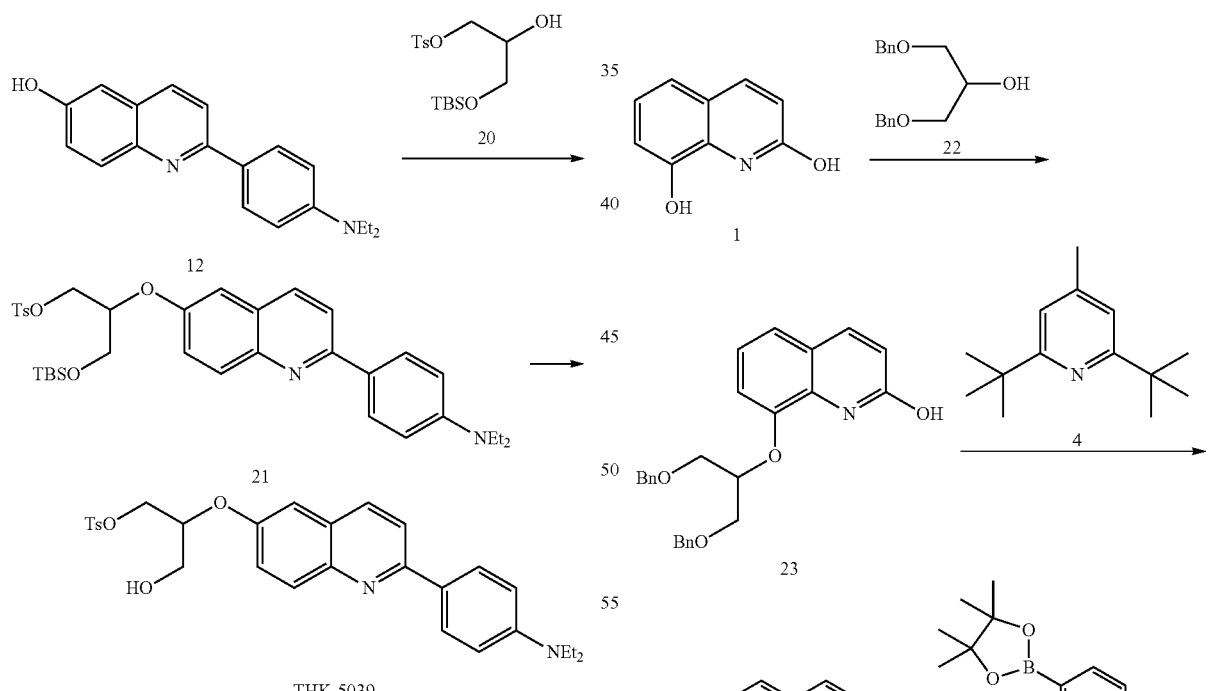

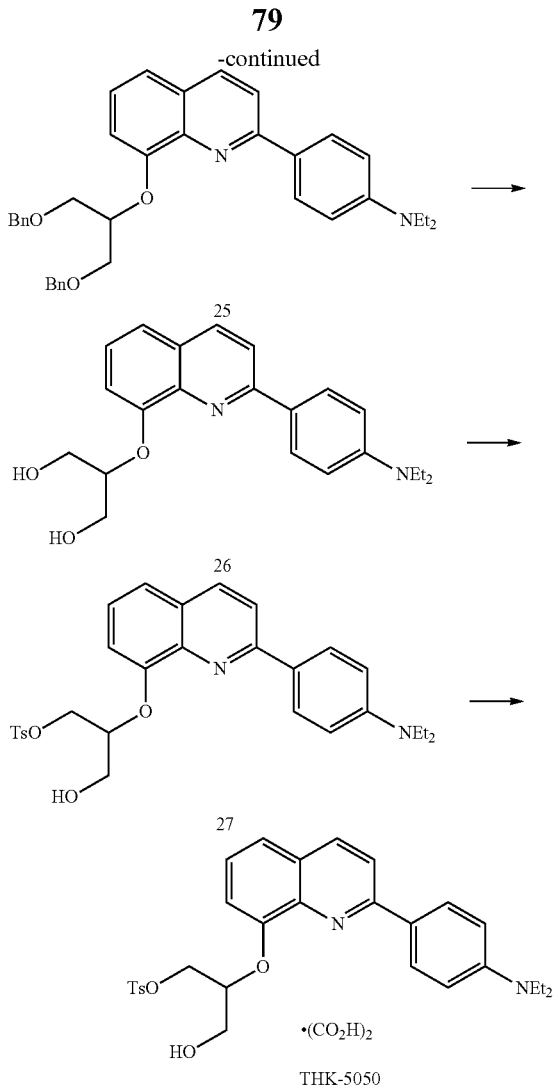

Synthesis of 23

To a mixture of 1 (2.00 g, 12.4 mmol), 22 (4.06 g, 14.9 mmol), triphenylphosphine (3.91 g, 14.9 mmol) and tetrahydrofuran (40 ml), diisopropyl azodicarboxylate (2.95 ml, 14.9 mmol) was added dropwise under ice cooling and stirring, and the mixture was stirred at room temperature for 3 days. The solvent of the reaction solution was distilled off under reduced pressure and the residue was purified by silica gel column chromatography (eluting solvent: ethyl acetate/n-hexane=1/4, 2/3) to obtain 23 (3.45 g, 67%) as a pale yellow oily substance.

APCI-MS m/z 416[M+H]$^+$

Synthesis of 24

To a methylene chloride (40 ml) solution of 23 (3.44 g, 8.28 mmol) and 4 (2.38 g, 11.6 mmol), trifluoromethanesulfonic anhydride (1.67 ml, 9.94 mmol) was added dropwise under ice cooling and stirring, and the mixture was stirred at room temperature for 1 hour. Water was added to the reaction solution and the solution was extracted with ethyl acetate. The extraction liquid was washed with water and dried, and then the solvent was distilled off under reduced pressure. The residue was purified by silica gel column chromatography (eluting solvent: n-hexane→n-hexane/ethyl acetate=9/1) to obtain 24 (4.16 g, 92%) as a colorless oily substance.

APCI-MS m/z 548[M+H]$^+$

Synthesis of 25

To a mixture of 24 (2.00 g, 3.65 mmol), 6 (1.01 g, 3.65 mmol) and 1,2-dimethoxyethane (30 ml), potassium carbonate (1.51 g, 11 mmol) and water (0.63 ml) were added, and tetrakistriphenylphosphine palladium (210 mg, 0.183 mmol) was added under an argon atmosphere and the mixture was stirred at 80° C. for 2 hours. The reaction solution was allowed to return to room temperature and water was added, and then solution was extracted with ethyl acetate. The extraction liquid was washed with water and dried, and then the solvent was distilled off under reduced pressure. The residue was purified by silica gel column chromatography (eluting solvent: n-hexane/ethyl acetate=9/1) to obtain 25 (1.95 g, 98%) as a pale yellow oily substance.

APCI-MS m/z 547[M+H]$^+$

Synthesis of 26

To a mixture of 25 (1.94 g, 3.55 mmol) and anisole (3 ml), methanesulfonic acid (9 ml) was added dropwise under ice cooling and stirring, and the mixture was stirred at room temperature for 20 minutes. To the reaction solution, ice water and then ethyl acetate were added, and the solution was extracted with ethyl acetate after adjusting the pH to 9 using an aqueous potassium carbonate solution. The extraction liquid was washed with saturated saline and dried, and then the solvent was distilled off under reduced pressure. The residue was purified by silica gel column chromatography (eluting solvent: n-hexane/ethyl acetate=4/1→1/2→1/3) to obtain 26 (1.22 g, 94%) as a yellow powder.

APCI-MS m/z 367[M+H]$^+$

Synthesis of 27

To a 1,2-dimethoxyethane (120 ml) solution of 26 (1.36 g, 3.71 mmol), paratoluenesulfonic anhydride (1.21 g, 3.71 mmol) and triethylamine (0.78 ml, 5.57 mmol) were added and the mixture was stirred at room temperature for 16 hours. The reaction solution was washed with saturated saline and dried, and then the solvent was distilled off under reduced pressure. The residue was purified by silica gel column chromatography (eluting solvent: n-hexane/ethyl acetate=3/1) to obtain 27 (500 mg, 26%) as an orange foam-like substance.

Synthesis of THK-5050

27 (638 mg, 1.23 mmol) was dissolved in ethyl acetate and the solution was subjected to short silica gel column chromatography (eluting solvent: ethyl acetate) to remove an origin substance. After dissolving by adding oxalic acid (221 mg, 2.45 mmol) to the eluate, the solvent was concentrated to about 100 ml under reduced pressure. After dissolving the precipitate by adding ethanol (100 ml), the solvent was concentrated to about 100 ml under reduced pressure. Insolubles were removed by filtration and the filtrate was concentrated to about 50 ml under reduced pressure. Isopropanol (50 ml) was added and the solvent was concentrated under reduced pressure to precipitate a crystal. After standing at 5° C. for 16 hours, the precipitated crystals were collected by filtration and dried to obtain THK-5050 (520 mg, 69%) as orange crystals.

mp 124-125° C., $^1$H NMR (400 MHz, DMSO-$d_6$) δ 1.15 (6H, t, J=7.0 Hz), 2.30 (3H, s), 3.50 (4H, q, J=7.0 Hz), 3.82-3.88 (2H, m), 4.42 to 4.49 (1H, m), 4.85 (1H, dd, J=14, 3.0 Hz), 4.92 (1H, dd, J=14, 9.4 Hz), 6.93 (2H, d, J=9.1 Hz), 7.15 (2H, d, J=7.9 Hz), 7.46 (2H, d, J=7.9 Hz), 7.66-7.70 (3H, m), 7.85 (1H, t, J=8.2 Hz), 7.93 (1H, dd, J=8.2, 1.2 Hz), 8.06 (1H, d, J=9.0 Hz), 8.95 (1H, d, J=9.0 Hz)

IR (Nujol) 1633, 1590 cm$^{-1}$

APCI-MS m/z 521[M+H]$^+$

Synthesis Method of THK-5051

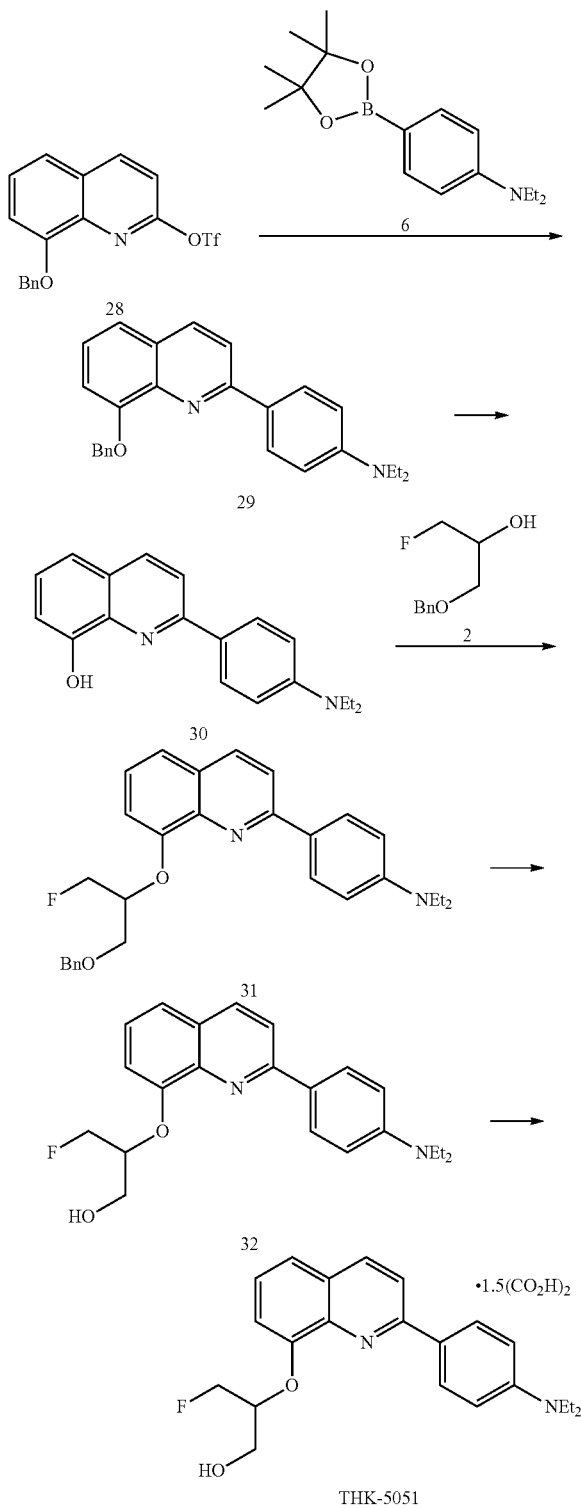

Synthesis of 29

To a mixture of 28 (894 mg, 2.30 mmol), 6 (706 mg, 2.57 mmol) and 1,2-dimethoxyethane (10 ml), an aqueous 2M sodium carbonate solution (2.5 ml, 5.0 mmol) and tetrakis-triphenylphosphine palladium (119 mg, 0.10 mmol) were added under an argon atmosphere and the mixture was stirred at 90° C. for 2 hours. The reaction solution was allowed to return to room temperature and insolubles were removed by filtration, and then the solution was washed with chloroform. The filtrate and the wash were combined and the mixture was extracted with chloroform. The extraction liquid was dried and the solvent was distilled off under reduced pressure. The residue was purified by silica gel column chromatography (eluting solvent: n-hexane/ethyl acetate=9/1→4/1) to obtain 29 (880 mg, 100%) as a pale yellow oily substance.

APCI-MS m/z 383[M+H]$^+$

Synthesis of 30

To a mixture of 29 (880 mg, 2.30 mmol) and anisole (1 ml), methanesulfonic acid (5 ml) was added dropwise under ice cooling and stirring, and the mixture was stirred at room temperature for 1 hour. To the reaction solution, ice water was added and the solution was washed with ethyl acetate. The aqueous layer was extracted with chloroform after adjusting the pH to 9 using an aqueous saturated sodium hydrogen carbonate solution. The extraction liquid was dried and the solvent was distilled off under reduced pressure to obtain 30 (670 mg, 100%) as a yellow oily substance.

APCI-MS m/z 293[M+H]$^+$

Synthesis of 31

To a mixture of 30 (670 mg, 2.3 mmol), 2 (516 mg, 2.8 mmol), triphenylphosphine (918 mg, 3.5 mmol) and tetrahydrofuran (10 ml), a tetrahydrofuran (10 ml) solution of diisopropyl azodicarboxylate (708 mg, 3.5 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: ethyl acetate/n-hexane=1/19→1/9) to obtain 31 (780 mg, 73%) as a pale green oily substance.

APCI-MS m/z 459[M+H]$^+$

Synthesis of 32

To a mixture of 31 (775 mg, 1.69 mmol) and anisole (1 ml), methanesulfonic acid (5 ml) was added under ice cooling and stirring, and the mixture was stirred at room temperature for 1.5 hours. To the reaction solution, ice water was added and the solution was washed with ethyl acetate. The aqueous layer was made basic with an aqueous saturated sodium hydrogen carbonate solution and extracted with chloroform. The extraction liquid was dried and the solvent was distilled off under reduced pressure, and then the residue was purified by silica gel column chromatography (eluting solvent: ethyl acetate/n-hexane=1/4) to obtain 32 (608 mg, 97%) as an orange oily substance.

APCI-MS m/z 369[M+H]$^+$

Synthesis of THK-5051

To an acetone solution of 32 (576 mg, 1.56 mmol), oxalic acid (281 mg, 3.12 mmol) was added to form an oxalate, which was recrystallized from methanol-diethyl ether to obtain THK-5051 (414 mg, 53%) as orange crystals.

mp 126-128° C., $^1$H NMR (400 MHz, DMSO-d$_6$+D$_2$O) δ 1.15 (6H, t, J=7.0 Hz), 3.44 (4H, q, J=7.0 Hz), 3.6-3.8 (1H, m), 4.7 to 4.9 (3H, m), 6.84 (2H, d, J=9.0 Hz), 7.39 (1H, d, J=7.4 Hz), 7.44 (1H, t, J=7.7 Hz), 7.60 (1H, d, J=7.7 Hz), 8.05 (1H, d, J=9.0 Hz), 8.12 (2H, d, J=9.0 Hz), 8.35 (1H, d, J=9.0 Hz)

APCI-MS m/z 369[M+H]$^+$

Synthesis Method of THK-5058

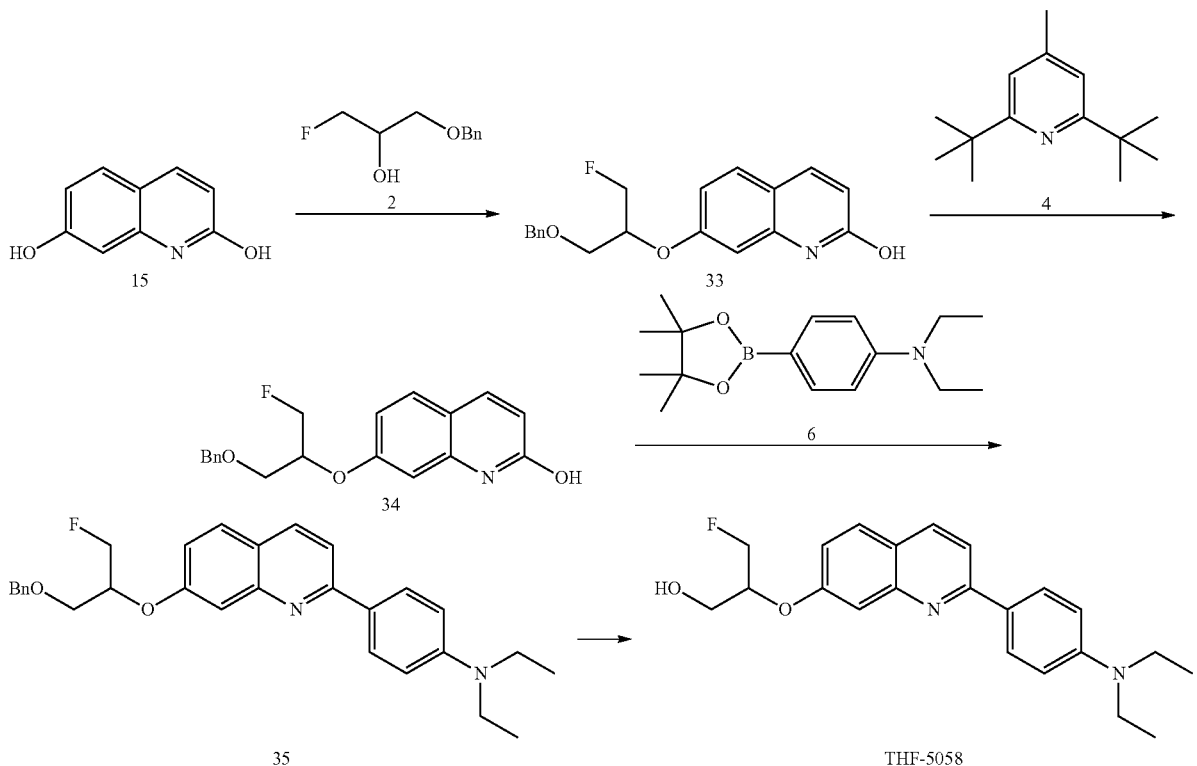

Synthesis of 33

To a mixture of 15 (1.00 g, 6.2 mmol), 2 (1.37 g, 7.45 mmol), triphenylphosphine (1.95 g, 7.45 mmol) and tetrahydrofuran (50 ml), diisopropyl azodicarboxylate (1.48 ml, 7.45 mmol) was added dropwise under ice cooling and stirring, and the mixture was stirred at room temperature for 16 hours. To the reaction solution, 2 (0.67 g, 3.73 mmol), triphenylphosphine (0.98 g, 3.73 mmol), tetrahydrofuran (10 ml) and diisopropyl azodicarboxylate (0.74 ml, 3.73 mmol) were added, followed by further stirring at room temperature for 6 hours. The solvent of the reaction solution was distilled off under reduced pressure and the residue was purified by silica gel column chromatography (eluting solvent: chloroform, chloroform/methanol/concentrated ammonia water=50/1/0.1) to obtain 33 (1.66 g, 82%) as a pale brown oily substance.

APCI-MS m/z 328[M+H]$^+$

Synthesis of 34

To a methylene chloride (25 ml) solution of 33 (1.65 g, 5.0 mmol) and 4 (1.45 g, 7.06 mmol), trifluoromethanesulfonic anhydride (1.02 ml, 6.05 mmol) was added dropwise under ice cooling and stirring, and the mixture was stirred at room temperature for 2 hours. 4 (0.21 g, 1.01 mmol) and trifluoromethanesulfonic anhydride (0.17 ml, 1.01 mmol) were added, followed by further stirring at room temperature for 30 minutes. To the reaction solution, ice water was added and the solution was extracted with ethyl acetate. The extraction liquid was washed with water and dried, and then the solvent was distilled off under reduced pressure. The residue was purified by silica gel column chromatography (eluting solvent: n-hexane, n-hexane/ethyl acetate=4/1) to obtain 34 (1.94 g, 84%) as a colorless solid. mp 81-82° C., APCI-MS m/z 460[M+H]$^+$ Synthesis of 35

To a mixture of 34 (1.00 g, 2.18 mmol), 6 (0.6 g, 2.18 mmol) and 1,2-dimethoxyethane (18 ml), potassium carbonate (0.90 g, 6.54 mmol), water (0.38 ml) and tetrakistriphenylphosphine palladium (130 mg, 0.109 mmol) were added under an argon atmosphere and the mixture was stirred at 80° C. for 1.5 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=9/1, 6/1) to obtain 35 (1.00 g, 100%) as a pale yellow oily substance.

APCI-MS m/z 459[M+H]$^+$

Synthesis of THK-5058

To a mixture of 35 (0.99 g, 2.16 mmol) and anisole (3 ml), methanesulfonic acid (9 ml) was added under ice cooling and stirring, and the mixture was stirred at room temperature for 1 hour. To the reaction solution, ice water and then ethyl acetate were added. The solution was made basic with an aqueous potassium carbonate solution and extracted with ethyl acetate. The extraction liquid was dried and the solvent was distilled off under reduced pressure, and then the residue was purified by silica gel column chromatography (eluting solvent: n-hexane/ethyl acetate=4/1, 2/1) and then washed with n-hexane/ethyl acetate (4/1) to obtain THK-5058 (636 mg, 80%) as pale yellow crystals.

mp 89-90° C., $^1$H NMR (500 MHz, DMSO-d) 1.14 (6H, t, J=7.0 Hz), 3.42 (4H, q, J=7.0 Hz), 3.65-3.77 (2H, m), 4.65-4.87 (3H, m), 5.14 (1H, t, J=5.6 Hz), 6.78 (2H, d, J=8.7 Hz), 7.17 (1H, dd, J=8.8, 2.4 Hz), 7.47 (1H, d, J=2.4 Hz), 7.82 (1H, d, J=8.8 Hz), 7.85 (1H, d, J=8.8 Hz), 8.10 (2H, d, J=8.8 Hz), 8.21 (1H, d, J=8.8 Hz)
IR (Nujol) 1598 cm$^{-1}$
APCI-MS m/z 369[M+H]$^+$ Synthesis Method of THK-5059

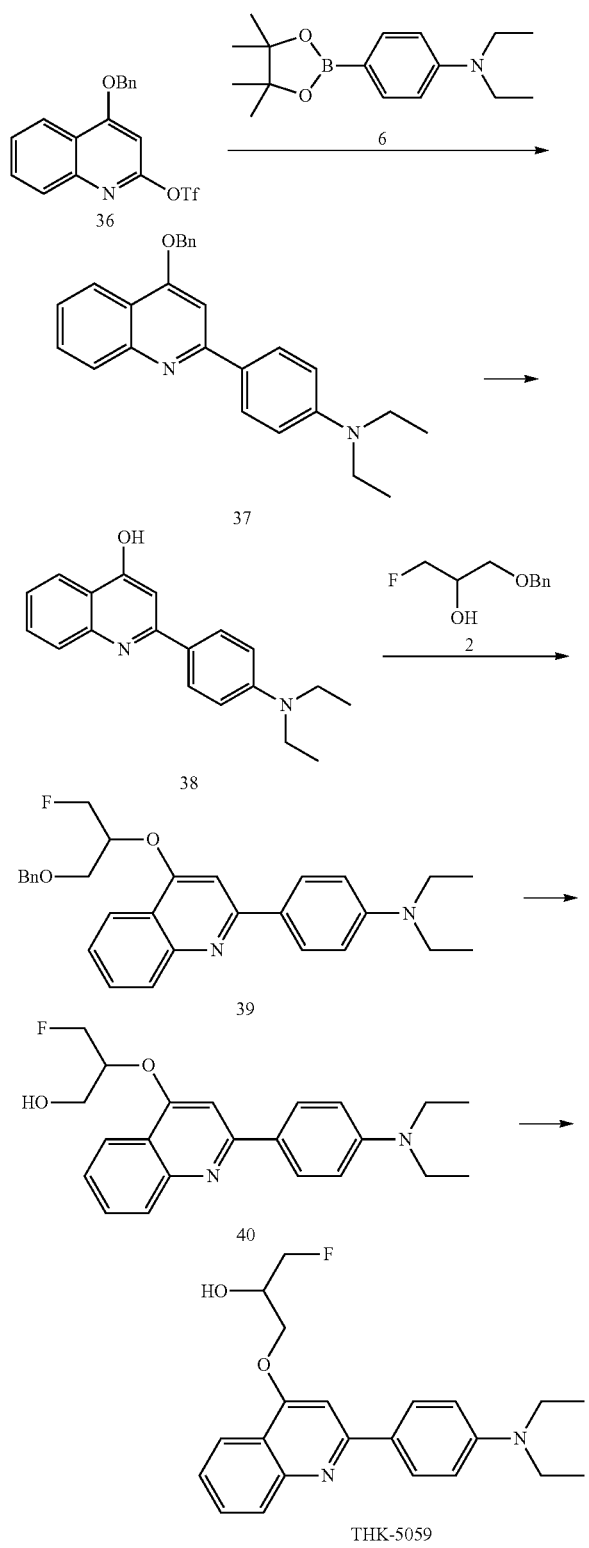

Synthesis of 37

To a mixture of 36 (1.68 g, 4.38 mmol), 6 (1.21 g, 4.38 mmol) and 1,2-dimethoxyethane (36 ml), potassium carbonate (1.82 g, 13.2 mmol), water (0.76 ml) and tetrakistriphenylphosphine palladium (250 mg, 0.22 mmol) were added under an argon atmosphere and the mixture was stirred at 80° C. for 1.5 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=20/1, 9/1) to obtain 37 (1.73 g) as a pale yellow oily substance.

APCI-MS m/z 383[M+H]$^+$

Synthesis of 38

To a mixture of 37 (1.73 g) and anisole (4 ml), methanesulfonic acid (12 ml) was added under ice cooling and stirring, and the mixture was stirred at room temperature for 3 days. To the reaction solution, ice water and then ethyl acetate were added. The solution was made basic with an aqueous potassium carbonate solution and extracted with ethyl acetate. The extraction liquid was dried and the solvent was distilled off under reduced pressure, and then the residue was washed with n-hexane/ethyl acetate (1/1) and then dried to obtain 38 (1.20 g, 94% from 36) as pale yellow crystals.

mp 290-291° C., APCI-MS m/z 293[M+H]$^+$

Synthesis of 39

To a mixture of 38 (600 mg, 2.05 mmol), 2 (454 mg, 2.46 mmol), triphenylphosphine (646 mg, 2.46 mmol) and tetrahydrofuran (20 ml), diisopropyl azodicarboxylate (0.49 ml, 2.46 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: n-hexane/ethyl acetate=9/1) to obtain 39 (940 mg, 100%) as a pale yellow oily substance.

APCI-MS m/z 459[M+H]$^+$

Synthesis of 40

To a mixture of 39 (940 mg, 2.05 mmol) and anisole (2 ml), methanesulfonic acid (6 ml) was added under ice cooling and stirring, and the mixture was stirred at room temperature for 10 minutes. To the reaction solution, ice water and then ethyl acetate were added. The solution was made basic with an aqueous potassium carbonate solution and extracted with ethyl acetate. The extraction liquid was dried and the solvent was distilled off under reduced pressure, and then the residue was purified by silica gel column chromatography (eluting solvent: n-hexane/ethyl acetate=4/1, 2/1) and then recrystallized from ethyl acetate to obtain 40 (627 mg, 83%) as pale yellow crystals.

mp 146-147° C., APCI-MS m/z 369[M+H]$^+$

Synthesis of THK-5059

To an ethyl acetate (100 ml) solution of 40 (700 mg, 1.90 mmol), an ethyl acetate suspension (10 g/20 ml) of silica gel was added and the mixture was stirred at room temperature for 3 days. The silica gel was removed by filtration and the solution was washed with ethyl acetate. The filtrate and the wash were combined and the solvent was distilled off under reduced pressure. The residue was recrystallized from n-hexane/ethyl acetate (1/1) to obtain THK-5059 (484 mg, 69%) as pale yellow crystals.

mp 155-155.5° C., $^1$H NMR (400 MHz, DMSO-d$_6$) δ 1.15 (6H, t, J=7.0 Hz), 3.42 (4H, q, J=7.0 Hz), 4.19-4.41 (3H, m), 4.61 (1H, ddd, J=48, 9.7, 5.0 Hz), 4.65 (1H, ddd, J=48, 10, 4.5 Hz), 5.64 (1H, d, J=5.4 Hz), 6.77 (2H, d, J=9.1 Hz), 7.42 (1H, s), 7.42-7.47 (1H, m), 7.66-7.71 (1H, m), 7.89 (1H, d, J=8.2 Hz), 8.10-8.13 3H, m)

IR (Nujol) 3150, 1610 cm$^{-1}$

APCI-MS m/z 369[M+H]$^+$

Synthesis Method of THK-5064

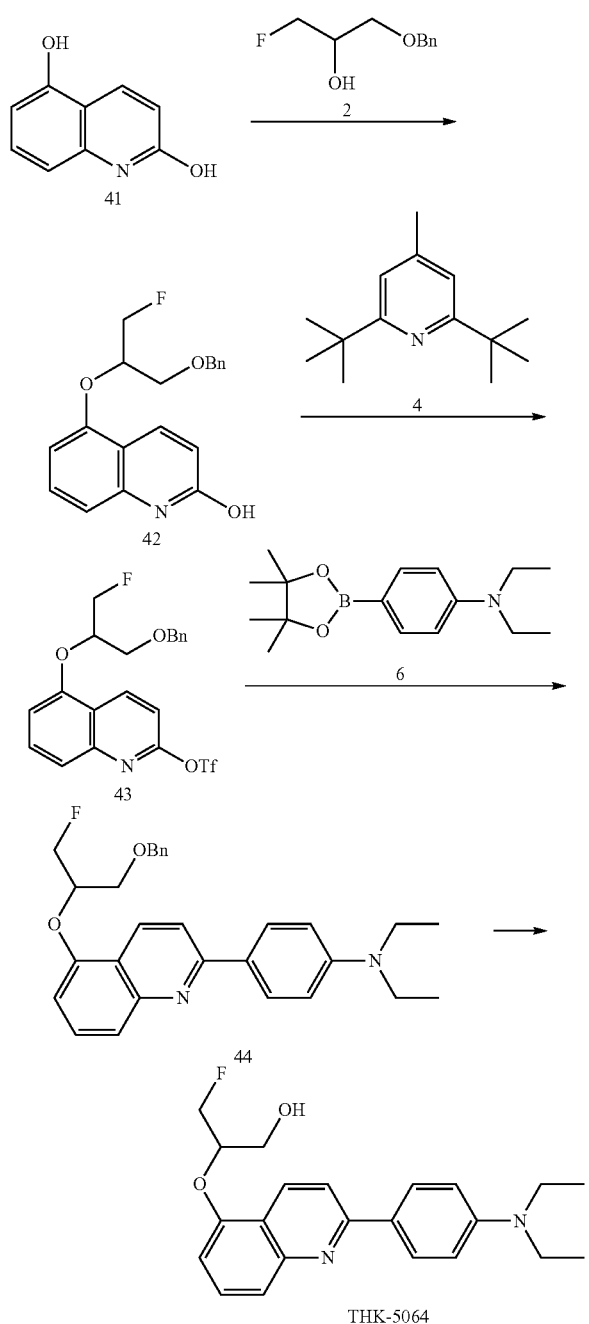

Synthesis of 42

To a mixture of 41 (520 mg, 3.23 mmol), 2 (710 mg, 3.87 mmol), triphenylphosphine (1.02 g, 3.87 mmol) and tetrahydrofuran (30 ml), diisopropyl azodicarboxylate (0.77 ml, 3.87 mmol) was added dropwise under ice cooling and stirring, and the mixture was stirred at room temperature for 16 hours. To the reaction solution, 2 (360 mg, 1.94 mmol), triphenylphosphine (0.51 g, 1.94 mmol), diisopropyl azodicarboxylate (0.38 ml, 1.94 mmol) and tetrahydrofuran (10 ml) were added, followed by further stirring at room temperature for 2 hours. The solvent of the reaction solution was distilled off under reduced pressure and the residue was purified by silica gel column chromatography (eluting solvent: n-hexane/ethyl acetate=2/1, 1/1) to obtain 42 (600 mg, 57%) as a pale brown solid.

APCI-MS m/z 328[M+H]$^+$

Synthesis of 43

To a methylene chloride (15 ml) solution of 42 (590 mg, 1.80 mmol) and 4 (520 mg, 2.52 mmol), trifluoromethanesulfonic anhydride (0.36 ml, 2.16 mmol) was added dropwise under ice cooling and stirring, and the mixture was stirred at room temperature for 1 hour. 4 (74 mg, 0.36 mmol) and trifluoromethanesulfonic anhydride (0.061 ml, 0.37 mmol) were added, followed by further stirring at room temperature for 30 minutes. To the reaction solution, ice water was added and the solution was extracted with ethyl acetate. The extraction liquid was washed with water and dried, and then the solvent was distilled off under reduced pressure. The residue was purified by silica gel column chromatography (eluting solvent: n-hexane, n-hexane/ethyl acetate=9/1) to obtain 43 (560 mg, 68%) as a pale yellow oily substance.

APCI-MS m/z 460[M+H]$^+$

Synthesis of 44

To a mixture of 43 (550 mg, 1.20 mmol), 6 (330 mg, 1.20 mmol) and 1,2-dimethoxyethane (20 ml), potassium carbonate (500 mg, 3.59 mmol), water (0.21 ml) and tetrakistriphenylphosphine palladium (69 mg, 0.06 mmol) were added under an argon atmosphere, and the mixture was stirred at 80° C. for 1.5 hours. The reaction solution was allowed to return to room temperature, diluted with ethyl acetate and washed with water. The organic layer was dried and the solvent was distilled off under reduced pressure. The residue was purified by silica gel column chromatography (eluting solvent: n-hexane/ethyl acetate=4/1) to obtain 44 (550 mg, 100%) as a pale yellow oily substance.

APCI-MS m/z 459[M+H]$^+$

Synthesis of THK-5064

To a mixture of 44 (540 mg, 1.18 mmol) and anisole (1.0 ml), methanesulfonic acid (3.0 ml) was added under ice cooling and stirring, and the mixture was stirred at room temperature for 20 minutes. To the reaction solution, ice water and then ethyl acetate were added. The solution was made basic with an aqueous potassium carbonate solution and extracted with ethyl acetate. The extraction liquid was washed with water and dried, and then the solvent was distilled off under reduced pressure. The residue was purified by silica gel column chromatography (eluting solvent: n-hexane/ethyl acetate=4/1) to obtain THK-5064 (403 mg, 93%) as an orange powder.

$^1$H NMR (500 MHz, DMSO-d$_6$) δ 1.14 (6H, t, J=7.0 Hz), 3.42 (4H, q, J=7.0 Hz), 3.73-3.78 (2H, m), 4.70-4.88 (3H, m), 5.14 (1H, t, J=5.3 Hz), 6.79 (2H, d, J=9.0 Hz), 7.10 (1H, d, J=7.4 Hz), 7.56 (1H, d, J=8.7 Hz), 7.61 (1H, t, J=8.4 Hz), 7.98 (1H, d, J=8.7 Hz), 8.11 (2H, d, J=9.0 Hz), 8.51 (1H, d, J=9.0 Hz)

IR (Nujol) 3400, 1610 cm$^{-1}$

APCI-MS m/z 369[M+H]$^+$

Synthesis Method of THK-5065

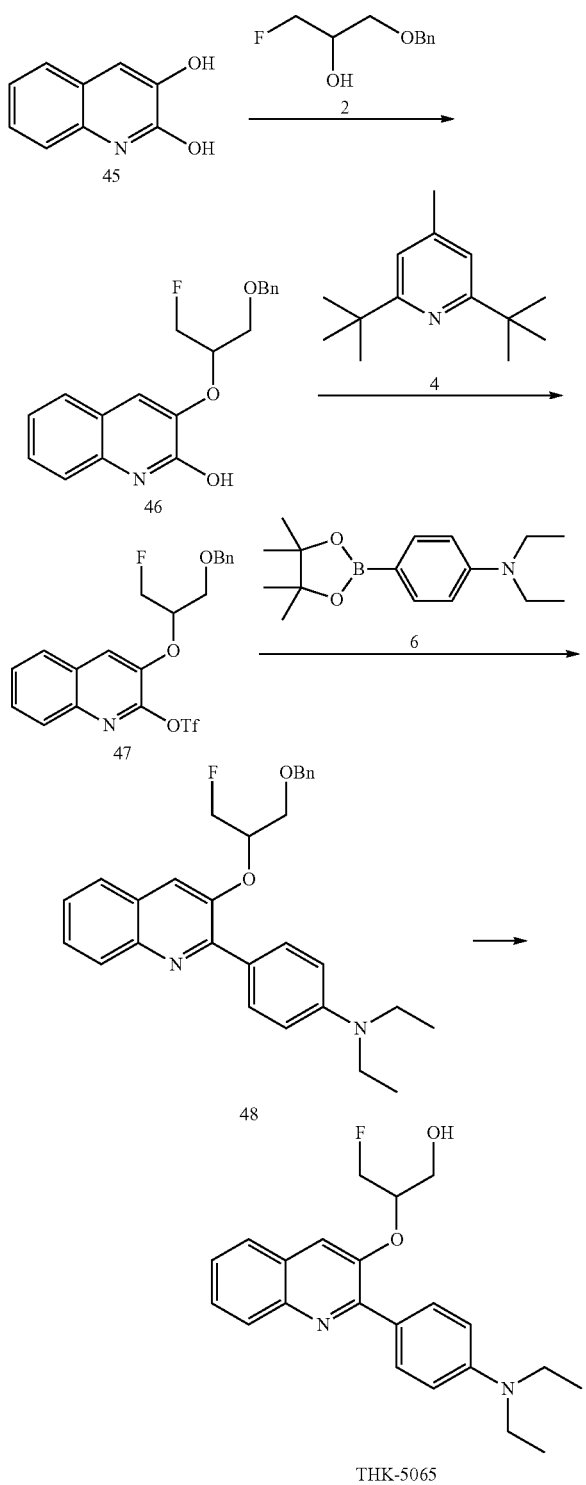

Synthesis of 46

To a mixture of 45 (3.0 g, 18.6 mmol), 2 (3.5 g, 19.0 mmol), triphenylphosphine (5.77 g, 22.0 mmol) and tetrahydrofuran (60 ml), diisopropyl azodicarboxylate (4.45 g, 22.0 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: n-hexane/ethyl acetate=2/1, 1/1) to obtain 46 (3.0 g, 49%) as a colorless solid.

mp 124-125° C.

Synthesis of 47

To a methylene chloride (20 ml) solution of 46 (2.62 g, 8.0 mmol) and 4 (2.2 g, 10.4 mmol), a methylene chloride (10 ml) solution of trifluoromethanesulfonic anhydride (2.7 g, 9.6 mmol) was added dropwise under ice cooling and stirring, and the mixture was stirred at room temperature for 16 hours. 4 (2.2 g, 10.4 mmol) and trifluoromethanesulfonic anhydride (2.7 g, 9.6 mmol) were added, followed by further stirring at room temperature for 16 hours. To the reaction solution, ice water was added and the solution was extracted with chloroform. The extraction liquid was dried and the solvent was distilled off under reduced pressure, and then the residue was purified by silica gel column chromatography (eluting solvent: n-hexane/ethyl acetate=20/1) to obtain 47 (1.47 g, 40%) as a colorless oily substance.

APCI-MS m/z 460[M+H]$^+$

Synthesis of 48

To a mixture of 47 (1.20 g, 2.61 mmol), 6 (0.72 g, 2.61 mmol) and 1,2-dimethoxyethane (30 ml), sodium carbonate (560 mg, 5.28 mmol), water (3 ml) and tetrakistriphenylphosphine palladium (150 mg, 0.13 mmol) were added under an argon atmosphere, and the mixture was heated at reflux for 3 hours. The reaction solution was allowed to return to room temperature, diluted with ethyl acetate, washed in turn with water and saturated saline and then dried. The solvent was distilled off under reduced pressure and the residue was purified by silica gel flash column chromatography (eluting solvent: n-hexane/ethyl acetate=8/1, 6/1) to obtain 48 (1.06 g, 88%) as a pale yellow oily substance.

APCI-MS m/z 459[M+H]$^+$

Synthesis of THK-5065

To a mixture of 48 (1.27 g, 2.77 mmol) and anisole (1.0 ml), methanesulfonic acid (10 ml) was added and the mixture was stirred at room temperature for 30 minutes. The reaction solution was diluted with ethyl acetate and poured into ice water, followed by liquid separation. The aqueous layer was made basic with concentrated ammonia water and extracted with ethyl acetate. The extraction liquid was washed in turn with water and saturated saline and then dried. The solvent was distilled off under reduced pressure and the residue was recrystallized from diisopropylether to obtain THK-5065 (758 mg, 74%) as pale yellow crystals.

mp 135-136° C., $^1$H NMR (400 MHz, CDCl$_3$) δ 1.20 (6H, t, J=7.1 Hz), 1.95 (1H, br), 3.42 (4H, q, J=7.1 Hz), 3.77-3.88 (2H, m), 4.56-4.65 (1H, m), 4.65-4.69 (1H, m), 4.77-4.81 (1H, m), 6.75 (2H, d, J 9.0 Hz), 7.47 (1H, m), 7.57 (1H, m), 7.61 (1H, s), 7.68 (1H, dd, J=8.2, 1.5 Hz), 7.93 (2H, d, J=9.0 Hz), 8.07 (1H, d, J=8.5 Hz)

IR (Nujol) 3200, 1617, 1606 cm$^{-1}$

APCI-MS m/z 369[M+H]$^+$

Synthesis Method of THK-5066

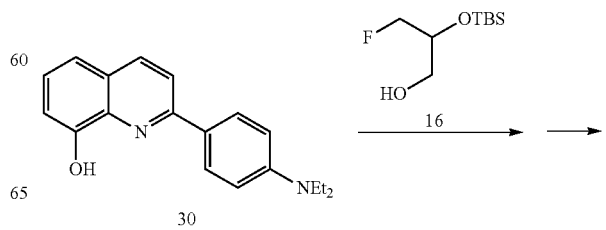

-continued

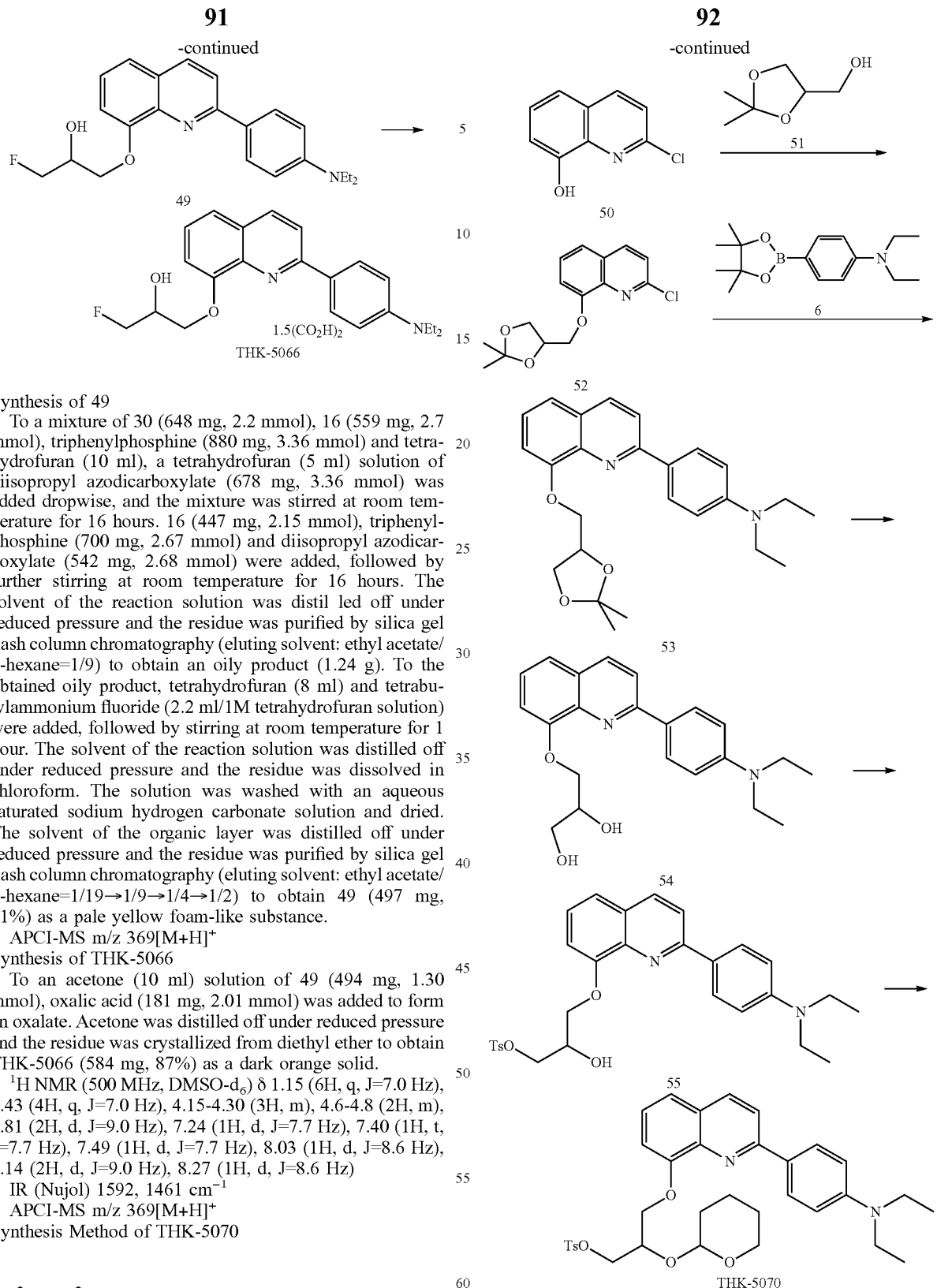

Synthesis of 49

To a mixture of 30 (648 mg, 2.2 mmol), 16 (559 mg, 2.7 mmol), triphenylphosphine (880 mg, 3.36 mmol) and tetrahydrofuran (10 ml), a tetrahydrofuran (5 ml) solution of diisopropyl azodicarboxylate (678 mg, 3.36 mmol) was added dropwise, and the mixture was stirred at room temperature for 16 hours. 16 (447 mg, 2.15 mmol), triphenylphosphine (700 mg, 2.67 mmol) and diisopropyl azodicarboxylate (542 mg, 2.68 mmol) were added, followed by further stirring at room temperature for 16 hours. The solvent of the reaction solution was distil led off under reduced pressure and the residue was purified by silica gel flash column chromatography (eluting solvent: ethyl acetate/ n-hexane=1/9) to obtain an oily product (1.24 g). To the obtained oily product, tetrahydrofuran (8 ml) and tetrabutylammonium fluoride (2.2 ml/1M tetrahydrofuran solution) were added, followed by stirring at room temperature for 1 hour. The solvent of the reaction solution was distilled off under reduced pressure and the residue was dissolved in chloroform. The solution was washed with an aqueous saturated sodium hydrogen carbonate solution and dried. The solvent of the organic layer was distilled off under reduced pressure and the residue was purified by silica gel flash column chromatography (eluting solvent: ethyl acetate/ n-hexane=1/19→1/9→1/4→1/2) to obtain 49 (497 mg, 61%) as a pale yellow foam-like substance.

APCI-MS m/z 369[M+H]$^+$

Synthesis of THK-5066

To an acetone (10 ml) solution of 49 (494 mg, 1.30 mmol), oxalic acid (181 mg, 2.01 mmol) was added to form an oxalate. Acetone was distilled off under reduced pressure and the residue was crystallized from diethyl ether to obtain THK-5066 (584 mg, 87%) as a dark orange solid.

$^1$H NMR (500 MHz, DMSO-d$_6$) δ 1.15 (6H, q, J=7.0 Hz), 3.43 (4H, q, J=7.0 Hz), 4.15-4.30 (3H, m), 4.6-4.8 (2H, m), 6.81 (2H, d, J=9.0 Hz), 7.24 (1H, d, J=7.7 Hz), 7.40 (1H, t, J=7.7 Hz), 7.49 (1H, d, J=7.7 Hz), 8.03 (1H, d, J=8.6 Hz), 8.14 (2H, d, J=9.0 Hz), 8.27 (1H, d, J=8.6 Hz)

IR (Nujol) 1592, 1461 cm$^{-1}$

APCI-MS m/z 369[M+H]$^+$

Synthesis Method of THK-5070

Synthesis of 50

To a N,N-dimethylformamide (20 ml) suspension of 1 (2.00 g, 12.4 mmol), thionyl chloride (3.56 ml, 49.6 mmol) was added dropwise under ice cooling and stirring, and the mixture was stirred at room temperature for 2 hours, and then thionyl chloride (3.56 ml, 49.6 mmol) was added, followed by further stirring at 50° C. for 3.5 hours. The reaction solution was allowed to return to room temperature, poured into ice water and extracted with ethyl acetate. The extraction liquid was washed with water and dried, and then the solvent was distilled off under reduced pressure. The residue was purified by silica gel column chromatography (eluting solvent: ethyl acetate/n-hexane=1/20) to obtain 50 (1.72 g, 77%) as a pale yellow solid.

mp 79-80° C., APCI-MS m/z 180/182[M+H]$^+$

Synthesis of 52

To a mixture of 50 (1.71 g, 9.52 mmol), 51 (1.51 g, 11.4 mmol), triphenylphosphine (3.00 g, 11.4 mmol) and tetrahydrofuran (50 ml), diisopropyl azodicarboxylate (2.27 ml, 11.4 mmol) was added dropwise under ice cooling and stirring, and the mixture was stirred at room temperature for 16 hours. The solvent of the reaction solution was distilled off under reduced pressure and the residue was purified by silica gel column chromatography (eluting solvent: ethyl acetate/n-hexane=1/19, 1/9) to obtain 52 (2.05 g, 73%) as a colorless solid.

mp 94-95° C., APCI-MS m/z 294/296[M+H]$^+$

Synthesis of 53

To a mixture of 52 (600 mg, 2.04 mmol), 6 (560 mg, 2.04 mmol) and 1,2-dimethoxyethane (20 ml), potassium carbonate (850 mg, 6.12 mmol), water (0.36 ml), tetrakistriphenylphosphine palladium (120 mg, 0.102 mmol) were added under an argon atmosphere, and the mixture was stirred at 80° C. for 16 hours. The reaction solution was allowed to return to room temperature, and water and ethyl acetate were added and insolubles were removed by filtration with celite, followed by liquid separation of the filtrate. The organic layer was washed with water and dried, and then the solvent was distilled off under reduced pressure. The residue was purified by silica gel column chromatography (eluting solvent: ethyl acetate/n-hexane=1/9) to obtain 53 (820 mg, 98%) as a pale yellow solid.

mp 87-89° C.

Synthesis of 54

A mixture of 53 (820 mg, 2.02 mmol), methanol (50 ml) and 1N hydrochloric acid (2.02 ml) was stirred at 70° C. for 1 hour. The reaction solution was allowed to return to room temperature and neutralized with sodium hydrogen carbonate, and then ethyl acetate and sodium sulfate were added, followed by stirring at room temperature. Insolubles were removed by filtration and the solvent of the filtrate was distilled off under reduced pressure. The residue was purified by silica gel column chromatography (eluting solvent: ethyl acetate/n-hexane=1/1, ethyl acetate) to obtain 54 (720 mg, 97%) as a pale yellow foam-like substance.

Synthesis of 55

To a pyridine (5 ml)-tetrahydrofuran (5 ml) solution of 54 (480 mg, 1.31 mmol), a tetrahydrofuran (5 ml) solution of paratoluenesulfonic anhydride (641 mg, 1.97 mmol) was added dropwise over 20 minutes under ice cooling and stirring, and the mixture was stirred at the same temperature for 10 minutes. To the reaction solution, methanol was added and the solvent was distilled off under reduced pressure, and then toluene containing triethylamine was added and the solvent was distilled off under reduced pressure. The residue was purified by silica gel column chromatography (eluting solvent: ethyl acetate/n-hexane=1/2, 1/1) to obtain 55 (340 mg, 50%) as a yellow foam-like substance.

Synthesis of THK-5070

To a tetrahydrofuran (20 ml) solution of 55 (390 mg, 0.749 mmol), 3,4-dihydro-2H-pyran (0.204 ml, 2.25 mmol) and paratoluenesulfonic acid monohydrate (168 mg, 0.976 mmol) were added, and the mixture was stirred at room temperature for 18 hours, and then 3,4-dihydro-2H-pyran (0.475 ml, 5.24 mmol) was added, followed by further stirring at room temperature for 24 hours. The reaction solution was neutralized with triethylamine and the solvent was distilled off under reduced pressure. The residue was purified by silica gel column chromatography (eluting solvent: ethyl acetate/n-hexane=1/2) and then purified by NH silica gel column chromatography (eluting solvent: ethyl acetate/n-hexane=1/1) and crystallized from methanol (15 ml) to obtain THK-5070 (96 mg, 21%) as pale yellow crystals.

mp 80-81° C.

IR (Nujol) 1597 cm$^{-1}$, APCI-MS m/z 605[M+H]$^+$

Synthesis Method of THK-5071

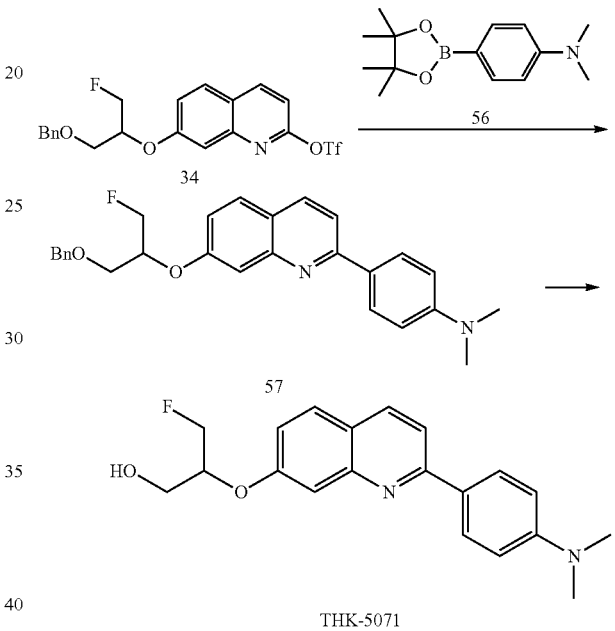

Synthesis of 57

To a mixture of 34 (735 mg, 1.6 mmol), 56 (435 mg, 1.76 mmol) and 1,2-dimethoxyethane (8 ml), an aqueous 2M sodium carbonate solution (1.6 ml, 3.2 mmol) and tetrakistriphenylphosphine palladium (92 mg, 0.08 mmol) were added under an argon atmosphere, and the mixture was stirred at 90° C. for 16 hours. The reaction solution was allowed to return to room temperature and insolubles were removed by filtration, and the solution was washed with chloroform. The filtrate and the wash were combined and the mixture was dried, and then the solvent was distilled off under reduced pressure. The residue was purified by silica gel flash column chromatography (eluting solvent: ethyl acetate/n-hexane=1/5, 1/2) to obtain 57 (678 mg, 98%) as a pale yellow oily substance.

APCI-MS m/z 431[M+H]$^+$

Synthesis of THK-5071

To a mixture of 57 (638 mg, 1.48 mmol) and anisole (5 ml), methanesulfonic acid (1 ml) was added under ice cooling and stirring, and the mixture was stirred at room temperature for 30 minutes. To the reaction solution, ice water was added and the solution was washed with ethyl acetate. The aqueous layer was made basic with potassium carbonate and extracted with chloroform. The extraction liquid was dried and the solvent was distilled off under reduced pressure, and then the residue was purified by silica gel flash column chromatography (eluting solvent: ethyl acetate/n-hexane=1/4) and then washed with diisopropyl-ether-chloroform to obtain THK-5071 (394 mg, 78%) as a yellow solid.

mp 134-135.5° C., $^1$H NMR (500 MHz, DMSO-$d_6$) δ 3.01 (6H, s), 3.7-3.8 (2H, m), 4.7-4.9 (3H, m), 6.84 (2H, d, J=9 Hz), 7.18 (1H, dd, J=8.7, 2.3 Hz), 7.48 (1H, d, J=2.3 Hz), 7.83 (1H, d, J=9 Hz), 7.88 (1H, d, J=8.7 Hz), 8.13 (2H, d, J=9 Hz), 8.23 (1H, d, J=8.4 Hz)

IR (Nujol) 1597, 1505, 1202 cm$^{-1}$

APCI-MS m/z 341[M+H]$^+$

Synthesis Method of THK-5072

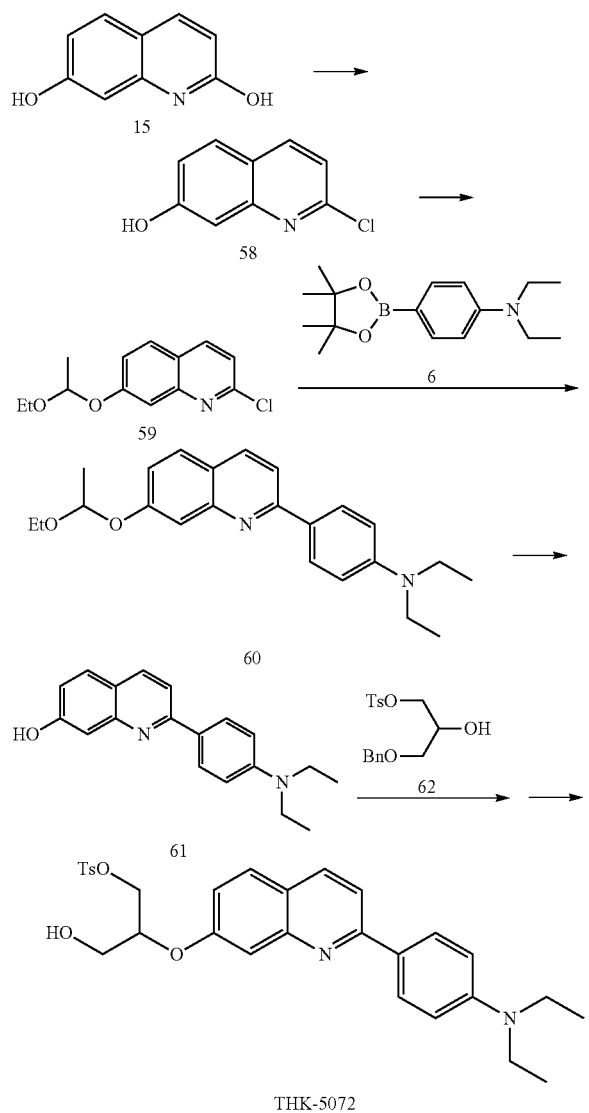

Synthesis of 58

To an N,N-dimethylformamide (30 ml) suspension of 15 (2.87 g, 17.81 mmol), thionyl chloride (5.11 ml, 71.23 mmol) was added dropwise under ice cooling and stirring, and the mixture was stirred at room temperature for 30 minutes, followed by stirring at 70° C. for 30 minutes. The reaction solution was allowed to return to room temperature, poured into ice water and extracted with ethyl acetate. The extraction liquid was washed with water and dried, and then the solvent was distilled off under reduced pressure. The residue was purified by silica gel column chromatography (eluting solvent: ethyl acetate/n-hexane=1/1, ethyl acetate) to obtain 58 (3.04 g, 95%) as a brownish solid.

APCI-MS m/z 180/182[M+H]$^+$

Synthesis of 59

To a tetrahydrofuran (30 ml) solution of 58 (1.50 g, 8.35 mmol) and ethyl vinyl ether (1.21 g, 16.7 mmol), a para-toluenesulfonic acid pyridine salt (210 mg, 0.84 mmol) was added, and the mixture was stirred at room temperature for 16 hours. After the pH of the reaction solution was adjusted to 8 using triethylamine, the solvent was distilled off under reduced pressure and the residue was purified by silica gel column chromatography (eluting solvent: ethyl acetate/n-hexane=1/20, 1/3) to obtain 59 (1.91 g, 91%) as a pink oily substance.

APCI-MS m/z 252[M+H]$^+$

Synthesis of 60

To a 1,2-dimethoxyethane (62 ml) solution of 59 (1.90 g, 7.55 mmol) and 6 (2.08 g, 7.55 mmol), potassium carbonate (3.13 g, 22.65 mmol), water (1.31 ml) and tetrakistriphenyl-phosphine palladium (436 mg, 0.38 mmol) were added under an argon atmosphere, and the mixture was stirred at 80° C. for 27 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/19) and then recrystallized from ethyl acetate-n-hexane (1/9) to obtain 60 (1.50 g, 54%) as yellow crystals.

mp 86-87° C.

APCI-MS m/z 365[M+H]$^+$

Synthesis of 61

To a methylene chloride (12 ml) solution of 60 (1.50 g, 4.12 mmol), trifluoroacetic acid (8 ml) was added dropwise under ice cooling and stirring, and the mixture was stirred at room temperature for 15 minutes. To the reaction solution, ice water and ethyl acetate were added and extracted with ethyl acetate after adjusting the pH to 9 using an aqueous potassium carbonate solution. The extraction liquid was washed with water and dried, and then the solvent was distilled off under reduced pressure. The residue was recrystallized from ethyl acetate-n-hexane to obtain 61 (1.13 g, 94%) as yellow crystals.

mp 223-224° C.

APCI-MS m/z 293[M+H]$^+$

Synthesis of THK-5072

To a mixture of 61 (500 mg, 1.71 mmol), 62 (690 mg, 2.05 mmol), triphenylphosphine (540 mg, 2.05 mmol) and tetrahydrofuran (25 ml), diisopropyl azodicarboxylate (0.41 ml, 2.05 mmol) was added dropwise under ice cooling and stirring, and the mixture was stirred at room temperature for 16 hours. To the reaction solution, 62 (690 mg, 2.05 mmol), triphenylphosphine (540 mg, 2.05 mmol) and tetrahydrofuran (5 ml) were added under ice cooling and stirring, and diisopropyl azodicarboxylate (0.41 ml, 2.05 mmol) was added dropwise, followed by further stirring at room temperature for 6 hours. The solvent of the reaction solution was distilled off under reduced pressure and the residue was purified by silica gel column chromatography (eluting solvent: ethyl acetate/n-hexane=1/4) to obtain a pale yellow oily substance (1.47 g). To an anisole (4 ml) solution of the present product, methanesulfonic acid (12 ml) was added dropwise under ice cooling and stirring, followed by stirring at room temperature for 15 minutes. The reaction solution was poured into ice water and ethyl acetate was added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/9, 1/1) to obtain THK-5072 (620 mg, 69%) as a yellow foam-like substance.

$^1$H NMR (400 MHz, DMSO-$d_6$) δ 1.15 (6H, t, J=7.3 Hz), 2.33 (3H, s), 3.43 (4H, q, J=7.3 Hz), 3.57-3.71 (2H, m), 4.30 (1H, dd, J=11, 5.7 Hz), 4.38 (1H, dd, J=11, 3.0 Hz), 4.71-4.77 (1H, m), 5.11 (1H, t, J=5.6 Hz), 6.79 (2H, d, J=9.1 Hz), 7.01 (1H, dd, J=8.8, 2.4 Hz), 7.32 (1H, d, J=2.1 Hz), 7.39 (2H, d, J=8.2 Hz), 7.75 (2H, d, J=8.5 Hz), 7.78 (1H, d, J=8.8 Hz), 7.85 (1H, d, J=8.5 Hz), 8.10 (2H, d, J=9.1 Hz), 8.21 (1H, d, J=8.8 Hz)

IR (Nujol) 1619, 1593 cm$^{-1}$,
APCI-MS m/z 521[M+H]$^+$

Synthesis Method of THK-5073

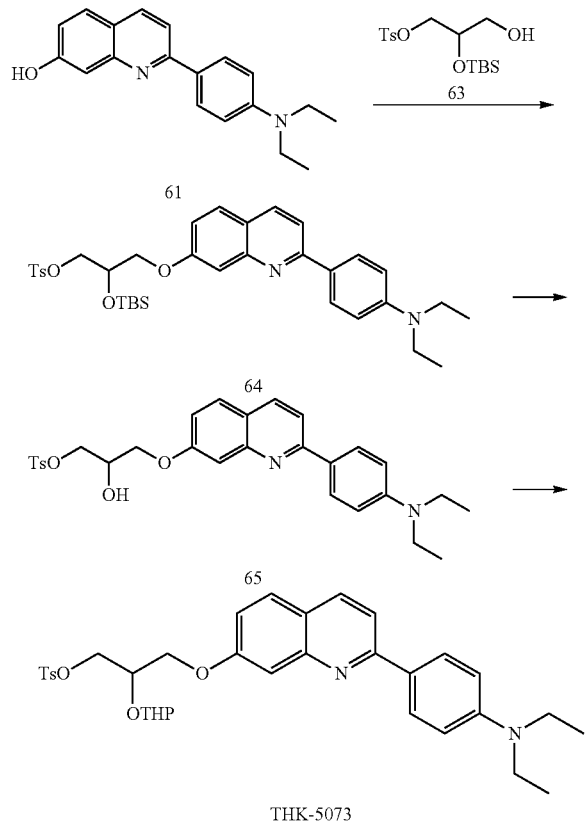

Synthesis of 64

To a tetrahydrofuran (45 ml) solution of 61 (630 mg, 2.16 mmol), 63 (932 mg, 2.59 mmol) and triphenylphosphine (678 mg, 2.59 mmol), diisopropyl azodicarboxylate (0.513 ml, 2.59 mmol) was added dropwise under ice cooling and stirring, and the mixture was stirred at room temperature for 16 hours. To the reaction solution, 63 (788 mg, 2.18 mmol), triphenylphosphine (573 mg, 2.18 mmol) and tetrahydrofuran (5 ml) were added under ice cooling and stirring, and diisopropyl azodicarboxylate (0.433 ml, 2.18 mmol) was added dropwise, followed by further stirring at room temperature for 3 days. The solvent of the reaction solution was distilled off under reduced pressure and the residue was purified by silica gel column chromatography (eluting solvent: ethyl acetate/n-hexane=1/9) to obtain 64 (720 mg, 53%) as a pale yellow foam-like substance.

APCI-MS m/z 635[M+H]$^+$

Synthesis of 65

To a methylene chloride (12 ml) solution of 64 (710 mg, 1.12 mmol), trifluoroacetic acid (8 ml) was added dropwise under ice cooling and stirring, and water (2 ml) was added and the mixture was stirred at room temperature for 5.5 hours. To the reaction solution, ice water and ethyl acetate were added and the solution was extracted with ethyl acetate after adjusting the pH to 8 using an aqueous saturated sodium hydrogen carbonate solution. The extraction liquid was washed with water and dried, and then the solvent was distilled off under reduced pressure. The residue was purified by silica gel column chromatography (eluting solvent: ethyl acetate/n-hexane=1/4, 1/2) to obtain 65 (520 mg, 85%) as a yellow foam-like substance.

APCI-MS m/z 221[M+H]$^+$

Synthesis of THK-5073

To a methylene chloride (60 mil) solution of 65 (290 mg, 0.557 mmol), 3,4-dihydro-2H-pyran (0.51 ml, 5.6 mmol) and a paratoluenesulfonic acid pyridine salt (182 mg, 0.724 mmol) were added, and the mixture was stirred at room temperature for 3 days. To the reaction solution, paratoluenesulfonic acid monohydrate (125 mg, 0.724 mmol) and 3,4-dihydro-2H-pyran (0.51 ml, 5.6 mmol) were added, followed by further stirring at room temperature for 1 hour. The reaction solution was neutralized with triethylamine and the solvent was distilled off under reduced pressure. The residue was purified by silica gel column chromatography (eluting solvent: ethyl acetate/n-hexane=1/3, 1/2) to obtain THK-5073 (336 mg, 100%) as a yellow oily substance.

$^1$H NMR (500 MHz, DMSO-$d_6$) δ 1.15 (6H, t, J=7.2 Hz), 1.36-1.74 (7H, m), 2.34 (3H, s), 3.43 (4H, q, J=7.2 Hz), 3.69-3.75, 3.84-3.90 (1H, m), 4.13-4.37 (5H, m), 4.71-4.76, 4.86-4.88 (1H, m), 6.79 (2H, d, J=9.0 Hz), 7.04 (1H, dd, J=9.0, 1.9 Hz), 7.25-7.29 (1H, m), 7.39-7.44 (2H, m), 7.77-7.82 (3H, m), 7.86 (1H, d, J=8.7 Hz), 8.11 (2H, d, J=8.7 Hz), 8.19-8.25 (1H, m)

APCI-MS m/z 605[M+H]$^+$

Synthesis Method of THK-5077

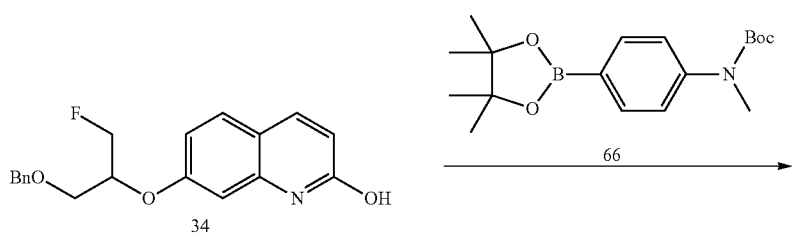

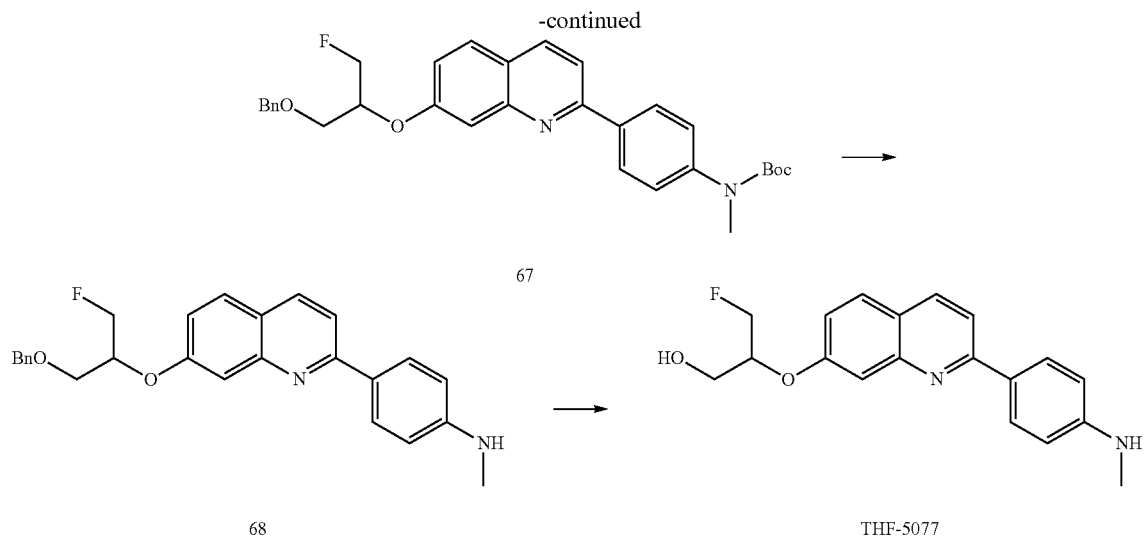

Synthesis of 67

To a mixture of 34 (1.50 g, 3.3 mmol), 66 (1.2 g, 3.6 mmol) and 1,2-dimethoxyethane (15 ml), an aqueous 2M sodium carbonate solution (3.3 ml, 6.6 mmol) and tetrakis-triphenylphosphine palladium (189 mg, 0.16 mmol) were added under an argon atmosphere, and the mixture was stirred at 90° C. for 1.5 hours. The reaction solution was allowed to return to room temperature and insolubles were removed by filtration, and the solution was washed with chloroform. The filtrate and the wash were combined and the mixture was washed with an aqueous saturated sodium hydrogen carbonate solution and dried, and then the solvent was distilled off under reduced pressure. The residue was purified by silica gel flash column chromatography (eluting solvent: ethyl acetate/n-hexane=1/9, 1/4, 1/2) to obtain 67 (1.70 g, 100%) as a colorless oily substance.

APCI-MS m/z 517[M+H]$^+$

Synthesis of 68

To a methylene chloride (8 ml) solution of 67 (1.70 g, 3.29 mmol), trifluoroacetic acid (2 ml) was added dropwise under ice cooling and stirring, and the mixture was stirred at room temperature for 16 hours. The solvent of the reaction solution was distilled off under reduced pressure and chloroform was added. The solution was made basic with an aqueous saturated sodium hydrogen carbonate solution and potassium carbonate and extracted with chloroform. The extraction liquid was dried and the solvent was distilled off under reduced pressure, and then the residue was purified by NH silica gel flash column chromatography (eluting solvent: n-hexane/ethyl acetate=3/1) to obtain 68 (1.34 g, 972) as a yellow oily substance.

APCI-MS m/z 417[M+H]$^+$

Synthesis of THK-5077

To a mixture of 68 (101 mg, 0.243 mmol) and thioanisole (2 ml), methanesulfonic acid (0.4 ml) was added under ice cooling and stirring, and the mixture was stirred at room temperature for 2 hours. To the reaction solution, ice water was added and the solution washed with ethyl acetate. The ethyl acetate layer was extracted with water, and the extract layer and the previous aqueous layer were combined. The mixture was made basic with potassium carbonate and extracted with chloroform. The extraction liquid was dried and the solvent was distilled off under reduced pressure, and then the residue was purified by NH silica gel flash column chromatography (eluting solvent: n-hexane/ethyl acetate=2/1, 1/1, 1/2) and then recrystallized from methanol-diisopropylether to obtain THK-5077 (54 mg, 68%) as a yellow solid.

mp 143.5-145.5° C., $^1$H NMR (400 MHz, DMSO-d$_6$) δ 2.75 (3H, d, J=4.9 Hz), 3.6-3.8 (2H, m), 4.6 to 4.9 (3H, m), 5.10 to 5.13 (1H, m), 5.12 (1H, q, J=4.9 Hz), 6.10 (1H, brs), 6.66 (2H, d, J=9.0 Hz), 7.16 (1H, dd, J=8.8, 2.4 Hz), 7.45 (1H, d, J=2.4 Hz), 7.81 (1H, d, J=8.9 Hz), 7.84 (1H, d, J=8.8 Hz), 8.07 (2H, d, J=9.0 Hz), 8.20 (1H, d, J=7.5 Hz)

IR (Nujol) 2854, 1612, 1461 cm$^{-1}$

APCI-MS m/z 327[M+H]$^+$

Synthesis Method of THK-5078

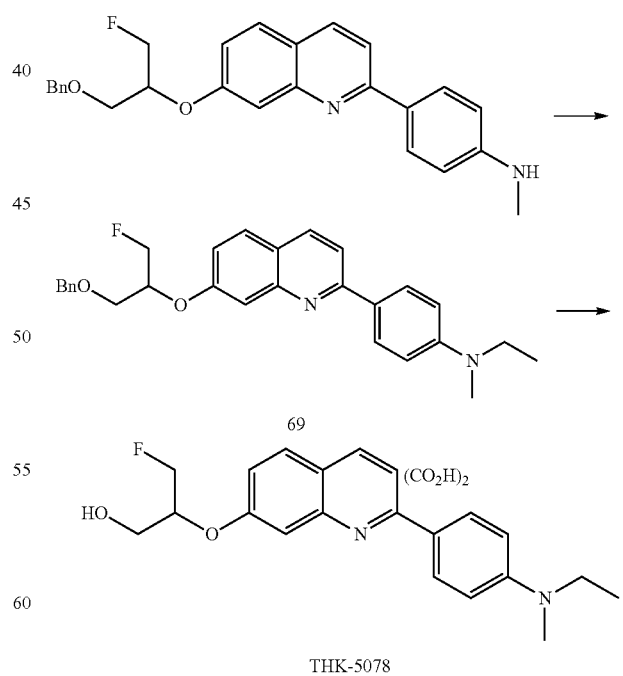

Synthesis of 69

A mixture of 68 (637 mg, 1.50 mmol), acetoaldehyde (115 mg, 2.60 mmol), a picoline borane complex (279 mg, 2.60 mmol) and methanol (10 ml)-acetic acid (1 ml) was stirred at room temperature for 16 hours. Acetoaldehyde (1.15 g, 26 mmol) and a picoline borane complex (279 mg, 2.60 mmol) were added, followed by further stirring at room temperature for 16 hours. The solvent of the reaction solution was distilled off under reduced pressure and aqueous 10% hydrochloric acid (10 ml) was added to the residue. After stirring at room temperature for 30 minutes, the solution was made basic by adding potassium carbonate. The reaction solution was extracted with chloroform and the extraction liquid was dried, and the solvent was distilled off under reduced pressure. The residue was purified by silica gel flash column chromatography (eluting solvent: n-hexane/ethyl acetate=4/1) to obtain 69 (640 mg, 94%) as a yellow oily substance.

APCI-MS m/z 445[M+H]+

Synthesis of THK-5078

To a mixture of 69 (639 mg, 1.44 mmol) and thioanisole (5 ml), methanesulfonic acid (1 ml) was added under ice cooling and stirring, and the mixture was stirred at room temperature for 1 hour. To the reaction solution, ice water was added and the solution was washed with ethyl acetate. The ethyl acetate layer was extracted with water, and the extraction layer and the previous aqueous layer were combined. The mixture was made basic with potassium carbonate and extracted with chloroform. The extraction liquid was dried and the solvent was distilled off under reduced pressure, and then the residue was purified by NH silica gel flash column chromatography (eluting solvent: n-hexane/ethyl acetate=2/1, 1/1) and then an oxalate was formed in acetone to obtain THK-5078 (460 mg, 71%) as orange crystals.

mp 134-136° C., $^1$H NMR (400 MHz, DMSO-$d_6$) δ 1.10 (3H, t, J=7.0 Hz), 3.49 (2H, q, J=7.0 Hz), 3.7-3.8 (2H, m), 4.6-4.9 (3H, m), 6.83 (2H, d, J=9.0 Hz), 7.20 (1H, dd, J=8.8, 2.4 Hz), 7.49 (1H, d, J=2.4 Hz), 7.85 (1H, d, J=9.0 Hz), 7.89 (1H, d, J=7.3 Hz), 8.11 (2H, d, J=9.0 Hz), 8.26 (1H, d, J=9.0 Hz)

IR (Nujol) 1603, 1458, 1214 cm$^{-1}$

APCI-MS m/z 355[M+H]+

Synthesis Method of THK-5090

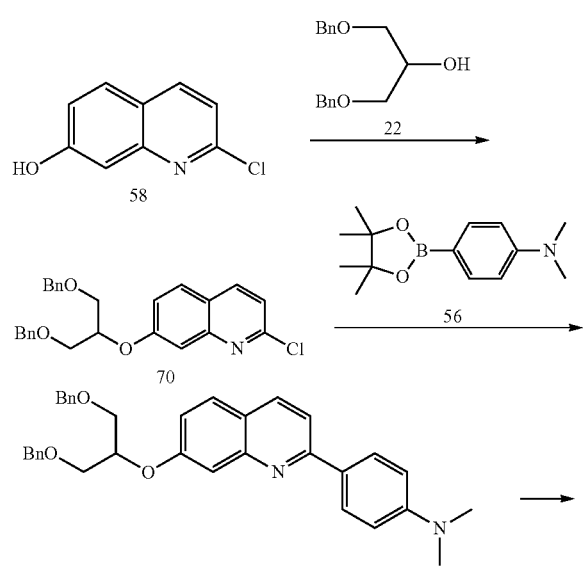

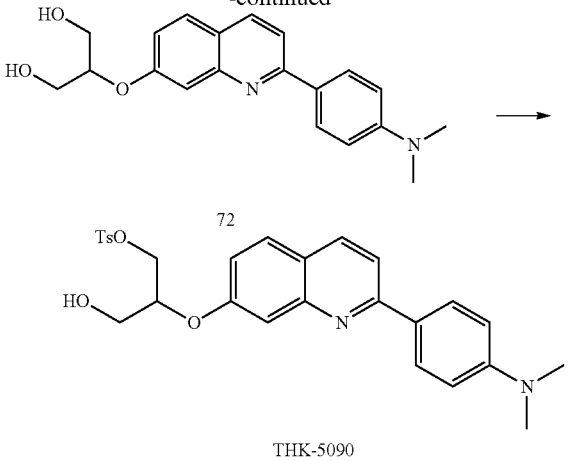

THK-5090

Synthesis of 70

To a tetrahydrofuran (60 ml) solution of 58 (1.36 g, 7.57 mmol), 22 (2.48 g, 9.09 mmol) and triphenylphosphine (2.38 g, 9.09 mmol), diisopropyl azodicarboxylate (1.8 ml, 9.09 mmol) was added dropwise under ice cooling and stirring, and the mixture was stirred at room temperature for 16 hours. To the reaction solution, 22 (1.24 g, 4.55 mmol), triphenylphosphine (1.19 g, 4.55 mmol) and tetrahydrofuran (10 ml) were added under ice cooling and stirring, and diisopropyl azodicarboxylate (0.9 ml, 4.55 mmol) was added dropwise, followed by further stirring at room temperature for 4 hours. The solvent of the reaction solution was distilled off under reduced pressure and the residue was purified by silica gel column chromatography (eluting solvent: ethyl acetate/n-hexane=1/9) to obtain 70 (3.04 g, 93%) as a pale pink oily substance.

APCI-MS m/z 434[M+H]+

Synthesis of 71

To a 1,2-dimethoxyethane (40 ml) solution of 70 (2.00 g, 4.61 mmol) and 56 (1.14 g, 4.61 mmol), potassium carbonate (1.91 g, 13.83 mmol), water (0.8 ml) and tetrakistriphenylphosphine palladium (270 mg, 0.23 mmol) were added under an argon atmosphere, and the mixture was stirred at 80° C. for 2 days. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9) to obtain 71 (1.22 g, 51%) as a yellow oily substance.

APCI-MS m/z 519[M+H]+

Synthesis of 72

To a mixture of 71 (1.21 g, 2.33 mmol) and anisole (3 ml), methanesulfonic acid (9 ml) was added dropwise under ice cooling and stirring, and the mixture was stirred at room temperature for 30 minutes. The reaction solution was poured into ice water and the solution was extracted with ethyl acetate-tetrahydrofuran. The extraction liquid was dried and the solvent was distilled off under reduced pressure, and then the residue was washed with ethyl acetate-n-hexane (1/2) to obtain 72 (680 mg, 86%) as yellow crystals.

mp 193-194° C.

APCI-MS m/z 339[M+H]+

Synthesis of THK-5090

To a pyridine (15 ml) solution of 72 (690 mg, 2.04 mmol), a tetrahydrofuran (15 ml) solution of paratoluenesulfonic anhydride (1.00 g, 3.06 mmol) was added dropwise over 35 minutes under ice cooling and stirring, and the mixture was stirred at the same temperature for 30 minutes. To the reaction solution, ice water was added and the solution was extracted with ethyl acetate after adjusting the pH to 9 using an aqueous potassium carbonate solution. The extraction liquid was dried and the solvent was distilled off under reduced pressure (toluene azeotrope). The residue was purified by silica gel column chromatography (eluting solvent: ethyl acetate/n-hexane=1/2, 1/1) and then recrystallized from ethyl acetate-n-hexane to obtain THK-5090 (459 mg, 46%) as pale yellow crystals.

mp 100-102° C., $^1$H NMR (400 MHz, DMSO-$d_6$) δ 2.33 (3H, s), 3.03 (6H, s), 3.56-3.71 (2H, m), 4.30 (1H, dd, J=11, 6.0 Hz), 4.39 (1H, dd, J=11, 2.7 Hz), 4.72-4.78 (1H, m), 5.12 (1H, t, J=5.4 Hz), 6.84 (2H, d, J=9.1 Hz), 7.02 (1H, dd, J=9.1, 2.4 Hz), 7.33 (1H, d, J=2.4 Hz), 7.39 (2H, d, J=7.9 Hz), 7.75 (21H, d, J=8.2 Hz), 7.79 (1H, d, J=9.1 Hz), 7.88 (1H, d, J=8.5 Hz), 8.13 (2H, d, J=9.1 Hz), 8.23 (1H, d, J=7.9 Hz)

IR (Nujol) 1731, 1609, 1597 cm$^{-1}$
APCI-MS m/z 493[M+H]$^+$

Synthesis Method of THK-5075

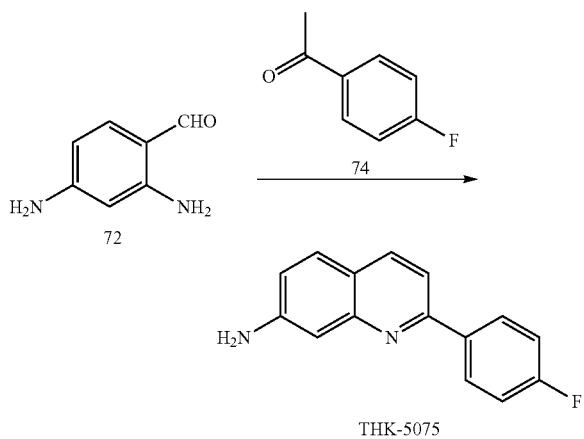

THK-5075

Synthesis of THK-5075

A mixture of 73 (1.19 g, 8.74 mmol), 74 (1.06 ml, 8.74 mmol), potassium hydroxide (590 mg, 10.5 mmol) and toluene (40 ml) was heated at reflux for 16 hours. The reaction solution was allowed to return to room temperature, and water and an aqueous saturated ammonium chloride solution were added and the solution was extracted with ethyl acetate. Insolubles were removed by filtration with celite. The extraction liquid was washed with water and dried, and then the solvent was distilled off under reduced pressure. The residue was purified by silica gel column chromatography (eluting solvent: n-hexane/ethyl acetate=9/1, 2/1) and then recrystallized from ethyl acetate-n-hexane to obtain THK-5075 (737 mg, 35%) as pale yellow crystals.

mp 160-161° C., $^1$H NMR (500 MHz, DMSO-$d_6$) δ 5.80 (2H, s), 6.96-7.00 (2H, m), 7.33 (2H, t, J=8.8 Hz), 7.63 (1H, d, J=9.6 Hz), 7.68 (1H, d, J=8.4 Hz), 8.11 (1H, d, J=8.4 Hz), 8.24 (2H, dd, J=9.0, 5.5 Hz)

IR (Nujol) 3388, 1619, 1600 cm$^{-1}$
APCI-MS m/z 239[M+H]$^+$

Synthesis Method of THK-5076

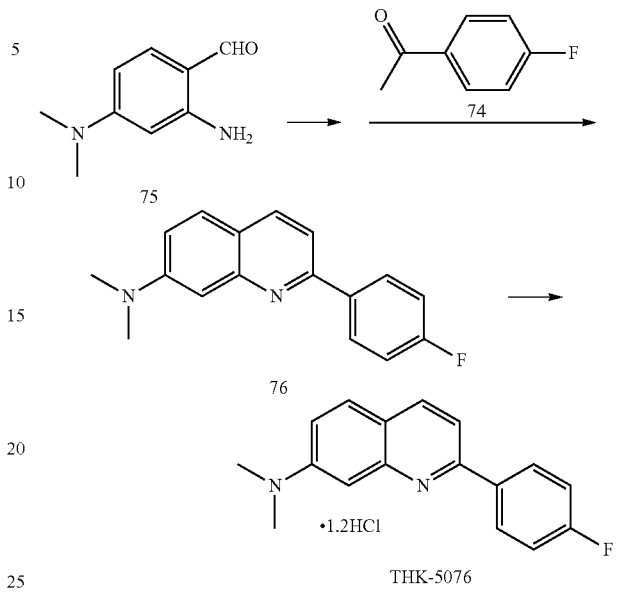

THK-5076

Synthesis of 76

To an ethanol (20 ml) suspension of 75 (1.00 g, 5.15 mmol), an iron powder (1.15 g) and 0.1N hydrochloric acid (2.58 ml) were added and the mixture was heated at reflux for 16 hours, and then 0.1N hydrochloric acid (7.72 ml) were added, followed by further heating at reflux for 6 hours. To the reaction solution, 74 (0.625 ml, 5.15 mmol) and potassium hydroxide (0.347 g, 6.18 mmol) were added, and the mixture was heated at reflux for 3 days. The reaction solution was allowed to return to room temperature and insolubles were removed by filtration, and the solution was washed with methanol. The filtrate and the wash were combined and the solvent was distilled off under reduced pressure. Water was added to the residue and the solution was extracted with ethyl acetate. The ethyl acetate layer was extracted with aqueous 10% hydrochloric acid, and the hydrochloric acid extraction liquid was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=9/1, 4/1) to obtain 76 (225 mg, 16%) as a yellow oily substance.

APCI-MS m/z 267[M+H]$^+$

Synthesis of THK-5076

To a methanol (20 ml) solution of 76 (540 mg, 2.03 mmol), 4M hydrochloric acid/ethyl acetate (1.02 ml) was added dropwise and the solvent was distilled off under reduced pressure. The residue was recrystallized from ethyl acetate-isopropanol to obtain THK-5076 (478 mg) as orange crystals.

mp 250-251° C., $^1$H NMR (400 MHz, DMSO-$d_6$) δ 3.26 (6H, s), 7.46-7.57 (4H, m), 7.85 (1H, d, J=8.2 Hz), 8.06 (1H, d, J=9.4 Hz), 8.23 to 8.29 (2H, m), 8.77 (1H, d, J=8.2 Hz), 15.0 (1H, br)

IR (Nujol) 1634, 1599 cm$^{-1}$
APCI-MS m/z 267[M+H]$^+$

Synthesis Method of THK-5079

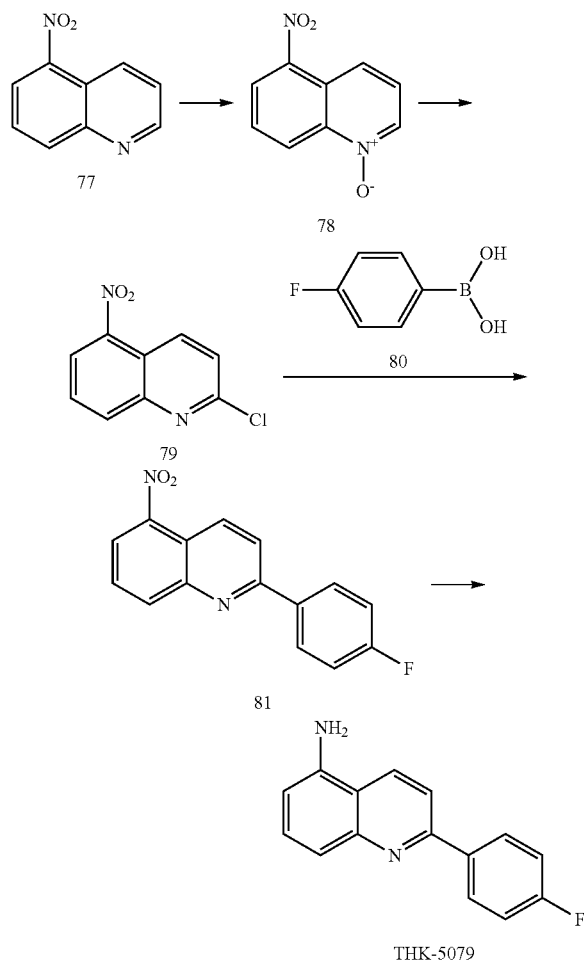

Synthesis of 78

To a chloroform (65 ml) solution of 77 (5.00 g, 28.71 mmol), a chloroform (27 ml)-methanol (7 ml) solution of metachlorobenzoic acid (10.9 g, 63.16 mmol) was added dropwise at room temperature, and the mixture was stirred at room temperature for 16 hours. To the reaction solution, an aqueous sodium thiosulfate solution was added, and the mixed solution was stirred room temperature for 10 minutes and extracted with chloroform. The extraction liquid was washed with an aqueous potassium carbonate solution, purified as it is by silica gel column chromatography (eluting solvent: chloroform) and then washed with n-hexane-ethyl acetate (2/1) to obtain 78 (4.96 g, 91%) as yellow crystals.

mp 164-165° C.

APCI-MS m/z 191[M+H]$^+$

Synthesis of 79

To 78 (4.94 g, 26 mmol), phosphorus oxychloride (22 ml) was added dropwise under ice cooling and stirring, and the mixture was heated at reflux for 3 hours. The reaction solution was ice-cooled and ice water was added, and then the solution was made basic with ammonia water and extracted with chloroform. The extraction liquid was washed with saturated saline and dried, and then the solvent was distilled off under reduced pressure. The residue was purified by silica gel flash column chromatography (eluting solvent: n-hexane/methylene chloride=2/1, 1/1, 1/2) and then washed with n-hexane to obtain 79 (2.25 g, 42%) as a pale yellow solid.

APCI-MS m/z 209/211[M+H]$^+$

Synthesis of 81

To a mixture of 79 (1.04 g, 5 mmol), 80 (770 mg, 5.5 mmol) and 1,2-dimethoxyethane (25 ml), an aqueous 2M sodium carbonate solution (5 ml, 10 mmol) and tetrakistriphenylphosphine palladium (289 mg, 0.25 mmol) were added under an argon atmosphere, and the mixture was stirred at 90° C. for 3 hours. The reaction solution was allowed to return to room temperature and the solvent was distilled off under reduced pressure. To the residue, chloroform was added and insolubles were removed by filtration, and the solution was washed with chloroform. The filtrate and the wash were combined and the mixture was washed with saturated saline and dried, and then the solvent was distilled off under reduced pressure. The residue was purified by silica gel flash column chromatography (eluting solvent: methylene chloride/n-hexane=1/1) and then washed with n-hexane to obtain 81 (1.30 g, 97%) as a pale yellow solid.

APCI-MS m/z 269[M+H]$^+$

Synthesis of THK-5079

A mixture of 81 (1.29 g, 4.81 mmol), 10% Pd—C (130 mg) and ethanol (30 ml) was stirred under a hydrogen atmosphere at room temperature for 2 hours. The catalyst was removed by filtration and the solvent of the filtrate was distilled off under reduced pressure, and then the residue was washed with n-hexane to obtain THK-5079 (1.087 g, 95%) as a yellowish orange solid.

mp 105-108° C., $^1$H NMR (400 MHz, DMSO-d$_6$) δ 5.9-6.3 (2H, brs), 6.70 (1H, dd, J=8.1 Hz), 7.23 (1H, d, J=8 Hz), 7.36 (2H, t, J=9 Hz), 7.44 (1H, t, J=8 Hz), 7.98 (1H, d, J=9 Hz), 8.31 (2H, dd, J=9.5 Hz), 8.63 (1H, d, J=9 Hz)

IR (Nujol) 1614, 1592 cm$^{-1}$

APCI-MS m/z 239[M+H]$^+$

Synthesis Method of THK-5080

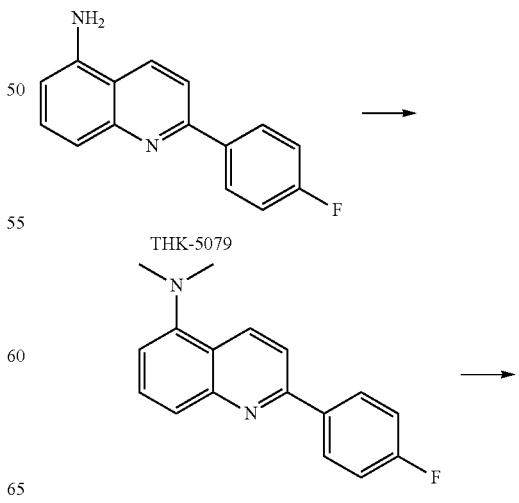

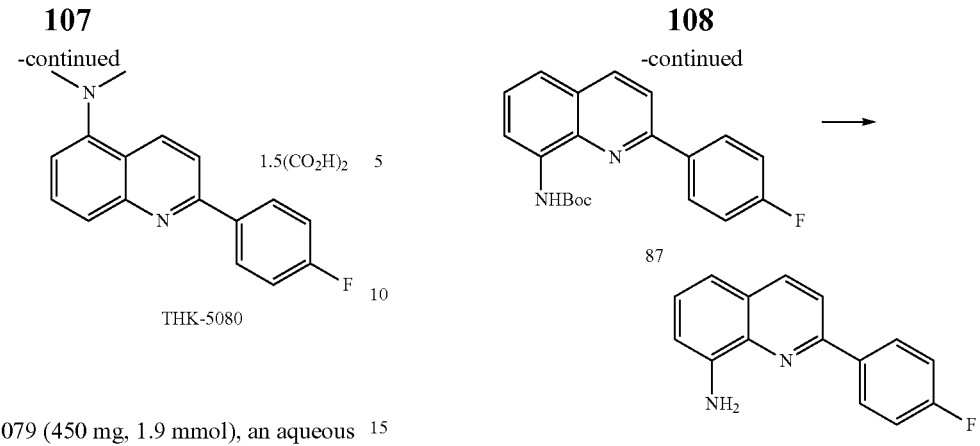

THK-5080

Synthesis of 82

A mixture of THK-5079 (450 mg, 1.9 mmol), an aqueous 35% formalin solution (0.81 g, 9.4 mmol), a picoline borane complex (303 mg, 2.8 mmol) and methanol (10 ml)-acetic acid (1 ml) was stirred at room temperature for 30 minutes and a picoline borane complex (100 mg, 0.93 mmol) was added, followed by stirring at room temperature for 30 minutes. The solvent of the reaction solution was distilled off under reduced pressure and aqueous 10% hydrochloric acid (5 ml) was added to the residue. After stirring at room temperature for 30 minutes, the solution was made basic by adding potassium carbonate. The reaction solution was extracted with chloroform, and the extraction liquid was dried and the solvent was distilled off under reduced pressure. The residue was purified by silica gel flash column chromatography (eluting solvent: n-hexane/ethyl acetate=49/1, 19/1) to obtain 82 (465 mg, 92) as a greenish yellow oily substance.

APCI-MS m/z 267[M+H]$^+$

Synthesis of THK-5080

After dissolving by adding oxalic acid (312 mg, 3.47 mmol) to an acetone (10 ml) solution of 82 (462 mg, 1.73 mmol), the solvent was distilled off under reduced pressure. The residue was washed with diisopropylether to obtain THK-5080 (620 mg, 89%) as an orange solid.

mp 118-120° C., $^1$H NMR (500 MHz, DMSO-d$_6$) δ 2.87 (2H, s), 7.15 (1H, dd, J=6, 1.5 Hz), 7.39 (2H, t, J=9 Hz), 7.6-7.7 (2H, m), 8.11 (1H, d, J=9 Hz), 8.33 (2H, dd, J=9.5 Hz), 8.59 (1H, d, J=9 Hz)

IR (Nujol) 1638, 1603 cm$^{-1}$

APCI-MS m/z 267[M+H]$^+$

Synthesis Method of THK-5081

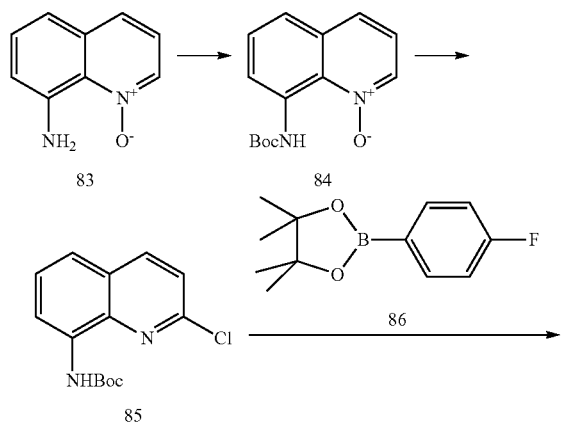

THK-5081

Synthesis of 84

A mixture of 83 (4.78 g, 29.84 mmol) and Boc$_2$O (10.28 ml, 44.8 mmol) was stirred at 80° C. for 2 hours, at 100° C. for 1 hour, followed by stirring at 120° C. for 30 minutes. The reaction solution was purified by silica gel column chromatography (eluting solvent: n-hexane/ethyl acetate=4/1, 1/1) to obtain 84 (6.54 g, 84%) as a yellow solid.

mp 126-128° C.

APCI-MS m/z 261[M+H]$^+$

Synthesis of 85

To a chloroform (120 ml) solution of 84 (6.62 g, 25.43 mmol), paratoluenesulfonyl chloride (5.82 g, 30.5 mmol) and potassium carbonate (4.22 g, 30.5 mmol) were added at room temperature under stirring, and the mixture was heated at reflux for 5 hours. The reaction solution was allowed to return to room temperature and water was added, and the solution was extracted with chloroform. The extraction liquid was purified as it is by NH silica gel column chromatography (eluting solvent: chloroform) and then silica gel column chromatography (eluting solvent: n-hexane/ethyl acetate=100/1 to ethyl acetate) to obtain 85 (3.70 g, 52%) as a pale yellow solid.

mp 99-100° C.

APCI-MS m/z 279[M+H]$^+$

Synthesis of 87

To a 1,2-dimethoxyethane (44 ml) solution of 85 (1.50 g, 5.38 mmol) and 86 (1.20 g, 5.38 mmol), potassium carbonate (2.23 g, 16.13 mmol), water (0.94 ml) and tetrakistriphenylphosphine palladium (310 mg, 0.27 mmol) were added under an argon atmosphere, and the mixture was stirred at 80° C. for 3 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/500, 1/100) to obtain 87 (1.68 g, 92%) as a colorless solid.

APCI-MS m/z 339[M+H]$^+$

Synthesis of THK-5081

To a chloroform (12 ml) solution of 87 (1.50 g, 4.43 mmol), trifluoroacetic acid (8 ml) was added dropwise under ice cooling and stirring, and the mixture was stirred at room temperature for 3 hours. To the reaction solution, water was added and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/9) and then recrystallized from n-hexane to obtain THK-5081 (404 mg, 38%) as pale yellow crystals.

mp 87.5-88° C., $^1$H NMR (500 MHz, DMSO-d$_6$) δ 6.25 (2H, br), 6.91 (1H, d, J=7.7 Hz), 7.09 (1H, d, J=8.0 Hz), 7.29 (1H, t, J=8.0 Hz), 7.35 (2H, t, J=9.0 Hz), 8.08 (1H, d, J=8.7 Hz), 8.26 (1H, d, J=8.7 Hz), 8.43 (2H, dd, J=8.7, 5.5 Hz)

IR (Nujol) 3433, 1616, 1600 cm$^{-1}$

APCI-MS m/z 239[M+H]$^+$

Synthesis Method of THK-5082

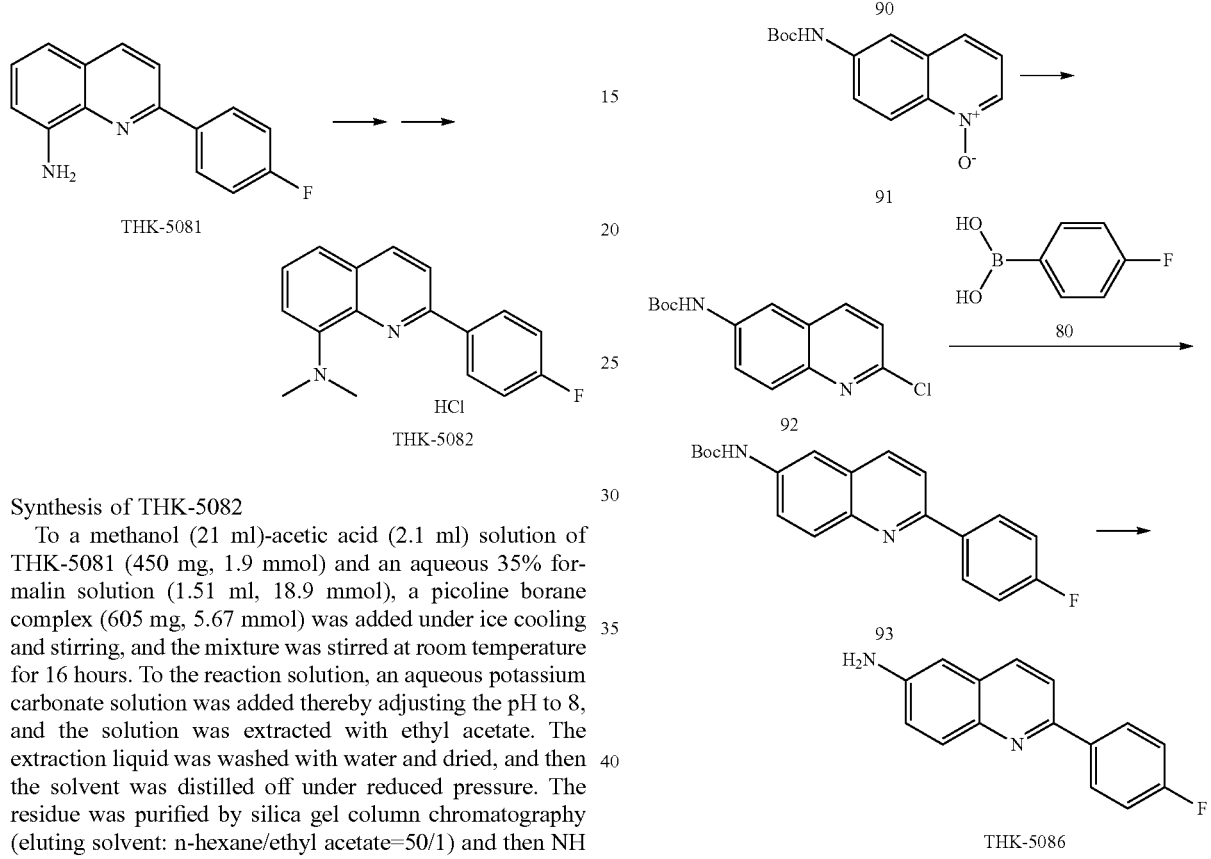

Synthesis of THK-5082

To a methanol (21 ml)-acetic acid (2.1 ml) solution of THK-5081 (450 mg, 1.9 mmol) and an aqueous 35% formalin solution (1.51 ml, 18.9 mmol), a picoline borane complex (605 mg, 5.67 mmol) was added under ice cooling and stirring, and the mixture was stirred at room temperature for 16 hours. To the reaction solution, an aqueous potassium carbonate solution was added thereby adjusting the pH to 8, and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=50/1) and then NH silica gel column chromatography (eluting solvent: n-hexane/ethyl acetate=100/1) to obtain a free form (430 mg) of THK-5082 as a yellow oily substance. The present product was dissolved in ethyl acetate (10 ml) and 4M hydrochloric acid/ethyl acetate (0.4 ml) was added dropwise, followed by stirring at room temperature for 30 minutes. The precipitate was collected by filtration and dried to obtain THK-5082 (430 mg, 75%) as colorless crystals.

mp 216-216.5° C., $^1$H NMR (400 MHz, DMSO-d$_6$) δ 3.57 (6H, s), 7.41-7.48 (2H, m), 7.76 (1H, t, J=7.9 Hz), 8.15 (1H, d, J=7.9 Hz), 8.24 (1H, d, J=7.6 Hz), 8.38 (1H, d, J=8.8 Hz), 8.56-8.62 (2H, m), 8.66 (1H, d, J=8.8 Hz), 12.2 (1H, br)

IR (Nujol) 2252, 1602 cm$^{-1}$

APCI-MS m/z 267[M+H]$^+$

Synthesis Method of THK-5086

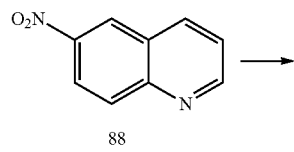

88

Synthesis of 89

To a methanol (50 ml)-tetrahydrofuran (50 ml) suspension of 88 (5.00 g, 28.71 mmol), 10% Pd—C (moisture of about 50%; 1.00 g) was added under a hydrogen atmosphere, and the mixture was stirred at room temperature for 2 hours. The catalyst was removed by filtration and the solvent of the filtrate was distilled off under reduced pressure to obtain 89 (4.14 g, 100%) as a pale yellow solid.

mp 116-117° C.

APCI-MS m/z 145[M+H]$^+$

Synthesis of 90

A mixture of 89 (4.14 g, 28.71 mmol) and Boc$_2$O (9.9 ml, 43.1 mmol) was stirred at 120° C. for 30 minutes. To the reaction solution, silica gel (30 ml) and toluene (100 ml) were added, followed by stirring at 80° C. for 1 hour. The reaction solution was allowed to return to room temperature and purified as it is by silica gel column chromatography (eluting solvent: n-hexane/ethyl acetate=2/1, ethyl acetate) to obtain 90 (5.92 g, 84%) as a pale yellow solid.

mp 132-133° C.

APCI-MS m/z 245[M+H]$^+$

Synthesis of 91

To a chloroform (55 ml) solution of 90 (5.91 g, 24.19 mmol), a chloroform (22 ml)-methanol (6 ml) solution of metachlorobenzoic acid (9.19 g, 53.2 mmol) was added dropwise at room temperature, and the mixed solution was stirred at room temperature for 16 hours. To the reaction solution, an aqueous sodium thiosulfate solution was added, followed by stirring at room temperature for 10 minutes and further extraction with chloroform. The extraction liquid was washed with an aqueous potassium carbonate solution, purified as it is by silica gel column chromatography (eluting solvent: chloroform) and then washed with n-hexane-ethyl acetate (2/1) to obtain 91 (5.25 g, 83%) as colorless crystals.

mp 212-213° C.

APCI-MS m/z 261[M+H]$^+$

Synthesis of 92

To a chloroform (200 ml) solution of 91 (5.25 g, 20.17 mmol), paratoluenesulfonyl chloride (4.61 g, 24.2 mmol) and potassium carbonate (3.35 g, 24.2 mmol) were added at room temperature under stirring, and the mixture was heated at reflux for 3.5 hours. The reaction solution was allowed to return to room temperature and water was added, and the solution was extracted with chloroform. The extraction liquid was purified as it is by NH silica gel column chromatography (eluting solvent: chloroform) and then silica gel column chromatography (eluting solvent: n-hexane/ethyl acetate=9/1, 4/1) to obtain 92 (1.87 g, 33%) as a colorless solid.

mp 152-153° C.

APCI-MS m/z 279/281[M+H]$^+$

Synthesis of 93

To a 1,2-dimethoxyethane (30 ml) solution of 92 (1.00 g, 3.59 mmol) and 80 (0.60 g, 4.31 mmol), potassium carbonate (1.50 g, 10.8 mmol), water (0.62 ml) and tetrakistriphenylphosphine palladium (210 mg, 0.18 mmol) were added under an argon atmosphere, and the mixture was stirred at 80° C. for 5.5 hours. The reaction solution was allowed to return to room temperature and water was added, and the solution was extracted with ethyl acetate. The extraction liquid was dried and the solvent was distilled off under reduced pressure. The residue was purified by silica gel column chromatography (eluting solvent: ethyl acetate/n-hexane=1/4) and then recrystallized from ethyl acetate-n-hexane to obtain 93 (990 mg, 82%) as colorless crystals.

mp 194-195° C.

APCI-MS m/z 339[M+H]$^+$

Synthesis of THK-5086

To a chloroform (12 ml) suspension of 93 (980 mg, 2.90 mmol), trifluoroacetic acid (8 ml) was added dropwise under ice cooling and stirring, and the mixture was stirred at room temperature for 1.5 hours. To the reaction solution, water was added and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/2) and then recrystallized from ethyl acetate-n-hexane to obtain THK-5086 (635 mg, 92%) as pale yellow crystals.

mp 145.5-146° C., $^1$H NMR (500 MHz, DMSO-d$_6$) δ 5.71 (2H, s), 6.82 (1H, d, J=2.6 Hz), 7.19 (1H, dd, J=9.0, 2.6 Hz), 7.29-7.35 (2H, m), 7.75 (1H, d, J=9.0 Hz), 7.89 (1H, d, J=8.7 Hz), 8.03 (1H, d, J=8.7 Hz), 8.19-8.24 (2H, m)

IR (Nujol) 3342, 1628 cm$^{-1}$

APCI-MS m/z 239[M+H]$^+$

Synthesis Method of THK-5087

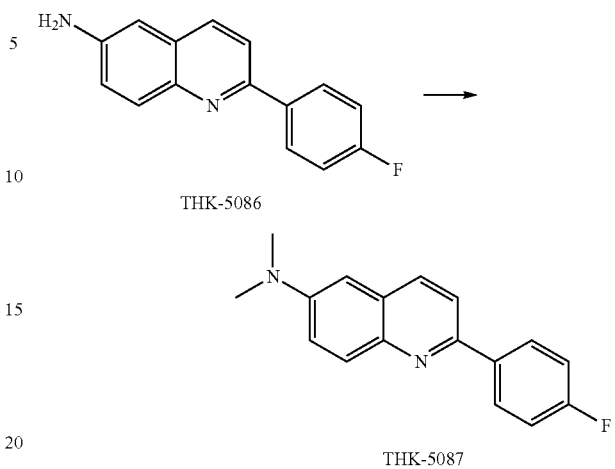

Synthesis of THK-5087

To a methanol (21 ml)-acetic acid (2.1 ml) solution of THK-5086 (440 mg, 1.85 mmol) and an aqueous 37% formalin solution (1.48 ml, 18.5 mmol), a picoline borane complex (590 mg, 5.55 mmol) was added under ice cooling and stirring, and the mixture was stirred at room temperature for 3.5 hours. After adjusting the pH of the reaction solution to 9 by adding an aqueous potassium carbonate solution, the solution was extracted with ethyl acetate. The extraction liquid was washed with water and dried, and then the solvent was distilled off under reduced pressure. The residue was purified by silica gel column chromatography (eluting solvent: n-hexane/ethyl acetate=9/1, 4/1) and then recrystallized from n-hexane-ethyl acetate to obtain THK-5087 (415 mg, 84%) as pale yellow crystals.

mp 172-173° C., $^1$H NMR (400 MHz, DMSO-d$_6$) δ 3.06 (6H, s), 6.96 (1H, d, J=2.7 Hz), 7.30-7.37 (2H, m), 7.47 (1H, dd, J=9.4, 3.0 Hz), 7.88 (1H, d, J=9.4 Hz), 7.96 (1H, d, J=8.8 Hz), 8.17 (1H, d, J=8.8 Hz), 8.22-8.28 (2H, m)

IR (Nujol) 1618 cm$^{-1}$

APCI-MS m/z 267[M+H]$^+$

Synthesis Method of THK-932

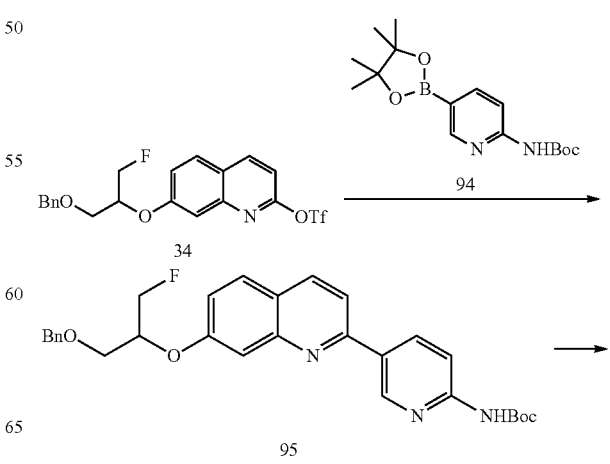

Synthesis Method of THK-5088

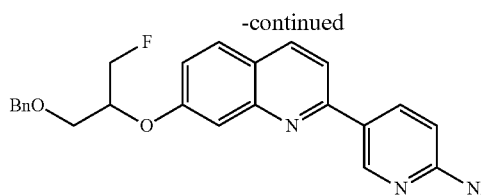

96

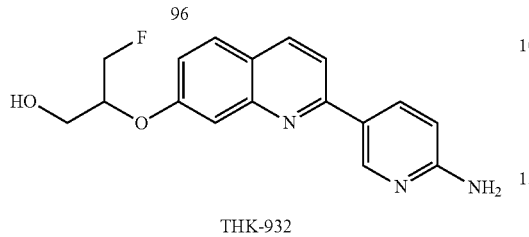

THK-932

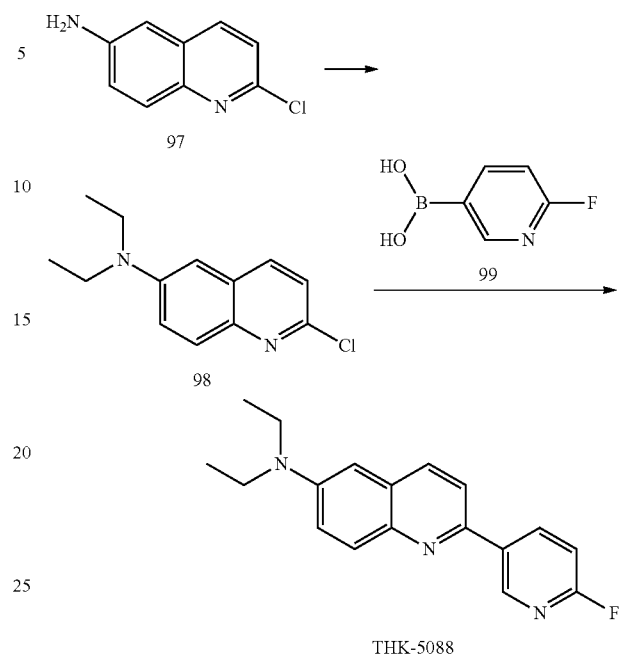

THK-5088

Synthesis of 95

To a 1,2-dimethoxyethane (27 ml) solution of 34 (1.05 g, 2.28 mmol) and 94 (720 mg, 2.28 mmol), potassium carbonate (940 mg, 6.83 mmol), water (0.57 ml) and tetrakistriphenylphosphine palladium (131 mg, 0.114 mmol) were added under an argon atmosphere, and the mixture was stirred at 80° C. for 1.5 hours. The reaction solution was allowed to return to room temperature, diluted with ethyl acetate, washed with water and then dried. The solvent was distilled off under reduced pressure and the residue was purified by silica gel column chromatography (eluting solvent: n-hexane/ethyl acetate=4/1→3/1) to obtain 95 (900 mg, 78%) as a pale yellow solid.

mp 150-152° C., APCI-MS m/z 504[M+H]$^+$

Synthesis of 96

To a chloroform (12 ml) solution of 95 (900 mg, 1.79 mmol), trifluoroacetic acid (8 ml) was added dropwise under ice cooling and stirring, and the mixture was stirred at room temperature for 2 hours. The reaction solution was ice-cooled, neutralized with an aqueous potassium carbonate solution and extracted with ethyl acetate. The organic layer was washed with water and dried, and then solvent was concentrated under reduced pressure to obtain 96 (720 mg, 99%) as a pale yellow oily substance.

APCI-MS m/z 404[M+H]$^+$

Synthesis of THK-932

To an anisole (5 ml) solution of 96 (720 mg, 1.78 mmol), methanesulfonic acid (20 ml) was added dropwise under ice cooling and stirring, and the mixture was stirred at room temperature for 30 minutes. The reaction solution was ice-cooled and ice water was added dropwise, and the solution was washed with ethyl acetate. The aqueous layer was extracted with ethyl acetate after adjusting the pH to 9 using an aqueous potassium carbonate solution. The organic layer was washed with water and dried, and the solvent was distilled off under reduced pressure. The residue was purified by NH silica gel column chromatography (eluting solvent: n-hexane/ethyl acetate=1/1→ethyl acetate) and then recrystallized from ethyl acetate to obtain THK-932 (390 mg, 69%) as colorless crystals.

mp 160-161° C., 1H NMR (500 MHz, DMSO-d$_6$) δ 3.66-3.77 (2H, m), 4.65-4.86 (3H, m), 5.14 (1H, t, J=5.8 Hz), 6.41 (2H, s), 6.57 (1H, d, J=9.0 Hz), 7.20 (1H, dd, J=8.8, 2.4 Hz), 7.48 (1H, d, J=2.4 Hz), 7.84 (1H, d, J=8.8 Hz), 7.87 (1H, d, J=8.8 Hz), 8.18-8.38 (2H, m), 8.83 (1H, d, J=2.4 Hz)

IR (Nujol) 3335, 1638, 1613 cm$^{-1}$

APCI-MS m/z 314[M+H]$^+$

Synthesis of 98

To a mixture of 97 (387 mg, 2.17 mmol), acetoaldehyde (2.39 g, 54.3 mmol) and methanol (10 ml)-acetic acid (1 ml), a picoline borane complex (1.16 g, 10.8 mmol) was added under ice cooling and stirring, and the mixture was stirred at room temperature for 3.5 hours. The solvent of the reaction solution was distilled off under reduced pressure and aqueous 10% hydrochloric acid (5 ml) was added to the residue. After stirring at room temperature for 30 minutes, the solution was made basic by adding potassium carbonate. The reaction solution was extracted with chloroform and the extraction liquid was dried, and the solvent was distilled off under reduced pressure. The residue was purified by silica gel flash column chromatography (eluting solvent: n-hexane/ethyl acetate=19/1) to obtain 98 (353 mg, 69%) as a yellow oily substance.

APCI-MS m/z 235/237[M+H]$^+$

Synthesis of THK-5088

To a mixture of 98 (348 mg, 1.48 mmol), 99 (230 mg, 1.6 mmol) and 1,2-dimethoxyethane (7.5 ml), an aqueous 2M sodium carbonate solution (1.5 ml, 3.0 mmol) and tetrakistriphenylphosphine palladium (86 mg, 0.074 mmol) were added under an argon atmosphere, and the mixture was stirred at 90° C. for 6 hours. To the reaction solution, 99 (115 mg, 0.816 mmol), an aqueous 2M sodium carbonate solution (0.75 ml, 1.5 mmol) and tetrakistriphenylphosphine palladium (43 mg, 0.037 mmol) were added under an argon atmosphere, followed by further stirring at 90° C. for 6 hours. The solvent of the reaction solution was distilled off under reduced pressure and the solution was extracted with chloroform. The extraction liquid was dried and the solvent was distilled off under reduced pressure. The residue was purified by silica gel flash column chromatography (eluting solvent: n-hexane/ethyl acetate=9/1) and then NH silica gel flash column chromatography (eluting solvent: n-hexane, n-hexane/ethyl acetate=49/1, 19/1) and then washed with cold n-hexane to obtain THK-5088 (380 mg, 87%) as a yellowish brown solid.

mp 118-120° C., $^1$H NMR (500 MHz, DMSO-$d_6$) δ 1.18 (6H, t, J=7.0 Hz), 3.50 (4H, q, J=7.0 Hz), 6.94 (1H, s), 7.32 (1H, dd, J=6.1, 1.5 Hz), 7.43 (1H, d, J=8.4 Hz), 7.89 (1H, d, J=9 Hz), 8.01 (1H, d, J=9 Hz), 8.20 (1H, d, J=8.3 Hz), 8.74 (1H, dt, J=8.3, 2.6 Hz), 9.01 (1H, d, J=2.6 Hz)
IR (Nujol) 1465, 1376 cm$^{-1}$
APCI-MS m/z 296[M+H]$^+$ Synthesis Method of THK-5089

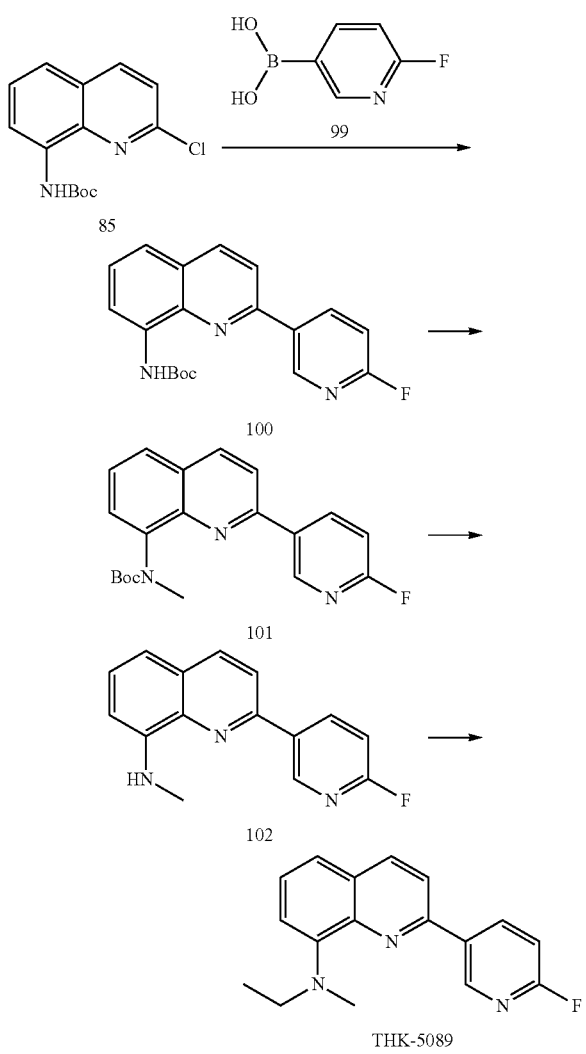

Synthesis of 100

To a mixture of 85 (1.00 g, 3.59 mmol), 99 (0.61 g, 4.31 mmol) and 1,2-dimethoxyethane (30 ml), potassium carbonate (1.49 g, 10.76 mmol), water (0.62 ml) and tetrakistriphenylphosphine palladium (210 mg, 0.18 mmol) were added under an argon atmosphere, and the mixture was stirred at 80° C. for 2.5 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9, 1/4) and then recrystallized from ethyl acetate-n-hexane to obtain 100 (1.01 g, 83%) as colorless crystals.
mp 189.5-190° C.
APCI-MS m/z 340[M+H]$^+$ Synthesis of 101

To an N,N-dimethylformamide (33 ml) solution of 100 (1.00 g, 2.95 mmol), 60% sodium hydride (131 mg, 3.28 mmol) was added under ice cooling and stirring under an argon atmosphere, and the mixture was stirred at the same temperature for 10 minutes and methyl iodide (0.22 ml, 3.54 mmol) was added dropwise at the same temperature, followed by stirring at room temperature for 30 minutes. To the reaction solution, ice water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9, 1/4) to obtain 101 (1.03 g, 98%) as a colorless solid.
mp 147-148° C.
APCI-MS m/z 354[M+H]$^+$ Synthesis of 102

To a chloroform (12 ml) solution of 101 (1.02 g, 2.89 mmol), trifluoroacetic acid (8 ml) was added dropwise under ice cooling and stirring, and the mixture was stirred at room temperature for 1.5 hours. To the reaction solution, water was added and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/9) to obtain 102 (732 mg, 100%) as a yellow oily substance.
APCI-MS m/z 254[M+H]$^+$ Synthesis of THK-5089

To a methanol (32 ml)-acetic acid (3.2 ml) solution, 102 (730 mg, 2.88 mmol) and acetoaldehyde (1.63 ml, 28.8 mmol), a picoline borane complex (930 mg, 8.64 mmol) was added little by little under ice cooling and stirring, and the mixture was stirred at room temperature for 16 hours. To the reaction solution, water and an aqueous potassium carbonate solution were added thereby adjusting the pH to 9, and the solution was extracted with ethyl acetate. The extraction liquid was washed with water and dried, and then the solvent was distilled off under reduced pressure. The residue was purified by silica gel column chromatography (eluting solvent: n-hexane/ethyl acetate=9/1, 4/1) and then recrystallized from n-hexane to obtain THK-5089 (680 mg, 84%) as pale yellow crystals.
mp 71-72° C., $^1$H NMR (400 MHz, DMSO-$d_6$) δ 1.20 (3H, t, J=7.1 Hz), 3.04 (3H, s), 3.72 (2H, q, J=7.1 Hz), 7.07-7.12 (1H, br), 7.39 (1H, dd, J=8.5, 2.7 Hz), 7.42-7.49 (2H, m), 8.16 (1H, d, J=8.5 Hz), 8.40 (1H, d, J=8.5 Hz), 8.79 (1H, td, J=8.3, 2.7 Hz), 9.09 (1H, d, J=2.7 Hz)
IR (Nujol) 1598 cm$^{-1}$
APCI-MS m/z 282[M+H]$^+$ Synthesis Method of THK-5095

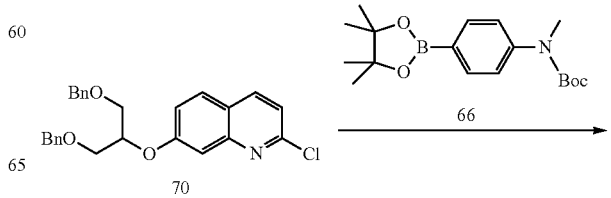

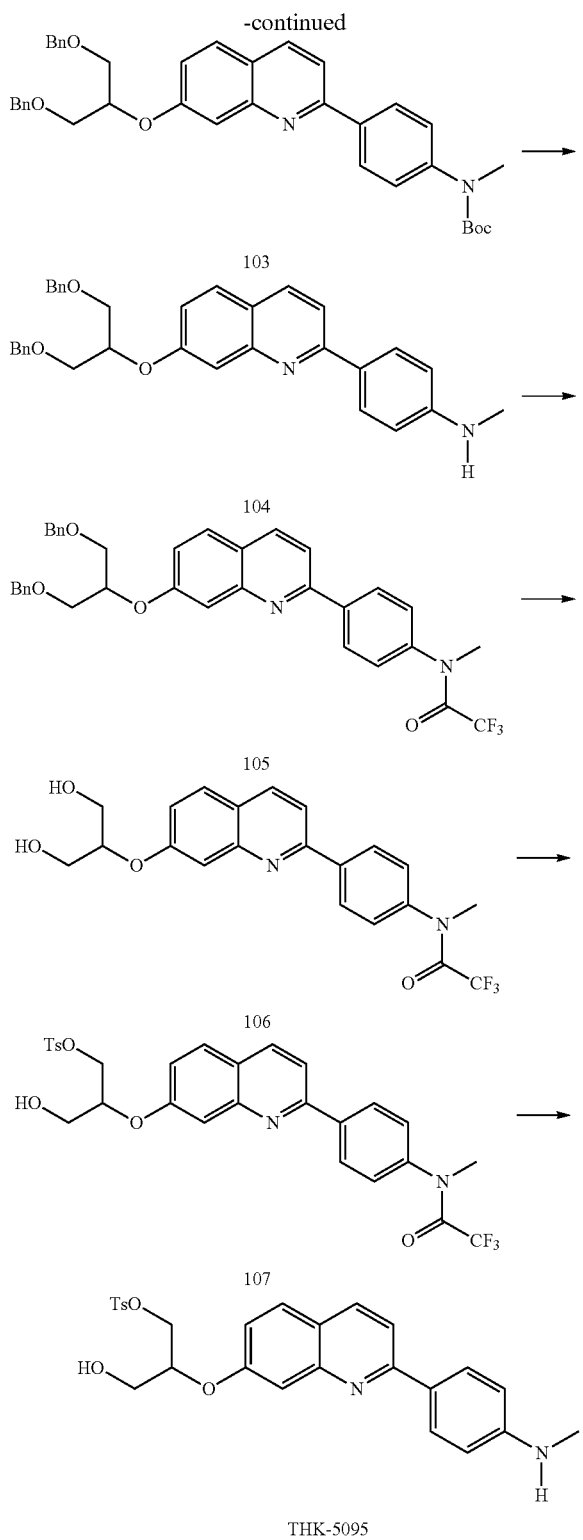

Synthesis of 103

To a 1,2-dimethoxyethane (38 ml) solution of 70 (2.02 g, 4.66 mmol) and 66 (1.55 g, 4.66 mmol), potassium carbonate (1.93 g, 13.97 mmol), water (0.81 ml) and tetrakistriphenylphosphine palladium (540 mg, 0.47 mmol) were added under an argon atmosphere, and the mixture was stirred at 80° C. for 16 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4) to obtain 103 (2.82 g, 100%) as a pale pink oily substance.

APCI-MS m/z 605[M+H]$^+$

Synthesis of 104

To a chloroform (24 ml) solution of 103 (2.81 g, 4.65 mmol), trifluoroacetic acid (16 ml) was added dropwise under ice cooling and stirring, and the mixture was stirred at room temperature for 1 hour. To the reaction solution, water and ethyl acetate were added, and the solution was made basic with an aqueous potassium carbonate solution and extracted with ethyl acetate. The extraction liquid was washed with water and dried, and then the solvent was distilled off under reduced pressure. The residue was purified by silica gel column chromatography (eluting solvent: n-hexane/ethyl acetate=3/1, 2/1) to obtain 104 (2.28 g, 97%) as a pale yellow oily substance.

APCI-MS m/z 505[M+H]$^+$

Synthesis of 105

To a chloroform (20 ml) solution of 104 (1.14 g, 2.26 mmol), triethylamine (0.473 ml, 3.39 mmol) and then trifluoroacetic anhydride (0.383 ml, 2.71 mmol) were added dropwise under ice cooling and stirring, and the mixture was stirred at the same temperature for 2 hours. To the reaction solution, ice water was added and the solution was extracted with ethyl acetate. The extraction liquid was washed with water and dried and then the solvent was distilled off under reduced pressure. The residue was purified by silica gel column chromatography (eluting solvent: ethyl acetate/n-hexane=1/4) to obtain 105 (1.36 g, 100%) as a pale yellow oily substance.

APCI-MS m/z 601[M+H]$^+$

Synthesis of 106

To a mixture of 105 (1.36 g, 2.26 mmol) and anisole (2 ml), methanesulfonic acid (6 ml) was added dropwise under ice cooling and stirring, and the mixture was stirred at room temperature for 20 minutes. The reaction solution was ice-cooled and ice water was added, and the solution was made basic with an aqueous potassium carbonate solution and extracted with ethyl acetate. The extraction liquid was washed with water and dried and then the solvent was distilled off under reduced pressure. The residue was purified by silica gel column chromatography (eluting solvent: ethyl acetate/n-hexane=1/1, ethyl acetate) to obtain 106 (890 mg, 94%) as a pale yellow amorphous.

APCI-MS m/z 421[M+H]$^+$

Synthesis of 107

To a pyridine (10 ml) solution of 106 (880 mg, 2.09 mmol), a tetrahydrofuran (15 ml) solution of paratoluenesulfonic anhydride (1.03 g, 3.14 mmol) was added dropwise over 20 minutes under ice cooling and stirring, and the mixture was stirred at the same temperature for 1 hour. To the reaction solution, ice water was added, and the solution was extracted with ethyl acetate after adjusting the pH to 9 using an aqueous potassium carbonate solution. The extraction liquid was washed with water and dried the solvent was distilled off under reduced pressure (toluene azeotrope). The residue was purified by silica gel column chromatography (eluting solvent: ethyl acetate/n-hexane=1/2, 1/1, ethyl acetate) to obtain 107 (750 mg, 63%) as a colorless amorphous.

APCI-MS m/z 575[M+H]$^+$

Synthesis of THK-5095

To a tetrahydrofuran (10 ml)-water (1 ml) solution of 107 (750 mg, 1.31 mmol), lithium hydroxide monohydrate (82 mg, 1.97 mmol) was added under ice cooling and stirring, and the mixture was stirred at the same temperature for 1 hour, followed by stirring at room temperature for 1 hour. To the reaction solution, ice water was added and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/1, 2/1) and then recrystallized from ethyl acetate-n-hexane to obtain THK-5095 (563 mg, 90%) as colorless crystals.

mp 109-111° C., $^1$H NMR (400 MHz, DMSO-d$_6$) δ 2.33 (3H, s), 2.76 (3H, d, J=4.5 Hz), 3.56-3.71 (2H, m), 4.30 (1H, dd, J=11, 5.7 Hz), 4.38 (1H, dd, J=11, 3.0 Hz), 4.71-4.76 (1H, m), 5.11 (1H, t, J=5.6 Hz) 6.14 (1H, br), 6.66 (2H, d, J=8.8 Hz), 7.01 (1H, dd, J=8.8, 2.4 Hz), 7.31 (1H, d, J=2.1 Hz), 7.39 (2H, d, J=8.5 Hz), 7.75 (2H, d, J=8.8 Hz), 7.78 (1H, d, J=9.1 Hz), 7.84 (1H, d, J=8.8 Hz), 8.06 (2H, d, J=8.8 Hz), 8.20 (1H, d, J=8.5 Hz)

IR (Nujol) 3359, 1741, 1608 cm$^{-1}$

APCI-MS m/z 479[M+H]$^+$

Synthesis Method of THK-5096

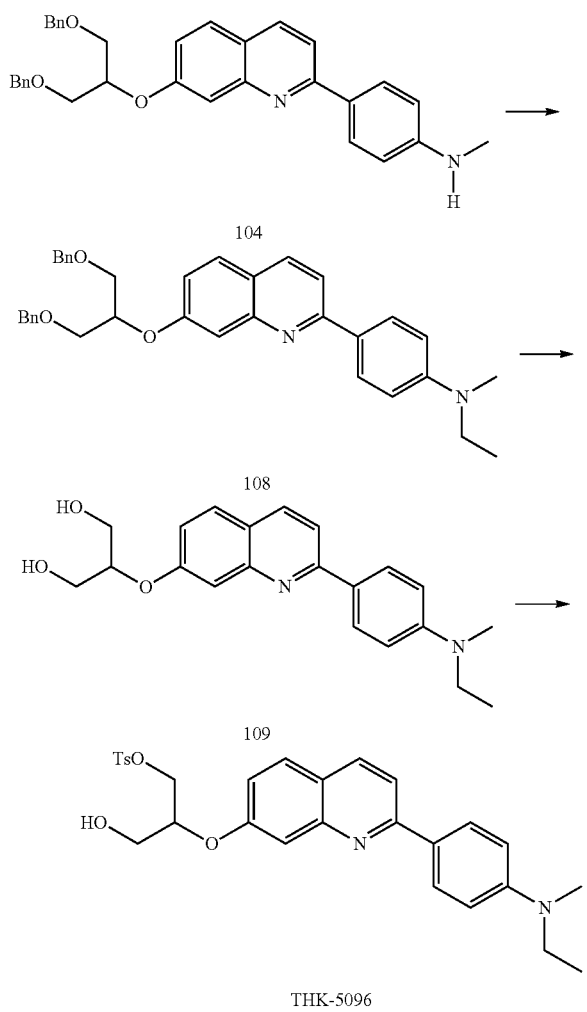

Synthesis of 108

To a methanol (25 ml)-acetic acid (2.5 ml) solution of 104 (1.13 g, 2.24 mmol) and acetoaldehyde (1.26 ml, 22.4 mmol), a picoline borane complex (720 mg, 6.72 mmol) was added under ice cooling and stirring, and the mixture was stirred at room temperature for 16 hours. To the reaction solution, ice water was added, and the solution was extracted with ethyl acetate by adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=9/1, 4/1) to obtain 108 (1.08 g, 91%) as a pale yellow oily substance.

APCI-MS m/z 533[M+H]$^+$

Synthesis of 109

To a mixture of 108 (1.15 g, 2.16 mmol) and anisole (3 ml), methanesulfonic acid (9 ml) was added dropwise under ice cooling and stirring, and the mixture was stirred at room temperature for 20 minutes. The reaction solution was ice-cooled and ice water was added, and the solution was extracted with ethyl acetate after adjusting the pH to 9 using an aqueous potassium carbonate solution. The extraction liquid was washed with water and dried, and then the solvent was distilled off under reduced pressure. The residue was washed with ethyl acetate-n-hexane (1/1) to obtain 109 (640 mg, 84%) as yellow crystals.

mp 136-137° C.

APCI-MS m/z 353[M+H]$^+$

Synthesis of THK-5096

To a pyridine (10 ml) solution of 109 (630 mg, 1.79 mmol), a tetrahydrofuran (10 ml) solution of paratoluenesulfonic anhydride (875 mg, 2.68 mmol) was added dropwise over 30 minutes under ice cooling and stirring, and the mixture was stirred at the same temperature for 20 minutes. To the reaction solution, ice water was added, and the solution was extracted with ethyl acetate after adjusting the pH to 9 using an aqueous potassium carbonate solution. The extraction liquid was washed with water and dried, and then the solvent was distilled off under reduced pressure (toluene azeotrope). The residue was purified by silica gel column chromatography (eluting solvent: ethyl acetate/n-hexane=1/2, ethyl acetate) and then recrystallized from ethyl acetate-n-hexane to obtain THK-5096 (450 mg, 50%) as yellow crystals.

mp 89-90° C., $^1$H NMR (400 MHz, DMSO-d$_6$) δ 1.10 (3H, t, J=7.0 Hz), 2.33 (3H, s), 2.96 (3H, s), 3.48 (2H, q, J=7.0 Hz), 3.37-3.71 (2H, m), 4.30 (1H, dd, J=11, 5.7 Hz), 4.38 (1H, dd, J=11, 2.7 Hz), 4.71-4.78 (1H, m), 5.11 (1H, t, J=5.4 Hz), 6.83 (2H, d, J=9.1 Hz), 7.02 (1H, dd, J=8.9, 2.3 Hz), 7.33 (1H, d, J=1.8 Hz), 7.39 (2H, d, J=7.9 Hz), 7.75 (2H, d, J=8.2 Hz), 7.79 (1H, d, J=8.8 Hz), 7.87 (1H, d, J=8.8 Hz), 8.11 (2H, d, J=9.1 Hz), 8.21 (1H, d, J=9.1 Hz)

IR (Nujol) 1620, 1597 cm$^{-1}$

APCI-MS m/z 507[M+H]$^+$

Synthesis Method of THK-5099

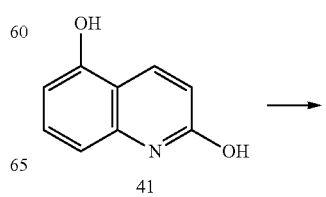

41

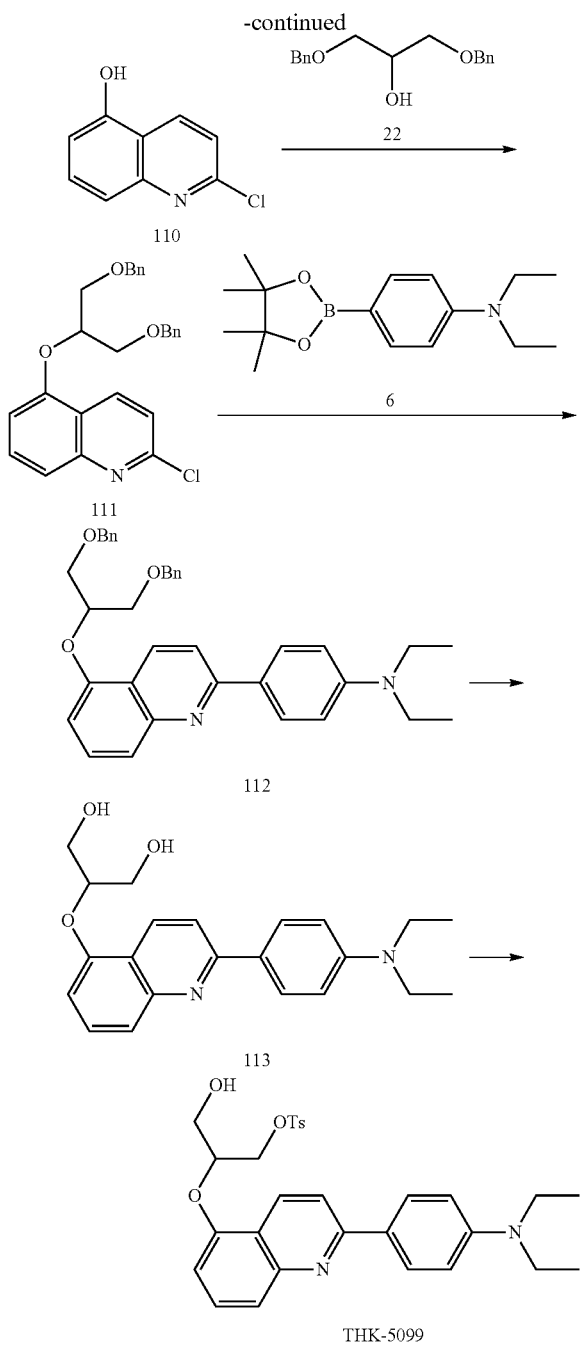

Synthesis of 111

To a tetrahydrofuran (30 ml) solution of 110 (700 mg, 3.90 mmol), 22 (1.27 g, 4.68 mmol) and triphenylphosphine (1.23 g, 4.68 mmol), a tetrahydrofuran (5 ml) solution of diisopropyl azodicarboxylate (0.93 ml, 4.68 mmol) was added dropwise under ice cooling and stirring, and the mixture was stirred at room temperature for 3 days. To the reaction solution, a tetrahydrofuran (5 ml) solution of 22 (1.27 g, 4.68 mmol) and diisopropyl azodicarboxylate (0.93 ml, 4.68 mmol) were added, followed by further stirring at room temperature for 2 hours. The solvent of the reaction solution was distilled off under reduced pressure and the residue was purified by silica gel column chromatography (eluting solvent: ethyl acetate/n-hexane=1/20, 1/15) to obtain 111 (1.18 g, 70%) as a pale yellow oily substance.

APCI-MS m/z 434[M+H]$^+$

Synthesis of 112

To a 1,2-dimethoxyethane (25 ml) solution of 111 (1.17 g, 2.70 mmol) and 6 (740 mg, 2.70 mmol), potassium carbonate (1.12 g, 8.09 mmol), water (0.5 ml) and tetrakistriphenylphosphine palladium (310 mg, 0.27 mmol) were added under an argon atmosphere, and the mixture was stirred at 80° C. for 7 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9, 1/4) to obtain 112 (1.48 g, 100%) as a yellow oily substance.

APCI-MS m/z 547[M+H]$^+$

Synthesis of 113

To a mixture of 112 (1.47 g, 2.69 mmol) and anisole (4 ml), methanesulfonic acid (12 ml) was added dropwise under ice cooling and stirring, and the mixture was stirred at room temperature for 1 hour. The reaction solution was poured into ice water, and the solution was extracted with ethyl acetate after adjusting the pH to 8 using an aqueous potassium carbonate solution. The extraction liquid was washed with water and dried and then the solvent was distilled off under reduced pressure. The residue was washed with hexane to obtain 113 (900 mg, 91%) as pale yellow crystals.

mp 165-166° C.

APCI-MS m/z 367[M+H]$^+$

Synthesis of THK-5099

To a pyridine (15 ml) solution of 113 (890 mg, 2.43 mmol), a tetrahydrofuran (15 ml) solution of paratoluenesulfonic anhydride (1.19 g, 3.64 mmol) was added dropwise over 30 minutes under ice cooling and stirring, and the mixture was stirred at the same temperature for 30 minutes. To the reaction solution, ice water was added, and the solution was extracted with ethyl acetate after adjusting the pH to 9 using an aqueous potassium carbonate solution. The extraction liquid was washed with water and dried, and then the solvent was distilled off under reduced pressure (toluene azeotrope). The residue was purified by silica gel column chromatography (eluting solvent: ethyl acetate/n-hexane=1/4) and then recrystallized from ethyl acetate to obtain THK-5099 (658 mg, 52%) as yellow crystals.

mp 143-143.5° C., $^1$H NMR (400 MHz, DMSO-$d_6$) δ 1.15 (6H, t, J=7.0 Hz), 2.31 (3H, s), 3.43 (4H, q, J=7.0 Hz), 3.67-3.72 (2H, m), 4.37 (1H, dd, J=11, 5.7 Hz), 4.42 (1H, dd, J=11, 3.0 Hz), 4.71-4.77 (1H, m), 5.13 (1H, t, J=5.6 Hz), 6.80 (2H, d, J=9.1 Hz), 6.94 (1H, dd, J=5.6, 3.2 Hz), 7.28

Synthesis of 110

To an N,N-dimethylformamide (30 ml) suspension of 41 (5.84 g, 36.24 mmol), thionyl chloride (10.39 ml, 145 mmol) was added dropwise under ice cooling and stirring, and the mixture was stirred at the same temperature for 30 minutes, followed by stirring at room temperature for 16 hours. The reaction solution was ice-cooled and ice water was added, and the solution was extracted with ethyl acetate after adjusting the pH to 7 using an aqueous potassium carbonate solution. The extraction liquid was washed with water, dried, purified by silica gel column chromatography (eluting solvent: ethyl acetate/n-hexane=1/9, 1/4) and then recrystallized from ethyl acetate-n-hexane to obtain 110 (3.88 g, 60%) as pale yellow crystals.

mp 176-177° C.

APCI-MS m/z 180[M+H]$^+$ (2H, d, J=8.2 Hz), 7.51-7.54 (2H, m), 7.68 (2H, d, J=8.2 Hz), 7.93 (1H, d, J=9.1 Hz), 8.12 (2H, d, J=9.1 Hz), 8.25 (1H, d, J=8.8 Hz)
IR (Nujol) 1593 cm$^{-1}$
APCI-MS m/z 521[M+H]$^+$ Synthesis Method of THK-5105

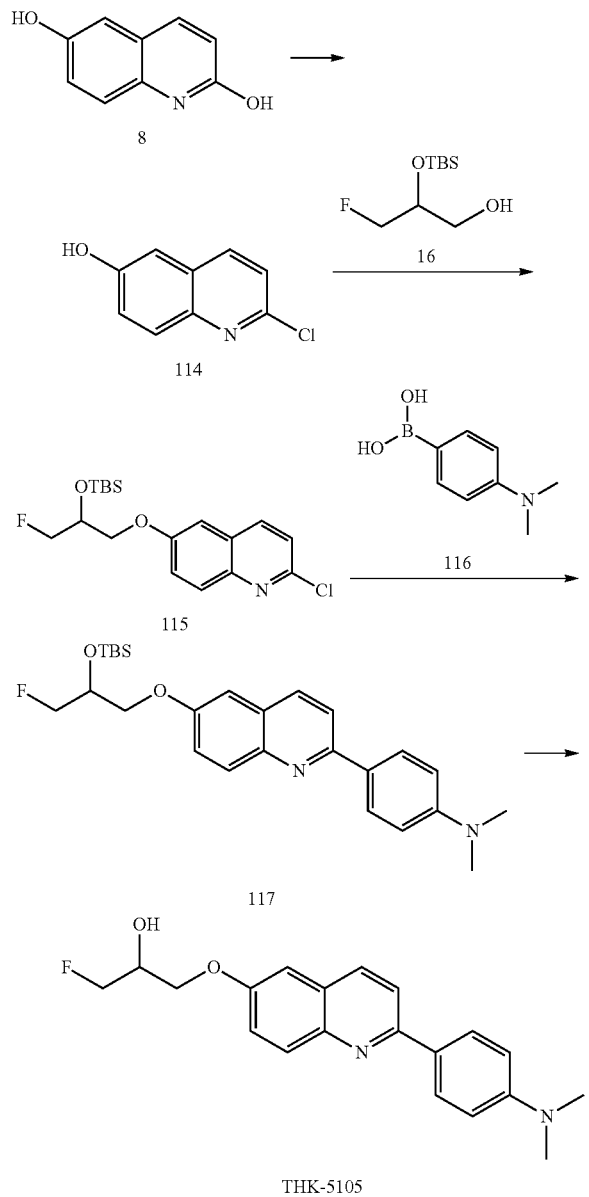

Synthesis of 114
To an N,N-dimethylformamide (20 ml) suspension of 8 (1.16 g, 10 mmol), thionyl chloride (5 g, 42 mmol) was added dropwise under ice cooling and stirring, and the mixture was stirred at room temperature for 16 hours. To the reaction solution, an aqueous saturated sodium hydrogen carbonate solution was added and the solution was extracted with ethyl acetate. The extraction liquid was washed with water and dried, and then the solvent was distilled off under reduced pressure. The residue was purified by silica gel flash column chromatography (eluting solvent: ethyl acetate/n-hexane=1/4) to obtain 114 (1.12 g, 62%) as a colorless solid.
mp 190-191° C.

Synthesis of 115
To a tetrahydrofuran (20 ml) solution of 114 (1.0 g, 5.57 mmol), 16 (1.2 g, 5.76 mmol) and triphenylphosphine (1.9 g, 7.24 mmol), diisopropyl azodicarboxylate (1.46 g, 7.22 mmol) was added dropwise under ice cooling and stirring, and the mixture was stirred at room temperature for 16 hours. The solvent of the reaction solution was distilled off under reduced pressure and the residue was purified by silica gel flash column chromatography (eluting solvent: ethyl acetate/n-hexane=1/7) to obtain 115 (1.78 g, 86%) as a pale yellow solid.
mp 50 to 52° C.

Synthesis of 117
To a 1,2-dimethoxyethane (14 ml) solution of 115 (600 mg, 1.62 mmol) and 116 (294 mg, 1.78 mmol), potassium carbonate (670 mg, 4.87 mmol), water (0.28 ml) and tetrakistriphenylphosphine palladium (190 mg, 0.16 mmol) were added under an argon atmosphere, and the mixture was stirred at 80° C. for 3 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/19, 1/9) to obtain 117 (690 mg, 94%) as a pale yellow solid.
mp 131-133° C.
APCI-MS m/z 455[M+H]$^+$ Synthesis of THK-5105
To a tetrahydrofuran (20 ml) solution of 117 (690 mg, 1.52 mmol), tetrabutylammonium fluoride (1.52 ml/1M tetrahydrofuran solution) was added, and the mixture was stirred at room temperature for 1 hour. Water was added to the reaction solution and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4, 1/1) and then recrystallized from ethyl acetate to obtain THK-5105 (437 mg, 85%) as pale yellow crystals.
mp 178-179° C., 1H NMR (400 MHz, DMSO-d$_6$) δ 4.07-4.18 (3H, m), 4.44-4.65 (2H, m), 5.52 (1H, br), 6.84 (2H, d, J=9.1 Hz), 7.36-7.41 (2H, m), 7.90 (1H, d, J=10 Hz), 7.99 (1H, d, J=8.8 Hz), 8.10 (2H, d, J=9.1 Hz), 8.23 (1H, d, J=8.8 Hz)
IR (Nujol) 3406, 1616 cm$^{-1}$
APCI-MS m/z 341[M+H]$^+$ Synthesis Method of THK-5106

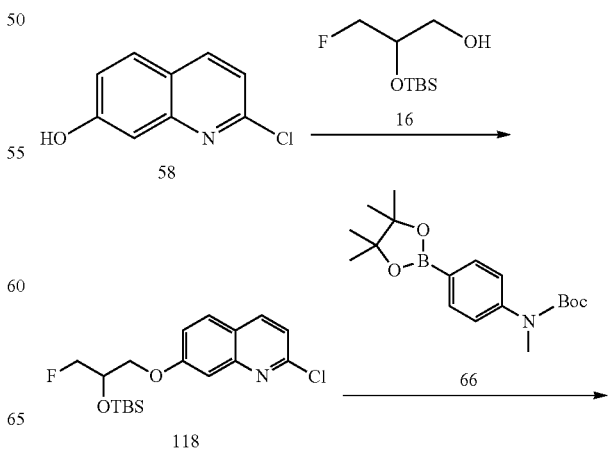

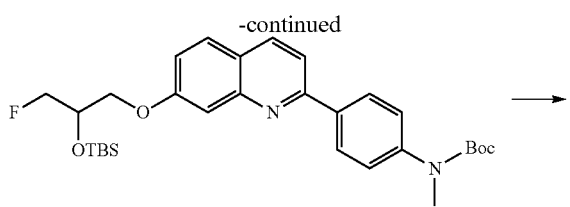

Synthesis of 118

To a tetrahydrofuran (40 ml) solution of 58 (2.00 g, 10.6 mmol), 16 (2.64 g, 12.7 mmol) and triphenylphosphine (3.32 g, 12.7 mmol), a tetrahydrofuran (10 ml) solution of diisopropyl azodicarboxylate (2.51 ml, 12.7 mmol) was added dropwise under ice cool ing and stirring, and the mixture was stirred at the same temperature for 30 minutes, followed by stirring at room temperature for 16 hours. The solvent of the reaction solution was distilled off under reduced pressure and the residue was purified by silica gel column chromatography (eluting solvent: ethyl acetate/n-hexane=1/20) to obtain 118 (3.90 g, 100%) as a pale yellow oily substance.

APCI-MS m/z 370/372[M+H]$^+$

Synthesis of 119

A mixture of 118 (1.83 g, 4.9 mmol), 66 (1.73 g, 5.2 mmol), potassium carbonate (1.37 g, 9.9 mmol), tetrakistriphenylphosphine palladium (300 mg, 0.26 mmol) and 1,2-dimethoxyethane (45 ml)-water (5 ml) was stirred under an argon atmosphere at 85° C. for 2 hours and tetrakistriphenylphosphine palladium (283 mg, 0.245 mmol) and potassium carbonate (678 mg, 4.9 mmol) were added, followed by stirring at the same temperature for 4 hours. The reaction solution was allowed to return to room temperature and water was added, and the solution was extracted with ethyl acetate. The extraction liquid was dried and the solvent was distilled off under reduced pressure and then the residue was purified by silica gel flash column chromatography (eluting solvent: n-hexane, ethyl acetate/n-hexane=1/9) to obtain 119 (2.28 g, 85%) as a pale yellow oily substance.

APCI-MS m/z 541[M+H]$^+$

Synthesis of THK-5106

To a chloroform (21 ml) solution of 119 (2.25 g, 3.33 mmol), trifluoroacetic acid (14 ml) was added dropwise under ice cooling and stirring, and the mixture was stirred at room temperature for 1 hour and water (7 ml) was added dropwise, followed by further stirring at room temperature for 1 hour. The solvent of the reaction solution was distilled off under reduced pressure and chloroform was added, and the solution was made basic with an aqueous saturated sodium hydrogen carbonate solution and extracted with chloroform/methanol (19/1). The extraction liquid was dried and the solvent was distilled off under reduced pressure. The residue was purified by silica gel flash column chromatography (eluting solvent: chloroform, chloroform/methanol=19/1) and then washed with n-hexane and diisopropylether to obtain THK-5106 (1.0 g, 92%) as a yellow solid.

mp 137-139° C., $^1$H NMR (500 MHz, DMSO-d$_6$) δ 2.76 (3H, d, J=4.4 Hz), 4.1-4.2 (3H, m), 4.4-4.7 (2H, m), 5.53 (1H, d, J=4.8 Hz), 6.13 (1H, brs) 6.66 (2H, d, J=8.7 Hz), 7.15 (1H, dd, J=9.0, 2.6 Hz), 7.35 (1H, d, J=2.6 Hz), 7.80 (1H, d, J=9.0 Hz), 7.83 (1H, d, J=8.7 Hz), 8.06 (2H, d, J=9.0 Hz), 8.20 (1H, d, J=8.3 Hz)

IR (Nujol) 1612, 1598 cm$^{-1}$

APCI-MS m/z 327[M+H]$^+$

Synthesis Method of THK-5107

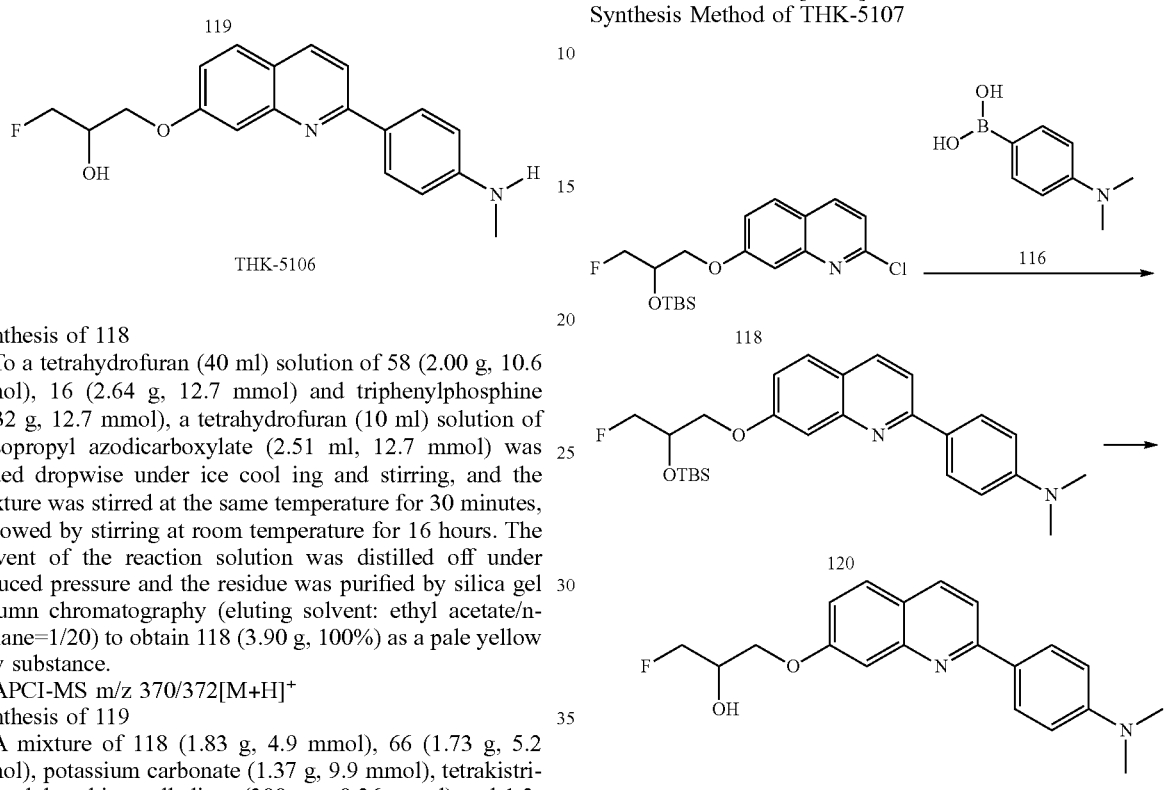

Synthesis of 120

To a 1,2-dimethoxyethane (20 ml) solution of 118 (800 mg, 2.16 mmol) and 116 (390 mg, 2.38 mmol), potassium carbonate (900 mg, 6.49 mmol), water (0.38 ml) and tetrakistriphenylphosphine palladium (380 mg, 0.22 mmol) were added under an argon atmosphere, and the mixture was stirred 80° C. for 3.5 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/19) to obtain 120 (860 mg, 88%) as a pale yellow solid.

mp 102-106° C.

APCI-MS m/z 455[M+H]$^+$

Synthesis of THK-5107

To a tetrahydrofuran (10 ml) solution of 120 (850 mg, 1.87 mmol), tetrabutylammonium fluoride (1.87 ml/1M tetrahydrofuran solution) was added, and the mixture was stirred at room temperature for 30 minutes. Water was added to the reaction solution and the solution was extracted with ethyl acetate. The extraction liquid was washed with water and dried and then the solvent was distilled off under reduced pressure. The residue was purified by silica gel column chromatography (eluting solvent: ethyl acetate/n-hexane=1/4, 1/2) to obtain THK-5107 (352 mg, 55%) as yellow crystals.

mp 163.5-164° C., $^1$H NMR (400 MHz, DMSO-$d_6$) δ 3.01 (6H, s), 4.09-4.22 (3H, m), 4.44-4.65 (2H, m), 5.53 (1H, br), 6.84 (2H, d, J=9.1 Hz), 7.18 (1H, dd, J=8.8, 2.4 Hz), 7.38 (1H, d, J=2.4 Hz), 7.83 (1H, d, J=9.1 Hz), 7.89 (1H, d, J=8.5 Hz), 8.13 (2H, d, J=9.1 Hz), 8.25 (1H, d, J=8.8 Hz)

IR (Nujol) 1619, 1608, 1595 cm$^{-1}$

APCI-MS m/z 341[M+H]$^+$

Synthesis Method of THK-5111

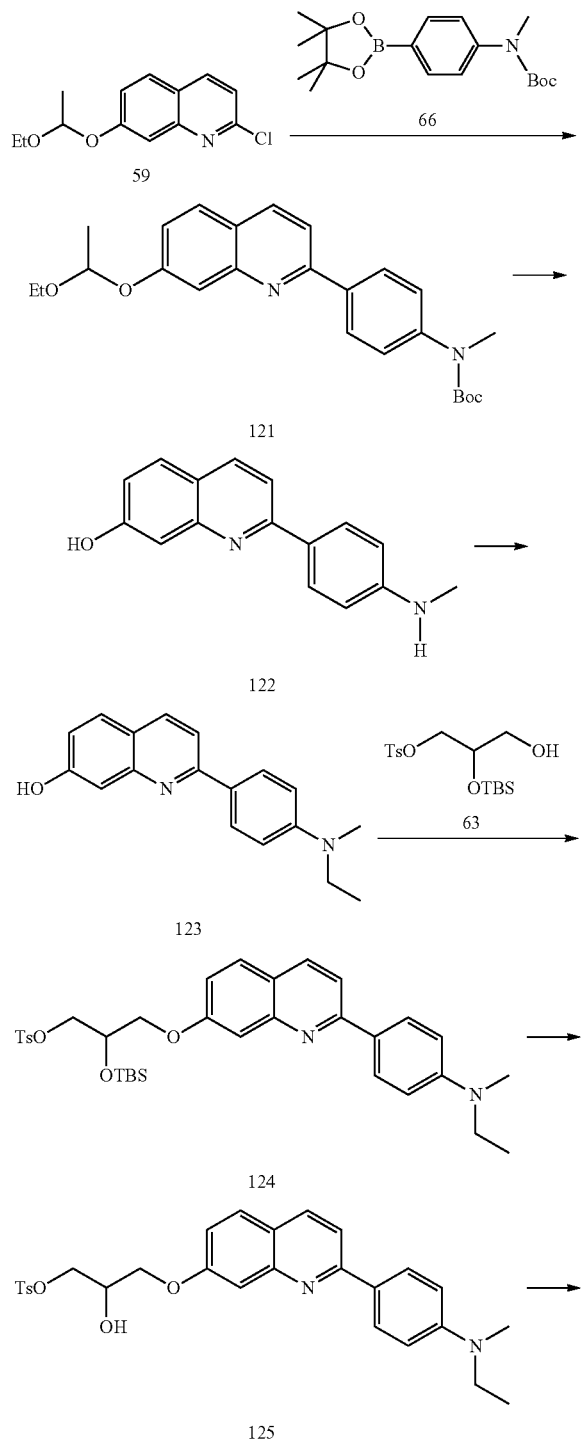

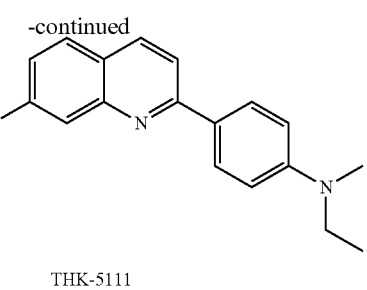

THK-5111

Synthesis of 121

To a 1,2-dimethoxyethane (65 ml) solution of 59 (2.01 g, 7.99 mmol) and 66 (2.66 g, 7.99 mmol), potassium carbonate (3.31 g, 24.0 mmol), water (1.39 ml) and tetrakistriphenylphosphine palladium (920 mg, 0.80 mmol) were added under an argon atmosphere, and the mixture was stirred at 80° C. for 8 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/19, 1/9, 1/4) to obtain 121 (3.38 g, 100%) as a pale yellow oily substance.

APCI-MS m/z 423[M+H]$^+$

Synthesis of 122

To a chloroform (12 ml) solution of 121 (3.37 g, 7.98 mmol), trifluoroacetic acid (8 ml) was added dropwise under ice cooling and stirring, and the mixture was stirred at room temperature for 2 hours. To the reaction solution, water was added, and the solution was extracted with ethyl acetate after adjusting the pH to 9 using an aqueous potassium carbonate solution. The extraction liquid was washed with water and dried, and then the solvent was distilled off under reduced pressure. The residue was recrystallized from ethyl acetate to obtain 122 (1.71 g, 86%) as yellow crystals.

mp 262-265° C.

APCI-MS m/z 251[M+H]$^+$

Synthesis of 123

To a methanol (35 ml)-acetic acid (3.5 ml) solution of 122 (800 mg, 3.20 mmol) and acetoaldehyde (1.80 ml, 32.0 mmol), a picoline borane complex (1.03 g, 9.59 mmol) was added under ice cooling and stirring, and the mixture was stirred at room temperature for 16 hours. To the reaction solution, ice water was added, and the solution was extracted with ethyl acetate after adjusting the pH to 9 using an aqueous potassium carbonate solution. The extraction liquid was washed with water and dried, and then the solvent was distilled off under reduced pressure. The residue was recrystallized from ethyl acetate to obtain 123 (840 mg, 94%) as yellow crystals.

mp 212-213° C.

APCI-MS m/z 279[M+H]$^+$

Synthesis of 124

To a tetrahydrofuran (30 ml) solution of 123 (830 mg, 2.98 mmol), 63 (1.29 g, 3.58 mmol) and triphenylphosphine (940 mg, 3.58 mmol), a tetrahydrofuran (10 ml) solution of diisopropyl azodicarboxylate (0.71 ml, 3.58 mmol) was added dropwise over 1 hour under ice cooling and stirring, and the mixture was stirred at the same temperature 1 hour, followed by stirring at room temperature for 16 hours. To the reaction solution, 63 (540 mg, 1.49 mmol) and triphenylphosphine (390 mg, 1.49 mmol) were added under ice cooling and stirring, and diisopropyl azodicarboxylate (0.3 ml, 1.49 mmol) and tetrahydrofuran (10 ml) were added, followed by further stirring at room temperature for 3 days. The solvent of the reaction solution was distilled off under reduced pressure and the residue was purified by silica gel column chromatography (eluting solvent: ethyl acetate/n-hexane=1/9) to obtain 124 (2.21 g) as a pale yellow oily substance.

APCI-MS m/z 621[M+H]$^+$

Synthesis of 125

To a chloroform (12 ml) solution of 124 (2.21 g), trifluoroacetic acid (8 ml) was added dropwise under ice cooling and stirring and water (2 ml) was added, and the mixture was stirred at room temperature for 16 hours. To the reaction solution, ice water and ethyl acetate were added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/2, 1/1) to obtain 125 (1.27 g, 84% from 123) as a yellow foam-like substance.

APCI-MS m/z 507[M+H]$^+$

Synthesis of THK-5111

To a methylene chloride (30 ml) solution of 125 (940 mg, 1.86 mmol), 3,4-dihydro-2H-pyran (3.36 ml, 37.2 mmol) and paratoluenesulfonic acid monohydrate (415 mg, 2.42 mmol) were added, and the mixture was stirred at room temperature for 40 minutes. The reaction solution was neutralized with triethylamine and the solvent was distilled off under reduced pressure. The residue was purified by silica gel column chromatography (eluting solvent: ethyl acetate/n-hexane=1/4) to obtain THK-5111 (1.05 g, 96%) as a yellow amorphous.

$^1$H NMR (500 MHz, DMSO-d$_6$) δ 1.10 (3H, t, J=7.2 Hz), 1.36-1.70 (6H, m), 2.34 (3H, s), 2.97 (3H, s), 3.37-3.45 (1H, m), 3.49 (2H, q, J=7.2 Hz), 3.68-3.74, 3.84-3.90 (1H, m), 4.13-4.37 (5H, m), 4.71-4.74, 4.86-4.88 (1H, m), 6.84 (2H, d, J=8.7 Hz), 7.06 (1H, d, J=8.7 Hz), 7.31 (1H, br), 7.39-7.44 (2H, m), 7.78-7.84 (3H, m), 7.90 (1H, d, J=9.0 Hz), 8.12 (2H, d, J=9.0 Hz), 8.27 (1H, br)

APCI-MS m/z 591[M+H]$^+$

Synthesis Method of THK-5112

Synthesis of THK-5112

To a methanol (10 ml)-acetic acid (1 ml) solution of THK-5106 (478 mg, 1.46 mmol) and acetoaldehyde (323 mg, 7.3 mmol), a picoline borane complex (204 mg, 1.9 mmol) was added under ice cooling and stirring and the mixture was stirred at room temperature for 1 hour, and acetoaldehyde (323 mg, 7.3 mmol) and a picoline borane complex (204 mg, 1.9 mmol) were added, followed by further stirring at room temperature for 5 hours. The solvent of the reaction solution was distilled off under reduced pressure and aqueous 10% hydrochloric acid (5 ml) was added to the residue. After stirring at room temperature for 30 minute, the solution was made basic by adding potassium carbonate. The reaction solution was extracted with chloroform and the extraction liquid was dried, and then the solvent was distilled off under reduced pressure. The residue was purified by NH silica gel flash column chromatography (eluting solvent: n-hexane, n-hexane/ethyl acetate=1/1) to obtain as a yellow oily substance. After dissolving by adding oxalic acid (292 mg, 2.9 mmol) to an acetone (10 ml) solution of the present product, the solvent was distilled off under reduced pressure. The residue was washed with diisopropylether and diethyl ether to obtain THK-5112 (660 mg, 91%) as an orange solid.

mp 193-194.5° C. (dec), $^1$H NMR (400 MHz, DMSO-d$_6$) δ 1.10 (3H, t, J=7.0 Hz), 2.97 (3H, s), 3.49 (2H, q, J=7.0 Hz), 4.0-4.2 (3H, m), 4.4-4.7 (2H, m), 6.83 (2H, d, J=9.1 Hz), 7.18 (1H, dd, J=8.7, 2.4 Hz), 7.38 (1H, d, J=2.4 Hz), 7.84 (1H, d, J=9.1 Hz), 7.89 (1H, d, J=8.7 Hz), 8.12 (2H, d, J=9.0 Hz), 8.27 (1H, d, J=8.8 Hz)

IR (Nujol) 2922, 2852 cm$^{-1}$

APCI-MS m/z 355[M+H]$^+$

Synthesis Method of THK-5113

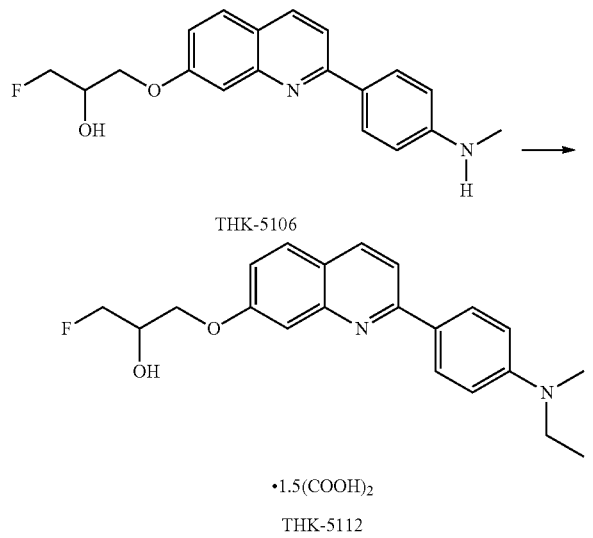

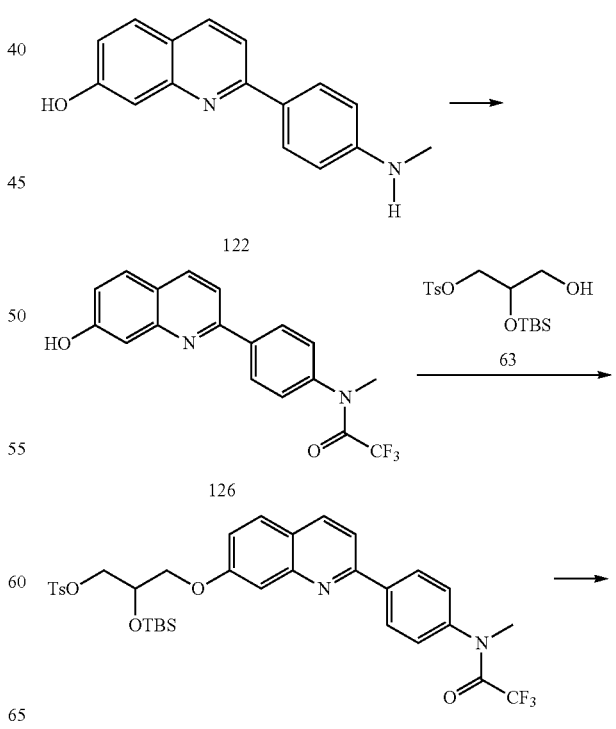

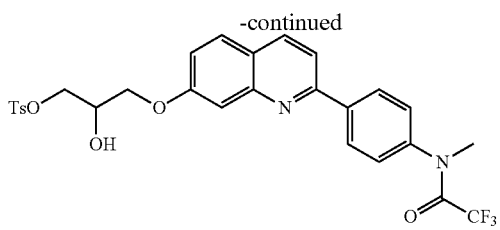

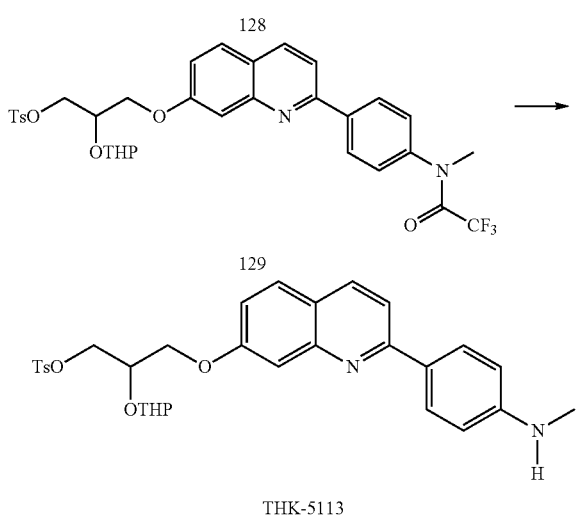

THK-5113

Synthesis of 126

To a methylene chloride (20 ml) suspension of 122 (900 mg, 3.60 mmol) and triethylamine (1.51 ml, 10.79 mmol), trifluoro acid anhydride (1.22 ml, 8.63 mmol) was added dropwise under ice cooling and stirring, and the mixture was stirred at the same temperature for 30 minutes. To the reaction solution, ice water was added and the solution was extracted with chloroform/methanol. The extraction liquid was dried and the solvent was distilled off under reduced pressure, and then the residue was recrystallized from ethyl acetate-n-hexane to obtain 126 (1.24 g, 99%) as orange crystals.

mp 176-178° C.

APCI-MS m/z 347[M+H]$^+$

Synthesis of 127

To a tetrahydrofuran (30 ml) suspension of 126 (1.23 g, 3.55 mmol), 63 (1.54 g, 4.26 mmol) and triphenylphosphine (1.12 g, 4.26 mmol), a tetrahydrofuran (10 ml) solution of diisopropyl azodicarboxylate (0.84 ml, 4.26 mmol) was added dropwise over 20 minutes under ice cooling and stirring, and the mixture was stirred at the same temperature 2 hours, followed by stirring at room temperature for 16 hours. To the reaction solution, 63 (640 mg, 1.78 mmol), triphenylphosphine (470 mg, 1.78 mmol) and diisopropyl azodicarboxylate (0.35 ml, 1.78 mmol) were added, followed by stirring at room temperature for 4 hours. Furthermore, 63 (640 mg, 1.78 mmol), triphenylphosphine (470 mg, 1.78 mmol) and diisopropyl azodicarboxylate (0.35 ml, 1.78 mmol) were added to the reaction solution, followed by stirring at room temperature for 16 hours. The solvent of the reaction solution was distilled off under reduced pressure and the residue was purified by silica gel column chromatography (eluting solvent: ethyl acetate/n-hexane=1/4) to obtain 127 (3.28 g) as a pale yellow oily substance.

APCI-MS m/z 347[M+H]$^+$

Synthesis of 128

To a chloroform (12 ml) solution of 127 (3.27 g), trifluoroacetic acid (8 ml) was added dropwise and water (2 ml) was added under ice cooling and stirring, and the mixture was stirred at room temperature for 8 hours. To the reaction solution, ice water and ethyl acetate were added, and the solution was extracted with ethyl acetate after adjusting the pH to 7 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/2, 1/1) to obtain 128 (1.85 g, 91% from 126) as a pale yellow foam-like substance.

APCI-MS m/z 575[M+H]$^+$

Synthesis of 129

To a tetrahydrofuran (60 ml) solution of 128 (1.84 g, 3.20 mmol) and 3,4-dihydro-2H-pyran (5.81 ml, 64.1 mmol), paratoluenesulfonic acid monohydrate (720 mg, 4.16 mmol) was added, and the mixture was stirred at room temperature for 16 hours. The reaction solution was neutralized with triethylamine and the solvent was distilled off under reduced pressure. The residue was purified by silica gel column chromatography (eluting solvent: ethyl acetate/n-hexane=1/9, 1/4, 1/2) to obtain 129 (2.10 g, 99%) as a pale yellow foam-like substance.

APCI-MS m/z 659[M+H]$^+$

Synthesis of THK-5113

To a tetrahydrofuran (25 ml)-water (10 ml) solution of 129 (2.09 g, 3.17 mmol), lithium hydroxide monohydrate (200 mg, 4.76 mmol) was added under ice cooling and stirring, and the mixture was stirred at the same temperature for 30 minutes. The reaction solution was extracted with ethyl acetate, and the extraction liquid was dried and the solvent was distilled off under reduced pressure. The residue was purified by silica gel column chromatography (eluting solvent: ethyl acetate/n-hexane=1/2) to obtain THK-5113 (1.70 g, 95%) as a pale yellow amorphous.

$^1$H NMR (400 MHz, DMSO-d$_6$) δ 1.36-1.72 (6H, m), 2.34 (3H, s), 2.76 (3H, d, J=4.2 Hz), 3.35-3.48, 3.67-3.76, 3.83-3.91 (2H, m), 4.11-4.37 (5H, m), 4.70-4.74, 4.85-4.88 (1H, m), 6.14 (1H, br), 6.66 (2H, d, J=8.8 Hz), 7.03 (1H, dd, J=8.8, 2.4 Hz), 7.24-7.28 (1H, m), 7.39-7.44 (2H, m), 7.76-7.87 (4H, m), 8.07 (2H, d, J=8.8 Hz), 8.21 (1H, d, J=8.8 Hz)

IR (Nujol) 3422, 1609, 1596 cm$^{-1}$

APCI-MS m/z 563[M+H]$^+$

Synthesis Method of THK-5115

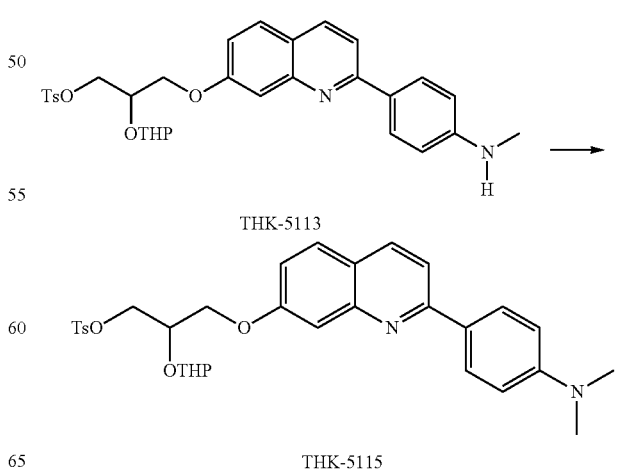

THK-5113

THK-5115

Synthesis of THK-5115

To a methanol (20 ml)-acetic acid (2 ml) solution of THK-5113 (1.02 g, 1.81 mmol) and an aqueous 37% formalin solution (1.45 ml, 18.1 mmol), a picoline borane complex (580 mg, 5.44 mmol) was added under ice cooling and stirring, and the mixture was stirred at the same temperature for 5 minutes, followed by stirring at room temperature for 1 hour. To the reaction solution, ice water was added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=4/1) to obtain THK-5115 (980 mg, 93%) as a yellow amorphous.

$^1$H NMR (500 MHz, DMSO-$d_6$) δ 1.36-1.71 (6H, m), 2.34 (3H, s), 3.01 (6H, s), 3.37-3.47 (1H, m), 3.69-3.74, 3.84-3.90 (1H, m), 4.13-4.37 (5H, m), 4.71-4.74, 4.85-4.88 (1H, m), 6.85 (2H, d, J=9.0 Hz), 7.05 (1H, d, J=8.7 Hz), 7.30 (1H, br), 7.40-7.44 (2H, m), 7.78-7.84 (3H, m), 7.90 (1H, d, J=9.3 Hz), 8.14 (2H, d, J=8.7 Hz), 8.25 (1H, br)

IR (Nujol) 1731, 1620, 1595 cm$^{-1}$

APCI-MS m/z 577[M+H]$^+$

Synthesis Method of THK-5116

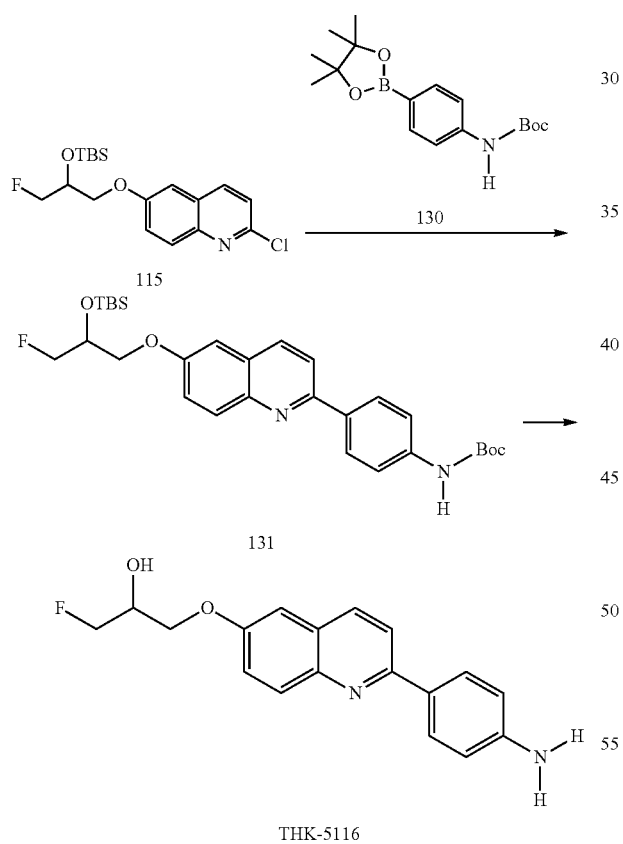

Synthesis of 131

A mixture of 115 (625 mg, 1.69 mmol), 130 (593 mg, 1.86 mmol), potassium carbonate (467 mg, 3.40 mmol), tetrakistriphenylphosphine palladium (195 mg, 0.169 mmol) and 1,2-dimethoxyethane (4.5 ml)-water (0.5 ml) was stirred under an argon atmosphere at 85° C. for 16 hours, and tetrakistriphenylphosphine palladium (98 mg, 0.085 mmol) was added, followed by further stirring at the same temperature for 8 hours. The reaction solution was allowed to return to room temperature and chloroform was added, and then insolubles were removed by filtration and the solution was washed with chloroform. The chloroform layers were combined and dried, and then the solvent was distilled off under reduced pressure. The residue was purified by silica gel flash column chromatography (eluting solvent: ethyl acetate/n-hexane=1/19, 1/9, 1/6) to obtain 131 (799 mg, 90%) as a pale brown solid.

APCI-MS m/z 527[M+H]$^+$

Synthesis of THK-5116

To a chloroform (10 ml) solution of 131 (790 mg, 1.50 mmol), trifluoroacetic acid (5 ml) was added dropwise under ice cooling and stirring, and the mixture was stirred at room temperature for 1 hour and water (5 ml) was added dropwise, followed by further stirring at room temperature for 1 hour. After the organic the solvent was distilled off under reduced pressure, the reaction solution was made basic under ice cooling using an aqueous saturated potassium carbonate solution. The precipitate was collected by filtration, washed with water and then dried. The obtained solid was purified by NH silica gel flash column chromatography (eluting solvent: chloroform, chloroform/methanol=9/1, 1/1) and then washed with methanol to obtain THK-5116 (396 mg, 84%) as a yellow solid.

mp 219-221° C., $^1$H NMR (500 MHz, DMSO-$d_6$) δ4.0-4.2 (3H, m), 4.4-4.7 (2H, m), 5.53 (3H, brs), 6.67 (2H, d, J=8.6 Hz), 7.3-7.4 (2H, m), 7.87 (1H, d, J=7.3 Hz), 7.92 (1H, d, J=8.6 Hz), 7.95 (2H, d, J=8.7 Hz), 8.19 (1H, d, J=8.6 Hz)

IR (Nujol) 1623, 1600 cm$^{-1}$

APCI-MS m/z 313[M+H]$^+$

Synthesis Method of THK-5117

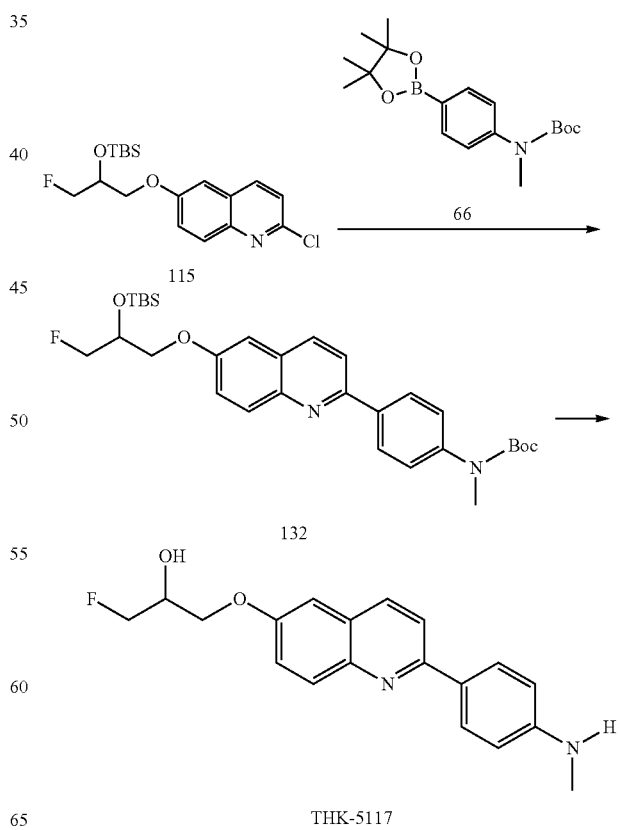

Synthesis of 132

A mixture of 115 (625 mg, 1.69 mmol), 66 (619 mg, 1.86 mmol), potassium carbonate (467 mg, 3.4 mmol), tetrakis-triphenylphosphine palladium (195 mg, 0.169 mmol) and 1,2-dimethoxyethane (4.5 ml)-water (0.5 ml) was stirred under an argon atmosphere at 85° C. for 16 hours. The reaction solution was allowed to return to room temperature and water was added, and the solution was extracted with ethyl acetate. The extraction liquid was dried and the solvent was distilled off under reduced pressure, and then the residue was purified by silica gel flash column chromatography (eluting solvent: n-hexane, ethyl acetate/n-hexane=1/19, 1/9, 1/6) to obtain 132 (920 mg, 100%) as a colorless oily substance.

APCI-MS m/z 541[M+H]$^+$

Synthesis of THK-5117

To a chloroform (10 ml) solution of 132 (912 mg, 1.69 mmol), trifluoroacetic acid (5 ml) was added dropwise under ice cooling and stirring, and the mixture was stirred at room temperature for 1 hour and water (5 ml) was added dropwise, followed by further stirring at room temperature for 1 hour. After the organic the solvent was distilled off under reduced pressure, the reaction solution was made basic under ice cooling using an aqueous saturated potassium carbonate solution, and the solution was extracted with chloroform-methanol. The extraction liquid was dried and the solvent was distilled off under reduced pressure, and then the residue was washed with diisopropylether to obtain THK-5117 (468 mg, 85%) as a yellow solid.

mp 158-159° C., $^1$H NMR (500 MHz, DMSO-d$_6$) δ 2.75 (3H, d, J=1.8 Hz), 4.0-4.2 (3H, m), 4.4-4.7 (2H, m), 5.53 (1H, d, J=4.8 Hz), 6.09 (1H, brs), 6.65 (2H, d, J=8.9 Hz), 7.3-7.4 (2H, m), 7.87 (1H, d, J=8.7 Hz), 7.94 (1H, d, J=8.7 Hz), 8.03 (2H, d, J=8.6 Hz), 8.20 (1H, d, J=8.7 Hz)

IR (Nujol) 1600 cm$^{-1}$

APCI-MS m/z 327[M+H]$^+$

Synthesis Method of THK-5100

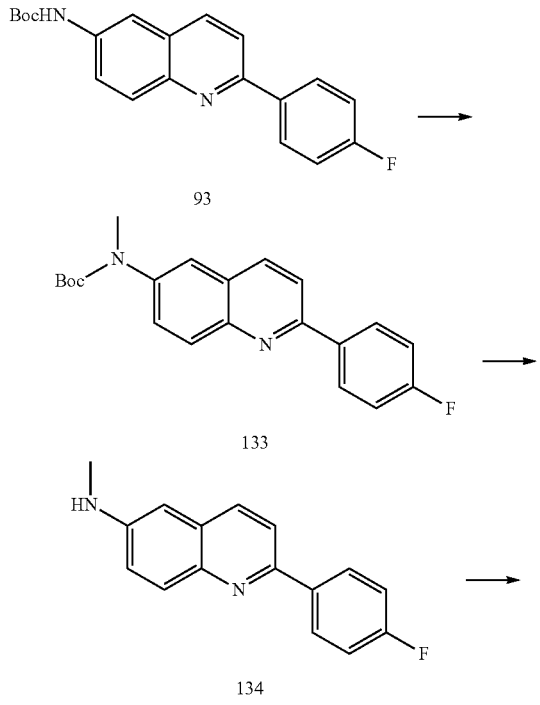

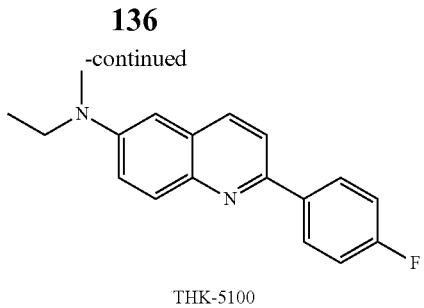

THK-5100

Synthesis of 133

To a N,N-dimethylformamide (10 ml) solution of 93 (790 mg, 2.34 mmol), 60% sodium hydride (112 mg, 2.81 mmol) was added under ice cooling and stirring under an argon atmosphere, and the mixture was stirred at the same temperature for 5 minutes and methyl iodide (0.22 ml, 3.5 mmol) was added dropwise, followed by stirring at the same temperature for 10 minutes. To the reaction solution, ice water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9, 1/4) to obtain 133 (800 mg, 97%) as a pale yellow solid.

mp 144-145° C.

APCI-MS m/z 353[M+H]$^+$

Synthesis of 134

To a chloroform (12 ml) solution of 133 (790 mg, 2.24 mmol), trifluoroacetic acid (8 ml) was added dropwise under ice cooling and stirring, and the mixture was stirred at room temperature for 1 hour. To the reaction solution, ice water was added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/4) to obtain 134 (568 mg, 100%) as a pale yellow solid.

mp 134-134.5° C.

APCI-MS m/z 253[M+H]$^+$

Synthesis of THK-5100

To a methanol (24 ml)-acetic acid (2.4 ml) solution of 134 (560 mg, 2.22 mmol) and acetoaldehyde (1.25 ml, 22.2 mmol), a picoline borane complex (710 mg, 6.66 mmol) was added little by little under ice cooling and stirring, and the mixture was stirred at room temperature for 16 hours. To the reaction solution, ethyl acetate was added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=9/1) and then washed with n-hexane to obtain THK-5100 (475 mg, 76%) as pale yellow crystals.

mp 137-138° C., $^1$H NMR (400 MHz, DMSO-d$_6$) δ 1.11 (3H, t, J=7.1 Hz), 3.01 (3H, s), 3.55 (2H, q, J=7.1 Hz), 6.93 (1H, d, J=2.7 Hz), 7.33 (2H, t, J=8.9 Hz), 7.46 (1H, dd, J=9.4, 3.0 Hz), 7.87 (1H, d, J=9.4 Hz), 7.95 (1H, d, J=8.8 Hz), 8.15 (1H, d, J=8.8 Hz), 8.24 (2H, dd, J=9.1, 5.7 Hz)

IR (Nujol) 1618 cm$^{-1}$

APCI-MS m/z 281[M+H]$^+$

Synthesis Method of THK-5091 and THK-5092

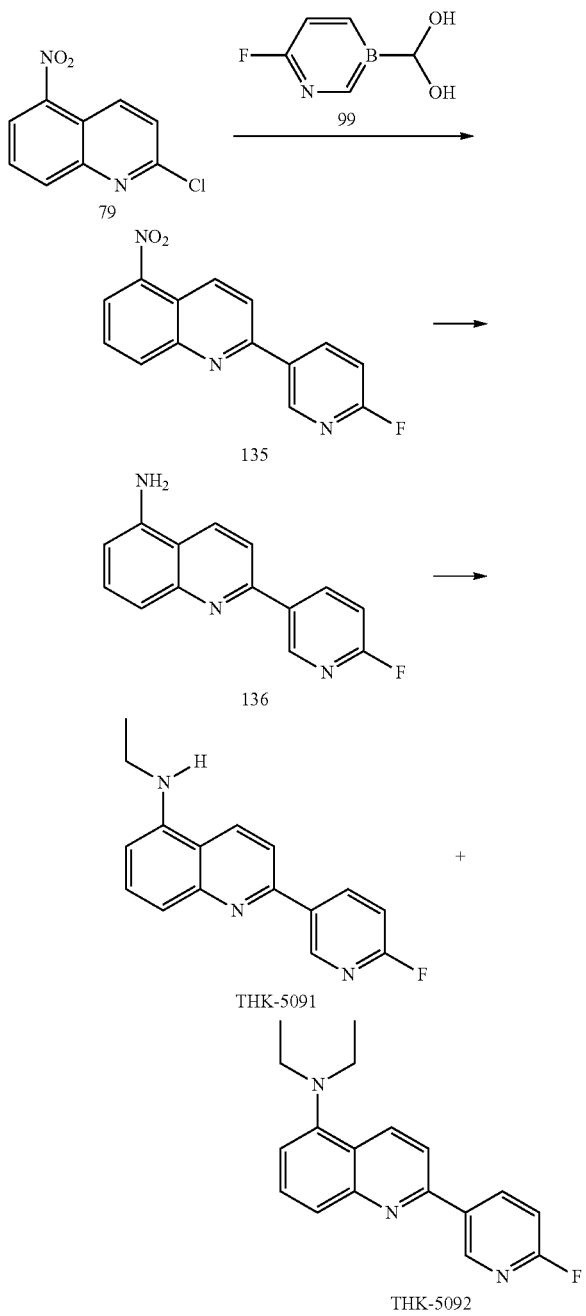

Synthesis of 135

To a mixture of 79 (627 mg, 3.0 mmol), 99 (465 mg, 3.3 mmol) and 1,2-dimethoxyethane (20 ml), an aqueous 2M sodium carbonate solution (3 ml, 6.0 mmol) and tetrakistriphenylphosphine palladium (173 mg, 0.15 mmol) were added under an argon atmosphere, and the mixture was heated at reflux for 3 hours. The reaction solution was allowed to return to room temperature, diluted with ethyl acetate and then washed in turn with water and saturated saline. The organic layer was dried and the solvent was distilled off under reduced pressure, and then the residue was purified by silica gel flash column chromatography (eluting solvent: n-hexane/ethyl acetate=4/1, 3/1) to obtain 135 (700 mg, 87%) as a pale yellow solid.

mp 159-161° C.
APCI-MS m/z 270[M+H]$^+$

Synthesis of 136

A mixture of 135 (260 mg, 0.96 mmol), 10% Pd—C (100 mg), ethanol (30 ml) and ethyl acetate (10 ml) was stirred under a hydrogen atmosphere at room temperature for 16 hours. The catalyst was removed by filtration and the solvent of the filtrate was distilled off under reduced pressure, and then the residue was washed with diisopropylether to obtain 136 (178 mg, 77%) as a solid.

mp 156-157° C.
APCI-MS m/z 240[M+H]$^+$

Synthesis of THK-5091, THK-5092

To a methanol (20 ml)-acetic acid (1 ml) solution of 136 (170 mg, 0.71 mmol) and acetoaldehyde (300 mg, 7 mmol), a picoline borane complex (230 mg, 2.14 mmol) was added little by little under ice cooling and stirring, and the mixture was stirred at room temperature for 8 hours. To the reaction solution, saturated saline was added and the solution was extracted with ethyl acetate. The extraction liquid was washed with saturated saline and dried, and then the solvent was distilled off under reduced pressure. The residue was purified by silica gel column chromatography (eluting solvent: n-hexane/ethyl acetate=10/1) to obtain THK-5092 (120 mg, 57%) and THK-5091 (70 mg, 41%) in the order of elution.

THK-5092

Yellow oily substance, $^1$H NMR (400 MHz, CDCl$_3$) δ 1.07 (6H, t, J=7.2 Hz), 3.22 (4H, q, J=7.2 Hz), 7.09 (1H, dd, J=8.2, 2.4 Hz), 7.20 (1H, dd, J=7.3, 0.9 Hz), 7.67 (1H, dd, J=9.6, 8.6 Hz), 7.80 (1H, d, J=9.1 Hz), 7.85 (1H, d, J=8.5 Hz), 8.66 (1H, m), 8.72 (1H, dd, J=8.8, 0.9 Hz), 8.94 (1H, d, J=2.7 Hz)

IR (Nujol) 1586 cm$^{-1}$
APCI-MS m/z 296[M+H]$^+$

THK-5091 mp 175-176° C., 1H NMR (400 MHz, CDCl$_3$) δ 1.48 (3H, t, J=7.3 Hz), 3.35 (2H, q, J=7.3 Hz), 4.27 (1H, brs), 6.66 (1H, d, J=7.0 Hz), 7.08 (1H, dd, J=7.9, 2.1 Hz), 7.52 (1H, d, J=8.5 Hz), 7.61 (1H, t), 7.75 (1H, d, J=8.8 Hz), 8.27 (1H, d, J=8.8 Hz), 8.66 (1H, m), 8.93 (1H, d, J=2.7 Hz)

IR (Nujol) 3332, 1610 cm$^{-1}$
APCI-MS m/z 268[M+H]$^+$

Synthesis Method of THK-5097

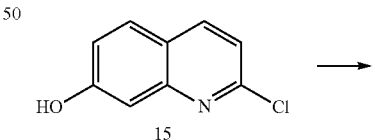

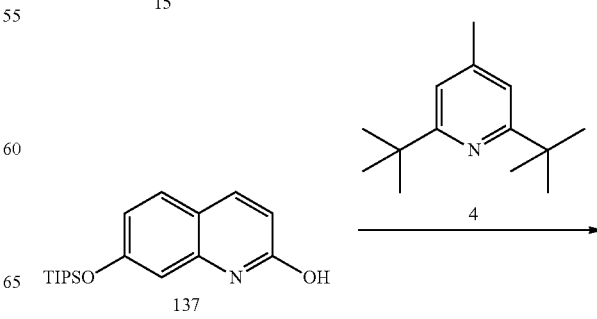

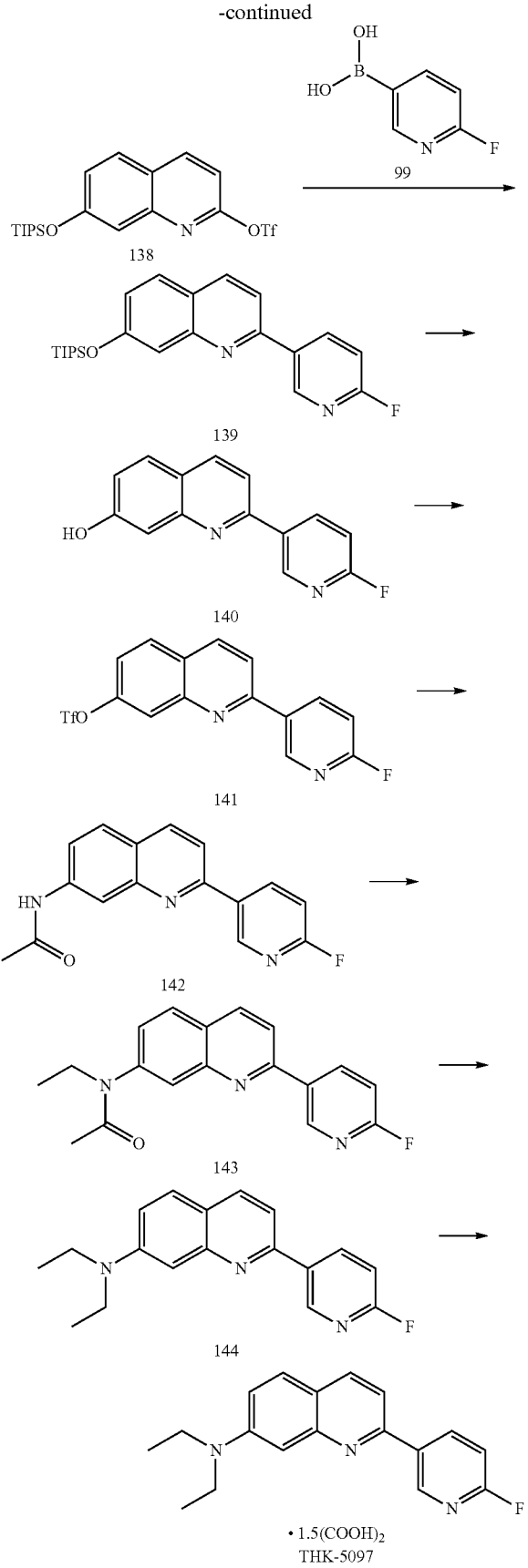

Synthesis of 137

A mixture of 15 (3.73 g, 23 mmol), triisopropylsilane chloride (5.0 q, 26 mmol), imidazole (2.07 g, 26 mmol) and N,N-dimethylformamide (50 ml) was stirred at room temperature for 16 hours. To the reaction solution, ice water was added and the solution was extracted with ethyl acetate. The extraction liquid was washed with water and dried, and then the solvent was distilled off under reduced pressure. The residue was purified by silica gel flash column chromatography (eluting solvent: n-hexane, n-hexane/ethyl acetate=3/1, 1/1) and then washed with n-hexane to obtain 137 (6.52 g, 89%) as a pale brown solid.

Synthesis of 138

To a methylene chloride (40 ml) solution of 137 (6.36 g, 20 mmol) and 4 (5.76 g, 28 mmol), a methylene chloride (10 ml) solution of trifluoromethanesulfonic anhydride (4.3 ml, 26 mmol) was added dropwise under ice cooling and stirring, and the mixture was stirred at the same temperature 1 hour. To the reaction solution, ice water was added and insolubles were removed by filtration, followed by washing with chloroform. The organic layers were combined and dried, and then the solvent was distilled off under reduced pressure. The residue was purified by silica gel flash column chromatography (eluting solvent: n-hexane, n-hexane/ethyl acetate=19/1, 9/1) to obtain 138 (8.60 g, 95%) as a brown oily substance.

Synthesis of 139

To a mixture of 138 (4.24 g, 9.4 mmol), 99 (1.54 g, 10.9 mmol) and 1,2-dimethoxyethane (80 ml), tripotassium phosphate (3.98 g) and tetrakistriphenylphosphine palladium (575 mg, 0.498 mmol) were added under an argon atmosphere, and the mixture was heated at reflux for 16 hours. The reaction solution was allowed to return to room temperature and insolubles were removed by filtration, followed by washing with chloroform. The organic layers were combined and the solvent was distilled off under reduced pressure. To the residue, chloroform-water was added and the solution was extracted with chloroform. The extraction liquid was dried and the solvent was distilled off under reduced pressure, and then the residue was purified by silica gel flash column chromatography (eluting solvent: n-hexane, n-hexane/ethyl acetate=50/1, 20/1) to obtain 139 (3.31 g, 88%) as a pale brown oily substance.

Synthesis of 140

To 139 (3.31 g, 8.35 mmol), tetrahydrofuran (4 ml) and then tetrabutylammonium fluoride (8.5 ml/1M tetrahydrofuran solution) were added, and the mixture was stirred at room temperature for 1 hour. The solvent of the reaction solution was distilled off under reduced pressure, and the residue was dissolved in chloroform and washed with water. The organic layer was dried and then the solvent was distilled off under reduced pressure. The residue was purified by silica gel flash column chromatography (eluting solvent: chloroform, chloroform/methanol=50/1, 20/1, 10/1) and then washed with n-hexane and diisopropylether to obtain 140 (1.87 g, 93%) as a pale brown solid.

Synthesis of 141

To a methylene chloride (20 ml) solution of 140 (1.87 g, 7.8 mmol) and ethyldiisopropylamine (2.6 ml, 15.3 mmol), a methylene chloride (10 ml) solution of trifluoromethanesulfonic anhydride (2.35 ml, 14.3 mmol) was added dropwise under ice cooling and stirring, and the mixture was stirred at room temperature for 1.5 hours. The reaction solution was poured into ice water and the solution was extracted with chloroform. The extraction liquid was dried and the solvent was distilled off under reduced pressure, and then residue was purified by silica gel flash column chromatography (eluting solvent: n-hexane, n-hexane/ethyl acetate=50/1, 20/1, 10/1) to obtain 141 (1.81 g, 62%) as a pale yellow solid.

Synthesis of 142

To a mixture of 141 (2.03 g, 5.3 mmol), acetoamide (393 mg, 6.65 mmol) and 1,4-dioxane (50 ml), cesium carbonate (2.49 g), Pd$_2$(dba)$_2$ (251 mg) and Xantphos (316 mg) were added under an argon atmosphere, and the mixture was heated at reflux for 16 hours. The reaction solution was allowed to return to room temperature and insolubles were removed by filtration, followed by washing with chloroform. The organic layers were combined and the solvent was distilled off under reduced pressure. To the residue, chloroform-water was added and the solution was extracted with chloroform. The extraction liquid was dried and the solvent was distilled off under reduced pressure, and then the residue was purified by silica gel flash column chromatography (eluting solvent: chloroform, chloroform/methanol=50/1, 20/1) to obtain 142 (1.35 g, 88%) as a pale brown solid.

Synthesis of 143

To an N,N-dimethylformamide (8 ml) solution of 142 (650 mg, 2.3 mmol), 60% sodium hydride (111 mg, 2.7 mmol) was added under ice cooling and stirring under an argon atmosphere, and the mixture was stirred at the same temperature for 20 minutes and an N,N-dimethylformamide (4 ml) solution of ethyl iodide (396 mg, 2.5 mmol) was added dropwise at the same temperature, followed by stirring at room temperature for 1 hour. To the reaction solution, ice water was added and the solution was extracted with ethyl acetate. The extraction liquid was washed with water and dried, and then the solvent was distilled off under reduced pressure. The residue was purified by silica gel flash column chromatography (eluting solvent: ethyl acetate/n-hexane=1/2, 1/1, 2/1) and then washed with n-hexane to obtain 143 (575 mg, 802) as a pale brown solid.

APCI-MS m/z 310[M+H]$^+$

Synthesis of 144

To a tetrahydrofuran (2 ml) solution of 143 (531 mg, 1.7 mmol), Zr(BH$_4$)$_2$ (14 ml/0.24M tetrahydrofuran solution) was added dropwise under ice cooling and stirring, and the mixture was stirred at the same temperature for 30 minutes. To the reaction solution, methanol was added and the solvent was distilled off under reduced pressure. To the residue, an aqueous saturated sodium hydrogen carbonate solution-chloroform was added and insolubles were removed by filtration, and then the aqueous layer was extracted with chloroform. The extraction liquid was dried and the solvent was distilled off under reduced pressure, and then the residue was purified by silica gel flash column chromatography (eluting solvent: ethyl acetate/n-hexane=1/20, 1/10) to obtain 144 (249 mg, 49%) as a yellow oily substance.

APCI-MS m/z 296[M+H]$^+$

Synthesis of THK-5097

After dissolving by adding oxalic acid (150 mg, 1.7 mmol) to an acetone (10 ml) solution of 144 (246 mg, 0.83 mmol), the solvent was distilled off under reduced pressure. The residue was washed with diisopropylether to obtain THK-5097 (305 mg, 84%) as an orange solid.

mp 127-129° C., $^1$H NMR (400 MHz, DMSO-d$_6$) δ 1.19 (6H, t, J=7.0 Hz), 3.52 (4H, q, J=7.0 Hz), 7.01 (1H, d, J=2.5 Hz), 7.27 (1H, d, J=2.5 Hz), 7.34 (1H, dd, J=8.6, 2.5 Hz), 7.7-7.8 (2H, m), 8.24 (1H, d, J=8.5 Hz), 8.7-8.8 (1H, m), 9.02 (1H, d, J=9.7 Hz)

IR (Nujol) 1659 cm$^{-1}$

APCI-MS m/z 296[M+H]$^+$

Synthesis of THK-5098

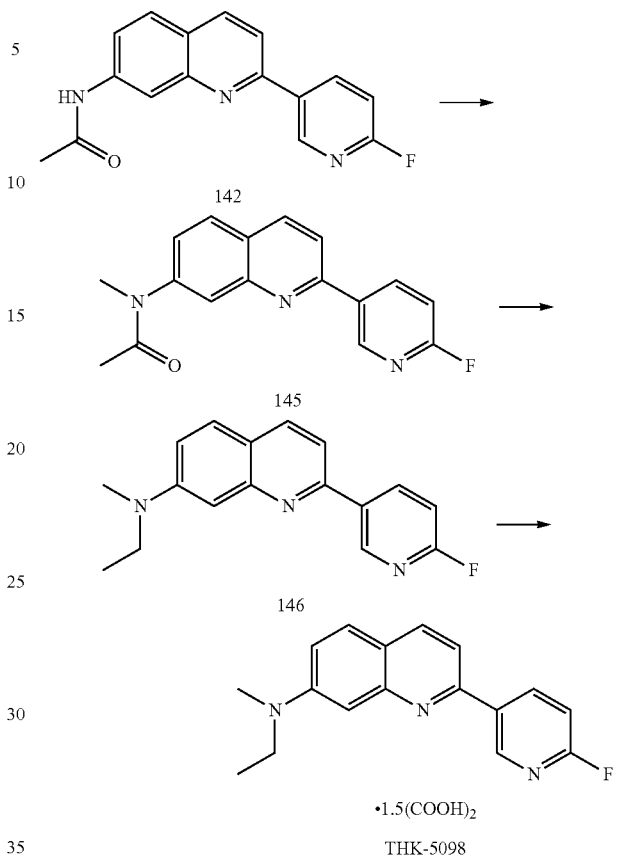

Synthesis of 145

To an N,N-dimethylformamide (6 ml) solution of 142 (650 mg, 2.3 mmol), 60% sodium hydride (111 mg, 2.7 mmol) was added under ice cooling and stirring under an argon atmosphere, and the mixture was stirred at the same temperature for 20 minutes and an N,N-dimethylformamide (4 ml) solution of ethyl iodide (360 mg, 2.5 mmol) was added dropwise at the same temperature, followed by stirring at room temperature for 1 hour. To the reaction solution, ice water was added and the solution was extracted with ethyl acetate. The extraction liquid was dried and the solvent was distilled off under reduced pressure. The residue was purified by silica gel flash column chromatography (eluting solvent: ethyl acetate/n-hexane=1/2, 1/1, 2/1) and then washed with n-hexane to obtain 145 (518 mg, 76%) as a pale brown solid.

Synthesis of 146

To a tetrahydrofuran (4 ml) solution of 145 (517 mg, 1.75 mmol), Zr(BH$_4$)$_2$ (14 ml/0.24M tetrahydrofuran solution) was added dropwise under ice cooling and stirring, and the mixture was stirred at room temperature for 30 minutes. The reaction solution was ice-cooled and methanol was added, and the solvent was distilled off under reduced pressure. To the residue, methanol was added and methanol was distilled off under reduced pressure. To the residue, an aqueous saturated sodium hydrogen carbonate solution-ethyl acetate was added and insolubles were removed by filtration, and then aqueous layer was extracted with ethyl acetate. The extraction liquid was dried and the solvent was distilled off under reduced pressure, and then the residue was purified by silica gel flash column chromatography (eluting solvent:

ethyl acetate/n-hexane=1/20, 1/10) to obtain 146 (258 mg, 52%) as a yellow oily substance.

Synthesis of THK-5098

After dissolving by adding oxalic acid (164 mg, 1.8 mmol) to an acetone (10 ml) solution of 146 (257 mg, 0.91 mmol), the solvent was distilled off under reduced pressure. The residue was washed with diisopropylether to obtain THK-5098 (333 mg, 88%) as an orange solid.

$^1$H NMR (400 MHz, DMSO-$d_6$) δ 1.13 (3H, t, J=7.0 Hz), 3.05 (3H, s), 3.58 (2H, q, J=7.0 Hz), 7.03 (1H, d, J=2.5 Hz), 7.3-7.4 (2H, m), 7.8-7.9 (2H, m), 8.25 (1H, d, J=8.1 Hz), 8.7-8.8 (1H, m), 9.03 (1H, d, J=2.5 Hz)

IR (Nujol) 1646 cm$^{-1}$

APCI-MS m/z 282[M+H]$^+$

Synthesis Method of THK-5119

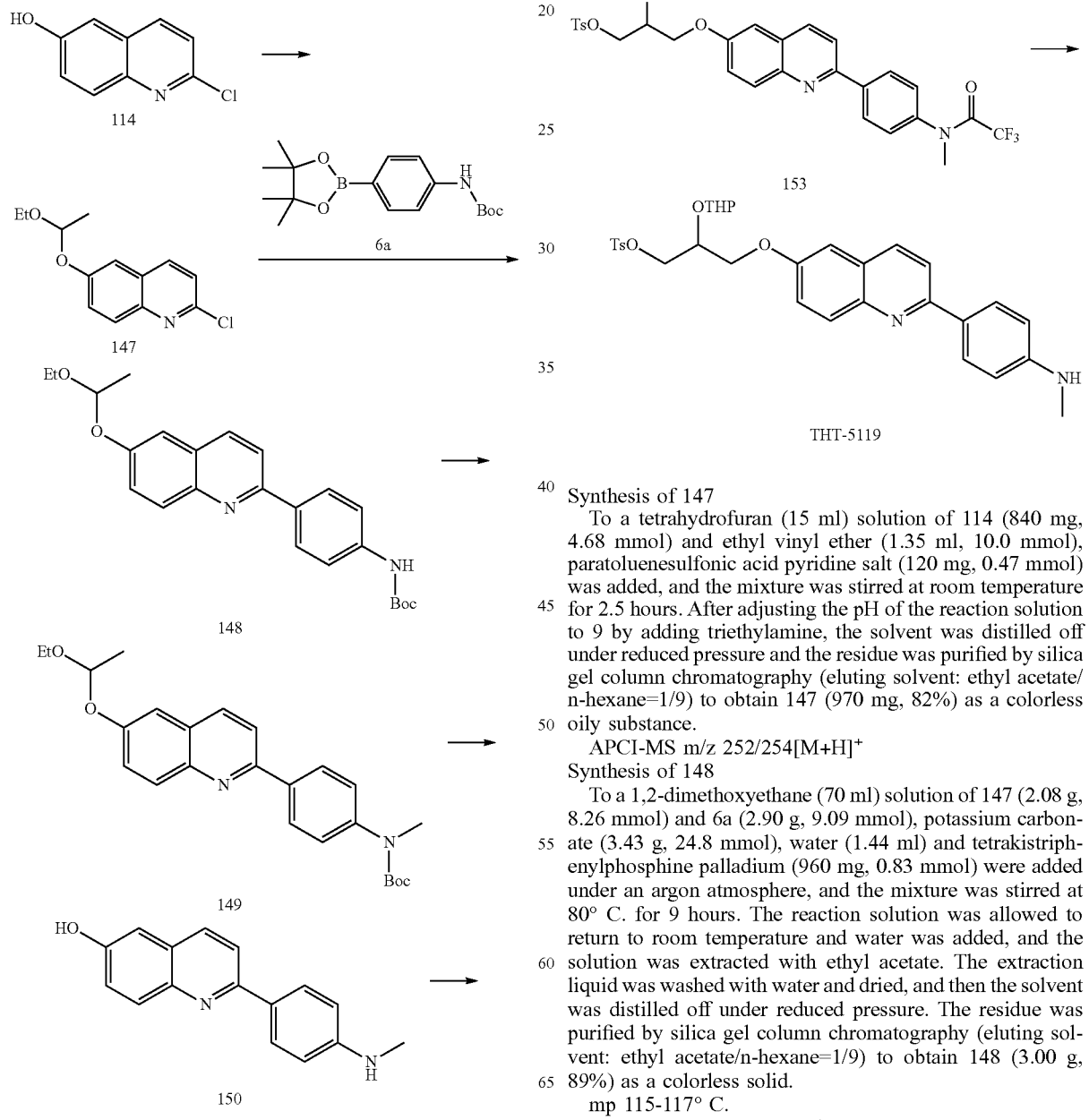

Synthesis of 147

To a tetrahydrofuran (15 ml) solution of 114 (840 mg, 4.68 mmol) and ethyl vinyl ether (1.35 ml, 10.0 mmol), paratoluenesulfonic acid pyridine salt (120 mg, 0.47 mmol) was added, and the mixture was stirred at room temperature for 2.5 hours. After adjusting the pH of the reaction solution to 9 by adding triethylamine, the solvent was distilled off under reduced pressure and the residue was purified by silica gel column chromatography (eluting solvent: ethyl acetate/n-hexane=1/9) to obtain 147 (970 mg, 82%) as a colorless oily substance.

APCI-MS m/z 252/254[M+H]$^+$

Synthesis of 148

To a 1,2-dimethoxyethane (70 ml) solution of 147 (2.08 g, 8.26 mmol) and 6a (2.90 g, 9.09 mmol), potassium carbonate (3.43 g, 24.8 mmol), water (1.44 ml) and tetrakistriphenylphosphine palladium (960 mg, 0.83 mmol) were added under an argon atmosphere, and the mixture was stirred at 80° C. for 9 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9) to obtain 148 (3.00 g, 89%) as a colorless solid.

mp 115-117° C.

APCI-MS m/z 409[M+H]$^+$

Synthesis of 149

To an N,N-dimethylformamide (25 ml) solution of 148 (1.79 g, 4.38 mmol), 60% sodium hydride (210 mg, 5.25 mmol) was added under ice cooling and stirring and an argon atmosphere at the same temperature. After stirring at the same temperature for 10 minutes, methyl iodide (0.41 ml, 6.57 mmol) was added dropwise and the mixture was stirred at the same temperature for 10 minutes. To the reaction solution, ice water was added and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4) to obtain 149 (1.85 g, 100%) as a colorless resinous substance.

APCI-MS m/z 423[M+H]$^+$

Synthesis of 150

To a chloroform (12 ml) solution of 149 (1.85 g, 4.38 mmol), trifluoroacetic acid (8 ml) was added dropwise under ice cooling and stirring, and the mixture was stirred at room temperature for 1 hour. To the reaction solution, ice water was added and the solution was extracted with ethyl acetate. The extraction liquid was washed with water and dried, and then the solvent was distilled off under reduced pressure. The residue was ground and then washed with ethyl acetate/n-hexane (1/4) to obtain 150 (1.04 g, 95%) as orange crystals.

mp 273-275° C.

APCI-MS m/z 251[M+H]$^+$

Synthesis of 151

To a methylene chloride (40 ml) suspension of 150 (1.03 g, 4.12 mmol) and triethylamine (1.72 ml, 12.36 mmol), trifluoroacetic anhydride (1.40 ml, 9.89 mmol) was added dropwise under ice cooling and stirring, and the mixture was stirred at the same temperature for 30 minutes. To the reaction solution, ice water was added and the solution was extracted with ethyl acetate. The extraction liquid was dried and the solvent was distilled off under reduced pressure. The residue was purified by silica gel column chromatography (eluting solvent: ethyl acetate/n-hexane=1/2) and then purified by NH silica gel column chromatography (eluting solvent: ethyl acetate/n-hexane=1/1, ethyl acetate) to obtain 151 (1.40 g, 98%) as a pale yellow solid.

mp 214-216° C.

APCI-MS m/z 347[M+H]$^+$

Synthesis of 152

To a tetrahydrofuran (40 ml) suspension of 151 (1.39 g, 4.01 mmol), 63 (1.74 g, 4.82 mmol) and triphenylphosphine (1.26 g, 4.82 mmol), a tetrahydrofuran (10 ml) solution of diisopropyl azodicarboxylate (0.95 ml, 4.82 mmol) added dropwise over 30 minutes under ice cooling and stirring, and the mixture was stirred at the same temperature for 1 hour, followed by stirring at room temperature for 16 hours. To the reaction solution, 63 (1.45 g, 4.01 mmol), triphenylphosphine (1.05 g, 4.01 mmol) and diisopropyl azodicarboxylate (0.80 ml, 4.01 mmol) were added, followed by further stirring at room temperature for 1 hour. The solvent of the reaction solution was distilled off under reduced pressure and the residue was purified by silica gel column chromatography (eluting solvent: ethyl acetate/n-hexane=1/4) to obtain a colorless oily substance (5.65 g). To a chloroform (24 ml) solution of the present product (5.65 g), trifluoroacetic acid (16 ml) was added dropwise under ice cooling and stirring and water was added (16 ml), followed by stirring at room temperature for 3 days. The reaction solution was extracted with ethyl acetate after adjusting the pH to 9 using an aqueous potassium carbonate solution. The extraction liquid was dried and the solvent was distilled off under reduced pressure and the residue was purified by silica gel column chromatography (eluting solvent: ethyl acetate/n-hexane=1/4, 2/3) to obtain 152 (2.15 g, 93%) as a yellow amorphous.

APCI-MS m/z 575[M+H]$^+$

Synthesis of 153

To a methylene chloride (60 ml) solution of 152 (2.14 g, 3.72 mmol) and 3,4-dihydro-2H-pyran (6.75 ml, 74 mmol), paratoluenesulfonic acid monohydrate (830 mg, 4.84 mmol) was added, and the mixture was stirred at room temperature for 1 hour. After adjusting the pH of the reaction solution to 9 suing triethylamine, the solvent was distilled off under reduced pressure. The residue was purified by silica gel column chromatography (eluting solvent: ethyl acetate/n-hexane=1/9, 1/2) to obtain 153 (2.36 g, 96%) as a pale yellow amorphous.

APCI-MS m/z 659[M+H]$^+$

Synthesis of THK-5119

To a tetrahydrofuran (28 ml)-water (11 ml) solution of 153 (2.35 g, 3.57 mmol), lithium hydroxide monohydrate (225 mg, 5.35 mmol) was added under ice cooling and stirring, and the mixture was stirred at the same temperature for 30 minutes. Water was added to the reaction solution and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=2/3) to obtain THK-5119 (1.78 g, 89%) as pale yellow crystals.

mp 126-126.5° C.

$^1$H NMR (500 MHz, DMSO-d$_6$) δ 1.35-1.71 (6H, m), 2.34, 2.34 (3H, s), 2.75 (3H, br), 3.38-3.46 (1H, m), 3.66-3.72, 3.81-3.88 (1H, m), 4.08-4.37 (5H, m), 4.69-4.72, 4.85-4.87 (1H, m), 6.10 (1H, br), 6.66 (2H, d, J=9.0 Hz), 7.22-7.25 (1H, m), 7.27-7.29 (1H, m), 7.39-7.43 (2H, m), 7.77-7.81 (2H, m), 7.85 (1H, d, J=9.0 Hz), 7.96 (1H, d, J=8.7 Hz), 8.03 (2H, d, J=8.7 Hz), 8.18 (1H, d, J=8.7 Hz)

IR (Nujol) 3377, 1621, 1610 cm$^{-1}$

APCI-MS m/z 563[M+H]$^+$

Synthesis Method of THK-5120

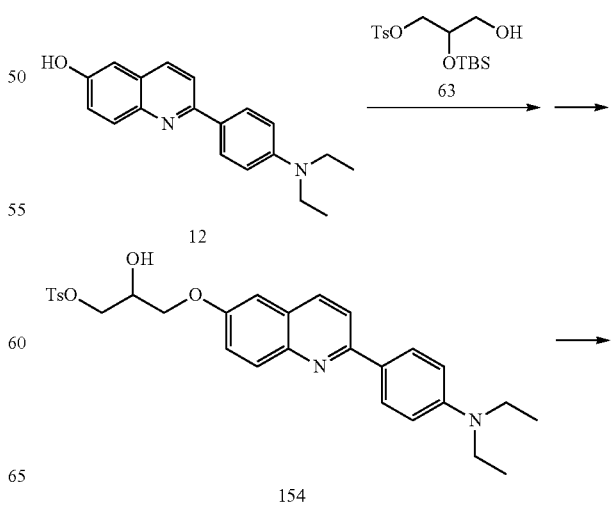

154

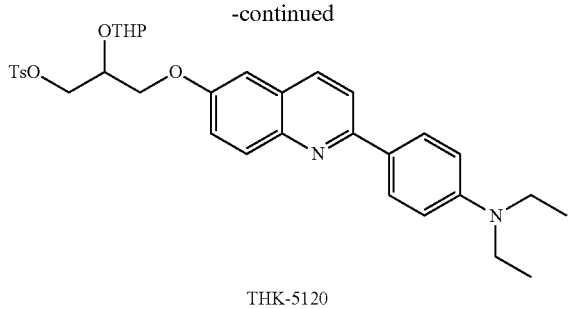

THK-5120

Synthesis of 154

To a tetrahydrofuran (25 ml) suspension of 12 (340 mg, 1.16 mmol), 63 (500 mg, 1.39 mmol) and triphenylphosphine (370 mg, 1.39 mmol), a tetrahydrofuran (5 ml) solution of diisopropyl azodicarboxylate (0.28 ml, 1.39 mmol) was added dropwise over 20 minutes under ice cooling and stirring, and the mixture was stirred at room temperature for 16 hours. To the reaction solution, 63 (500 mg, 1.39 mmol), triphenylphosphine (370 mg, 1.39 mmol) was added and diisopropyl azodicarboxylate (0.28 ml, 1.39 mmol) was added under ice cooling and stirring, followed by further stirring at room temperature for 3 days. To the reaction solution, 63 (170 mg, 0.46 mmol), triphenylphosphine (120 mg, 0.46 mmol) was added and diisopropyl azodicarboxylate (0.09 ml, 0.46 mmol) was added under ice cooling and stirring, followed by further stirring at room temperature for 1 day. The solvent of the reaction solution was distilled off under reduced pressure and the residue was purified by silica gel column chromatography (eluting solvent: ethyl acetate/n-hexane=1/9). To the chloroform (12 ml) solution of the obtained main fraction, trifluoroacetic acid (8 ml) was added dropwise under ice cooling and stirring and water (2 ml) was added, followed by further stirring at room temperature for 16 hours. To the reaction solution, ice water was added and the solution was extracted with ethyl acetate after adjusting the pH to 8 using an aqueous potassium carbonate solution. The extraction liquid was dried and the solvent was distilled off under reduced pressure. The residue was purified by silica gel column chromatography (eluting solvent: ethyl acetate/n-hexane=1/3, 1/1) and then washed with ethyl acetate/n-hexane (1/2) to obtain 154 (410 mg, 68%) as pale yellow crystals.

mp 167-168° C.
APCI-MS m/z 521[M+H]$^+$

Synthesis of THK-5120

To a methylene chloride (10 ml) solution of 154 (400 mg, 0.77 mmol), 3, 4-dihydro-2H-pyran (1.39 ml, 15.4 mmol) and paratoluenesulfonic acid monohydrate (172 mg, 1.00 mmol) were added, and the mixture was stirred at room temperature for 10 minutes. After adjusting the pH of the reaction solution to 9 using triethylamine, the solvent was distilled off under reduced pressure. The residue was purified by silica gel column chromatography (eluting solvent: ethyl acetate/n-hexane=1/4) to obtain THK-5120 (466 mg, 100%) as a pale yellow amorphous.

$^1$H NMR (500 MHz, DMSO-d$_6$) δ 1.14 (6H, t, J=6.9 Hz), 1.34-1.69 (6H, m), 2.33, 2.34 (3H, s), 3.22-3.32 (1H, m), 3.42 (4H, q, J=7.3 Hz), 3.66-3.72, 3.82-3.87 (1H, m), 4.09-4.37 (5H, m), 4.69-4.72, 4.85-4.87 (1H, m), 6.78 (2H, d, J=9.0 Hz), 7.22-7.26 (1H, m), 7.28-7.31 (1H, m), 7.38-7.43 (2H, m), 7.77-7.82 (2H, m), 7.86 (1H, d, J=9.0 Hz), 7.97 (1H, d, J=8.7 Hz), 8.07 (2H, d, J=9.0 Hz), 8.20 (1H, d, J=8.3 Hz)

APCI-MS m/z 605[M+H]$^+$

Synthesis Method of THK-5121

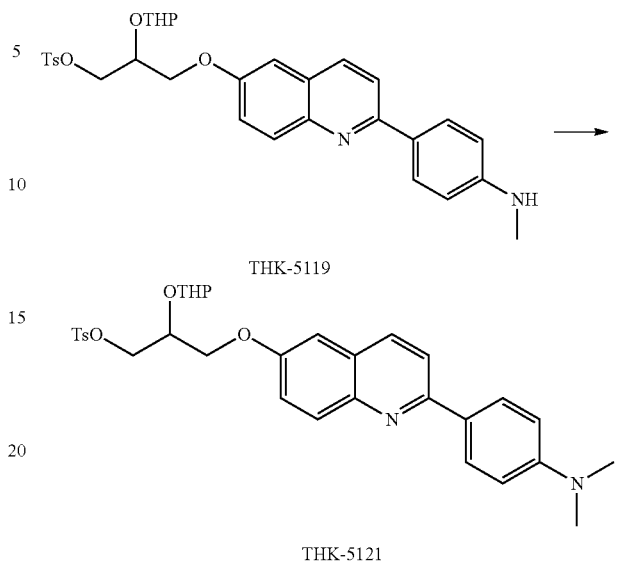

Synthesis of THK-5121

To a ethanol (12 ml)-acetic acid (1.2 ml)-chloroform (10 ml) solution of THK-5119 (600 mg, 1.07 mmol) and an aqueous 20% formaldehyde solution (1.60 ml, 10.7 mmol), picoline borane complex (342 mg, 3.21 mmol) was added little by little under ice cooling and stirring, and the mixture was stirred at room temperature for 1 hour. The reaction solution was diluted with ethyl acetate and extracted with ethyl acetate after adjusting the pH to 8 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=4/1) and then recrystallized from n-hexane/ethyl acetate to obtain THK-5121 (566 mg, 92%) as pale yellow crystals.

mp 152-154° C.
$^1$H NMR (500 MHz, DMSO-d$_6$) δ 1.34-1.68 (6H, m), 2.34 (3H, s), 3.01 (6H, s), 3.41-3.47 (1H, m), 3.65-3.72, 3.81-3.87 (1H, m), 4.10-4.37 (5H, m), 4.68-4.72, 4.85-4.87 (1H, m), 6.85 (2H, d, J=7.4 Hz), 7.25-7.37 (2H, m), 7.39-7.43 (2H, m), 7.77-7.81 (2H, m), 7.88-7.96 (1H, m), 8.01-8.07 (1H, m), 8.11 (2H, d, J=8.7 Hz), 8.23-8.32 (1H, m)

IR (Nujol) 1622 cm$^{-1}$
APCI-MS m/z 577[M+H]$^+$

Synthesis Method of THK-5122

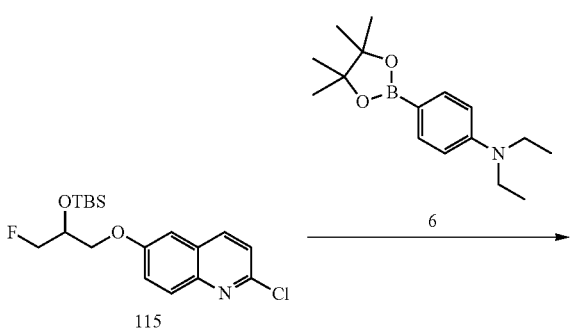

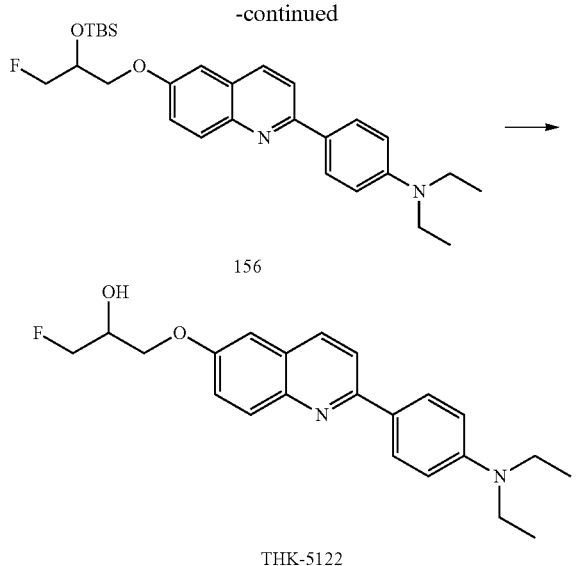

Synthesis of 156

To a mixture of 115 (650 mg, 1.76 mmol), 6 (580 mg, 2.11 mmol) and 1,2-dimethoxyethane (20 ml), sodium carbonate (372 mg, 3.50 mmol) and water (2 ml) were added and tetrakistriphenylphosphine palladium (102 mg, 0.088 mmol) was added under an argon atmosphere and the mixture was heated at reflux for 48 hours. To the reaction solution, tetrakistriphenylphosphine palladium (102 mg, 0.088 mmol) was added, and the mixture was heated at reflux for 24 hours under an argon atmosphere. The reaction solution was allowed to return to room temperature and silica gel was added, and then the solvent was distilled off under reduced pressure. The residue was purified by silica gel column chromatography (eluting solvent: n-hexane/ethyl acetate=10/1) to obtain 156 (750 mg, 89%) as a pale yellow solid.

mp 104-105° C.

Synthesis of THK-5122

To a mixture of 156 (740 mg, 1.55 mmol) and tetrahydrofuran (20 ml), 1M tetra-n-butylammonium fluoride/tetrahydrofuran (2.0 ml, 2.00 mmol) was added, and the mixture was stirred at room temperature for 1 hour. The reaction solution was poured into water, and the solution was extracted with ethyl acetate. The extraction liquid was washed with saturated saline and dried, and then the solvent was distilled off under reduced pressure. The residue was purified by silica gel column chromatography (eluting solvent: n-hexane/ethyl acetate=3/1, 2/1) and then recrystallized from ethyl acetate/n-hexane (1/1) to obtain THK-5122 (448 mg, 78%) as crystals.

mp 126-127° C.

$^1$H NMR (400 MHz, CDCl$_3$) δ 1.21 (6H, t, J=7.0 Hz), 2.60 (1H, brs), 3.43 (4H, q, J=7.0 Hz), 4.14-4.23 (2H, m), 4.26-4.37 (1H, m), 4.53-4.62 (1H, m), 4.66-4.74 (1H, m), 6.78 (2H, d, J=8.8 Hz), 7.06 (1H, d, J=2.7 Hz), 7.32 (1H, dd, J=9.0, 2.7 Hz), 7.78 (1H, d, J=9.0 Hz), 7.99 (1H, d, J=7.0 Hz), 8.01 (1H, d, J=7.0 Hz), 8.03 (2H, d, J=8.8 Hz)

IR (Nujol) 3378, 1620, 1596 cm$^{-1}$

APCI-MS m/z 369[M+H]$^+$

Synthesis Method of THK-5123

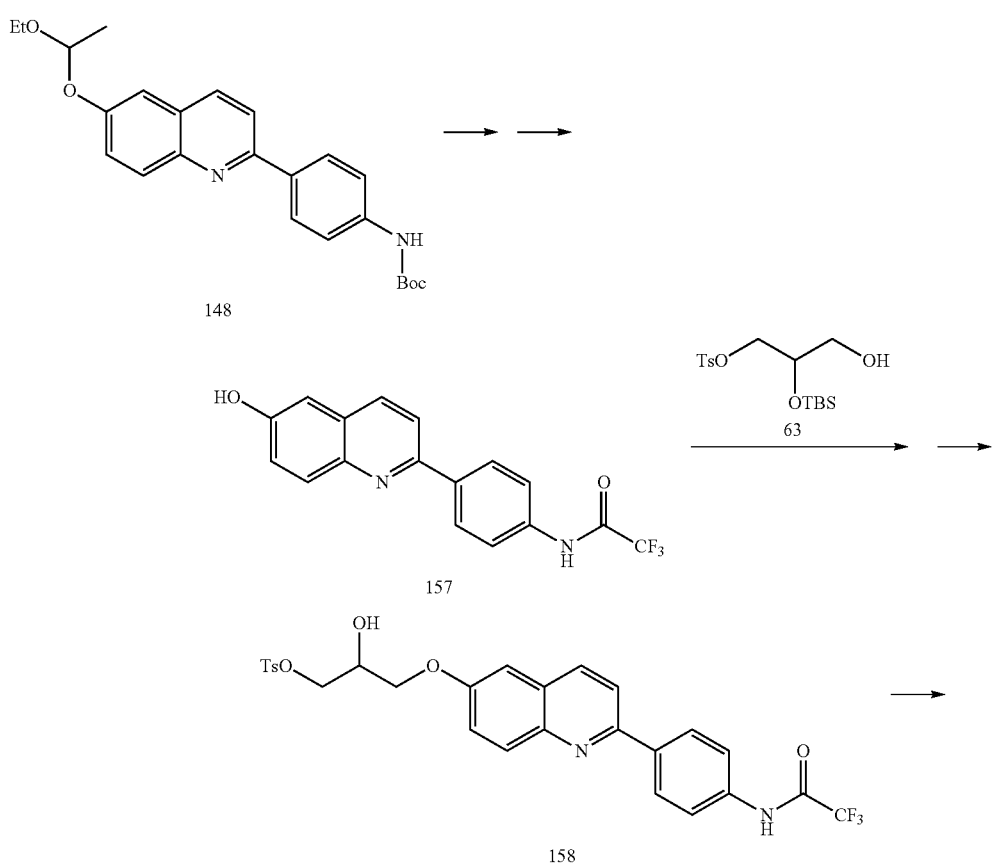

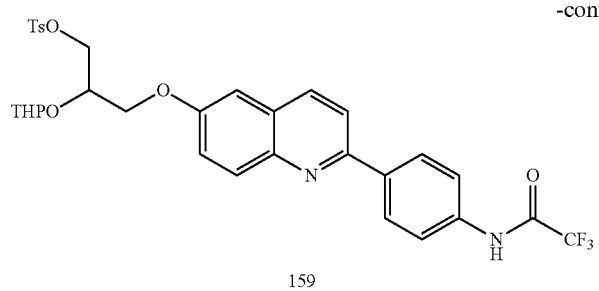

159

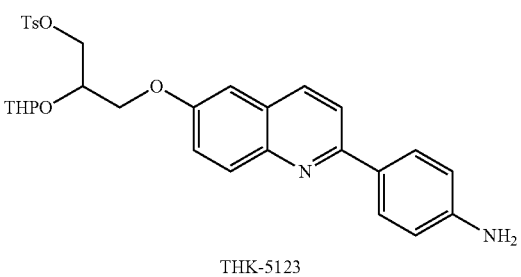

THK-5123

Synthesis of 157

To a chloroform (12 ml) solution of 148 (1.20 g, 2.94 mmol), trifluoroacetic acid (8 ml) was added dropwise under ice cooling and stirring, and the mixture was stirred at room temperature for 1.5 hours. To the reaction solution, ice water was added, and the solution was extracted with chloroform/methanol after adjusting the pH to 9 using an aqueous potassium carbonate solution. The extraction liquid was dried the solvent was distilled off under reduced pressure, and the residue was purified by silica gel column chromatography (eluting solvent: ethyl acetate/n-hexane=1/1, ethyl acetate).

To a methylene chloride (20 ml) suspension of the obtained orange solid (650 mg) and triethylamine (1.13 ml, 8.13 mmol), trifluoroacetic anhydride (0.92 ml, 6.5 mmol) was added dropwise under ice cooling and stirring, followed by stirring at the same temperature for 30 minutes. To the reaction solution, ice water was added and the solution was extracted with chloroform/methanol. The extraction liquid was dried the solvent was distilled off under reduced pressure. The residue was purified by silica gel column chromatography (eluting solvent: ethyl acetate/n-hexane=1/1) and then washed with ethyl acetate/n-hexane (1/4) to obtain 157 (360 mg, 37%) as pale brown crystals.

mp 253-254° C.

APCI-MS m/z 333[M+H]$^+$

Synthesis of 158

To a tetrahydrofuran (25 ml) suspension of 157 (350 mg, 1.05 mmol), 63 (911 mg, 2.53 mmol) and triphenylphosphine (664 mg, 2.53 mmol), a tetrahydrofuran (8 ml) solution of diisopropyl azodicarboxylate (0.5 ml, 2.52 mmol) was added dropwise over 20 minutes under ice cooling and stirring, and the mixture was stirred at the same temperature for 1 hour, followed by stirring at room temperature for 3 days. The solvent of the reaction solution was distilled off under reduced pressure, and the residue was purified by silica gel column chromatography (eluting solvent: ethyl acetate/n-hexane=1/4). To a chloroform (16 ml) solution of the obtained main fraction, trifluoroacetic acid (11 ml) was added dropwise under ice cooling and stirring and water (2.5 ml) was added, followed by further stirring at room temperature for 16 hours. The reaction solution was diluted with chloroform and extracted with chloroform after adjusting the pH to 8 using an aqueous potassium carbonate solution. The extraction liquid was dried and purified by silica gel column chromatography (eluting solvent: chloroform, ethyl acetate/n-hexane=1/2, 1/1) to obtain 158 (490 mg, 83%) as a pale yellow solid.

mp 186-188° C.

APCI-MS m/z 561[M+H]$^+$

Synthesis of 159

To a methylene chloride (20 ml) suspension of 158 (480 mg, 0.86 mmol) and 3,4-dihydro-2H-pyran (1.55 ml, 17.2 mmol), paratoluenesulfonic acid monohydrate (192 mg, 1.12 mmol) was added, and the mixture was stirred at room temperature for 10 minutes. After adjusting the pH of the reaction solution to 8 by adding triethylamine, the solvent was distilled off under reduced pressure. The residue was purified by silica gel column chromatography (eluting solvent: ethyl acetate/n-hexane=1/4, 1/2) to obtain 159 (480 mg, 87%) as a pale yellow solid.

mp 112-115° C.

APCI-MS m/z 645[M+H]$^+$

Synthesis of THK-5123

To a tetrahydrofuran (9 ml)-water (3 ml) solution of 159 (470 mg, 0.73 mmol), lithium hydroxide monohydrate (46 mg, 1.09 mmol) was added under ice cooling and stirring, and the mixture was stirred at the same temperature for 1.5 hours, followed by stirring at room temperature for 1 hour. Lithium hydroxide monohydrate (46 mg, 1.09 mmol) and methanol (2 ml) were added, followed by further stirring at room temperature for 16 hours. The reaction solution was diluted with ethyl acetate, washed with water and dried, and the solvent was distilled off under reduced pressure. The residue was purified by silica gel column chromatography (eluting solvent: ethyl acetate/n-hexane=2/3, 1/1) to obtain THK-5123 (380 mg, 95<) as a pale yellow amorphous.

$^1$H NMR (500 MHz, DMSO-d$_6$) δ 1.34-1.71 (6H, m), 2.33, 2.34 (3H, s), 3.37-3.46 (1H, m), 3.66-3.72, 3.82-3.87 (1H, m), 4.08-4.36 (5H, m), 4.69-4.72, 4.84-4.87 (1H, m), 5.52 (2H, br), 6.68 (2H, d, J=8.7 Hz), 7.21-7.25 (1H, m), 7.26-7.29 (1H, m), 7.38-7.43 (2H, m), 7.77-7.81 (2H, m), 7.84 (1H, d, J=9.3 Hz), 7.93 (1H, d, J=8.7 Hz), 7.96 (1H, d, J=8.7 Hz), 8.17 (1H, d, J=8.7 Hz)

IR (Nujol) 3452, 1728, 1622 cm$^{-1}$

APCI-MS m/z 549[M+H]$^+$

Synthesis Method of THK-5125

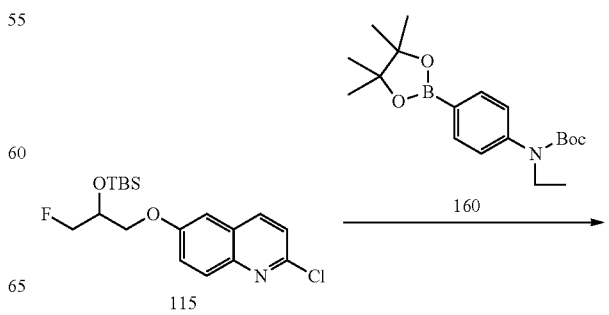

115

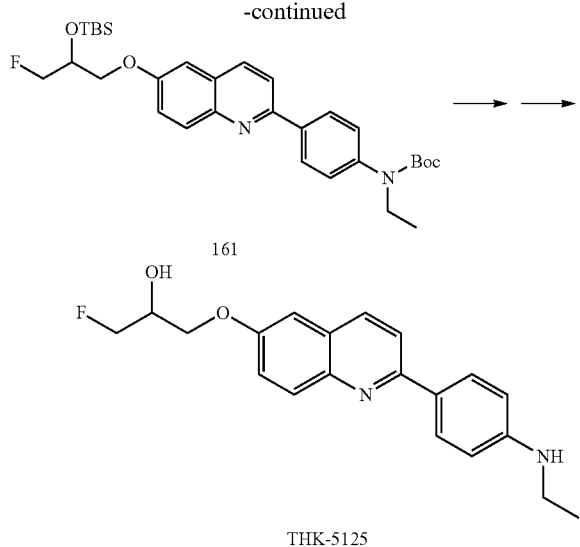

Synthesis of 161

To a mixture of 115 (650 mg, 1.76 mmol), 160 (733 mg, 2.11 mmol) and 1,2-dimethoxyethane (20 ml), sodium carbonate (372 mg, 3.50 mmol) and water (2 ml) were added, and tetrakistriphenylphosphine palladium (102 mg, 0.088 mmol) was added under an argon atmosphere, and then the mixture was heated at reflux for 33 hours. The reaction solution was allowed to return to room temperature, filtered with celite and then purified by silica gel flash column chromatography (eluting solvent: n-hexane/ethyl acetate=10/1) to obtain 161 (900 mg, 93%) as a viscous oily substance.

Synthesis of THK-5125

To a mixture of 161 (900 mg, 1.62 mmol) and tetrahydrofuran (20 ml), 1M tetra-n-butylammonium fluoride/tetrahydrofuran (2.0 ml, 2.00 mmol) was added, and the mixture was stirred at room temperature for 1 hour. The reaction solution was poured into water, and the solution was extracted with ethyl acetate. The extraction liquid was washed with saturated saline and dried, and then the solvent was distilled off under reduced pressure. To a methylene chloride (20 ml) solution of the residue, trifluoroacetic acid (4 ml) was added dropwise, followed by stirring at room temperature for 1.5 hours. The reaction solution was diluted with ethyl acetate and the solution was made basic with an aqueous saturated sodium hydrogen carbonate solution. The organic layer was washed with saturated saline and dried, and then the solvent was distilled off under reduced pressure. The residue was recrystallized from ethyl acetate to obtain THK-5125 (350 mg, 63%) as pale brown crystals.

mp 146-147° C.

$^1$H NMR (400 MHz, CDCl$_3$) δ 1.29 (3H, t, J=7.1 Hz), 2.61 (1H, br), 3.24 (2H, q, J=7.1 Hz), 3.80 (1H, br), 4.14-4.23 (2H, m), 4.32 (1H, brd, J=18 Hz), 4.54-4.62 (1H, m), 4.65-4.74 (1H, m), 6.71 (2H, d, J=8.8 Hz), 7.07 (1H, d, J=2.7 Hz), 7.33 (1H, dd, J=9.0, 2.7 Hz), 7.76 (1H, d, J=8.8 Hz), 8.01 (2H, d, J=8.8 Hz), 8.02 (1H, d, J=9.0 Hz), 7.90-8.20 (1H, br)

IR (Nujol) 3432, 3356, 1621, 1598 cm$^{-1}$

APCI-MS m/z 341[M+H]$^+$

Synthesis Method of THK-5131

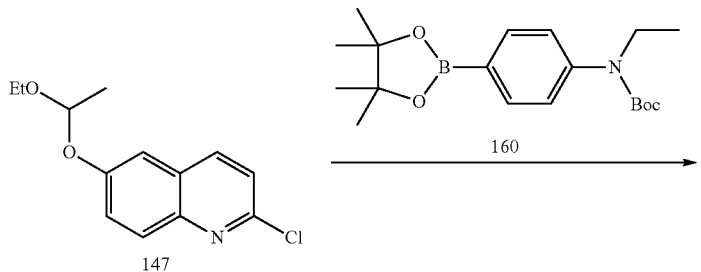

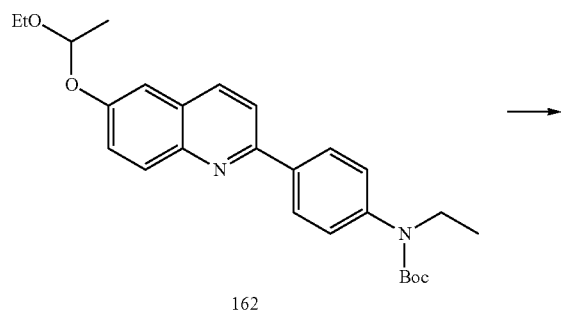

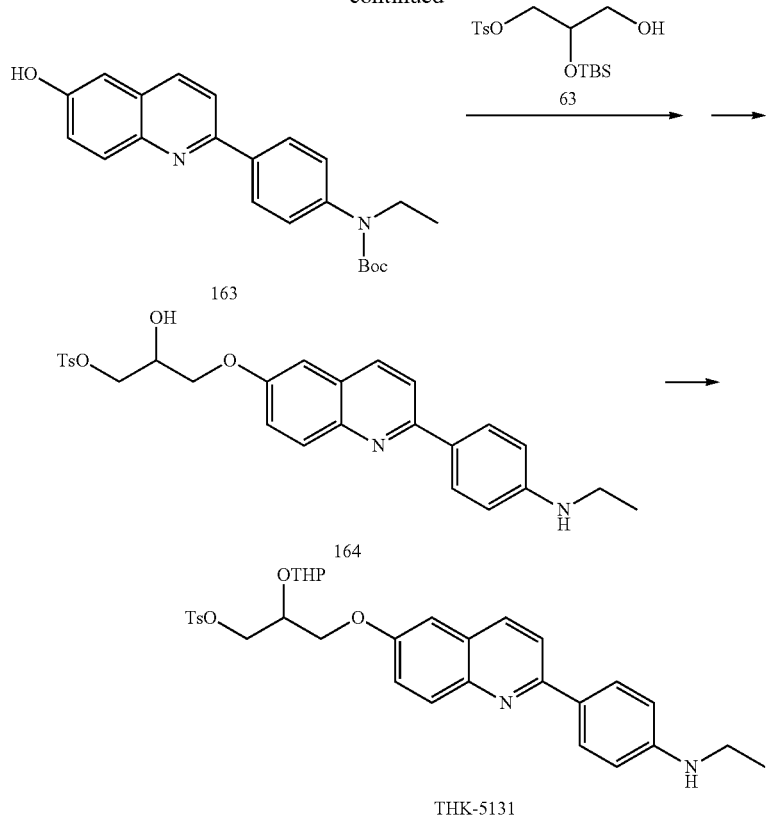

THK-5131

Synthesis of 162

To a 1,2-dimethoxyethane (20 ml) solution of 147 (600 mg, 2.38 mmol) and 160 (830 mg, 2.38 mmol), potassium carbonate (990 mg, 7.14 mmol), water (0.41 ml) and tetrakistriphenylphosphine palladium (275 mg, 0.24 mmol) were added under an argon atmosphere, and the mixture was stirred at 80° C. for 16 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/9) to obtain 162 (1.02 g, 98%) as a pale yellow viscous oily substance.

APCI-MS m/z 437[M+H]$^+$

Synthesis of 163

To a chloroform (10 ml) solution of 162 (1.01 g, 2.31 mmol), trifluoroacetic acid (1 ml) was added dropwise under ice cooling and stirring, and the mixture was stirred at the same temperature for 40 minutes and trifluoroacetic acid (0.5 ml) was added, followed by stirring at the same temperature for 10 minutes. To the reaction solution, ice water-ethyl acetate was added, and the solution was extracted with ethyl acetate after adjusting the pH to 9 using an aqueous potassium carbonate solution. The extraction liquid was dried and the solvent was distilled off under reduced pressure and the residue was purified by silica gel column chromatography (eluting solvent: n-hexane/ethyl acetate=4/1, 2/1) to obtain 163 (740 mg, 88%) as a pale yellow solid.

mp 205-206° C.

APCI-MS m/z 365[M+H]$^+$

Synthesis of 164

To a tetrahydrofuran (30 ml) solution of 163 (730 mg, 2.00 mmol), 63 (1.74 g, 4.81 mmol) and triphenylphosphine (1.26 g, 4.81 mmol), a tetrahydrofuran (10 ml) solution of diisopropyl azodicarboxylate (0.95 ml, 4.81 mmol) was added dropwise over 20 minutes under ice cooling and stirring, and the mixture was stirred at the same temperature for 1 hour, followed by stirring at room temperature for 4 days. The solvent of the reaction solution was distilled off under reduced pressure, and the residue was purified by silica gel column chromatography (eluting solvent: ethyl acetate/n-hexane=1/9). To a chloroform (24 ml) solution of the obtained colorless oily substance (2.53 g), trifluoroacetic acid (16 ml) was added dropwise under ice cooling and stirring and water (4 ml) was added, followed by stirring at room temperature for 16 hours. To the reaction solution, ice water and ethyl acetate were added and the solution was extracted with ethyl acetate by adjusting the pH to 8 using an aqueous potassium carbonate solution. The extraction liquid was dried and the solvent was distilled off under reduced pressure. The residue was purified by silica gel column chromatography (eluting solvent: ethyl acetate/n-hexane=1/2, ethyl acetate) and then washed with ethyl acetate/n-hexane (1/2) to obtain 164 (880 mg, 89%) as yellow crystals.

mp 162-164° C.

APCI-MS m/z 493[M+H]$^+$

Synthesis of THK-5131

To a methylene chloride (20 ml) suspension of 164 (440 mg, 0.893 mmol), 3,4-dihydro-2H-pyran (1.62 ml, 17.9 mmol) and paratoluenesulfonic acid monohydrate (200 mg, 1.16 mmol) were added, and the mixture was stirred at room temperature for 15 minutes. After adjusting the pH of the reaction solution to 8 using triethylamine, the solvent was distilled off under reduced pressure. The residue was purified by silica gel column chromatography (eluting solvent: ethyl acetate/n-hexane=1/2) and then recrystallized from ethyl acetate/n-hexane to obtain THK-5131 (389 mg, 76%) as pale yellow crystals.

mp 103-105° C.

$^1$H NMR (500 MHz, DMSO-d$_6$) δ 1.20 (3H, t, J=7.1 Hz), 1.34-1.69 (6H, m), 2.33, 2.34 (3H, s), 3.09-3.15 (2H, m), 3.37-3.46 (1H, m), 3.66-3.72, 3.80-3.88 (1H, m), 4.09-4.37 (5H, m), 4.69-4.72, 4.84-4.87 (1H, m), 6.01 (1H, br), 6.67 (2H, d, J=8.3 Hz), 7.23 (1H, d, J=9.0 Hz), 7.26-7.29 (1H, m), 7.38-7.43 (2H, m), 7.77-7.81 (2H, m), 7.85 (1H, d, J=9.0 Hz), 7.95 (1H, d, J=8.7 Hz), 8.01 (2H, d, J=8.7 Hz), 8.18 (1H, d, J=8.0 Hz)

IR (Nujol) 3360, 1619, 1608 cm$^{-1}$

APCI-MS m/z 577[M+H]$^+$

Synthesis Method of THK-5127

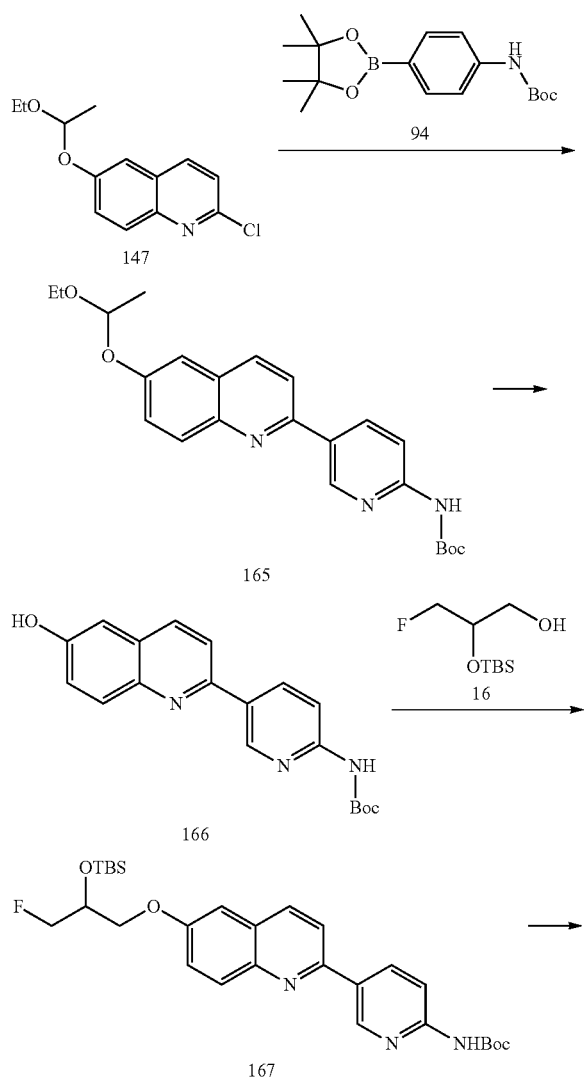

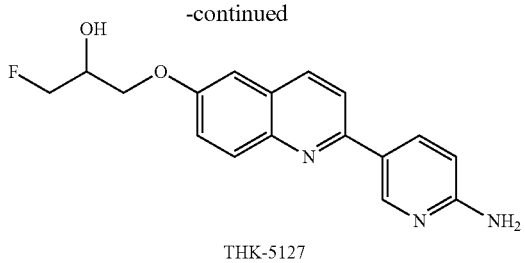

THK-5127

Synthesis of 165

To a 1,2-dimethoxyethane (63 ml) suspension of 147 (1.94 g, 7.71 mmol) and 94 (2.72 g, 8.48 mmol), potassium carbonate (3.20 g, 23.1 mmol), water (1.34 ml) and tetrakistriphenylphosphine palladium (890 mg, 0.77 mmol) were added under an argon atmosphere, and the mixture was stirred at 80° C. for 16 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4) and then recrystallized from ethyl acetate/n-hexane to obtain 165 (2.78 g, 88%) as pale yellow crystals.

mp 182-183° C.

APCI-MS m/z 410[M+H]$^+$

Synthesis of 166

To a chloroform (40 ml) solution of 165 (2.77 g, 6.76 mmol), trifluoroacetic acid (4 ml) was added dropwise under ice cooling and stirring, and the mixture was stirred at room temperature for 20 minutes. To the reaction solution, ice water was added and the solution was extracted with ethyl acetate-tetrahydrofuran after adjusting the pH to 9 using an aqueous potassium carbonate solution. The extraction liquid was dried and the solvent was distilled off under reduced pressure, and then the residue was recrystallized from ethyl acetate to obtain 166 (2.00 g, 88%) as pale yellow crystals.

mp 325-326° C.

APCI-MS m/z 338[M+H]$^+$

Synthesis of 167

To a tetrahydrofuran (40 ml) solution of 166 (1.50 g, 4.45 mmol), 16 (1.11 g, 5.35 mmol) and triphenylphosphine (1.40 g, 5.35 mmol), a tetrahydrofuran (10 ml) solution of diisopropyl azodicarboxylate (1.06 ml, 5.35 mmol) was added dropwise over 30 minutes under ice cooling and stirring, and the mixture was stirred at the same temperature for 1 hour, followed by stirring at room temperature for 3 days. To the reaction solution, 16 (830 mg, 4.00 mmol) and triphenylphosphine (1.05 g, 4.00 mmol) were additionally added, and the diisopropyl azodicarboxylate (0.79 ml, 4.00 mmol) was added dropwise under ice cooling and stirring, followed by further stirring at room temperature for 5 hours. The solvent of the reaction solution was distilled off under reduced pressure, and the residue was purified by silica gel column chromatography (eluting solvent: ethyl acetate/n-hexane=1/9, 1/4) and then recrystallized from ethyl acetate/n-hexane to obtain 167 (1.51 g, 64%) as colorless crystals.

mp 188-189° C.

APCI-MS m/z 528[M+H]$^+$

Synthesis of THK-5127

To a chloroform (24 ml) solution of 167 (1.50 g, 2.84 mmol), trifluoroacetic acid (16 ml) was added dropwise under ice cooling and stirring, and water (4 ml) was added, and the mixture was stirred at room temperature for 16 hours. To the reaction solution, ice water and then ethyl acetate were added, and the solution was extracted with ethyl acetate after adjusting the pH to 9 using an aqueous potassium carbonate solution. The extraction liquid was dried and the solvent was distilled off under reduced pressure. The residue was purified by silica gel column chromatography (eluting solvent: ethyl acetate) and then recrystallized from ethyl acetate to obtain THK-5127 (717 mg, 81%) as pale yellow crystals.

mp 196-197° C.

$^1$H NMR (400 MHz, DMSO-d$_6$) δ 4.06-4.19 (3H, m), 4.44-4.65 (2H, m), 5.54 (1H, d, J=5.7 Hz), 6.33 (2H, s), 6.57 (1H, d, J=8.8 Hz), 7.36-7.41 (2H, m), 7.87-7.91 (1H, m), 7.97 (1H, d, J=8.8 Hz), 8.21-8.27 (2H, m), 8.80 (1H, d, J=2.4 Hz)

IR (Nujol) 3440, 1651, 1619 cm$^{-1}$

APCI-MS m/z 314[M+H]$^+$

Synthesis Method of THK-5150

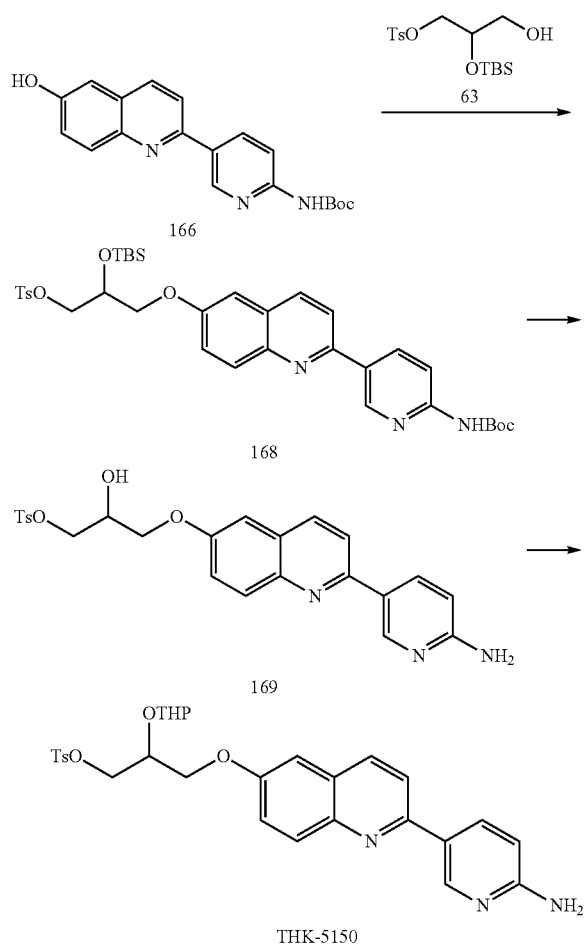

Synthesis of 168

To a tetrahydrofuran (30 ml) solution, 166 (980 mg, 2.91 mmol), 63 (2.51 g, 6.98 mmol) and triphenylphosphine (1.83 g, 6.98 mmol), a tetrahydrofuran (10 ml) solution of diisopropyl azodicarboxylate (1.38 ml, 6.98 mmol) was added dropwise over 10 minutes under ice cooling and stirring, and the mixture was stirred at the same temperature for 1 hour, followed by stirring at room temperature for 2 days. The solvent of the reaction solution was distilled off under reduced pressure, and the residue was washed with ethyl acetate/n-hexane=1/4) after grinding to obtain 168 (1.38 g, 70%) as colorless crystals.

mp 204-206° C.

APCI-MS m/z 680[M+H]$^+$

Synthesis of 169

To a chloroform (24 ml) solution of 168 (1.98 g, 2.91 mmol), trifluoroacetic acid (16 ml) was added dropwise under ice cooling and stirring, and water (4 ml) was added, and the mixture was stirred at room temperature for 16 hours. To reaction solution, ice water and ethyl acetate were added, and the solution was extracted with ethyl acetate after adjusting the pH to 8 using an aqueous potassium carbonate solution, and the solution was extracted with ethyl acetate after adjusting the pH to 8 using an aqueous potassium carbonate solution. The extraction liquid was dried and the solvent was distilled off under reduced pressure. The residue was purified by silica gel column chromatography (eluting solvent: ethyl acetate/n-hexane=1/1, ethyl acetate) and then washed with ethyl acetate/n-hexane (1/1) to obtain 169 (940 mg, 69%) as colorless crystals.

mp 168-169° C.

APCI-MS m/z 466[M+H]$^+$

Synthesis of THK-5150

To a ethylene chloride (20 ml) solution of 169 (930 mg, 2.00 mmol), 3,4-dihydro-2H-pyran (3.62 ml, 40.0 mmol) and paratoluenesulfonic acid monohydrate (447 mg, 2.60 mmol) were added, and the mixture was stirred at room temperature for 40 minutes. Paratoluenesulfonic acid monohydrate (344 mg, 2.0 mmol) was added, followed by stirring at room temperature for 10 minutes. After adjusting the pH of the reaction solution to 8 by adding triethylamine, ethyl acetate and water were added, followed by stirring at room temperature for 10 minutes. The organic layer was separated and dried, and then the solvent was distilled off under reduced pressure. The residue was purified by silica gel column chromatography (eluting solvent: ethylacetate/n-hexane=1/1, 2/1, ethyl acetate) to obtain THK-5150 (510 mg, 46%) as a colorless foam-like substance.

$^1$H NMR (500 MHz, DMSO-d$_6$) δ 1.35-1.68 (6H, m), 2.34, 2.34 (3H, s), 3.36-3.46 (1H, m), 3.66-3.71, 3.82-3.87 (1H, m), 4.09-4.37 (5H, m), 4.70, 4.84-4.87 (1H, m), 6.37 (2H, s), 6.57 (1H, d, J=8.7 Hz), 7.23-7.27 (1H, m), 7.29-7.31 (1H, m), 7.41 (2H, dd, J=8.2, 1.8 Hz), 7.79 (2H, dd, J=8.7, 2.6 Hz), 7.87 (1H, d, J=9.0 Hz), 7.98 (1H, d, J=8.7 Hz), 8.21 (1H, d, J=8.7 Hz), 8.25 (1H, dd, J=8.7, 2.6 Hz), 8.80 (1H, d, J=2.2 Hz)

IR (Nujol) 1621 cm$^{-1}$

APCI-MS m/z 550[M+H]$^+$

Synthesis Method of THK-5152

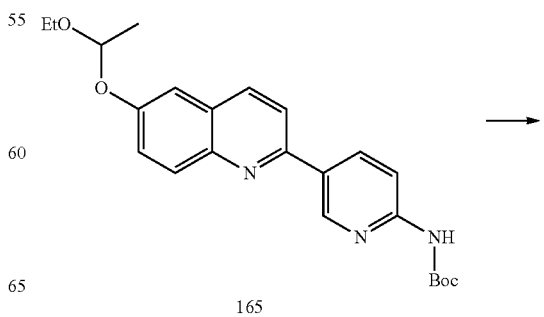

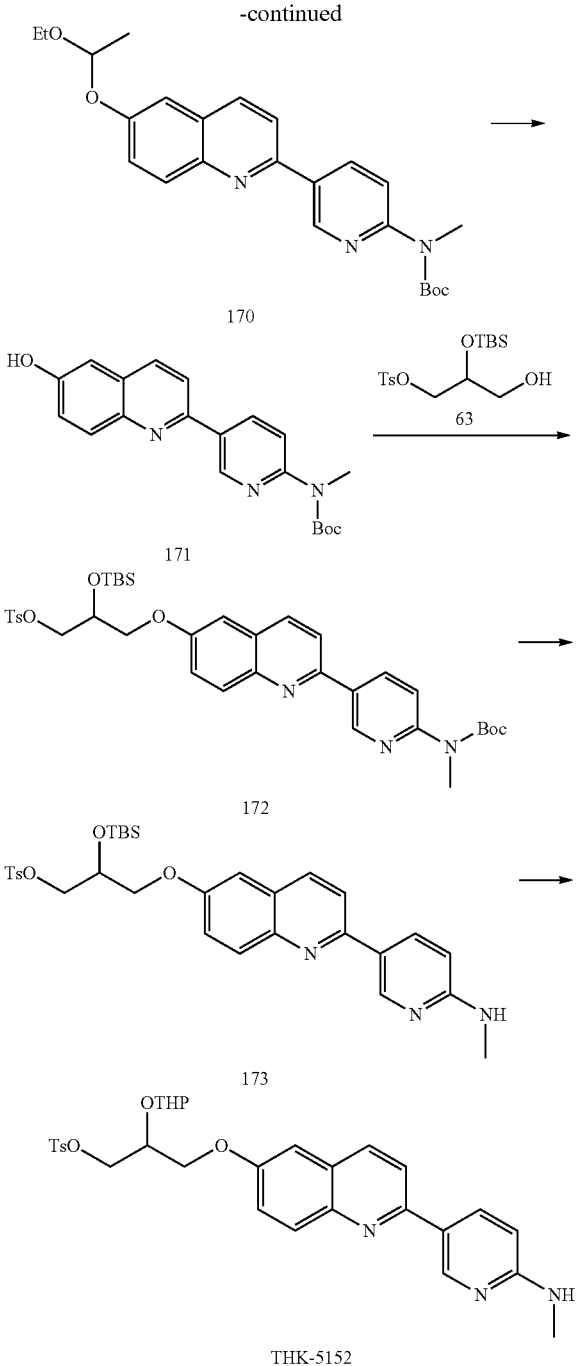

ethyl acetate/n-hexane=1/9, 1/4) to obtain 170 (1.93 g, 100%) as a pale yellow oily substance.

APCI-MS m/z 424[M+H]+

Synthesis of 171

To chloroform (20 ml) solution of 170 (1.93 g, 4.56 mmol), trifluoroacetic acid (4 ml) was added dropwise under ice cooling and stirring, and the mixture was stirred at the same temperature for 1 hour. To the reaction solution, water and ethyl acetate were added, and the solution was extracted with ethyl acetate after adjusting the pH to 8 using an aqueous potassium carbonate solution. The extraction liquid was dried and the solvent was distilled off under reduced pressure. The residue was purified by silica gel column chromatography (eluting solvent: n-hexane/ethyl acetate=2/1) and then washed with n-hexane/ethyl acetate=2/1 to obtain 171 (1.57 g, 98%) as pale yellow crystals.

mp 179-180° C.

APCI-MS m/z 352[M+H]+

Synthesis of 172

To a tetrahydrofuran (20 ml) suspension of 171 (500 mg, 1.42 mmol), 63 (1.23 g, 3.42 mmol) and triphenylphosphine (900 mg, 3.42 mmol), a tetrahydrofuran (10 ml) solution of diisopropyl azodicarboxylate (0.68 ml, 3.42 mmol) was added dropwise over 5 minutes under ice cooling and stirring, and the mixture was stirred at the same temperature for 1 hour, followed by stirring at room temperature for 16 hours. The solvent of the reaction solution was distilled off under reduced pressure, and the residue was purified by silica gel column chromatography (eluting solvent: ethyl acetate/n-hexane=1/9, 1/4) and then recrystallized from ethyl acetate/n-hexane (1/9) to obtain 172 (950 mg, 96%) as colorless crystals.

mp 112-113° C.

APCI-MS m/z 694[M+H]+

Synthesis of 173

To a chloroform (18 ml) solution of 172 (940 mg, 1.35 mmol), trifluoroacetic acid (12 ml) was added dropwise under ice cooling and stirring, and water (3 ml) was added, and the mixture was stirred at room temperature for 16 hours. To the reaction solution, ice water and ethyl acetate were added, and the solution was extracted with ethyl acetate after adjusting the pH to 8 using an aqueous potassium carbonate solution. The extraction liquid was dried and the solvent was distilled off under reduced pressure, and the residue was purified by silica gel column chromatography (eluting solvent: ethyl acetate/n-hexane=1/1, ethyl acetate) to obtain 173 (400 mg, 62%) as a pale yellow solid.

mp 162-163° C.

APCI-MS m/z 480[M+H]+

Synthesis of THK-5152

To a chloroform (20 ml) suspension of 173 (390 mg, 0.81 mmol), 3,4-dihydro-2H-pyran (1.47 ml, 16.3 mmol) and paratoluenesulfonic acid monohydrate (322 mg, 1.87 mmol) were added, and the mixture was stirred at room temperature for 20 minutes. After adjusting the pH of the reaction solution to 8 by adding triethylamine, the solvent was distilled off under reduced pressure. The residue was purified by silica gel column chromatography (eluting solvent: ethyl acetate/n-hexane=2/1, ethyl acetate) and then recrystallized from ethyl acetate/n-hexane to obtain THK-5152 (442 mg, 97%) as colorless crystals.

mp 129-130° C.

$^1$H NMR (400 MHz, DMSO-$d_6$) δ 1.33-1.71 (6H, m), 2.32 (3H, s), 2.85 (3H, d, J=4.8 Hz), 3.36-3.51 (1H, m), 3.65-3.73, 3.81-3.89 (1H, m), 4.09-4.38 (5H, m), 4.70, 4.86 (1H, m), 6.58 (1H, d, J=8.8 Hz), 6.89 (1H, q, J=4.8 Hz), 7.23-7.27 (1H, m), 7.29-7.32 (1H, m), 7.39-7.43 (2H, m),

Synthesis of 170

To an N,N-dimethylformamide (30 ml) suspension of 165 (1.87 g, 4.57 mmol), 60% sodium hydride (220 mg, 5.5 mmol) was added little by little under ice cooling and stirring an argon atmosphere, and the mixture was stirred at the same temperature for 15 minutes and methyl iodide (0.43 ml, 6.9 mmol) was added dropwise at the same temperature, followed by stirring at the same temperature for 5 minutes and further stirring at room temperature for 30 minutes. To the reaction solution, ice water was added and the solution was extracted with ethyl acetate. The extraction liquid was washed with water and dried, and then the solvent was distilled off under reduced pressure. The residue was purified by silica gel column chromatography (eluting solvent:

7.79 (2H, dd, J=8.3, 2.0 Hz), 7.87 (1H, d, J=9.1 Hz), 7.99 (1H, d, J=8.8 Hz), 8.21 (1H, d, J=8.8 Hz), 8.26 (1H, dd, J=8.8, 2.4 Hz), 8.87 (1H, d, J=2.4 Hz)

IR (Nujol) 3355, 1623, 1604 cm$^{-1}$

APCI-MS m/z 564[M+H]$^{+}$

Synthesis Method of THK-5129

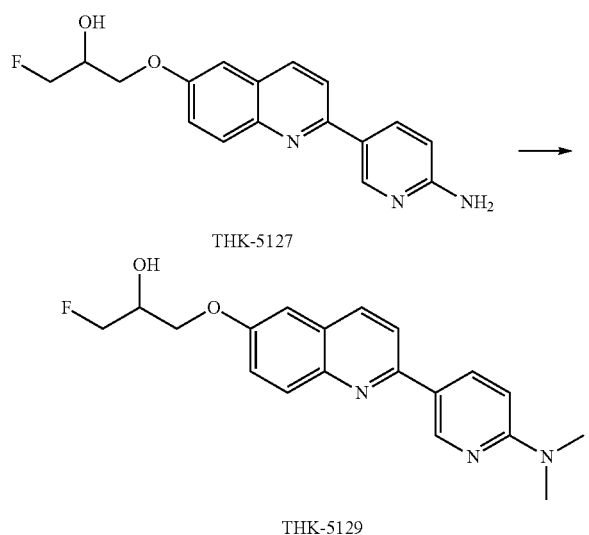

Synthesis of THK-5129

To a methanol (8.6 ml)-acetic acid (0.86 ml) solution of THK-5127 (123 mg, 0.39 mmol) and an aqueous 20% formaldehyde solution (1.18 ml, 7.8 mmol), a picoline borane complex (252 mg, 2.36 mmol) was added little by little under ice cooling and stirring, and the mixture was stirred at room temperature for 3 hours. To the reaction solution, water was added, and the solution was extracted with ethyl acetate. The extraction liquid was washed with water and dried, and then the solvent was distilled off under reduced pressure. The residue was purified by NH silica gel column chromatography (eluting solvent: n-hexane/ethyl acetate=1/2), purified by silica gel column chromatography (eluting solvent: n-hexane/ethyl acetate=1/2) and then recrystallized from ethyl acetate/n-hexane to obtain THK-5129 (100 mg, 75%) as pale yellow crystals.

mp 172-173° C.

$^{1}$H NMR (400 MHz, DMSO-d$_{6}$) δ 3.12 (6H, s), 4.06-4.19 (3H, m), 4.44-4.65 (2H, m), 5.54 (1H, d, J=4.8 Hz), 6.78 (1H, d, J=9.1 Hz), 7.37-7.41 (2H, m), 7.88-7.93 (1H, m), 8.01 (1H, d, J=8.8 Hz), 8.25 (1H, d, J=8.8 Hz), 8.36 (1H, dd, J=9.1, 2.4 Hz), 8.95 (1H, d, J=2.4 Hz)

IR (Nujol) 3378, 1620, 1611 cm$^{-1}$

APCI-MS m/z 342[M+H]$^{+}$

Synthesis Method of THK-5135

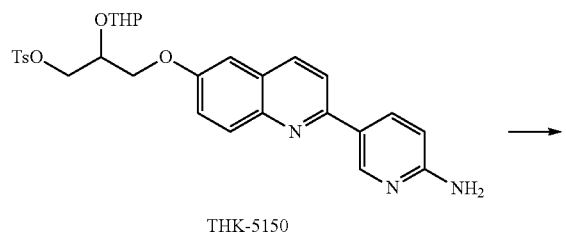

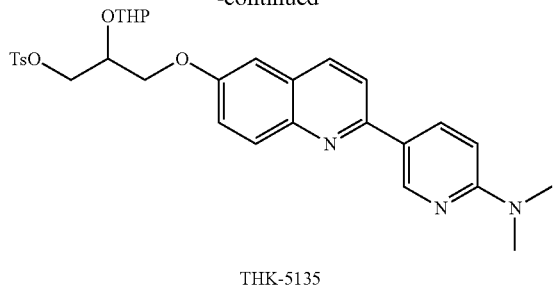

Synthesis of THK-5135

To a methanol (20 ml)-acetic acid (2 ml) solution of THK-5150 (500 mg, 0.91 mmol) and an aqueous 20% formaldehyde solution (2.73 ml, 18.2 mmol), a picoline borane complex (584 mg, 5.46 mmol) was added little by little at room temperature under stirring, and the mixture was stirred at room temperature for 1 hour. To the reaction solution, water and ethyl acetate were added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=1/1) and then recrystallized from ethyl acetate/n-hexane to obtain THK-5135 (331 mg, 63%) as pale yellow crystals.

mp 135-138° C.

$^{1}$H NMR (400 MHz, DMSO-d$_{6}$) δ 1.34-1.70 (6H, m), 2.34 (3H, s), 3.12 (6H, s), 3.38-3.51 (1H, m), 3.65-3.73, 3.81-3.89 (1H, m), 4.08-4.38 (5H, m), 4.69-4.73, 4.84-4.88 (1H, m), 6.79 (1H, d, J=9.1 Hz), 7.24-7.28 (1H, m), 7.30-7.33 (1H, m), 7.39-7.43 (2H, m), 7.79 (2H, dd, J=8.5, 2.1 Hz), 7.88 (1H, d, J=9.1 Hz), 8.02 (1H, d, J=8.8 Hz), 8.23 (1H, d, J=8.8 Hz), 8.37 (1H, dd, J=9.1, 2.41 Hz), 8.96 (1H, d, J=2.4 Hz)

IR (Nujol) 1624 cm$^{-1}$

APCI-MS m/z 578[M+H]$^{+}$

Synthesis Method of THK-5130

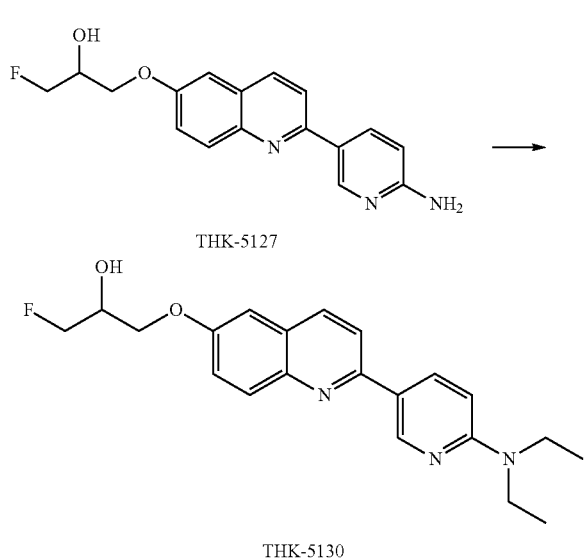

Synthesis of THK-5130

To a methanol (16 ml)-acetic acid (1.6 ml) suspension of THK-5127 (449 mg, 1.43 mmol) and acetaldehyde (78 mg/ml methanol solution: 3.24 ml, 5.73 mmol), a picoline borane complex (460 mg, 4.30 mmol) was added little by little under ice cooling and stirring, and the mixture was stirred at room temperature for 4 hours. Acetaldehyde (78 mg/ml methanol solution: 3.24 ml, 5.73 mmol) and a picoline borane complex (460 mg, 4.30 mmol) were added, followed by stirring at room temperature for 16 hours. To the reaction solution, water and ethyl acetate were added, and the solution was extracted with ethyl acetate after adjusting the pH to 9 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=2/1, 1/1) and then recrystallized from ethyl acetate/n-hexane to obtain THK-5130 (479 mg, 91%) as pale yellow crystals.

mp 131-132° C.

$^1$H NMR (400 MHz, DMSO-$d_6$) δ 1.15 (6H, t, J=7.1 Hz), 3.57 (4H, q, J=7.1 Hz), 4.00-4.19 (3H, m), 4.44-4.65 (2H, m), 5.54 (1H, d, J=4.81 Hz), 6.74 (1H, d, J=9.1 Hz), 7.36-7.41 (2H, m), 7.87-7.92 (1H, m), 8.00 (1H, d, J=8.8 Hz), 8.24 (1H, d, J=8.8 Hz), 8.33 (1H, dd, J=9.1, 2.4 Hz), 8.93 (1H, d, J=2.4 Hz)

IR (Nujol) 3275, 1622 cm$^{-1}$

APCI-MS m/z 370[M+H]$^+$

Synthesis Method of THK-5138

169

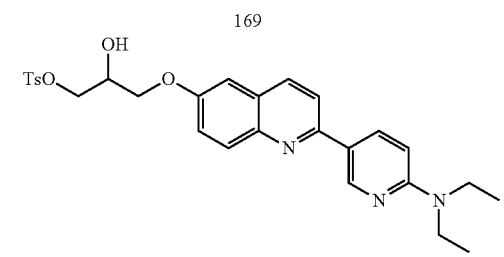

174

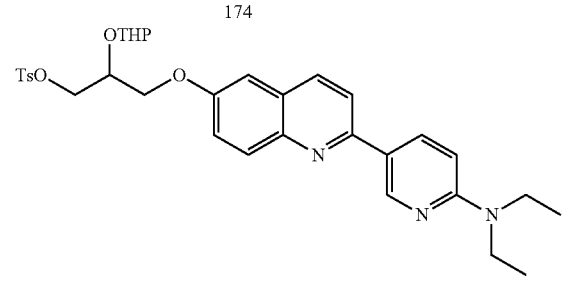

THK-5138

Synthesis of 174

To a methanol (13 ml)-acetic acid (1.3 ml)-chloroform (10 ml) solution of 169 (550 mg, 1.18 mmol) and acetaldehyde (0.66 ml, 11.8 mmol), picoline borane complex (890 mg, 8.32 mmol) was added little by little under ice cooling and stirring, and the mixture was stirred at room temperature for 4 days. To the reaction solution, water and ethyl acetate were added, and the solution was extracted with ethyl acetate after adjusting the pH to 8 using an aqueous potassium carbonate solution. The extraction liquid was washed with water and dried, and then the solvent was distilled off under reduced pressure. The residue was purified by silica gel column chromatography (eluting solvent: n-hexane/ethyl acetate=1/1, ethyl acetate) to obtain 174 (560 mg, 91%) as a pale yellow foam-like substance.

APCI-MS m/z 522[M+H]$^+$

Synthesis of THK-5138

To a chloroform (20 ml) solution of 174 (550 mg, 1.05 mmol), 3,4-dihydro-2H-pyran (1.19 ml, 21.1 mmol), para-toluenesulfonic acid monohydrate (420 mg, 2.43 mmol) was added, and the mixture was stirred at room temperature for 10 minutes. After adjusting the pH of the reaction solution to 8 by adding triethylamine, the solvent was distilled off under reduced pressure. The residue was purified by silica gel column chromatography (eluting solvent: ethyl acetate/n-hexane=1/4, 1/2) and then washed with ethyl acetate/n-hexane to obtain THK-5138 (477 mg, 75%) as pale yellow crystals.

mp 102-104° C.

$^1$H NMR (400 MHz, DMSO-$d_6$) δ 1.15 (6H, t, J=7.0 Hz), 1.30-1.50 (4H, m), 1.52-1.69 (2H, m), 2.34 (3H, s), 3.36-3.46 (1H, m), 3.57 (4H, q, J=6.7 Hz), 3.65-3.73, 3.81-3.88 (1H, m), 4.08-4.38 (5H, m), 4.69-4.72, 4.84-4.88 (1H, m), 6.73 (1H, d, J=9.1 Hz), 7.23-7.27 (1H, m), 7.29-7.32 (1H, m), 7.41 (2H, d, J=7.3 Hz), 7.79 (2H, dd, J=8.2, 2.1 Hz), 7.87 (1H, d, J=9.1 Hz), 8.00 (1H, d, J=8.8 Hz), 8.22 (1H, d, J=8.8 Hz), 8.34 (1H, dd, J=9.1, 2.4 Hz), 8.94 (1H, d, J=2.4 Hz)

IR (Nujol) 1620 cm$^{-1}$

APCI-MS m/z 606[M+H]$^+$

Synthesis Method of THK-5151

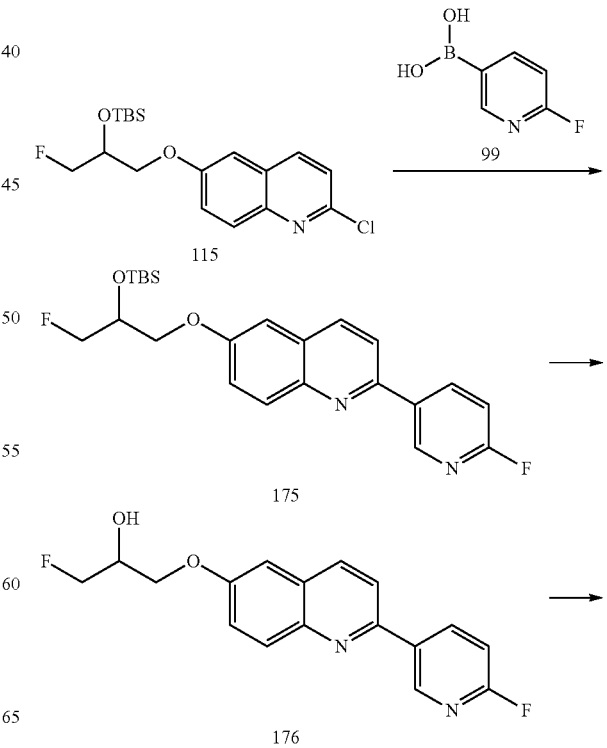

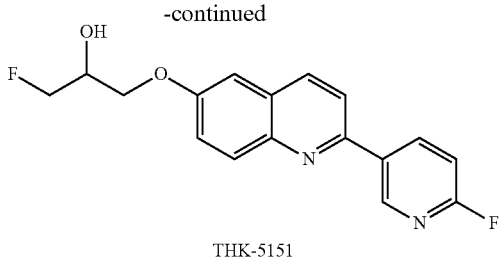

THK-5151

Synthesis of 175

To 115 (175 mg, 0.473 mmol), 99 (71.1 mg, 0.505 mmol), sodium carbonate (105 mg, 0.992 mmol) and dichlorobis(triphenylphosphine)palladium (3.6 mg, 0.00513 mmol), 2.5 ml of a mixed solution of water/ethanol/1,2-dimethoxyethane (each ratio=0.55:0.4:1.25) was added, and the mixture was heated at reflux at 90° C. for 90 minutes. The reaction solution was allowed to return to room temperature and water (40 ml) was added, and the solution was extracted with ethyl acetate (2×40 ml) and then dried over magnesium sulfate. The extraction solvent was distilled off and the residue was purified by silica gel flash column chromatography (eluting solvent: n-hexane/ethyl acetate=85/15, 60/40) to obtain 175 (191 mg, 94%) as crystalline substance. EI-MS m/z 430[M]$^+$ Synthesis of 176

175 (106 mg, 0.247 mmol) was dissolved in tetrahydrofuran (3.0 ml) and a 1M tetrabutylammonium fluoride/acetonitrile solution (0.37 ml, 0.37 mmol) was added, and the mixture was reacted at room temperature for 90 minutes reaction. To the reaction solution, water (30 ml) was added, and the solution was extracted with ethyl acetate (3×30 ml) and then dried over magnesium sulfate. The extraction solvent was distilled off, and the residue was purified by silica gel flash column chromatography (eluting solvent: n-hexane/ethyl acetate=45/55, 20/80) to obtain 176 (74.1 mg, 95%) as white crystals. EI-MS m/z 316[M]$^+$.

Synthesis of THK-5151

176 (52.4 mg, 0.166 mmol) was dissolved in methanol (2.0 ml) and a 40% monomethylamine/methanol solution (0.60 ml, 5.8 mmol) was added, and the mixture was heated at 40° C. for 7 hours, followed by stirring with heating at 50° C. for 17 hours. After the reaction solution returned to room temperature, the solvent was distilled off and the residue was purified by silica gel flash column chromatography (eluting solvent: ethyl acetate/methanol=100/0, 70/30) to obtain THK-5151 (46.0 mg, 85%) as yellow crystals. EI-MS m/z 327[M]$^+$.

$^1$H NMR (600 MHz, CDCl$_3$) δ 3.01 (3H, d, J=4.8 Hz), 4.20-4.25 (2H, m), 4.32-4.38 (1H, m), 4.59-4.65 (1H, m), 4.67-4.73 (1H, m), 4.85 (1H, br), 6.54 (1H, d, J=8.4 Hz), 7.11 (1H, d, J=3.0 Hz), 7.37 (1H, dd, J=3.0, 9.6 Hz), 7.76 (1H, d, J=8.4 Hz), 8.02 (1H, d, J=9.6 Hz), 8.06 (1H, d, J=8.4 Hz), 8.36 (1H, dd, J=1.8, 9.0 Hz), 8.82 (1H, d, J=1.8 Hz).

Synthesis Method of THK-5177

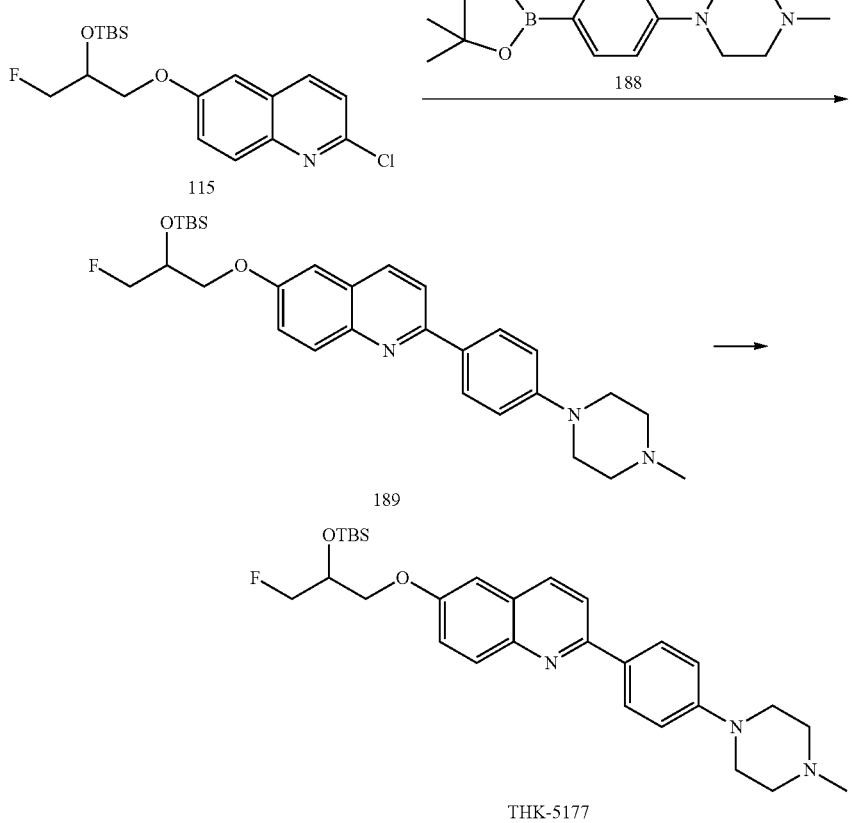

Synthesis of 189

From 115 (112 mg, 0.302 mmol) and 188 (91.0 mg, 0.301 mmol), 189 (a yellow crystal, 94.6 mg, 62%) was synthesized in the same manner as in the compound 175. EI-MS m/z 509[M]$^+$.

Synthesis of THK-5177

189 (75.0 mg, 0.147 mmol) was dissolved in tetrahydrofuran (3.0 ml) and a 1M tetrabutylammonium fluoride/acetonitrile solution (0.37 ml, 0.37 mmol) was added, and the mixture was reacted at room temperature for 90 minutes reaction. To the reaction solution, water (30 ml) was added, and the solution was extracted with ethyl acetate (3×30 ml) and then dried over magnesium sulfate. The extraction solvent was distilled off and the residue was purified by silica gel flash column chromatography (eluting solvent: n-hexane/ethyl acetate=45/55, 20/80) to synthesize THK-5177 (yellow crystals, 40.8 mg, 70%).

EI-MS m/z 395[M]$^+$.

$^1$H NMR (600 MHz, CDCl$_3$) δ 2.38 (3H, s), 2.54 (1H, br), 2.61 (4H, t, J=4.8 Hz), 3.33 (4H, t, J=4.8 Hz), 4.20-4.24 (2H, m), 4.31-4.38 (1H, m), 4.59-4.65 (1H, m), 4.67-4.73 (11H, m), 7.04 (1H, d, J=9.0 Hz), 7.10 (1H, d, J=3.0 Hz), 7.36 (1H, dd, J=3.0, 9.0 Hz), 7.81 (1H, d, J=8.4 Hz), 8.04 (1H, d, J=9.6 Hz), 8.05 (1H, d, J=9.0 Hz), 8.08 (2H, d, J=9.0 Hz).

Synthesis Method of THK-5178

Synthesis of 191

From 115 (134 mg, 0.361 mmol) and 190 (146 mg, 0.505 mmol), 191 (a yellow crystal, 144 mg, 80%) was synthesized in the same manner as in the compound 175. EI-MS m/z 496[M]$^+$.

Synthesis of THK-5178

From 191 (30.4 mg, 0.065 mmol), THK-5178 (a milk white crystal, 13.3 mg, 54%) was synthesized in the same manner as in THK-5177. EI-MS m/z 382 [M]$^+$.

$^1$H NMR (600 MHz, CDCl$_3$) δ 2.19 (1H, s), 2.54 (1H, br), 3.02 (4H, t, J=5.4 Hz), 3.63 (4H, t, J=5.4 Hz), 4.20-4.24 (2H, m), 4.32-4.38 (1H, m), 4.59-4.65 (1H, m), 4.67-4.73 (1H, m), 6.78 (1H, d, J=9.0 Hz), 7.11 (1H, d, J=2.4 Hz), 7.37 (1H, dd, J=2.4, 9.0 Hz), 7.78 (1H, d, J=9.0 Hz), 8.02 (1H, d, J=9.6 Hz), 8.06 (1H, d, J=8.4 Hz), 8.38 (1H, dd, J=2.4, 9.0 Hz), 8.90 (1H, d, J=2.4 Hz).

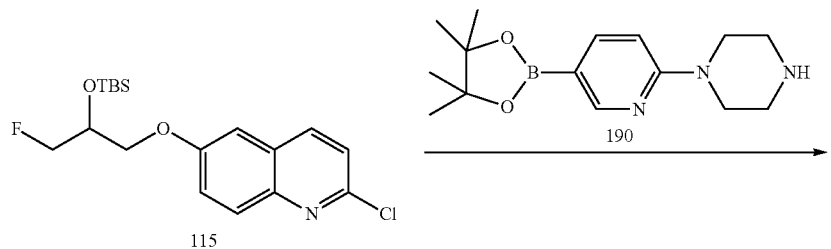

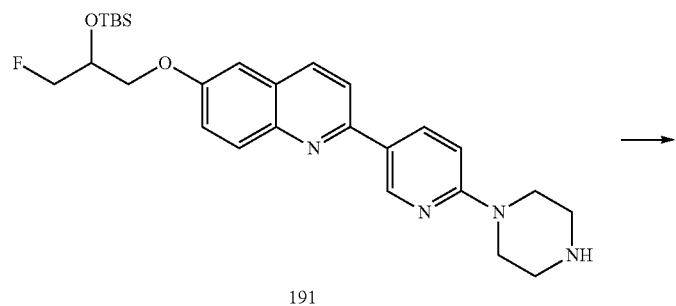

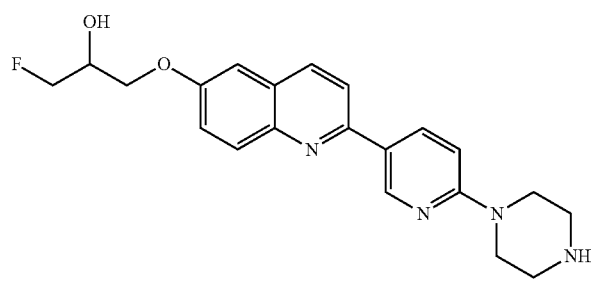

Synthesis Method of THK-5180

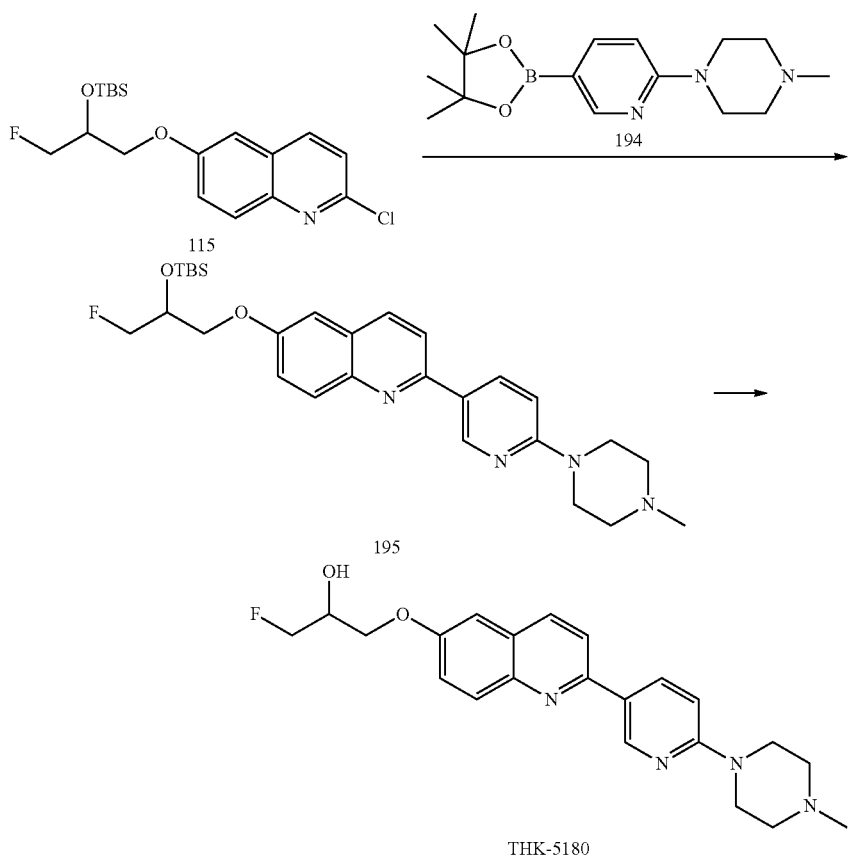

Synthesis of 195
From 115 (180 mg, 0.486 mmol) and 194 (157 mg, 0.517 mmol), 195 (a white crystal, 119 mg, 48%) was synthesized in the same manner as in the compound 175. EI-MS m/z 510[M]⁺.

Synthesis of THK-5180
From 195 (86.0 mg, 0.168 mmol), THK-5180 (white crystals, 48.6 mg, 73%) was synthesized in the same manner as in THK-5177. EI-MS m/z 396[M]⁺.
$^1$H NMR (600 MHz, CDCl$_3$) δ 2.37 (3H, s), 2.46 (1H, d, J=5.4 Hz), 2.55 (4H, t, J=5.4 Hz), 3.69 (4H, t, J=5.4 Hz), 4.20-4.25 (2H, m), 4.31-4.38 (1H, m), 4.59-4.65 (1H, m), 4.67-4.73 (1H, m), 6.79 (1H, d, J=9.0 Hz), 7.11 (1H, d, J=2.4 Hz), 7.37 (1H, dd, J=3.0, 9.6 Hz), 7.76 (1H, d, J=9.0 Hz), 8.02 (1H, d, J=9.0 Hz), 8.06 (1H, d, J=8.4 Hz), 8.38 (1H, dd, J=2.4, 9.0 Hz), 8.90 (1H, d, J=2.4 Hz).

Synthesis Method of THK-5142

-continued

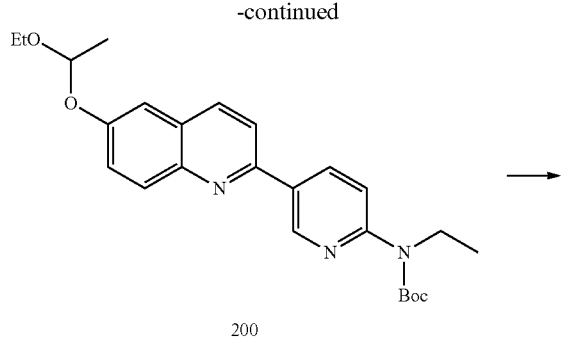

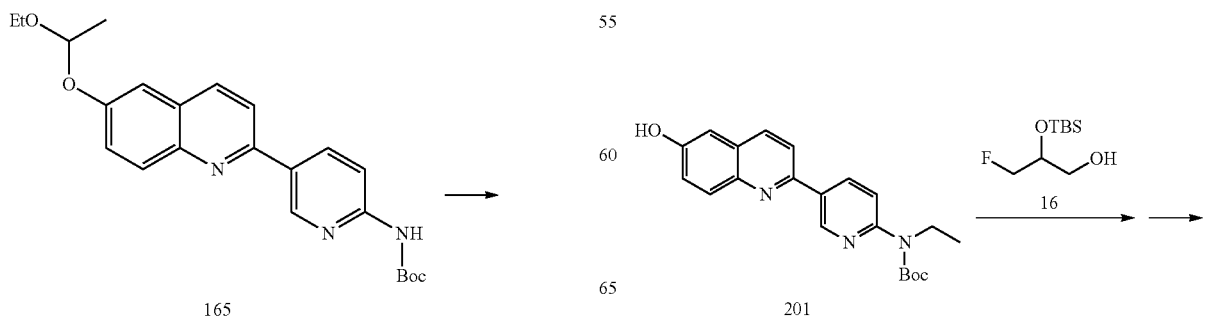

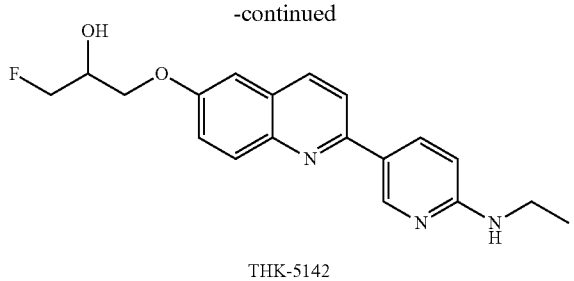

THK-5142

200

To an N,N-dimethylformamide (30 ml) suspension of 165 (2.09 g, 5.10 mmol), 60% sodium hydride (245 mg, 6.12 mmol) was added little by little under ice cooling and stirring and an argon atmosphere. After stirring at the same temperature for 10 minutes, ethyl iodide (0.616 ml, 7.66 mmol) was added dropwise, and the mixture was stirred at the same temperature for 1 hour, followed by stirring at room temperature for 30 minutes. To the reaction solution, ice water was added and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4) to obtain 200 (2.07 g, 92%) as a colorless oily substance.

APCI-MS m/z 438[M+H]$^+$

201

To a chloroform (30 ml) solution of 200 (2.06 g, 4.71 mmol), trifluoroacetic acid (5 ml) was added dropwise under ice cooling and stirring, and the mixture was stirred at the same temperature for 20 minutes. To the reaction solution, water was added, and the solution was extracted with ethyl acetate after adjusting the pH to 7 using an aqueous potassium carbonate solution. The extraction liquid was dried and the solvent was distilled off under reduced pressure, and the residue was purified by silica gel column chromatography (eluting solvent: n-hexane/ethyl acetate=2/1) and then recrystallized from n-hexane/ethyl acetate to obtain 201 (1.26 g, 73%) as pale yellow crystals.

mp 181-182° C.

APCI-MS m/z 366[M+H]$^+$

Synthesis of THK-5142

To a tetrahydrofuran (20 ml) solution of 201 (750 mg, 2.05 mmol), 16 (1.03 g, 4.93 mmol) and triphenylphosphine (1.29 g, 4.93 mmol), a tetrahydrofuran (10 ml) solution of diisopropyl azodicarboxylate (0.98 ml, 4.93 mmol) was added dropwise under ice cooling and stirring, and the mixture was stirred at the same temperature for 1 hour, followed by stirring at room temperature for 16 hours. The solvent of the reaction solution was distilled off under reduced pressure, and the residue was purified by silica gel column chromatography (eluting solvent: ethylacetate/n-hexane=1/20, 1/9) to obtain a colorless oily substance (1.69 g) containing the objective product. To a chloroform (18 ml) solution of the present product (1.69 q), trifluoroacetic acid (12 ml) was added dropwise under ice cooling and stirring, and water (3 ml) was added, followed by stirring at room temperature for 16 hours. To the reaction solution, ice water and then ethyl acetate were added, and the solution was extracted with ethyl acetate after adjusting the pH to 9 using an aqueous potassium carbonate solution. The extraction liquid was dried and the solvent was distilled off under reduced pressure, and the residue was purified by silica gel column chromatography (eluting solvent: ethyl acetate/n-hexane=1/1, 2/1) and then recrystallized from ethyl acetate to obtain THK-5142 (465 mg, 66%) as colorless crystals.

mp 154-155° C.

$^1$H NMR (400 MHz, DMSO-d$_6$) δ 1.17 (3H, t, J=7.3 Hz), 3.29-3.38 (2H, m), 4.06-4.20 (3H, m), 4.44-4.65 (2H, m), 5.53 (1H, d, J=5.7 Hz), 6.58 (1H, d, J=8.8 Hz), 6.90 (1H, t, J=5.4 Hz), 7.39 (1H, d, J=2.7 Hz), 7.39 (1H, dd, J=8.8, 2.7 Hz), 7.90 (1H, d, J=8.8 Hz), 7.97 (1H, d, J=8.5 Hz), 8.23 (1H, d, J=8.5 Hz), 8.25 (1H, dd, J=8.8, 2.7 Hz), 8.85 (1H, br)

IR (Nujol) 3333, 1625 cm$^{-1}$

APCI-MS m/z 342[M+H]$^+$

Synthesis Method of THK-5143

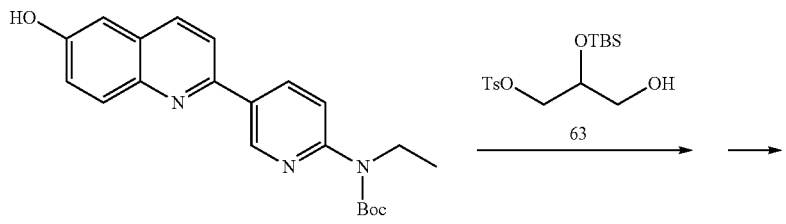

201

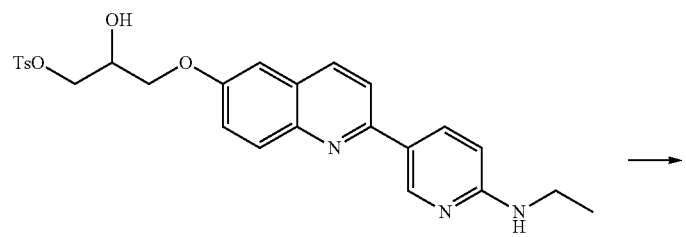

202

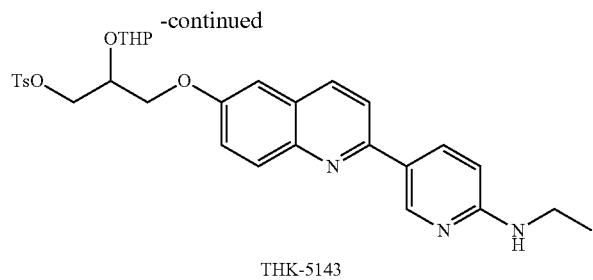

THK-5143

202

To a tetrahydrofuran (20 ml) solution of 201 (500 mg, 1.37 mmol), 63 (1.18 g, 3.28 mmol) and triphenylphosphine (860 mg, 3.28 mmol), a tetrahydrofuran (10 ml) solution of diisopropyl azodicarboxylate (0.65 ml, 3.28 mmol) was added dropwise under ice cooling and stirring, followed by stirring at the same temperature for 1 hour and further stirring at room temperature for 2 days. The solvent of the reaction solution was distilled off under reduced pressure, and the residue was purified by silica gel column chromatography (eluting solvent: ethyl acetate/n-hexane=1/4) to obtain a colorless solid (1.51 g) containing the objective product. To a chloroform (18 ml) solution of the present product (1.51 g), trifluoroacetic acid (12 ml) was added dropwise under ice cooling and stirring, and water (3 ml) was added, followed by stirring at room temperature for 3 days. To the reaction solution, ice water and ethyl acetate were added, and the solution was extracted with ethyl acetate after adjusting the pH to 8 using an aqueous potassium carbonate solution. The extraction liquid was dried and the solvent was distilled off under reduced pressure, and the residue was purified by silica gel column chromatography (eluting solvent: ethyl acetate/n-hexane=2/1, ethyl acetate) and then washed with ethyl acetate/n-hexane=1 to obtain 202 (520 mg, 77%) as colorless crystals.

mp 158-159° C.

APCI-MS m/z 494[M+H]$^+$

Synthesis of THK-5143

To a chloroform (20 ml) suspension of 202 (510 mg, 1.03 mmol), 3,4-dihydro-2H-pyran (1.87 ml, 20.7 mmol) and paratoluenesulfonic acid monohydrate (409 mg, 2.38 mmol) were added, and the mixture was stirred at room temperature for 20 minutes. After adjusting the pH of the reaction solution to 8 by adding triethylamine, the solvent was distilled off under reduced pressure. The residue was purified by silica gel column chromatography (eluting solvent: ethyl acetate/n-hexane=1/1, 2/1) and then recrystallized from ethyl acetate/n-hexane to obtain THK-5143 (508 mg, 85%) as colorless crystals.

mp 93-94° C.

$^1$H NMR (400 MHz, DMSO-d$_6$) δ 1.17 (3H, t, J=7.3 Hz), 1.33-1.72 (6H, m), 2.34 (3H, s), 3.30-3.37 (2H, m), 3.37-3.47 (1H, m), 3.69-3.73, 3.81-3.88 (1H, m), 4.09-4.37 (5H, m), 4.71, 4.84-4.88 (1H, m), 6.58 (1H, d, J=8.8 Hz), 6.91 (1H, t, J=5.3 Hz), 7.23-7.27 (1H, m), 7.29-7.31 (1H, m), 7.39-7.43 (2H, m), 7.77-7.82 (2H, m), 7.98 (1H, d, J=8.8 Hz), 7.97 (1H, d, J=8.5 Hz), 8.21 (1H, d, J=8.5 Hz), 8.25 (1H, dd, J=9.1, 2.4 Hz), 8.86 (1H, br)

IR (Nujol) 3347, 1622, 1602 cm$^{-1}$

APCI-MS m/z 578[M+H]$^+$

Synthesis Method of THK-5136

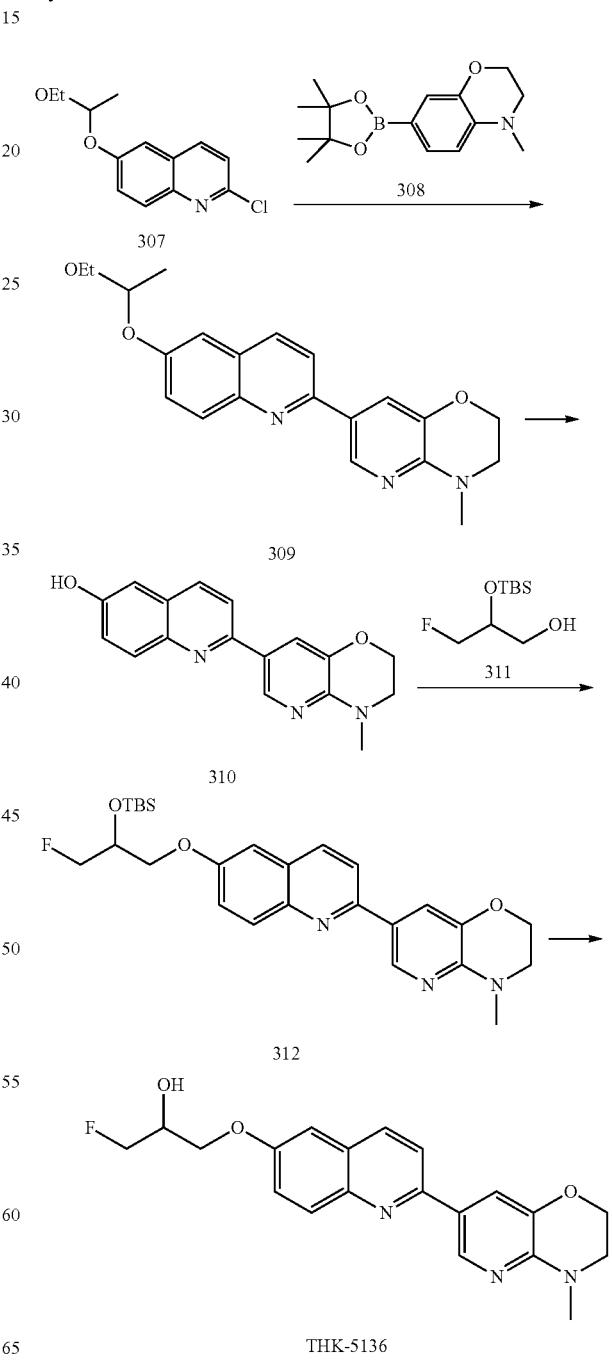

THK-5136

Synthesis of 309

To a 1,2-dimethoxyethane (30 ml) solution of 307 (900 mg, 3.58 mmol) and 308 (990 mg, 3.58 mmol), potassium carbonate (1.48 g, 10.7 mmol), water (0.62 ml) and tetrakistriphenylphosphine palladium (410 mg, 0.36 mmol) were added under an argon atmosphere, and the mixture was stirred at 80° C. for 16 hours. The reaction solution was allowed to return to room temperature and water was added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/2) to obtain 309 (1.31 g, 100%) as a pale yellow solid.

mp 112-113° C.

APCI-MS m/z 366[M+H]+

Synthesis of 310

To a chloroform (20 ml) solution of 309 (1.31 g, 3.58 mmol), trifluoroacetic acid (2 ml) was added dropwise under ice cooling and stirring, and the mixture was stirred at the same temperature for 30 minutes. To the reaction solution, ice water was added and the solution was extracted with ethyl acetate after adjusting the pH to 8 using an aqueous potassium carbonate solution. The extraction liquid was washed with water and dried, and then the solvent was distilled off under reduced pressure. The residue was washed with n-hexane/ethyl acetate=4/1 to obtain 310 (950 mg, 90%) as pale yellow crystals.

mp 273-274° C.

APCI-MS m/z 294[M+H]+

Synthesis of 312

To a tetrahydrofuran (20 ml) solution of 310 (500 mg, 1.71 mmol), 311 (852 mg, 4.09 mmol) and triphenylphosphine (1.07 g, 4.09 mmol), a tetrahydrofuran (10 ml) solution of diisopropyl azodicarboxylate (0.81 ml, 4.09 mmol) was added dropwise over 15 minutes under ice cooling and stirring, and the mixture was stirred at the same temperature for 1 hour, followed by stirring at room temperature for 4 days. The solvent of the reaction solution was distilled off under reduced pressure, and the residue was purified by silica gel column chromatography (eluting solvent: ethylacetate/n-hexane=1/4, 1/2) to obtain 312 (710 mg, 86%) as a pale yellow solid.

mp 139-140° C.

APCI-MS m/z 484[M+H]+

Synthesis of THK-5136

To a tetrahydrofuran (20 ml) solution of 312 (700 mg, 1.45 mmol), 1M tetra-n-butylammonium fluoride/tetrahydrofuran (1.45 ml, 1.45 mmol) was added dropwise at room temperature under stirring, and the mixture was stirred at room temperature for 1 hour. To the reaction solution, water was added, and the solution was extracted with ethyl acetate. The extraction liquid was dried and the solvent was distilled off under reduced pressure, and the residue was purified by silica gel column chromatography (eluting solvent: ethyl acetate/n-hexane=1/2, 2/1) and then recrystallized from ethyl acetate to obtain THK-5136 (466 mg, 87%) as pale yellow crystals.

mp 169-170° C.

$^1$H NMR (400 MHz, DMSO-$d_6$) δ 3.12 (3H, s), 3.52 (2H, t, J=4.5 Hz), 4.06-4.19 (3H, m), 4.27 (2H, t, J=4.5 Hz), 4.44-4.65 (2H, m), 5.53 (1H, d, J=4.2 Hz), 7.37-7.41 (2H, m), 7.78 (1H, d, J=1.8 Hz), 7.88-7.92 (1H, m), 8.00 (1H, d, J=8.5 Hz), 8.24 (1H, d, J=8.8 Hz), 8.56 (1H, d, J=2.1 Hz)

IR (Nujol) 1620 cm$^{-1}$

APCI-MS m/z 370[M+H]+

Synthesis Method of THK-5153

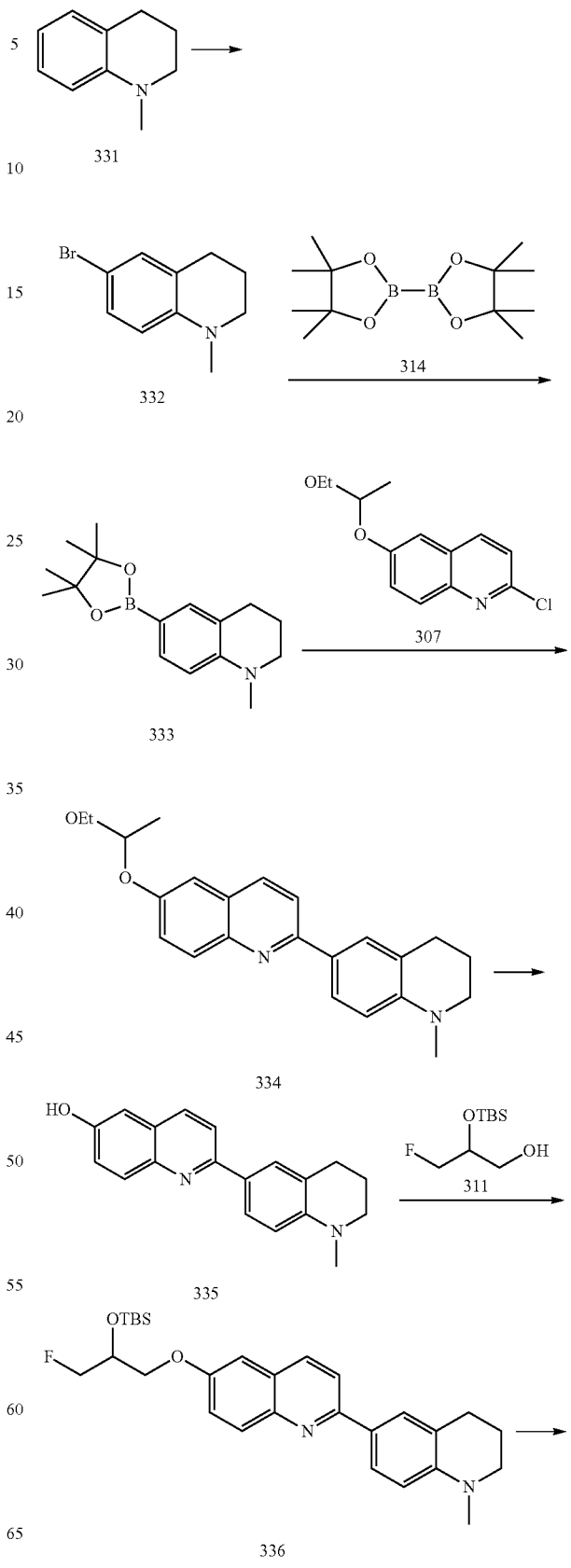

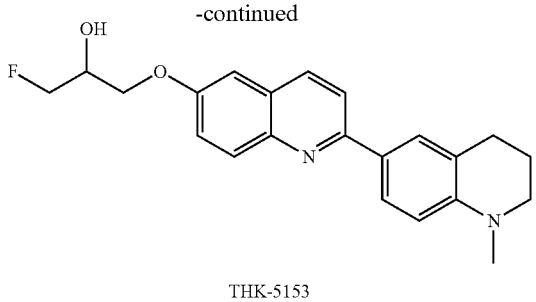

THK-5153

Synthesis of 332

To a tetrahydrofuran (70 ml) solution of 331 (5.25 g, 35.66 mmol), N-bromosuccinimide (6.35 g, 35.66 mmol) was added at −78° C. under an argon atmosphere, and the mixture was stirred at the same temperature for 3 hours, followed by stirring at room temperature for 16 hours. To the reaction solution, water and ethyl acetate were added, and the solution was extracted with ethyl acetate after adjusting the pH to 9 using an aqueous potassium carbonate solution. The extraction liquid was dried and the solvent was distilled off under reduced pressure, and the residue was purified by silica gel column chromatography (eluting solvent: ethyl acetate/n-hexane=1/50) to obtain 332 (7.38 g, 91%) as a colorless oily substance.

APCI-MS m/z 226/228[M+H]$^+$

Synthesis of 333

To a 1,4-dioxane (200 ml) solution of 332 (7.37 g, 32.6 mmol) and 314 (9.93 g, 39 mmol), potassium acetate (9.6 g, 97.8 mmol) and Pd(dppf)Cl$_2$·CH$_2$Cl$_2$ (1.19 g, 1.46 mmol) were added under an argon atmosphere, and the mixture was heated at reflux at 100° C. for 8 hours. The reaction solution was allowed to return to room temperature and insolubles were filtration with celite, and the solvent of the filtrate was distilled off under reduced pressure. The residue was purified by silica gel column chromatography (eluting solvent: ethyl acetate/n-hexane=1/50) to obtain 333 (4.71 g, 53%) as a pale yellow solid.

mp 129-130° C.

APCI-MS m/z 274[M+H]$^+$

Synthesis of 334

To a 1,2-dimethoxyethane (107 ml) solution of 333 (4.46 g, 16.3 mmol) and 307 (3.28 g, 13.0 mmol), potassium carbonate (5.40 g, 39.0 mmol), water (2.27 ml) and tetrakistriphenylphosphine palladium (1.51 g, 1.3 mmol) were added under an argon atmosphere, and the mixture was stirred at 80° C. for 16 hours. The reaction solution was allowed to return to room temperature and sodium sulfate was added, followed by drying and further filtration with celite. The solvent of the filtrate was distilled off under reduced pressure and the residue was purified by silica gel column chromatography (eluting solvent: ethyl acetate/n-hexane=1/9) to obtain 334 (4.52 g, 95%) as a yellow oily substance.

APCI-MS m/z 363[M+H]$^+$

Synthesis of 335

To a chloroform (24 ml) solution of 334 (4.51 g, 12.4 mmol), trifluoroacetic acid (16 ml) was added dropwise under ice cooling and stirring, and the mixture was stirred at the same temperature for 20 minutes. To the reaction solution, water and ethyl acetate were added and the solution was extracted with ethyl acetate after adjusting the pH to 8 using an aqueous potassium carbonate solution. The extraction liquid was washed with water and dried and the solvent was distilled off under reduced pressure, and then the residue was washed with ethyl acetate/n-hexane=1/1 to obtain 335 (3.17 q, 88%) as orange crystals.

mp 323-325° C.

APCI-MS m/z 291[M+H]$^+$

Synthesis of 336

To a mixture of 335 (500 mg, 1.72 mmol), 311 (861 mg, 4.13 mmol), triphenylphosphine (1.08 g, 4.13 mmol) and tetrahydrofuran (20 ml), a tetrahydrofuran (10 ml) solution of isopropyl azodicarboxylate (0.82 ml, 4.13 mmol) was added dropwise over 10 minutes under ice cooling and stirring, and the mixture was stirred at the same temperature for 1 hour, followed by stirring at room temperature for 4 days. The solvent of the reaction solution was distilled off under reduced pressure, and the residue was purified by silica gel column chromatography (eluting solvent: ethyl acetate/n-hexane=1/9) to obtain 336 (820 mg, 99%) as a pale yellow solid.

mp 84-85° C.

APCI-MS m/z 481[M+H]$^+$

Synthesis of THK-5153

To a tetrahydrofuran (10 ml) solution of 336 (810 mg, 1.69 mmol), 1M tetra-n-butylammonium fluoride/tetrahydrofuran (1.69 ml, 1.69 mmol) was added dropwise at room temperature under stirring, and the mixture was stirred at room temperature for 1 hour. To the reaction solution, water was added, and the solution was extracted with ethyl acetate. The extraction liquid was dried and the solvent was distilled off under reduced pressure, and the residue was purified by silica gel column chromatography (eluting solvent: ethyl acetate/n-hexane=1/2) and then recrystallized from ethyl acetate to obtain THK-5153 (353 mg, 57%) as pale yellow crystals.

mp 137-138° C.

$^1$H NMR (500 MHz, DMSO-d$_6$) δ 1.89-1.97 (2H, m), 2.81 (2H, t, J=6.4 Hz), 2.94 (3H, s), 3.30 (2H, t, J=5.8 Hz), 4.06-4.18 (3H, m), 4.46-4.63 (2H, m), 5.55 (1H, s), 6.68 (1H, d, J=9.0 Hz), 7.38-7.43 (2H, m), 7.84 (1H, d, J=1.9 Hz), 7.91 (1H, dd, J=8.7, 2.2 Hz), 7.92-7.95 (1H, m), 7.99 (1H, d, J=8.7 Hz), 8.26 (1H, d, J=8.7 Hz)

IR (Nujol) 1598 cm$^{-1}$

APCI-MS m/z 367[M+H]$^)$

Synthesis Method of THK-5157

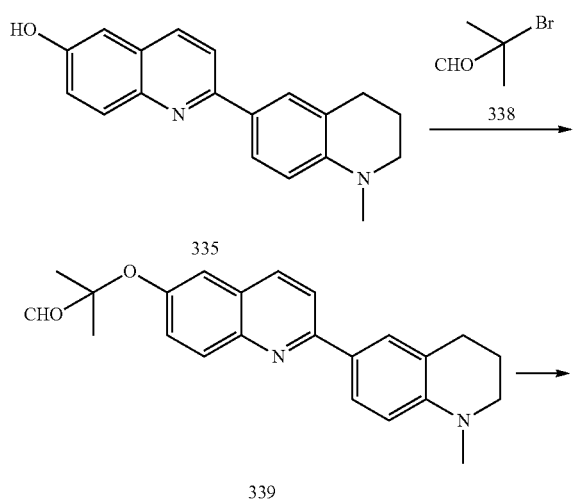

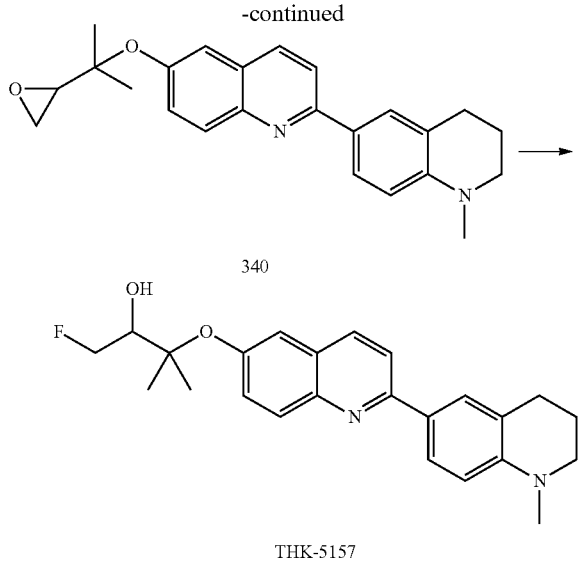

THK-5157

Synthesis of 339

To a tetrahydrofuran (100 ml) suspension of 335 (2.00 g, 6.89 mmol), 1M t-butoxy potassium/tetrahydrofuran (7.58 ml, 7.58 mmol) was added dropwise and dissolved at room temperature under stirring and an argon atmosphere. The solvent of the reaction solution was distilled off under reduced pressure, and 18-crown-6 (1.82 g, 6.89 mmol) and acetonitrile (40 ml) were added to the residue. After cooling to −78° C., an acetonitrile (10 ml) solution of 338 (1.87 g, 12.4 mmol) was added dropwise, the mixture was stirred under an argon atmosphere at room temperature for 16 hours. To the reaction solution, water was added and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/4, ethyl acetate) and then washed with ethyl acetate/n-hexane=1/100 to obtain 339 (1.81 g, 73%) as pale yellow crystals.

mp 135-136° C.

APCI-MS m/z 361[M+H]$^+$

Synthesis of 340

To a mixture of trimethylsulfoxonium iodide (1.65 g, 7.50 mmol) and DMSO (20 ml), 60% sodium hydride (300 mg, 7.50 mmol) was added under ice cooling and stirring, and the mixture was stirred at room temperature for 30 minutes. The reaction solution was ice-cooled and a tetrahydrofuran (10 ml) solution of 339 (1.80 g, 4.99 mmol) was added dropwise, followed by stirring at room temperature for 1 hour. To the reaction solution, ice water was added, and the solution was extracted with ethyl acetate. The extraction liquid was washed with water and died, and then the solvent was distilled off under reduced pressure and the residue was purified by silica gel column chromatography (eluting solvent: ethyl acetate/n-hexane=1/4) to obtain 340 (1.74 g, 93%) as a pale yellow oily substance.

APCI-MS m/z 375[M+H]$^+$

Synthesis of THK-5157

A mixture of 340 (1.73 g, 4.62 mmol), n-Bu$_4$NH$_2$F$_3$ (232 mg, 0.46 mmol) and KHF$_2$ (722 mg, 9.24 mmol) was stirred at 120° C. for 2 hours. The reaction solution was allowed to return to room temperature, water and ethyl acetate were added and the solution was extracted with ethyl acetate after adjusting the pH to 8 using an aqueous potassium carbonate solution. The extraction liquid was washed with water and dried, and then the solvent was distilled off under reduced pressure. The residue was purified by silica gel column chromatography (eluting solvent: ethyl acetate/n-hexane=1/4, 1/3) and then recrystallized from ethyl acetate to obtain THK-5157 (474 mg, 26%) as pale yellow crystals.

mp 163-164° C.

$^1$H NMR (400 MHz, DMSO-d$_6$) δ 1.21 (3H, s), 1.22 (3H, s), 1.90-1.96 (2H, m), 2.81 (2H, t, J=6.3 Hz), 2.93 (3H, s), 3.30 (2H, t, J=5.8 Hz), 4.54-4.61 (1H, m), 4.67 (1H, ddd, J=48, 10, 7.1 Hz), 4.93 (1H, ddd, J=48, 10, 2.9 Hz), 4.95 (1H, d, J=6.7 Hz), 6.68 (1H, d, J=8.7 Hz), 7.44-7.49 (2H, m), 7.85 (1H, d, J=2.2 Hz), 7.89-7.94 (2H, m), 7.97 (1H, d, J=8.7 Hz), 8.22 (1H, d, J=8.3 Hz)

IR (Nujol) 3267, 1620, 1599 cm$^{-1}$

APCI-MS m/z 395[M+H]$^+$

Synthesis Method of THK-5128

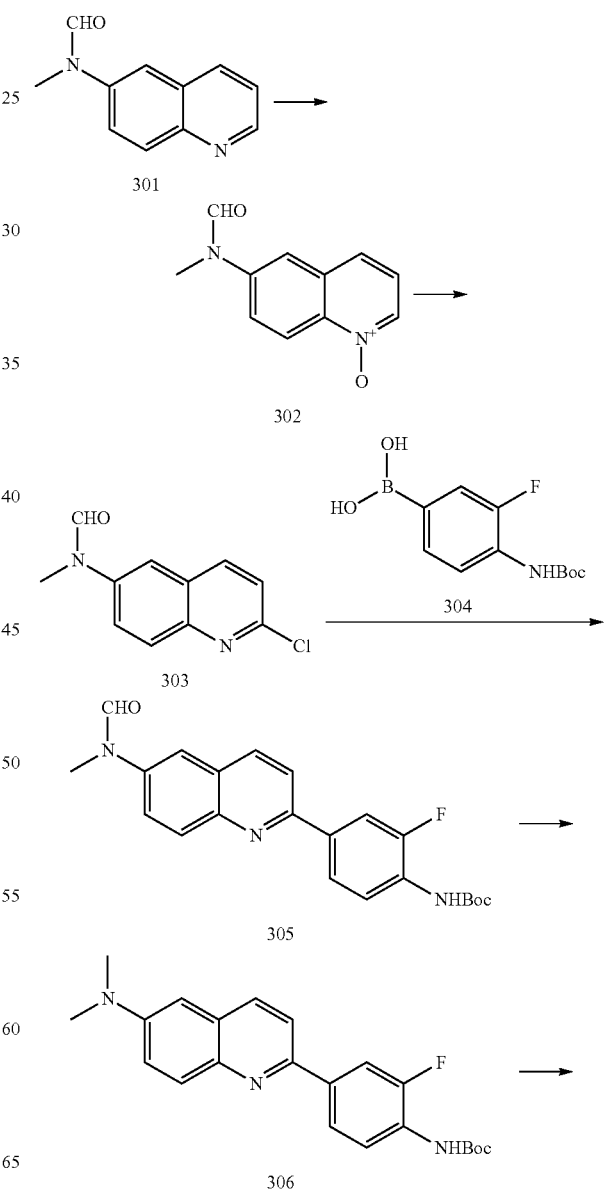

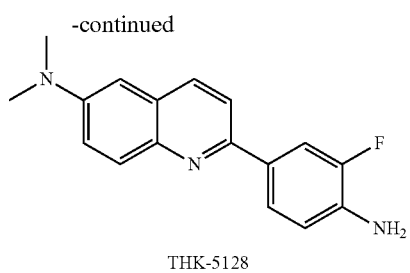

THK-5128

Synthesis of 302

A mixture of 301 (3.65 g, 19.6 mmol), 75% methachlorobenozic acid (5.20 g, 22.6 mmol) and chloroform (40 ml) was stirred at room temperature for 2 hours. The reaction solution was washed in turn with an aqueous sodium thiosulfate solution, an aqueous saturated sodium hydrogen carbonate solution and saturated saline. The organic layer was dried and the solvent was distilled off under reduced pressure. The residue was purified by silica gel column chromatography (eluting solvent: chloroform/methanol=30/1, 10/1) and the washed with diisopropyl ether to obtain 302 (3.30 g, 831) as a solid.

mp 145-146° C.

Synthesis of 303

A mixture of 302 (3.20 g, 16.3 mmol), paratoluenesulfonyl chloride (3.3 g, 17.3 mmol), potassium carbonate (2.5 g, 18.1 mmol) and chloroform (60 ml) was heated at reflux for 3 hours. The reaction solution was allowed to return to room temperature and water was added, and the solution was extracted with chloroform. The extraction liquid was washed in turn with an aqueous saturated sodium hydrogen carbonate solution and a saturated saline and, after drying, the solvent was distilled off under reduced pressure. The residue was purified by silica gel column chromatography (eluting solvent: n-hexane/ethyl acetate=2/1) to obtain 303 (2.30 g, 64%) as a colorless solid.

mp 110-111° C.

APCI-MS m/z 221[M+H]$^+$

Synthesis of 305

A mixture of 303 (883 mg, 4.0 mmol), 304 (1.224 g, 4.8 mmol), 1,2-dimethoxyethane (20 ml), sodium carbonate (848 mg, 8.0 mmol), water (2 ml) and tetrakistriphenylphosphine palladium (231 mg, 0.2 mmol) was heated at reflux under an argon atmosphere for 18 hours. The reaction solution was al lowed to return to room temperature and water was added, and the solution was extracted with ethyl acetate. The extraction liquid was washed in turn with water and saturated saline and, after drying, the solvent was distilled off under reduced pressure. The residue was purified by silica gel column chromatography (eluting solvent: ethyl acetate/toluene=1/10, 1/4) to obtain 305 (1.38 g, 87%) as a colorless solid.

mp 160-161° C.

Synthesis of 306

To a tetrahydrofuran (30 ml) suspension of NaBH$_4$ (380 mg, 10 mmol), a tetrahydrofuran (5 ml) solution of BF$_3$.Et$_2$O (1.86 g, 13.1 mmol) was added dropwise at 0° C., and the mixture was stirred at the same temperature for 30 minutes. To the present reaction solution, a tetrahydrofuran (10 ml) solution of 305 (1.30 g, 3.28 mmol) was added dropwise at 0 to 5° C., and the solution was stirred at the same temperature for 20 minutes, followed by stirring at room temperature for 1 hour. The reaction solution was ice-cooled and an aqueous saturated sodium hydrogen carbonate solution was added dropwise, and the solution was stirred and then extracted with ethyl acetate. The extraction liquid was washed in turn with water and saturated saline and, after drying, the solvent was distilled off under reduced pressure. The residue was purified by silica gel column chromatography (eluting solvent: ethyl acetate/n-hexane=1/4, 1/3) and then washed with n-hexane-diisopropyl ether to obtain 306 (980 mg, 78%) as an orange solid.

mp 175-176° C.

APCI-MS m/z 382[M+H]$^+$

Synthesis of THK-5128

To a methylene chloride (15 ml) solution of 306 (900 mg, 2.36 mmol), trifluoroacetic acid (3 ml) was added dropwise under ice cooling and stirring, and the mixture was stirred at room temperature for 1 hour. The reaction solution was ice-cooled and diluted with ethyl acetate, and the solution was made basic with 28 ammonia water, followed by liquid separation. The organic layer was washed in turn with water and saturated saline and, after drying, the solvent was distilled off under reduced pressure. The residue was purified by silica gel column chromatography (eluting solvent: toluene, ethyl acetate/toluene=1/3) and then recrystallized from ethyl acetate to obtain THK-5128 (545 mg, 82%) as yellow crystals.

mp 204-205° C. (dec.)

$^1$H NMR (400 MHz, CDCl$_3$) δ 3.08 (6H, s), 3.86 (2H, brs), 6.80 (1H, d, J=2.7 Hz), 6.87 (1H, dd, J=9.2, 8.8 Hz), 7.36 (1H, dd, J=9.4, 2.7 Hz), 7.66 (1H, d, J=8.8 Hz), 7.72 (1H, dd, J=8.8, 1.8 Hz), 7.86 (1H, dd, J=13, 1.8 Hz), 7.96 (1H, d, J=8.8 Hz), 7.97 (1H, d, J=9.4 Hz).

IR (Nujol) 3460, 3304, 3181, 1645, 1619, 1589 cm$^{-1}$

APCI-MS m/z 282[M+H]$^+$

Synthesis of THK-5147

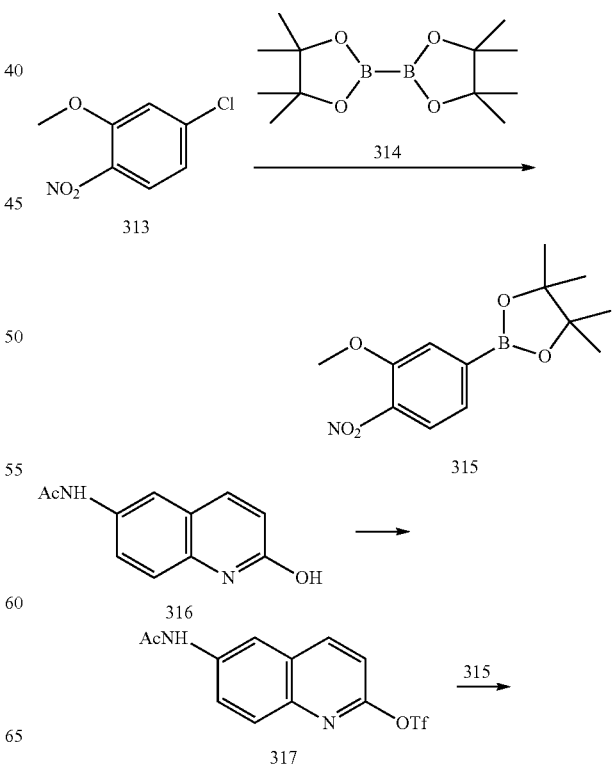

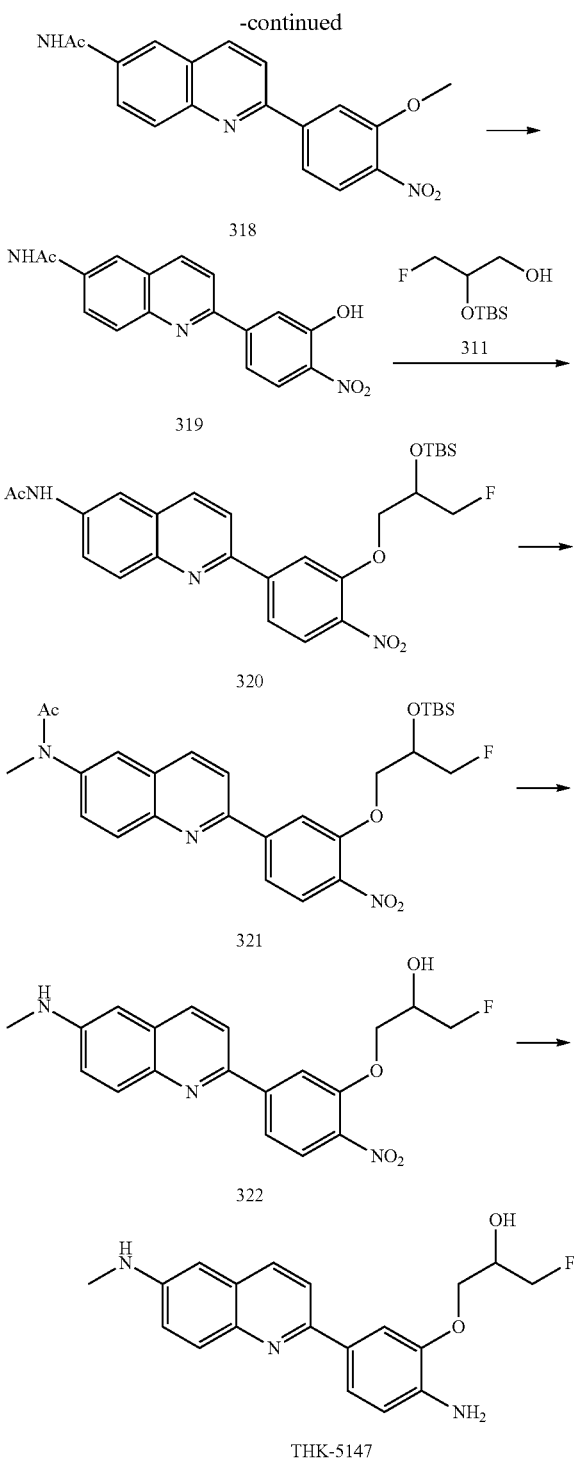

Synthesis of 315

A mixture of 313 (18.76 g, 0.1 mol), 314 (27.93 g, 0.11 mol), potassium acetate (14.72 g, 0.15 mol), Pd$_2$(dba)$_3$ (2.75 g, 3 mmol), tricyclohexylphosphine (2.02 g, 7.2 mmol) and 1,4-dioxane (200 ml) was stirred under an argon atmosphere at 90° C. for 16 hours. The reaction solution was allowed to return to room temperature and poured into ethyl acetate-water, and then the solution was extracted with ethyl acetate. The extraction liquid was washed with saturated saline and dried, and then the solvent was distilled off under reduced pressure. The residue was purified by silica gel flash column chromatography (eluting solvent: n-hexane→n-hexane/ethyl acetate=19/1, 9/1, 6/1, 4/1) to obtain 315 (26.74 g, 96%) as a pale yellow solid.

APCI-MS m/z 280[M+H]$^+$

Synthesis of 317

To a pyridine (1 L) suspension of 316 (29.51 g, 146 mmol), trifluoromethanesulfonic anhydride (48 ml, 292 mmol) was added dropwise at −30 to −20° C., and the mixture was stirred at 10° C. for 1 hour. To the reaction solution, ice water was added after distilling off a volatile substance at 40° C. or lower, the solution was extracted with ethyl acetate. The extraction liquid was washed with saturated saline and dried, and then the solvent was distilled off under reduced pressure. The residue was purified by silica gel flash column chromatography (eluting solvent: n-hexane→n-hexane/ethyl acetate=2/1, 1/1, 1/2, 1/5) and then recrystallized from ethyl acetate-diisopropyl ether to obtain 317 (30.86 g, 63%) as pale pink crystals.

APCI-MS m/z 335[M+H]$^+$

Synthesis of 318

A mixture of 317 (29.11 g, 87 mmol), 315 (26.74 g, 96 mmol), an aqueous 2M sodium carbonate solution (100 ml), tetrakistriphenylphosphine palladium (5 g, 4.3 mmol) and 1,2-dimethoxyethane (300 ml) was stirred under an argon atmosphere at 90° C. for 16 hours. The reaction solution was allowed to return to room temperature and 1,2-dimethoxyethane was distilled off under reduced pressure, and chloroform/methanol (=1/1) was added and then insolubles were removed by filtration. The filtrate was washed with saturated saline and dried the solvent was distilled off under reduced pressure. The residue was purified by silica gel flash column chromatography (eluting solvent: chloroform/tetrahydrofuran=4/1) and then washed with chloroform-diisopropyl ether to obtain 318 (20.5 g, 76%) as a yellow solid.

APCI-MS m/z 338[M+H]$^+$

Synthesis of 319

A mixture of 318 (1.0 g, 29.6 mmol), lithium chloride (1.26 g, 29.7 mmol) and hexamethylphosphoric triamide (5 ml) was stirred at 110° C. for 2 days. The reaction solution was allowed to return to room temperature and water was added. The solution was acidified with 10% hydrochloric acid water and made basic with an aqueous saturated sodium hydrogen carbonate solution, and then extracted with ethyl acetate-tetrahydrofuran. The extraction liquid was washed with saturated saline and dried, and then the solvent was distilled off under reduced pressure. The residue was purified by silica gel flash column chromatography (eluting solvent: chloroform/tetrahydrofuran=4/1, 3/2) and then recrystallized from tetrahydrofuran-diisopropyl ether to obtain 319 (745 mg, 781) as a yellow solid.

APCI-MS m/z 324[M+H]$^+$

Synthesis of 320

To a mixture of 319 (323 mg, 1.0 mmol), 311 (208 mg, 1.0 mmol), triphenylphosphine (394 mg, 1.5 mmol) and tetrahydrofuran (5 ml), a tetrahydrofuran (2 ml) solution of diisopropyl azodicarboxylate (300 mg, 1.5 mmol) was added dropwise under ice cooling and stirring, followed by stirring at the same temperature for 30 minutes and further stirring at room temperature for 20 hours. The reaction solution was purified by silica gel column chromatography (eluting solvent: ethyl acetate/n-hexane=1/1) to obtain 320 (403 mg, 78%) as a yellow caramel.

APCI-MS m/z 514[M+H]$^+$

Synthesis of 321

To a N,N-dimethylformamide (20 ml) suspension of 60% sodium hydride (345 mg, 8.6 mmol), an N,N-dimethylformamide (10 ml) solution of 320 (3.70 g, 7.2 mmol) was added dropwise under an argon atmosphere, and the mixture was stirred at 0 to 5° C., followed by stirring at −15° C. for 30 minutes. The reaction solution was allowed to return to 0 to 5° C. and an N,N-dimethylformamide (2 ml) solution of methyl iodide (2.2 g, 15 mmol) was added dropwise, and the solution was stirred at room temperature for 1 hour. The reaction solution was poured into ice water, and the solution was extracted with ethyl acetate. The extraction liquid was washed with saturated saline and dried, and then the solvent was distilled off under reduced pressure. The residue was purified by silica gel flash column chromatography (eluting solvent: ethyl acetate/n-hexane=1/1) to obtain 321 (3.30 g, 89%) as a pale yellow solid.

mp 97-99° C.

APCI-MS m/z 528[M+H]+

Synthesis of 322

A mixture of 321 (2.18 g, 4.13 mmol) and 48% HBr (25 ml) was stirred at 90 to 95° C. for 2 hours. The reaction solution was cooled and was made basic with 28% ammonia water, and then extracted with ethyl acetate. The extraction liquid was washed with saturated saline and dried, and then the solvent was distilled off under reduced pressure. The residue was washed with diisopropyl ether to obtain 322 (1.45 g, 95%) as an orange solid.

mp 130-132° C.

IR (Nujol) 3379, 1624, 1605 cm−1

APCI-MS m/z 372[M+H]+

Synthesis of THK-5147

A mixture of 322 (250 mg, 0.673 mmol), SnCl2.2H2O (450 mg, 1.99 mmol) and ethanol (10 ml) was heated at reflux for 1 hour. The reaction solution was allowed to return to room temperature, diluted with ethyl acetate and then made basic with 289 ammonia water. Insolubles were removed by filtration with celite, and the organic layer of the filtrate was separated and washed with saturated saline. After drying, the solvent was distilled off under reduced pressure. The residue was purified by NH silica gel column chromatography (eluting solvent: ethyl acetate/n-hexane=1/4) to obtain THK-5147 (175 mg, 76%) as a yellow solid.

mp 122-124° C.

1H NMR (400 MHz, CDCl3) δ 2.95 (3H, s), 3.96 (3H, br), 4.23-4.37 (3H, m), 4.49-4.61 (1H, m), 4.62-4.73 (1H, m), 6.69 (1H, d, J=2.7 Hz), 6.81 (1H, d, J=8.2 Hz), 7.08 (1H, dd, J=9.0, 2.7 Hz), 7.53 (1H, dd, J=8.2, 1.8 Hz), 7.68 (1H, d, J=8.8 Hz), 7.74 (1H, d, J=1.8 Hz), 7.91 (1H, d, J=9.0 Hz), 7.94 (1H, d, J=8.8 Hz)

IR (Nujol) 3429, 3342, 1625, 1595 cm−1

APCI-MS m/z 342[M+H]+

Synthesis Method of THK-5148

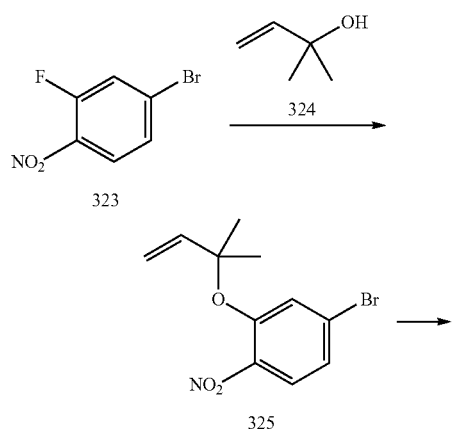

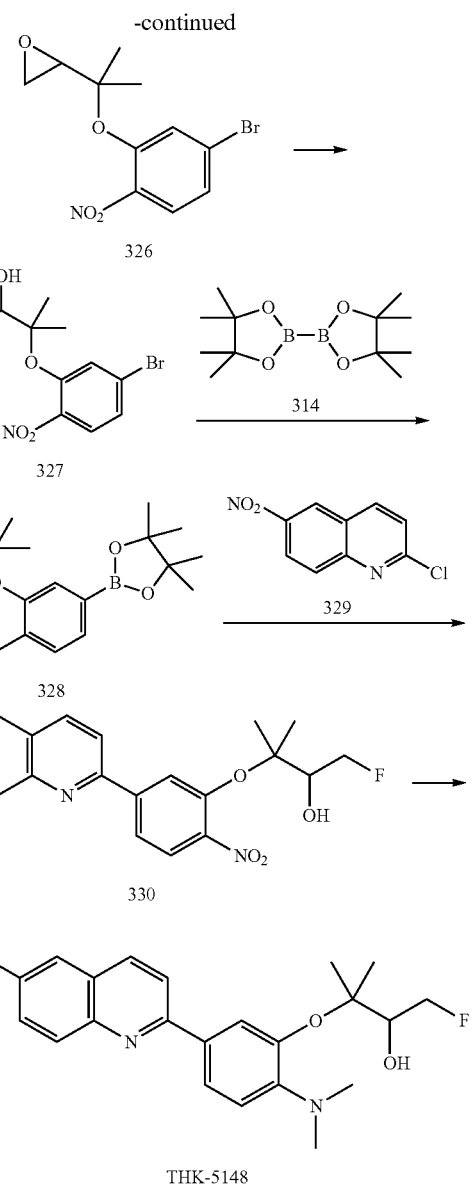

Synthesis of 325

Under an argon atmosphere, a tetrahydrofuran (15 ml) solution of 324 (3.1 g, 36 mmol) was added dropwise to a tetrahydrofuran (30 ml) suspension of 60% sodium hydride (1.44 g, 36 mmol) at room temperature, and the mixture was heated at reflux for 30 minutes. The reaction solution was cooled to 0 to 5° C. and a tetrahydrofuran (15 ml) solution of 323 (7.2 g, 33 mmol) was added dropwise, and the solution was stirred at room temperature for 16 hours. The reaction solution was poured into a cooled aqueous ammonium chloride solution, and then the solution was extracted with ethyl acetate. The extraction liquid was dried and the solvent was distilled off under reduced pressure, and then the residue was purified by silica gel flash column chromatography (eluting solvent: n-hexane→ethyl acetate/n-hexane=1/50, 1/20) to obtain 325 (8.46 g, 90%) as a yellow oily substance.

APCI-MS m/z 303/305[M+NH4]+

Synthesis of 326

A mixture of 325 (7.0 g, 24.5 mmol), 75% methachlorobenozic acid (20.26 g, 88.1 mmol) and chloroform (70 ml)

was stirred at room temperature for 2 days. The reaction solution was ice-cooled and an aqueous saturated sodium hydrogen carbonate solution was added, and the solution was extracted with chloroform. The extraction liquid was dried and the solvent was distilled off under reduced pressure, and then the residue was purified by silica gel flash column chromatography (eluting solvent: n-hexane→ethyl acetate/n-hexane=1/20, 1/10) to obtain 326 (4.197 g, 57%) as a yellow oily substance.

APCI-MS m/z 319/321[M+NH$_4$]$^+$

Synthesis of 327

A mixture of 326 (4.119 g, 13.6 mmol), n-Bu$_4$NH$_2$F$_3$ (410 mg, 1.36 mmol) and KHF$_2$ (2.13 g, 27.27 mmol) was stirred at 120° C. for 6 hours. The reaction solution was allowed to return to room temperature and chloroform was added, and then insolubles were removed by filtration. The filtrate was dried and the solvent was distilled off under reduced pressure, and then the residue was purified by silica gel flash column chromatography (eluting solvent: n-hexane→ethyl acetate/n-hexane=1/20, 1/10, 1/6, 1/4) to obtain 327 (1.3 g, 30%) as a yellow solid.

APCI-MS m/z 339/341[M+NH$_4$]$^+$

Synthesis of 328

A mixture of 327 (1.29 g, 4.0 mmol), 314 (1.06 g, 4.16 mmol), potassium acetate (1.18 g, 12 mmol), Pd(dppf)Cl$_2$·CH$_2$Cl$_2$ (229 mg, 0.28 mmol) and 1, 4-dioxane (20 ml) was heated at reflux for 16 hours under an argon atmosphere. The reaction solution was allowed to return to room temperature and the solvent was distilled off under reduced pressure. To the residue, ethyl acetate and an aqueous saturated sodium hydrogen carbonate solution were added, and then the solution was extracted with ethyl acetate. The extraction liquid was dried and the solvent was distilled off under reduced pressure, and then the residue was purified by silica gel flash column chromatography (eluting solvent: n-hexane→ethyl acetate/n-hexane=1/10, 1/4, 1/2) to obtain 328 (1.438 g, 97%) as a brown oily substance.

APCI-MS m/z 387[M+NH$_4$]$^+$

Synthesis of 330

A mixture of 328 (1.4 g, 3.8 mmol), 329 (729 mg, 3.5 mmol), an aqueous 2M sodium carbonate solution (3.5 ml), tetrakistriphenylphosphine palladium (202 mg, 0.175 mmol) and 1,2-dimethoxyethane (20 ml) was stirred at 90° C. for 5 hours under an argon atmosphere. The reaction solution was allowed to return to room temperature and 1,2-dimethoxyethane was distilled off under reduced pressure. Chloroform was added and insolubles were removed by filtration, followed by washing with chloroform/methanol (=9/1). The filtrate and the wash were combined, and the solvent was distilled off under reduced pressure. The residue was purified by silica gel flash column chromatography (eluting solvent: n-hexane→ethyl acetate/n-hexane=1/10, 1/4, 1/2) and then washed with n-hexane to obtain 330 (1.448 g, 99%) as a yellow solid.

APCI-MS m/z 416[M+H]$^+$

Synthesis of THK-5148

330 (1.44 g, 3.47 mmol), 10% Pd—C (300 mg) and ethanol-methanol (60 ml-20 ml) were stirred under hydrogen pressure (40 psi) at room temperature for 16 hours. The catalyst was removed by filtration and Pd—C (150 mg) was added to the filtrate, followed by further stirring under hydrogen pressure (40 psi) at room temperature for 1.5 hours. The catalyst was removed by filtration and the solvent of the filtrate was distilled off under reduced pressure. To the residue, methanol (50 ml)-acetic acid (5 ml), an aqueous 36% formaldehyde solution (3.1 g, 37.2 mmol) and a picoline borane complex (1.5 g, 14 mmol) were added, followed by stirring at room temperature for 16 hours. The solvent of the reaction solution was distilled off under reduced pressure and an aqueous saturated sodium hydrogen carbonate solution the residue, and the solution was extracted with chloroform. The extraction liquid was dried and the solvent was distilled off under reduced pressure. The residue was purified by silica gel flash column chromatography (eluting solvent: chloroform→chloroform/methanol=50/1) and then recrystallized from chloroform-n-hexane to obtain THK-5148 (832 mg, 58%) as a yellowish orange solid.

mp 182-184° C.

$^1$H NMR (400 MHz, DMSO-d$_6$) δ 1.25, 1.23 (6H, each s), 2.05 (6H, s), 2.82 (6H, s), 4.45-4.51 (1H, m), 4.81 (1H, ddd, J=48, 10, 6.5 Hz), 4.90 (1H, ddd, J=46, 10, 2.4 Hz), 5.09 (1H, brs), 6.94 (1H, d, J=2.7 Hz), 7.02 (1H, d, J=8.4 Hz), 7.44 (1H, dd, J=9.4, 2.7 Hz), 7.73 (1H, dd, J=8.5, 1.8 Hz), 7.85 (1H, d, J=9.4 Hz), 7.89 (1H, d, J=8.7 Hz), 7.91 (1H, d, J=2.1 Hz), 8.13 (1H, d, J=8.8 Hz)

IR (Nujol) 1819, 1375 cm$^{-1}$

APCI-MS m/z 412[M+H]$^+$

Synthesis Method of THK-5155

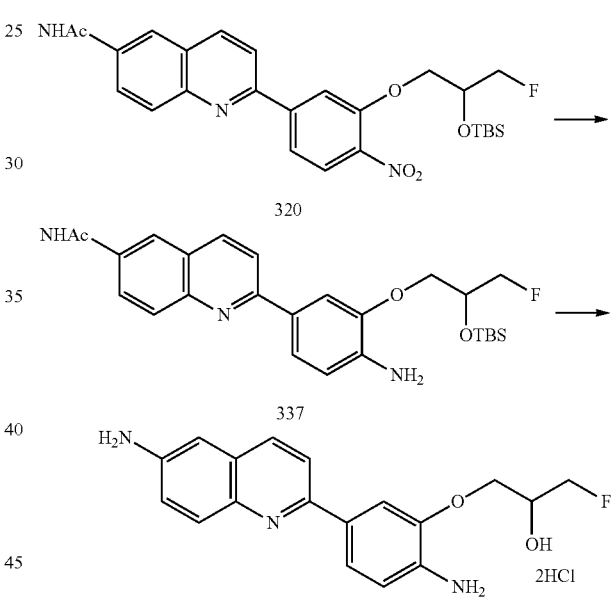

Synthesis of 337

320 (1.18 g, 2.3 mmol), 10% Pd—C (moisture 50%; 250 mg) and ethanol (30 ml) were stirred under hydrogen pressure (40 psi) at room temperature for 16 hours. The catalyst was removed by filtration and the solvent of the filtrate was distilled off under reduced pressure, and then the residue was purified by NH silica gel flash column chromatography (eluting solvent: chloroform) to obtain 337 (1.03 g, 93%) as a yellow foam-like substance.

Synthesis of THK-5155

A mixture of 337 (1.025 g, 2.12 mmol) and 48% HBr (10 ml) was stirred at 110° C. for 5 hours. The reaction solution was allowed to return to room temperature and the solvent was distilled off under reduced pressure. To the residue, an aqueous saturated sodium hydrogen carbonate solution was added, and the solution was extracted with ethyl acetate-tetrahydrofuran. The extraction liquid was dried and the solvent was distilled off under reduced pressure, and then the residue was purified by NH silica gel flash column chromatography (eluting solvent: chloroform/methanol=50/1) to obtain a pale yellow amorphous (684 mg). The present product was converted into a hydrochloride by a conventional method using 4M hydrochloric acid/ethyl acetate to obtain THK-5155 (670 mg, 79%) as an orange solid.

mp 232-235° C.

$^1$H NMR (400 MHz, DMSO-d$_6$) δ 4.05-4.25 (3H, m), 4.50-4.70 (2H, m), 6.94 (1H, d, J=8.2 Hz), 7.18 (1H, brs), 7.49 (1H, dd, J=9.0, 2.4 Hz), 7.72 (1H, dd, J=8.4, 1.8 Hz), 7.81 (1H, d, J=1.8 Hz), 8.19 (1H, d, J=9.0 Hz), 8.39 (1H, d, J=9.0 Hz), 8.62 (1H, d, J=9.0 Hz)

IR (Nujol) 1624, 1460 cm$^{-1}$

APCI-MS m/z 328[M+H]$^+$

Synthesis Method of THK-5156

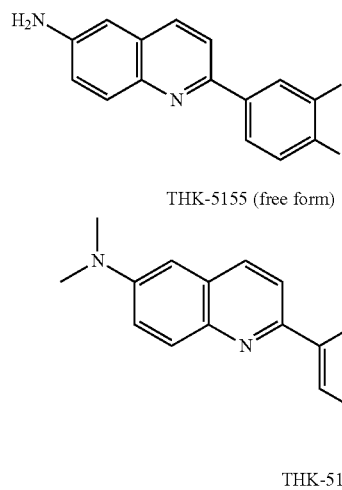

Synthesis of THK-5156

To a mixture of THK-5155 (free form) (450 mg, 1.4 mmol), an aqueous 36% formaldehyde solution (0.97 g, 11.6 mmol) and methanol (10 ml)-acetic acid (1 ml), a picoline borane complex (441 mg, 4.1 mmol) was added little by little, and the mixture was stirred at room temperature for 16 hours. The solvent of the reaction solution was distilled off under reduced pressure and 10% hydrochloric acid water was added to the residue, and the solution was stirred at room temperature for 10 minutes. The reaction solution was extracted with chloroform after being made basic with an aqueous potassium carbonate solution. The extraction liquid was dried and the solvent was distilled off under reduced pressure, and then the residue was purified by silica gel flash column chromatography (eluting solvent: chloroform-→chloroform/tetrahydrofuran=9/1, 6/1, 4/1) to obtain THK-5156 (328 mg, 62%) as an orange solid.

mp 187-188.5° C.

$^1$H NMR (400 MHz, DMSO-d$_6$) δ 2.82 (6H, s), 3.05 (6H, s), 4.10-4.20 (3H, m), 4.40-4.70 (2H, m), 5.50 (1H, brs), 6.95 (1H, d, J=2.4 Hz), 6.98 (1H, d, J=8.5 Hz), 7.45 (1H, dd, J=9.0, 2.4 Hz), 7.72 (1H, dd, J=8.4, 1.8 Hz), 7.78 (1H, d, J=1.8 Hz), 7.87 (1H, d, J=9.4 Hz), 7.95 (1H, d, J=8.8 Hz), 8.14 (1H, d, J=8.8 Hz)

IR (Nujol) 1620, 1463, 1375 cm$^{-1}$

APCI-MS m/z 384[M+H]$^+$

Synthesis Method of THK-5158

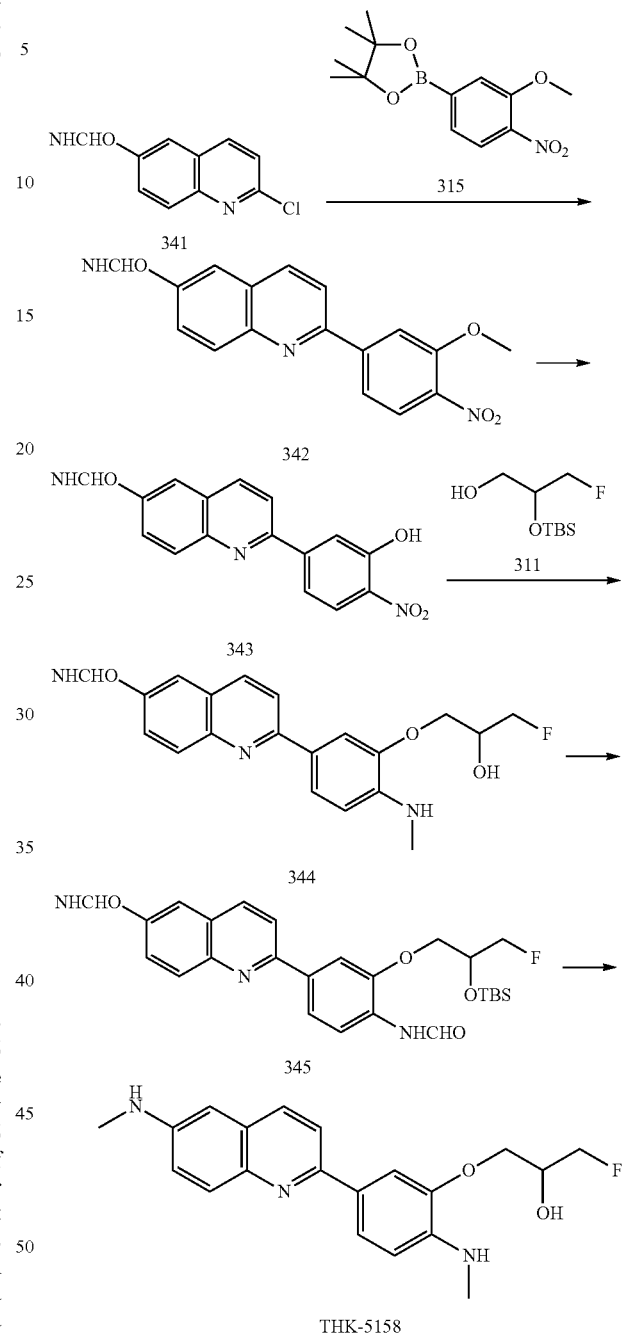

Synthesis of 342

To a 1,2-dimethoxyethane (364 ml) solution of 341 (9.14 g, 44.23 mmol) and 315 (14.57 g, 52.20 mmol), potassium carbonate (18.34 g, 133 mmol), water (7.7 ml) and tetrakistriphenylphosphine palladium (5.11 g, 4.42 mmol) were added under an argon atmosphere, and the mixture was stirred at 80° C. for 16 hours. The reaction solution was allowed to return to room temperature and ethyl acetate was added, and then insolubles were removed by filtration with celite and the solution was washed with chloroform/methanol (=1/1). The filtrate and the wash were combined, and the solvent was distilled off under reduced pressure. The residue was purified by silica gel column chromatography (eluting solvent: ethyl acetate/n-hexane=1/1, 3/1) and then washed with ethyl acetate to obtain 342 (9.55 g, 67%) as orange crystals.

mp 216-217° C.

APCI-MS m/z 324[M+H]$^+$

Synthesis of 343

A mixture of 342 (6.5 g, 20.1 mmol), lithium chloride (8.48 g, 0.2 mol) and hexamethylphosphoric triamide (65 ml) was stirred at 110° C. for 41 hour. The reaction solution was allowed to return to room temperature and poured into an aqueous citric acid solution, and the solution was stirred. The precipitate was collected by filtration, washed with water and then dissolved in tetrahydrofuran. The tetrahydrofuran solution was dried and the solvent was distilled off under reduced pressure, and then the residue was washed with ethyl acetate to obtain 343 (5.74 g, 92%) as a brown solid.

mp 222-223° C.

Synthesis of 344

To a tetrahydrofuran (110 ml) solution of 343 (5.73 g, 18.5 mmol), 311 (5.65 g, 27.1 mmol) and triphenylphosphine (8.26 g, 31.5 mmol), a tetrahydrofuran (20 ml) solution of diisopropyl azodicarboxylate (6.37 g, 31.5 mmol) was added dropwise at -5 to 0° C. over 20 minutes, and the mixture was stirred at the same temperature for 30 minutes, followed by stirring at room temperature for 66 hours. To the reaction solution, 311 (565 mg, 2.7 mmol), triphenylphosphine (826 mg, 3.15 mmol) and diisopropyl azodicarboxylate (638 mg, 3.15 mmol) were added, and the solution was further stirred at room temperature for 6 hours. The solvent of the reaction solution was distilled off under reduced pressure and the residue was purified by silica gel column chromatography (eluting solvent: ethyl acetate/n-hexane=1/2, 1/1) to obtain 344 (7.67 g, 83%) as a solid.

mp 150-152° C.

APCI-MS m/z 500[M+H]$^+$

Synthesis of 345

344 (1.0 g, 2 mmol), 10% Pd—C (150 mg) and ethanol (20 ml) were stirred under hydrogen pressure (40 psi) at room temperature for 16 hours. The catalyst was removed by filtration and the solvent was distilled off under reduced pressure. The pale yellow amorphous as the residue was dissolved by adding ethyl formate (20 ml) and the solution was heated at reflux for 16 hours. The reaction solution was allowed to return to room temperature and the solvent was distilled off under reduced pressure. The residue was purified by silica gel flash column chromatography (eluting solvent: tetrahydrofuran/chloroform=1/19, 1/9, 1/4, 1/3, 1/1, methanol/chloroform=1/9, 1/1) and then washed with ethyl acetate/n-hexane to obtain 345 (860 mg, 86%) as an orange solid.

APCI-MS m/z 498[M+H]$^+$

Synthesis of THK-5158

To a tetrahydrofuran (10 ml) suspension of NaBH$_4$ (392 mg, 10.4 mmol), a tetrahydrofuran (10 ml) solution of BF$_3$.Et$_2$O (1.96 g, 13.8 mmol) was added dropwise at 0° C., and the mixture was stirred at room temperature for 1 hour. To the present reaction solution, a tetrahydrofuran (10 ml) solution of 345 (855 mg, 1.7 mmol) was added dropwise at 0 to 5° C., and the solution was stirred at room temperature for 2 hours, followed by stirring under heating at reflux for 3 hours. The reaction solution was allowed to return to room temperature and the solvent was distilled off under reduced pressure. To the residue, 10% hydrochloric acid water was added, followed by stirring at room temperature for 1 hour. The reaction solution was made basic by adding potassium carbonate and then extracted with chloroform. The extraction liquid was dried and the solvent was distilled off under reduced pressure. The residue was purified by silica gel flash column chromatography (eluting solvent: chloroform→tetrahydrofuran/chloroform=1/19, 1/9, 1/4), purified again by silica gel flash column chromatography (eluting solvent: n-hexane→ethyl acetate/n-hexane=1/1, 6/4) and then washed with diisopropyl ether and then n-hexane to obtain THK-5158 (331 mg, 54%) as an orange solid.

mp 150-152° C.

$^1$H NMR (400 MHz, DMSO-d$_6$) δ 2.79 (3H, d, J=5.8 Hz), 2.80 (3H, d, J=5.1 Hz), 3.95-4.20 (3H, m), 4.50-4.70 (2H, m), 5.47 (1H, d, J=5.8 Hz), 5.53 (1H, d, J=5.1 Hz), 6.12 (1H, d, J=5.1 Hz), 6.56 (1H, d, J=8.8 Hz), 6.62 (1H, d, J=2.7 Hz), 7.13 (1H, dd, J=9.1, 2.4 Hz), 7.64-7.68 (2H, m), 7.70 (1H, d, J=9.1 Hz), 7.84 (1H, d, J=8.8 Hz), 7.99 (1H, d, J=8.7 Hz)

IR (Nujol) 1621 cm$^{-1}$

APCI-MS m/z 356[M+H]$^+$

Synthesis Method of THK-5159

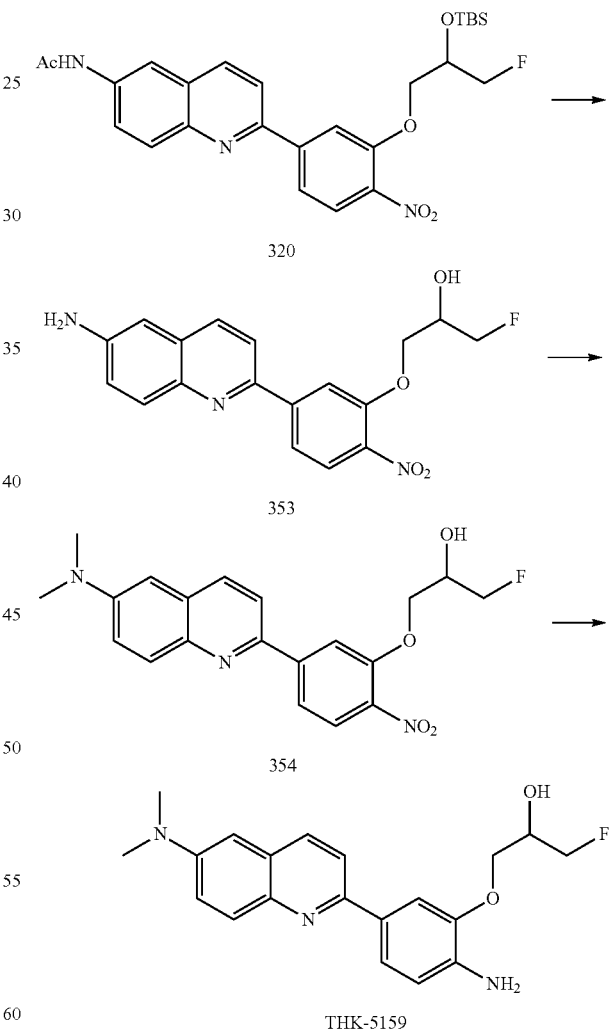

Synthesis of 353

A mixture of 320 (100 mg, 0.195 mmol) and 48% HBr (1 ml) was stirred at 90 to 95° C. for 1 hour. The reaction solution was allowed to return to room temperature and made basic concentrated ammonia water, followed by extraction with ethyl acetate. The extraction liquid was washed with saturated saline and dried, and then the solvent was distilled off under reduced pressure. The residue was washed with ethyl acetate-diisopropyl ether to obtain 353 (45 mg, 65%) as an orange solid.

mp 153-154° C.
APCI-MS m/z 358[M+H]⁺

Synthesis of 354

To a mixture of 353 (167 mg, 0.467 mmol), an aqueous 36% formaldehyde solution (1 ml) and ethanol (5 ml)-acetic acid (0.5 ml), a picoline borane complex (150 mg, 1.4 mmol) was added little by little, followed by stirring at room temperature for 3 hours. The reaction solution was diluted with ethyl acetate, washed in turn with an aqueous saturated sodium hydrogen carbonate solution and saturated saline and dried, and then the solvent was distilled off under reduced pressure. The residue was purified by silica gel column chromatography (eluting solvent: ethyl acetate/n-hexane=1/2) and then washed with ethyl acetate/n-hexane (=1/3) to obtain 354 (161 mg, 89%) as a brown solid.

mp 169-171° C.

Synthesis of THK-5159

A mixture of 354 (270 mg, 0.7 mmol), 10% Pd—C (moisture of about 50%; 100 mg), ammonium formate (440 mg, 7 mmol) and methanol (10 ml)-tetrahydrofuran (5 ml) was stirred under an argon atmosphere at room temperature for 3 hours. The reaction solution was diluted with ethyl acetate and insolubles were removed by filtration. The filtrate was washed in turn with water and saturated saline and dried, and then the solvent was distilled off under reduced pressure. The residue was purified by NH silica gel flash column chromatography (eluting solvent: n-hexane/ethyl acetate=1/1, 1/2, 1/3, 1/4, 1/5) and then washed with n-hexane/diisopropyl ether to obtain THK-5159 (216 mg, 87%) as a pale brown solid.

mp 169-170° C.
¹H NMR (400 MHz, CDCl₃) δ 2.94 (1H, br), 3.08 (6H, s), 3.96 (2H, br), 4.24-4.36 (3H, m), 4.52-4.61 (1H, m), 4.64-4.73 (1H, m), 6.81 (1H, d, J=3.0 Hz), 6.81 (1H, d, J=8.0 Hz), 7.36 (1H, dd, J=9.4, 3.0 Hz), 7.53 (1H, dd, J=8.0, 1.2 Hz), 7.68 (1H, d, J=8.8 Hz), 7.76 (1H, br), 7.96 (1H, d, J=8.8 Hz), 7.99 (1H, d, J=9.4 Hz)
IR (Nujol) 3345, 1621, 1590 cm⁻¹
APCI-MS m/z 356[M+H]⁺

Synthesis Method of THK-5160

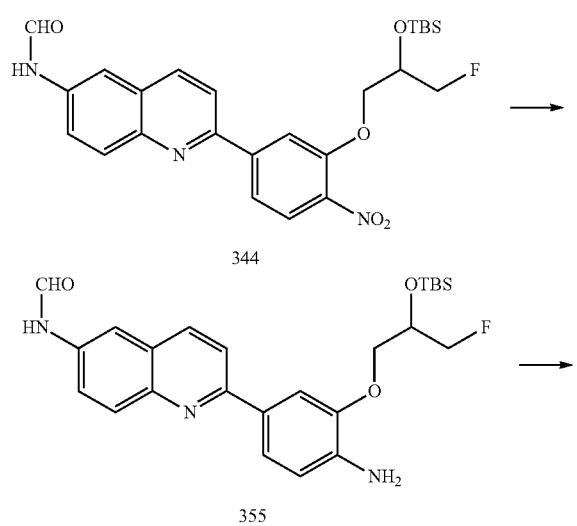

344

355

-continued

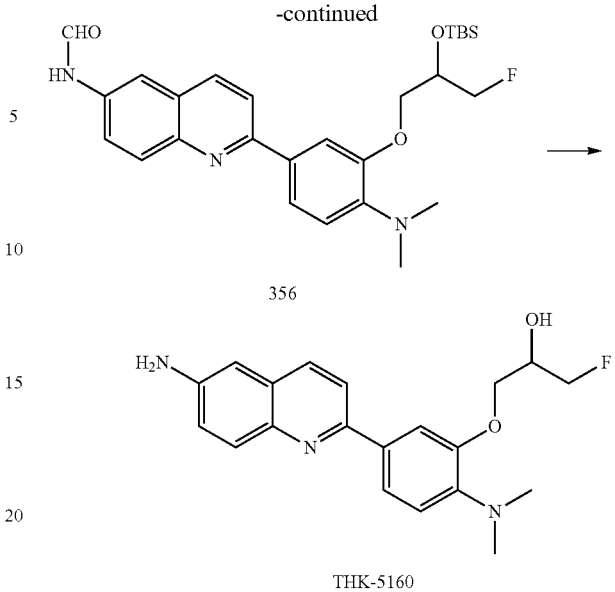

356

THK-5160

Synthesis of 355

344 (2.65 g, 5.3 mmol), 10% Pd—C (moisture of about 50%; 350 mg) and ethyl acetate (40 ml)-tetrahydrofuran (20 ml) were stirred under a hydrogen atmosphere at room temperature for 21 hour. The catalyst was removed by filtration and the solvent of the filtrate was distilled off under reduced pressure. The residue was dissolved in ethyl acetate (50 ml) and 10% Pd—C (moisture of about 50%; 300 mg) was added, and the solution was stirred under a hydrogen atmosphere at room temperature for 2 days. The catalyst was removed by filtration and the solvent of the filtrate was distilled off under reduced pressure, and the residue was purified by silica gel column chromatography (eluting solvent: n-hexane/ethyl acetate=1/1, 2/3, ethyl acetate) to obtain 355 (2.27 g, 91%).

APCI-MS m/z 470[M+H]⁺

Synthesis of 356

To a mixture of 355 (1.20 g, 2.55 mmol), an aqueous 35% formaldehyde solution (2.2 g, 26 mmol) and ethanol (20 ml)-acetic acid (2 ml), a picoline borane complex (545 mg, 5.1 mmol) was added little by little, followed by stirring at room temperature for 6 hours. To the reaction solution, an aqueous 35% formaldehyde solution (2.2 g, 26 mmol) and a picoline borane complex (545 mg, 5.1 mmol) were added, followed by further stirring at room temperature for 2 hours. The reaction solution was diluted with ethyl acetate, washed in turn with water, dilute ammonia water and saturated saline and dried, and then the solvent was distilled off under reduced pressure. The residue was washed with diisopropyl ether to obtain 356 (922 mg, 73%) as a pale brown solid.

mp 164-166° C.
APCI-MS m/z 498[M+H]⁺

Synthesis of THK-5160

A mixture of 356 (350 mg, 0.7 mmol) and 48% HBr (3 ml) was stirred at 90 to 95° C. for 1 hour. The reaction solution was allowed to return to room temperature and diluted with ethyl acetate and ice water was added. Then, the solution was made basic with concentrated ammonia water and extracted with ethyl acetate. The extraction liquid was washed in turn with water and saturated saline and dried, and then the solvent was distilled off under reduced pressure. The residue was purified by silica gel flash column chromatography (eluting solvent: n-hexane/ethyl acetate=1/2, 1/4, ethyl acetate) to obtain THK-5160 (179 mg, 72%) as a beige solid.

mp 158-160° C.

$^1$H NMR (400 MHz, CDCl$_3$) δ 2.85 (6H, s), 3.95 (2H, brs), 4.04-4.15 (1H, m), 4.24-4.35 (2H, m), 4.43-4.52 (1H, m), 4.55-4.63 (1H, m), 5.20 (1H, br), 6.92 (1H, d, J=2.4 Hz), 7.11 (1H, d, J=8.5 Hz), 7.17 (1H, dd, J=8.5, 2.7 Hz), 7.71 (1H, d, J=8.8 Hz), 7.72 (1H, dd, J=8.5, 2.1 Hz), 7.86 (1H, d, J=2.1 Hz), 7.94 (1H, d, J=8.5 Hz), 7.95 (1H, d, J=8.8 Hz)

IR (Nujol) 3462, 3345, 1633 cm$^{-1}$

APCI-MS m/z 356[M+H]$^+$

Synthesis Method of THK-5161

Synthesis of 357

Under an argon atmosphere, a tetrahydrofuran (5 ml) solution of BF$_3$.Et$_2$O (1.23 g, 8.7 mmol) was added dropwise to a tetrahydrofuran (10 ml) suspension of NaBH$_4$ (252 mg, 6.6 mmol) at 0° C., and the mixture was stirred at the same temperature for 20 minutes. To the present reaction solution, a tetrahydrofuran (3 ml) solution of 356 (630 mg, 1.27 mmol) was added dropwise at 0 to 5° C., followed by stirring at 5° C. for 1 hour. To the reaction solution, ice water and ethyl acetate were added, and the solution was made basic with concentrated ammonia water and then extracted with ethyl acetate. The extraction liquid was washed in turn with water and then saturated saline, and dried and then the solvent was distilled off under reduced pressure. The residue was purified by NH silica gel column chromatography (eluting solvent: ethyl acetate/n-hexane=1/8, 1/6) to obtain 357 (440 mg, 72%) as a pale yellow solid.

APCI-MS m/z 484[M+H]$^+$

Synthesis of THK-5161

A mixture of 357 (440 mg, 0.91 mmol) and 48% HBr (3 ml) was stirred at 50° C. for 10 minutes. The reaction solution was made basic with concentrated ammonia water under ice cooling, and then extracted with ethyl acetate. The extraction liquid was washed in turn with water and then saturated saline, and dried the solvent was distilled off under reduced pressure. The residue was purified by NH silica gel column chromatography (eluting solvent: ethyl acetate/n-hexane=2/1, 3/1) to obtain THK-5161 (280 mg, 83%) as a pale yellow solid.

mp 140-141° C.

$^1$H NMR (400 MHz, CDCl$_3$) δ 2.84 (6H, s), 2.96 (3H, brs), 4.00-4.15 (2H, m), 4.24-4.35 (2H, m), 4.43-4.51 (1H, m), 4.55-4.63 (1H, m), 5.26 (1H, br), 6.71 (1H, d, J=2.7 Hz), 7.10 (1H, d, J=9.0 Hz), 7.10 (1H, dd, J=9.0, 2.7 Hz), 7.71 (1H, d, J=8.5 Hz), 7.72 (1H, dd, J=8.5, 2.0 Hz), 7.86 (1H, d, J=2.0 Hz), 7.92 (1H, d, J=9.0 Hz), 7.98 (1H, d, J=8.8 Hz)

IR (Nujol) 3462, 1627 cm$^{-1}$

APCI-MS m/z 370[M+H]$^+$

Synthesis Method of THK-5162

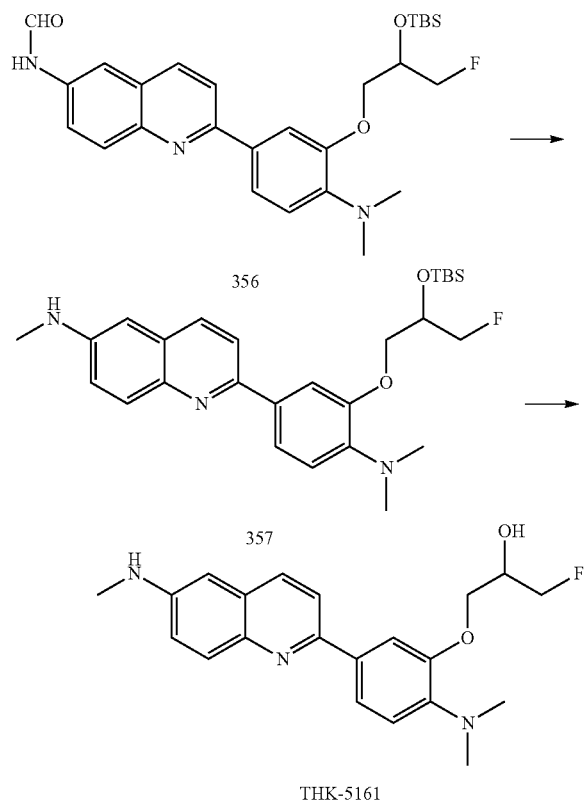

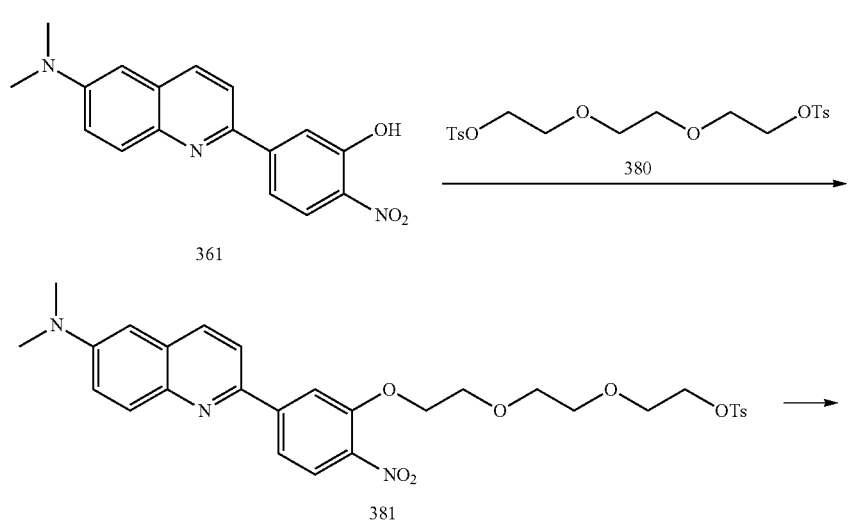

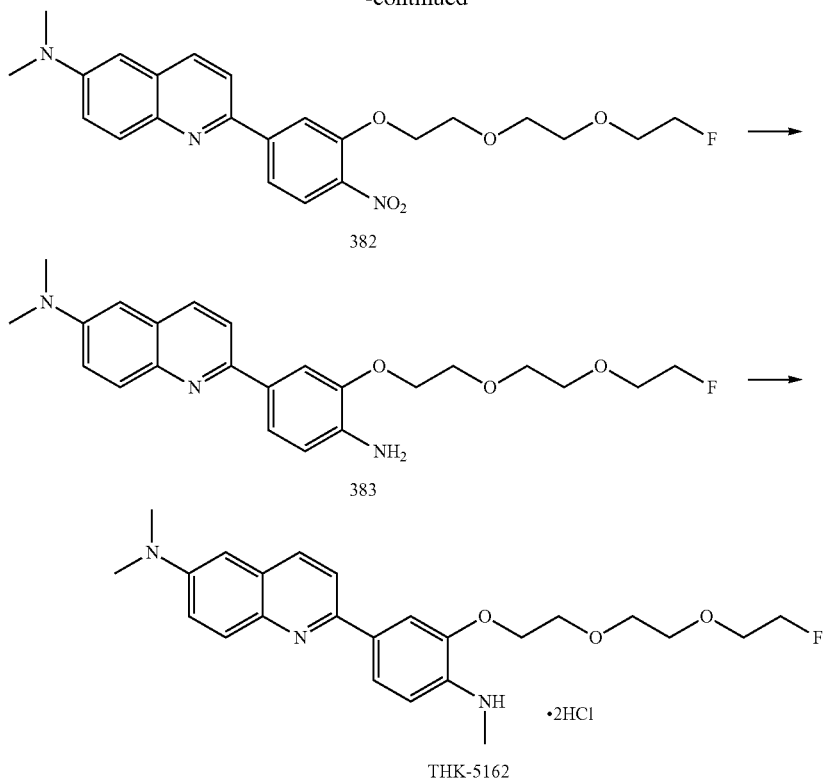

382

383

THK-5162 ·2HCl

Synthesis of 381

To an N,N-dimethylformamide (30 ml) suspension of 361 (900 mg, 2.91 b mmol) and 380 (4.00 g, 8.7 mmol), potassium carbonate (1.21 g, 8.7 mmol) was added at room temperature under stirring, and the mixture was stirred at room temperature for 4 days. The reaction solution was extracted with ethyl acetate after adding water and ethyl acetate. The extraction liquid was washed with water and dried, and then the solvent was distilled off under reduced pressure. The residue was purified by silica gel column chromatography (eluting solvent: ethyl acetate/n-hexane=1/2, 1/1) to obtain 381 (1.73 g, 100%) as a red oily substance.

APCI-MS m/z 596[M+H]$^+$

Synthesis of 382

A mixture of 381 (1.73 g, 2.9 mmol) and 1M tetra-n-butylammonium fluoride/tetrahydrofuran (14.6 ml, 14.6 mmol) was stirred at room temperature for 16 hours. The reaction solution was diluted with ethyl acetate, washed with water and dried, and then the solvent was distilled off under reduced pressure. The residue was purified by silica gel column chromatography (eluting solvent: ethyl acetate/n-hexane=1/2, 2/3) to obtain 382 (960 mg, 74%) as a red resinous substance.

APCI-MS m/z 444[M+H]$^+$

Synthesis of 383

A mixture of 382 (950 mg, 2.14 mmol), 10% Pd—C (moisture of about 50%; 190 mg), ammonium formate (1.35 g, 21.4 mmol) and methanol (20 ml)-tetrahydrofuran (10 ml) was stirred under an argon atmosphere at room temperature for 1 hour. The reaction solution was diluted with ethyl acetate and insolubles were removed by filtration, and then the solvent of the filtrate was distilled off under reduced pressure. The residue was purified by silica gel column chromatography (eluting solvent: ethyl acetate/n-hexane=1/2, 2/1) to obtain 383 (850 mg, 96%) as a yellow resinous substance.

APCI-MS m/z 414[M+H]$^+$

Synthesis of THK-5162

A mixture of 383 (600 mg, 1.45 mmol), an aqueous 35% formaldehyde solution (373 mg, 4.35 mmol), magnesium sulfate (7 g), tetrahydrofuran (40 ml) and isopropanol (20 ml) was stirred at room temperature for 3 hours. To the reaction solution, NaBH$_4$ (274 mg, 7.2 mmol) was added, and the solution was stirred at room temperature for 3 days. Insolubles were removed by filtration from the reaction solution, and the solvent of the filtrate was distilled off under reduced pressure. The residue was purified by silica gel column chromatography (eluting solvent: ethyl acetate/n-hexane=2/1) and the obtained orange resinous substance (580 mg; free form) was converted into a hydrochloride by treating with 4M hydrochloric acid/ethyl acetate, and then recrystallized from ethanol to obtain THK-5162 (516 mg, 71%) as orange crystals.

mp 197-198° C.

$^1$H NMR (400 MHz, DMSO-d$_6$) δ 2.87 (3H, s), 3.10 (6H, s), 3.56-3.64 (3H, m), 3.64-3.68 (2H, m), 3.69-3.72 (1H, m), 3.84-3.88 (2H, m), 4.38 (2H, dd, J=5.4, 3.9 Hz), 4.53 (2H, dt, J=48, 4.3 Hz), 6.72 (1H, d, J=8.8 Hz), 7.18 (1H, d, J=2.7 Hz), 7.68 (1H, dd, J=9.5, 2.9 Hz), 7.84 (1H, dd, J=8.5, 2.1 Hz), 7.90 (1H, d, J=2.1 Hz), 8.24 (1H, d, J=9.1 Hz), 8.58 (1H, d, J=9.4 Hz), 8.63 (1H, d, J=9.1 Hz)

IR (Nujol) 3376, 2582, 1643, 1603 cm$^{-1}$

APCI-MS m/z 428[M+H]$^+$

Synthesis Method of THK-5163

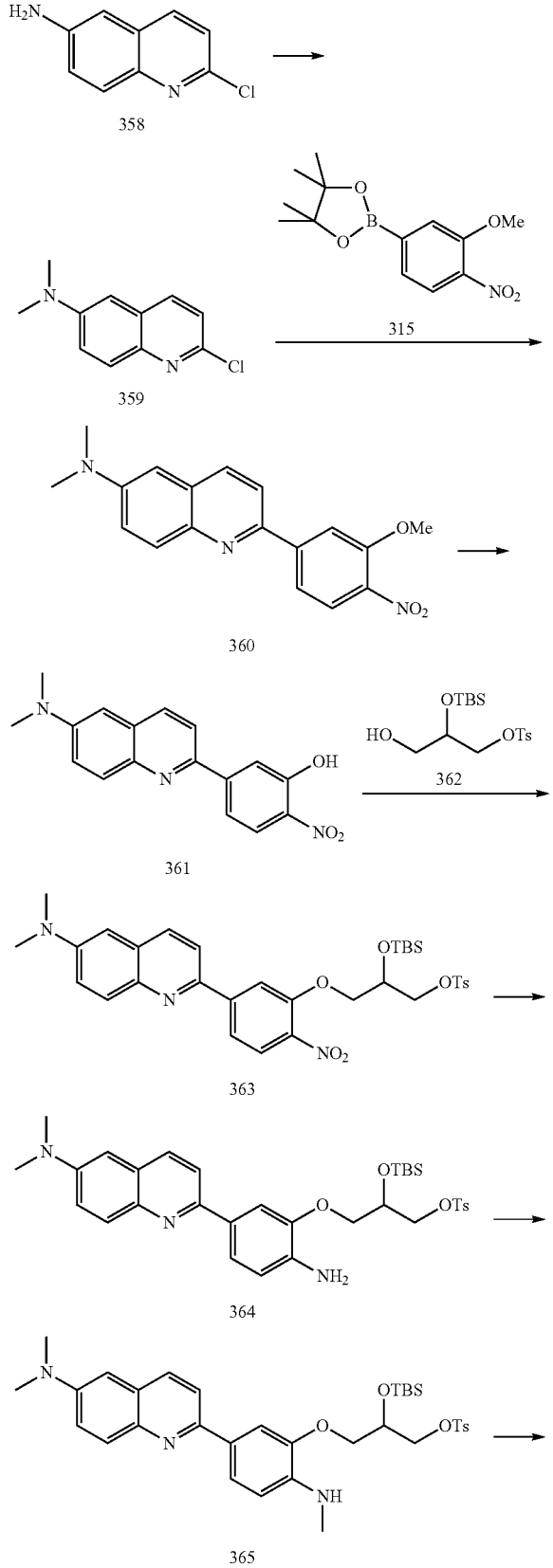

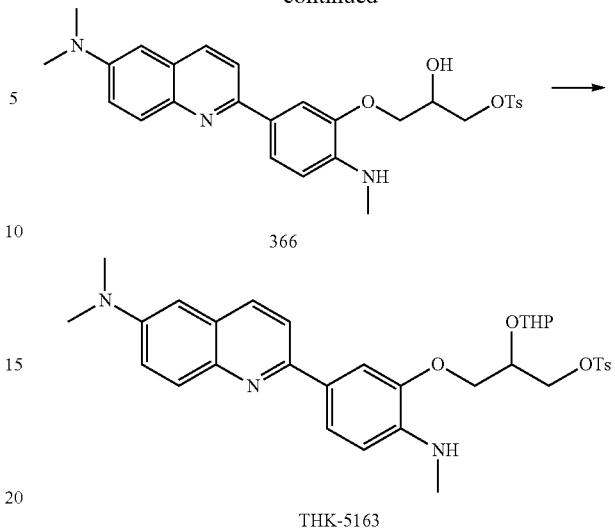

Synthesis of 359

To a mixture of 358 (2.20 g, 12.3 mmol), an aqueous 36% formaldehyde solution (20.5 g, 246 mmol) and methanol (250 ml)-acetic acid (20 ml), a picoline borane complex (7.91 g, 73.95 mmol) was added little by little, followed by stirring at room temperature for 16 hours. To the reaction solution, ethyl acetate-water was added and the solution was extracted with ethyl acetate after adjusting the pH to 8 using an aqueous potassium carbonate solution. The extraction liquid was washed with water and dried the solvent was distilled off under reduced pressure and the residue was purified by silica gel column chromatography (eluting solvent: ethyl acetate/n-hexane=1/4) to obtain 359 (2.54 g, 99%) as a pale yellow solid.

mp 74-75° C.
APCI-MS m/z 207[M+H]$^+$

Synthesis of 360

A mixture of 359 (2.54 g, 12.29 mmol), 315 (4.36 g, 15.6 mmol), potassium carbonate (5.10 g, 36.9 mmol), tetrakis-triphenylphosphine palladium (1.42 g, 1.23 mmol) and water (2.2 ml)-1,2-dimethoxyethane (100 ml) was stirred under an argon atmosphere at 80° C. for 16 hours. The reaction solution was allowed to return to room temperature, diluted with ethyl acetate, dried over sodium sulfate and then filtered with celite. The filtrate was concentrated to about 100 ml under reduced pressure, purified by silica gel column chromatography (eluting solvent: ethyl acetate/n-hexane=1/2) and then washed with ethyl acetate/n-hexane (=1/2) to obtain 360 (3.66 g, 92%) as an orange solid.

mp 175-175.5° C.
APCI-MS m/z 324[M+H]$^+$

Synthesis of 361

A mixture of 360 (3.11 g, 9.62 mmol), lithium chloride (4.08 g, 96.2 mmol) and hexamethylphosphoric tridamide (31 ml) was stirred under an argon atmosphere at 110° C. for 16 hours. The reaction solution was allowed to return to room temperature, and ethyl acetate and water were added, and the solution was extracted with ethyl acetate. The extraction liquid was washed with water and dried, and then the solvent was distilled off under reduced pressure. The residue was purified by silica gel column chromatography (eluting solvent: ethyl acetate/n-hexane=1/2) and then recrystallized from ethyl acetate/n-hexane to obtain 361 (2.97 g, 100%) as brown crystals.

mp 224-225° C.
APCI-MS m/z 310[M+H]$^+$

Synthesis of 363

To a mixture of 361 (1.00 g, 3.23 mmol), 362 (1.40 g, 3.88 mmol), triphenylphosphine (1.02 g, 3.88 mmol) and tetrahydrofuran (40 ml), a tetrahydrofuran (10 ml) solution of diisopropyl azodicarboxylate (0.77 ml, 3.88 mmol) was added dropwise over 20 minutes under ice cooling, followed by stirring at the same temperature for 1 hour and further stirring at room temperature for 16 hours. To the reaction solution, 362 (700 mg, 1.94 mmol), triphenylphosphine (510 mg, 1.94 mmol), diisopropyl azodicarboxylate (0.38 ml, 1.92 mmol) and tetrahydrofuran (10 ml) were added, and the solution was further stirred at room temperature for 3 hours. The solvent of the reaction solution was distilled off under reduced pressure, and the residue was purified by silica gel column chromatography (eluting solvent: ethyl acetate/n-hexane=1/9, 1/4) and then recrystallized from ethyl acetate/n-hexane=1/4 to obtain 363 (1.94 g, 92%) as orange crystals.

mp 144-145° C.

APCI-MS m/z 652[M+H]$^+$

Synthesis of 364

A mixture of 363 (1.00 g, 1.53 mmol), 10% Pd—C (moisture of about 50%; 130 mg), ammonium formate (965 mg, 15.3 mmol) and methanol (20 ml)-tetrahydrofuran (10 ml) was stirred under an argon atmosphere, followed by stirring at room temperature for 27 hours. The catalyst was removed by filtration and the solvent of the filtrate was distilled off under reduced pressure. The residue was purified by silica gel column chromatography (eluting solvent: n-hexane/ethyl acetate=4/1, 2/1) to obtain 364 (900 mg, 94%) as an orange amorphous.

APCI-MS m/z 622[M+H]$^+$

Synthesis of 365

364 (890 mg, 1.43 mmol) and an aqueous 35% formaldehyde solution (0.61 ml, 7.16 mmol) were nearly dissolved in methanol (50 ml)-tetrahydrofuran (10 ml) and magnesium sulfate (10 g) was added, and the mixture was stirred at room temperature for 1 hour. The reaction solution was ice-cooled and NaBH$_4$ (271 mg, 7.16 mmol) was added at the same temperature for 10 minutes, followed by stirring at room temperature for 16 hours. Insolubles were removed from the reaction solution by filtration, and the solvent of the filtrate was distilled off under reduced pressure. The residue was nearly dissolved in isopropyl alcohol (50 ml), and an aqueous 35% formaldehyde solution (0.61 ml, 7.16 mmol) and magnesium sulfate (10 g) were added, followed by stirring at room temperature for 30 minutes. The reaction solution was ice-cooled and NaBH$_4$ (271 mg, 7.16 mmol) was added. After stirring at room temperature for 2 days, NaBH$_4$ (271 mg, 7.16 mmol) was added, followed by further stirring at room temperature for 6 days. Insolubles were removed from the reaction solution by filtration and the solvent of the filtrate was distilled off under reduced pressure. The residue was dissolved in ethyl acetate, and the solution was washed with water and dried, and then the solvent was distilled off under reduced pressure. The residue was purified by silica gel column chromatography (eluting solvent: ethyl acetate/n-hexane=1/4) to obtain 365 (650 mg, 71%) as a pale yellow amorphous.

APCI-MS m/z 636[M+H]$^+$

Synthesis of 366

To chloroform (12 ml) solution of 365 (640 mg, 1.01 mmol), trifluoroacetic acid (8 ml) was added dropwise under ice cooling and stirring, and water (2 ml) was added, and then the mixture was stirred at room temperature for 2 days. To the reaction solution, ice water and then ethyl acetate were added, and the solution was extracted with ethyl acetate after adjusting the pH to 9 using an aqueous potassium carbonate solution. The extraction liquid was dried and the solvent was distilled off under reduced pressure and the residue was purified by silica gel column chromatography (eluting solvent: ethyl acetate/n-hexane=1/1) to obtain 366 (520 mg, 99%) as an orange amorphous.

APCI-MS m/z 522[M+H]$^+$

Synthesis of THK-5163

To a methylene chloride (20 ml) solution of 366 (510 mg, 0.98 mmol) and 3,4-dihydro-2H-pyran (1.77 ml, 19.6 mmol), paratoluenesulfonic acid monohydrate (387 mg, 2.25 mmol) was added, and the mixture was stirred at room temperature for 20 minutes. After adjusting the pH of the reaction solution to 8 by adding triethylamine, the solvent was distilled off under reduced pressure. The residue was purified by silica gel column chromatography (eluting solvent: ethyl acetate/n-hexane=1/2, 2/3, 1/1) to obtain THK-5163 (569 mg, 96%) as an orange amorphous.

$^1$H NMR (400 MHz, DMSO-d$_6$) δ 1.32-1.51 (4H, m), 1.52-1.74 (2H, m), 2.34 (3H, s), 2.78 (3H, d, J=3.6 Hz), 3.34-3.46 (1H, m), 3.64-3.72, 3.78-3.86 (1H, m), 4.10 (2H, d, J=5.4 Hz), 4.14-4.22 (1H, m), 4.29-4.44 (2H, m), 4.65-4.70, 4.85-4.88 (1H, m), 5.31 (1H, br), 6.57 (1H, dd, J=8.3, 1.4 Hz), 6.93 (1H, d, J=2.1 Hz), 7.39 (2H, d, J=7.9 Hz), 7.44 (1H, dd, J=9.1, 2.4 Hz), 7.61-7.64 (1H, m), 7.70 (1H, d, J=8.2 Hz), 7.79 (2H, dd, J=8.3, 2.9 Hz), 7.83 (1H, d, J=9.4 Hz), 7.92 (1H, d, J=8.8 Hz), 8.08 (1H, d, J=8.5 Hz)

IR (Nujol) 3433, 1733, 1619 cm$^{-1}$

APCI-MS m/z 606[M+H]$^+$

Synthesis Method of THK-5164

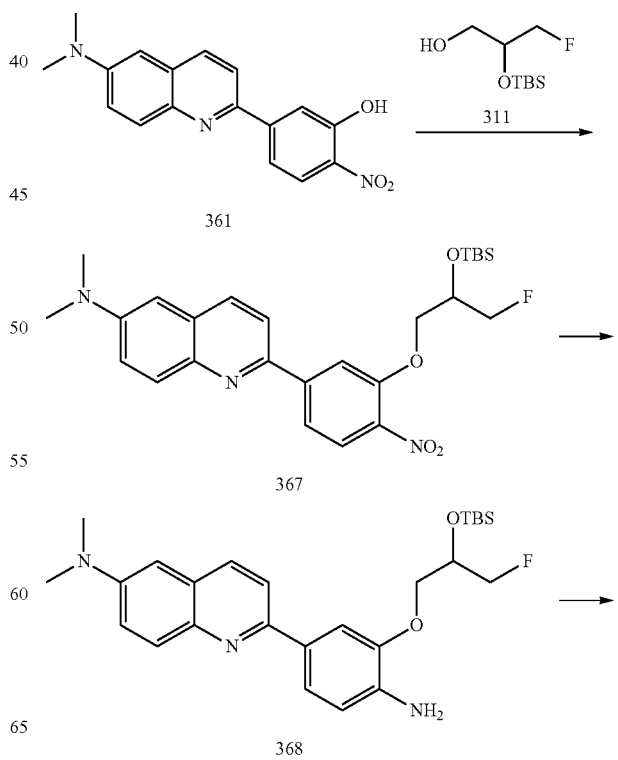

-continued

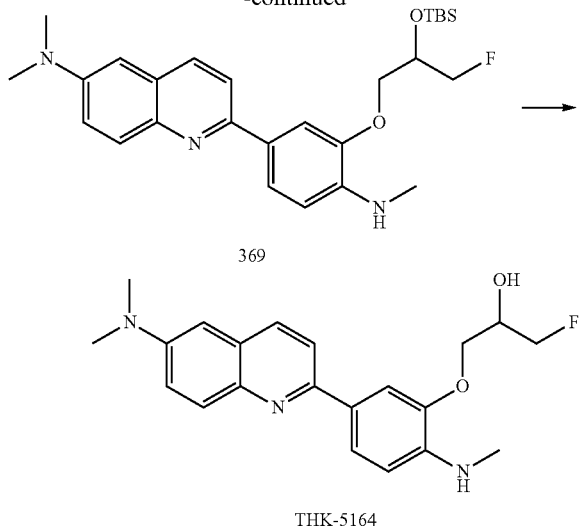

369

THK-5164

Synthesis of 367

To a mixture of 361 (1.09 g, 3.52 mmol), 311 (1.04 g, 5.0 mmol), triphenylphosphine (1.57 g, 5.98 mmol) and tetrahydrofuran (25 ml), a tetrahydrofuran (5 ml) solution of diisopropyl azodicarboxylate (1.21 g, 5.98 mmol) was added dropwise under ice cooling and stirring, followed by stirring at the same temperature for 1 hour and further stirring at room temperature for 16 hours. The reaction solution was purified by NH silica gel flash column chromatography (eluting solvent: ethyl acetate/n-hexane=1/9) to obtain 367 (1.66 g, 94%) as an orange solid.

mp 119-120° C.

APCI-MS m/z 500[M+H]$^+$

Synthesis of 368

A mixture of 367 (1.65 g, 3.3 mmol), 10% Pd—C (moisture of about 50%; 350 mg), ammonium formate (2.08 g, 33 mmol) and methanol (40 ml)-tetrahydrofuran (20 ml) was stirred under an argon atmosphere at room temperature for 2 hours. The catalyst was removed by filtration and the solvent of the filtrate was distilled off under reduced pressure. The residue was dissolved in ethyl acetate-tetrahydrofuran, and the solution was washed in turn with water and saturated saline and dried, and then the solvent was distilled off under reduced pressure. The residue was purified by silica gel flash column chromatography (eluting solvent: n-hexane/ethyl acetate=3/1) to obtain 368 (1.40 g, 90V) as a pale yellow solid.

mp 90-92° C.

APCI-MS m/z 470[M+H]$^+$

Synthesis of 369

To a mixture of 368 (800 mg, 1.7 mmol), an aqueous 36% formaldehyde solution (708 mg, 8.5 mmol) and isopropanol (20 ml)-tetrahydrofuran (5 ml), magnesium sulfate (5 g) was added, followed by stirring at room temperature for 1 hour. To the reaction solution, NaBH$_4$ (323 mg, 8.5 mmol) was added, and the solution was stirred at room temperature for 24 hours. Isopropanol (5 ml) and NaBH$_4$ (323 mg, 8.5 mmol) were added, followed by stirring at 80° C. for 1 hour. The reaction solution was allowed to return to room temperature and insolubles were removed by filtration, and the filtrate was purified by silica gel flash column chromatography (eluting solvent: ethyl acetate/n-hexane=1/5) to obtain 369 (720 mg, 889) as a pale yellow solid.

mp 134-135° C.

APCI-MS m/z 484[M+H]$^+$

Synthesis of THK-5164

A mixture of 369 (700 mg, 1.45 mmol) and 48% HBr (7 ml) was stirred at room temperature for 30 minutes. The reaction solution was poured into ice water, and the solution was made basic with concentrated ammonia water and then extracted with ethyl acetate. The extraction liquid was washed with saturated saline and dried, and then the solvent was distil led off under reduced pressure. The residue was washed with ethyl acetate/n-hexane=1/5 and then recrystallized from ethyl acetate to obtain THK-5164 (490 mg, 91%) as a pale yellow solid.

mp 193-194° C.

$^1$H NMR (400 MHz, CDCl$_3$) δ 2.75 (1H, br), 2.92 (3H, s), 3.08 (6H, s), 4.25-4.38 (3H, m), 4.40 (1H, br), 4.52-4.62 (1H, m), 4.65-4.74 (1H, m), 6.69 (1H, d, J=8.2 Hz), 6.81 (1H, d, J=2.7 Hz), 7.35 (1H, dd, J=9.4, 2.7 Hz), 7.63 (1H, dd, J=8.5, 1.8 Hz), 7.70 (1H, d, J=8.8 Hz), 7.79 (1H, d, J=1.8 Hz), 7.96 (1H, d, J=8.8 Hz), 8.00 (1H, brd, J=9.4 Hz)

IR (Nujol) 3417, 3250, 1620, 1592 cm$^{-1}$

APCI-MS m/z 370[M+H]$^+$

Synthesis Method of THK-5165

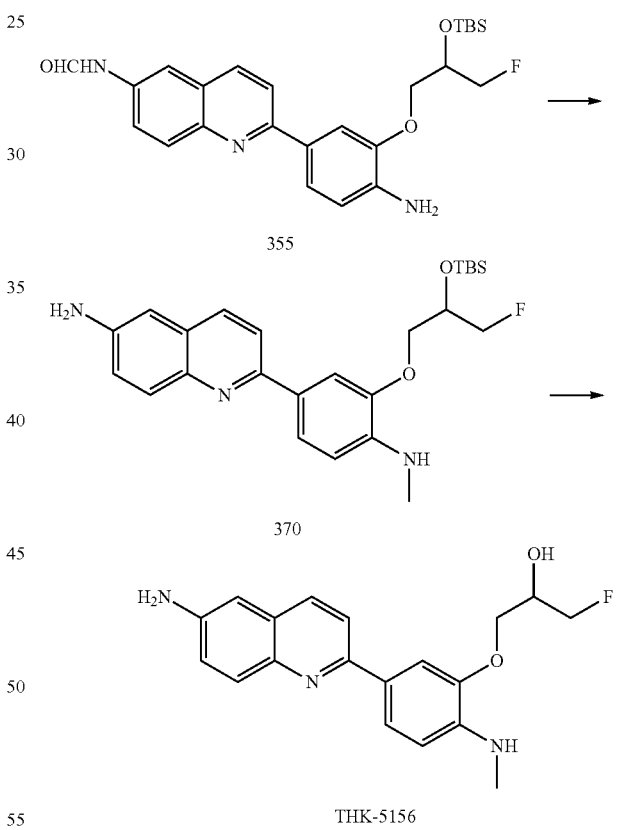

355

370

THK-5156

Synthesis of 370

To an isopropanol (50 ml) solution of 355 (836 mg, 1.78 mmol), an aqueous 35% formaldehyde solution (760 mg, 8.9 mmol) and magnesium sulfate (10 g) were added, and the mixture was stirred at room temperature for 2 hours. To the reaction solution, NaBH$_4$ (340 mg, 9 mmol) was added three times every 24 hours, and the solution was stirred at room temperature for 2 days and then heated at reflux for 1 hour. The reaction solution was allowed to return to room temperature and insolubles were removed by filtration, and then the solvent of the filtrate was distilled off under reduced pressure. The residue was purified by silica gel flash column chromatography (eluting solvent: ethyl acetate/n-hexane=1/2, 2/5) to obtain 370 (683 mg, 84%) as a pale yellow amorphous.

APCI-MS m/z 456[M+H]+

Synthesis of THK-5165

A mixture of 370 (676 mg, 1.48 mmol) and 1M tetra-n-butylammonium fluoride/tetrahydrofuran (5.0 ml, 5.0 mmol) was stirred at room temperature for 1 hour. The solvent of the reaction solution was distilled off under reduced pressure, and the residue was purified by silica gel flash column chromatography (eluting solvent: chloroform→chloroform/methanol=50/1, 24/1) and then washed with n-hexane-diisopropyl ether to obtain THK-5165 (453 mg, 85%) as an orange solid.

mp 79-82° C.

$^1$H NMR (400 MHz, DMSO-$d_6$) δ 2.80 (3H, d, J=4.9 Hz), 2.80 (3H, s), 4.00-4.20 (3H, m), 4.50-4.70 (2H, m), 5.45-5.55 (4H, m), 6.56 (1H, d, J=8.2 Hz), 6.77 (1H, d, J=2.5 Hz), 7.11 (1H, dd, J=8.8, 2.5 Hz), 7.60-7.70 (3H, m), 7.80 (1H, d, J=8.8 Hz), 7.90 (1H, d, J=8.8 Hz)

IR (Nujol) 1503, 1462, 1377 cm$^{-1}$

APCI-MS m/z 342[M+H]+

Synthesis Method of THK-5154

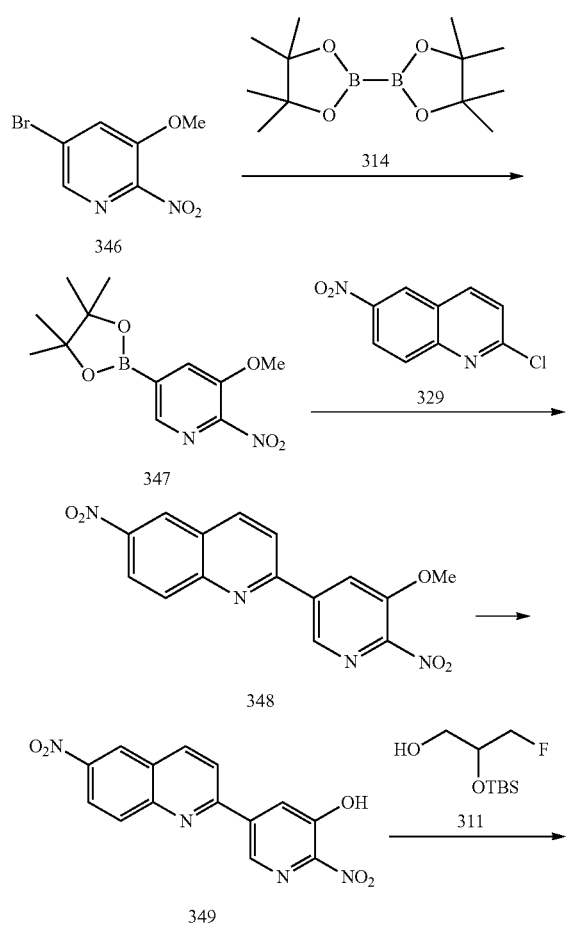

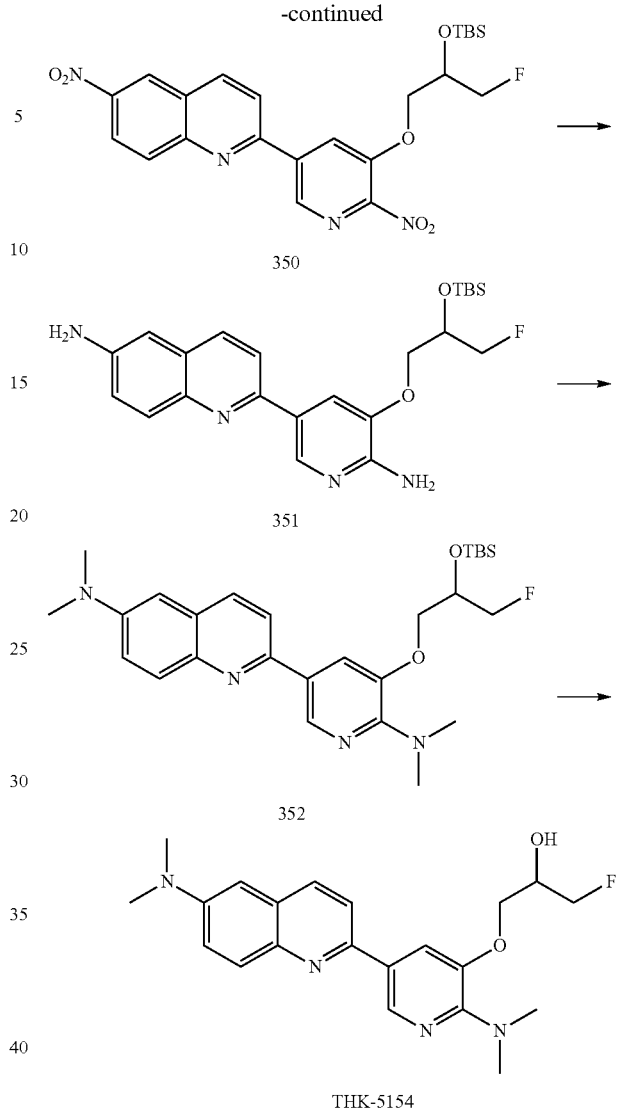

Synthesis of 347

A mixture of 346 (1.40 g, 6 mol), 314 (1.53 g, 6 mol), potassium acetate (2.36 g, 24 mol), PdCl$_2$(dppf).CH$_2$Cl$_2$ (245 mg, 0.3 mmol) and 1,4-dioxane (25 ml) was stirred under an argon atmosphere at 100° C. for 16 hours. The reaction solution was allowed to return to room temperature and insolubles were removed by filtration, and the solvent of the filtrate was distilled off under reduced pressure. The residue was purified by silica gel column chromatography (eluting solvent: n-hexane/ethyl acetate=2/1) and then washed with n-hexane to obtain 347 (1.17 g, 70%) as a colorless solid.

mp 130-131° C.

APCI-MS m/z 281[M+H]+

Synthesis of 348

A mixture of 347 (1.10 g, 3.39 mmol), 329 (840 mg, 4 mmol), sodium carbonate (850 mg, 8 mmol), tetrakistriphenylphosphine palladium (230 mg, 0.2 mmol) water (2 ml) and 1,2-dimethoxyethane (20 ml) was stirred under an argon atmosphere at 90° C. for 4 hours. The reaction solution was allowed to return to room temperature, and insolubles were collected by filtration and then dried to obtain 348 (836 mg, 66%).

mp 253-255° C.

APCI-MS m/z 327[M+H]+

Synthesis of 349

A mixture of 348 (326 mg, 1 mmol), lithium chloride (424 mg, 10 mmol) and hexamethylphosphoric triamide (7 ml) was stirred under an argon atmosphere at 110° C. for 19 hours. The reaction solution was allowed to return to room temperature and water was added, and the solution was acidified with an aqueous citric acid solution and then extracted with ethyl acetate. The extraction liquid was washed in turn with water and saturated saline, and dried, and then the solvent was distilled off under reduced pressure. The residue was washed with diisopropyl ether to obtain 349 (312 mg, 100%).

APCI-MS m/z 313[M+H]$^+$

Synthesis of 350

To a mixture of 349 (680 mg, 2.18 mmol), 311 (680 mg, 3.26 mmol), triphenylphosphine (973 mg, 3.71 mmol) and tetrahydrofuran (20 ml), a tetrahydrofuran (2 ml) solution of diisopropyl azodicarboxylate (750 mg, 3.71 mmol) was added dropwise under ice cooling and stirring, followed by stirring at room temperature for 20 hours. The reaction solution was purified by silica gel flash column chromatography (eluting solvent: ethyl acetate/n-hexane=1/9-1/5) and then washed with diisopropyl ether to obtain 350 (820 mg, 75%) as a grayish white solid.

mp 167-168° C.

APCI-MS m/z 503[M+H]$^+$

Synthesis of 351

A mixture of 350 (510 mg, 1.01 mmol), Fe (503 mg), NH$_4$Cl (325 mg, 6.09 mmol) and water (3 ml)-ethanol (15 ml) was stirred at 70 to 75° C. for 1.5 hours. The reaction solution was allowed to return to room temperature, and then diluted with ethyl acetate. Insolubles were removed by filtration with celite and the filtrate was washed in turn with ammonia water and saturated saline, and dried, and then the solvent was distilled off under reduced pressure. The residue was purified by silica gel flash column chromatography (eluting solvent: chloroform, chloroform/methanol=40/1) to obtain 351 (385 mg, 86%) as an orange solid.

mp 139-141° C.

APCI-MS m/z 443[M+H]$^+$

Synthesis of 352

To a mixture of 351 (520 mg, 1.17 mmol), an aqueous 36% formaldehyde solution (1.95 g, 23.4 mmol) and ethanol (30 ml)-acetic acid (3 ml), a picoline borane complex (751 mg, 7.02 mmol) was added little by little, followed by stirring at room temperature for 4 hours. The reaction was completed by adding an aqueous 36% formaldehyde solution (3 g, 27.8 mmol), acetic acid (1 ml) and a picoline borane complex (1.05 g, 9.82 mmol). The reaction solution was made basic with concentrated ammonia water under ice cooling and then extracted with ethyl acetate. The extraction liquid was washed in turn with water and saturated saline, and dried, and then the solvent was distilled off under reduced pressure. The residue was purified by silica gel flash column chromatography (eluting solvent: ethyl acetate/n-hexane=1/5) to obtain 352 (430 mg, 74%) as a yellow solid.

APCI-MS m/z 499[M+H]$^+$ mp 136-137° C.

Synthesis of THK-5154

A mixture of 352 (300 mg, 0.68 mmol) and 48% HBr (3 ml) was stirred at room temperature for 10 minutes. The reaction solution was diluted with water, and the solution was made basic with concentrated ammonia water and then extracted with ethyl acetate. The extraction liquid was washed in turn with water and saturated saline, and dried, and then the solvent was distilled off under reduced pressure. The residue was washed with ethyl acetate to obtain THK-5154 (220 mg, 84%) as a yellow solid.

mp 154-155° C.

$^1$H NMR (400 MHz, CDCl$_3$) δ 3.06 (6H, s), 3.10 (6H, s), 3.26 (1H, brs), 4.24-4.32 (3H, m), 4.51-4.60 (1H, m), 4.64-4.72 (1H, m), 6.81 (1H, d, J=2.7 Hz), 7.37 (1H, dd, J=9.3, 2.7 Hz), 7.70 (1H, d, J=8.8 Hz), 7.98 (1H, d, J=8.8 Hz), 7.98 (1H, d, J=9.3 Hz), 8.04 (1H, d, J=1.9 Hz), 8.53 (1H, d, J=1.9 Hz).

IR (Nujol) 1618, 1588 cm$^{-1}$

APCI-MS m/z 385[M+H]$^+$

Synthesis Method of THK-5166

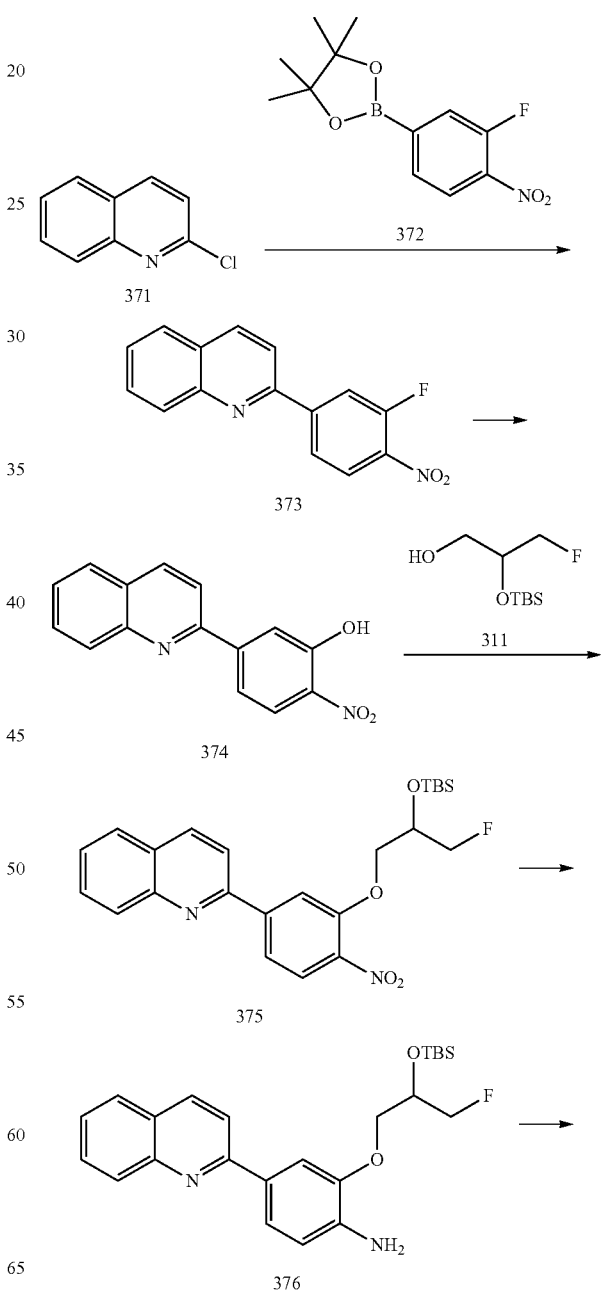

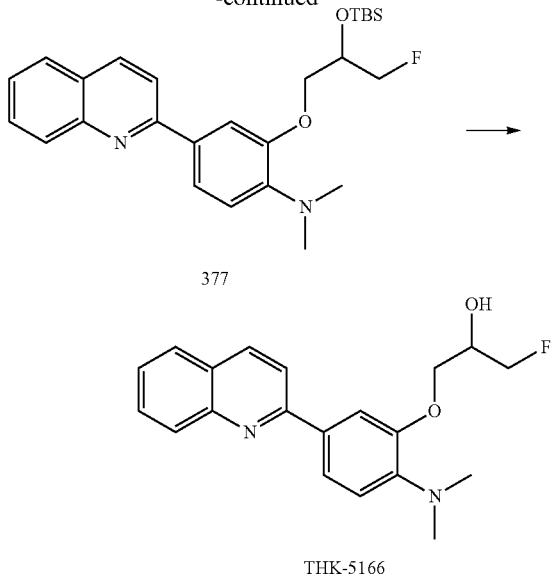

Synthesis of 373

A mixture of 371 (654 mg, 4 mmol), 372 (1.28 g, 4.8 mmol), 2M sodium carbonate (4 ml, 8 mmol), tetrakistriphenylphosphine palladium (231 mg, 0.2 mmol) and 1,2-dimethoxyethane (7 ml) was stirred under an argon atmosphere at 90° C. for 16 hours. The reaction solution was allowed to return to room temperature and the solvent was distilled off. Chloroform was added and insolubles were removed by filtration. The chloroform layer of the filtrate was separated and dried, and then the solvent was distilled off under reduced pressure. The residue was purified by silica gel flash column chromatography (eluting solvent: n-hexane, chloroform/n-hexane=1/4, 2/3, 3/2) and then washed with n-hexane to obtain 373 (986 mg, 92%) as a pale yellow solid.

APCI-MS m/z 269[M+H]$^+$

Synthesis of 374

To a N,N-dimethylformamide (15 ml) solution of 373 (982 mg, 3.6 mmol) and 2-methanesulfonylethanol (679 mg, 5.47 mmol), 60% NaH (438 mg, 10.9 mmol) was added at room temperature under stirring, and the mixture was stirred at room temperature for 2 hours. After the reaction solution was acidified by adding water and 10% hydrochloric acid water, the solution was made basic with an aqueous saturated sodium hydrogen carbonate solution and then extracted with ethyl acetate. The extraction liquid was washed with saturated saline and dried, and then the solvent was distilled off under reduced pressure. The residue was recrystallized from ethyl acetate/n-hexane to obtain 374 (778 mg, 80%) as pale brown crystals.

APCI-MS m/z 267[M+H]$^+$

Synthesis of 375

To a mixture of 374 (773 mg, 2.9 mmol), 311 (844 mg, 4.0 mmol), triphenylphosphine (1.21 g, 4.6 mmol) and tetrahydrofuran (10 ml), a tetrahydrofuran (5 ml) solution of diisopropyl azodicarboxylate (936 mg, 4.6 mmol) was added dropwise under ice cooling and stirring, followed by stirring at room temperature for 16 hours. The solvent of the reaction solution was distilled off under reduced pressure, and the residue was purified by silica gel flash column chromatography (eluting solvent: n-hexane, ethyl acetate/n-hexane=1/4) and then washed with n-hexane to obtain 375 (1.10 g, 83%) as a colorless solid.

APCI-MS m/z 457[M+H]$^+$

Synthesis of 376

A mixture of 375 (1.09 g, 2.4 mmol), 10% Pd—C (moisture of about 50%; 200 mg), ammonium formate (1.50 g, 24 mmol) and methanol (20 ml)-tetrahydrofuran (10 ml) was stirred under an argon atmosphere at room temperature for 1 hour. The catalyst was removed by filtration, and the solvent of the filtrate was distilled off under reduced pressure. To the residue, water was added and the solution was extracted from chloroform. The extraction liquid was dried and solvent was distilled off under reduced pressure to obtain 376 (1.02 g, 100%) as a yellow oily substance.

APCI-MS m/z 427[M+H]$^+$

Synthesis of 377

To a mixture of 376 (1.02 g, 2.4 mmol), an aqueous 35% formaldehyde solution (1.0 g, 11.7 mmol) and methanol (20 ml)-acetic acid (2 ml), a picoline borane complex (385 mg, 3.6 mmol) was added little by little under ice cooling and stirring, followed by stirring at room temperature for 2.5 hours. To the reaction solution, an aqueous 35% formaldehyde solution (0.5 g, 5.8 mmol) and a picoline borane complex (260 mg, 2.4 mmol) were added, and the solution was further stirred at room temperature for 16 hours. The solvent was distilled off from the reaction solution under reduced pressure, and an aqueous saturated sodium hydrogen carbonate solution was added to the residue, and then the solution was extracted with chloroform. The extraction liquid was dried and the solvent was distilled off under reduced pressure. The residue was purified by silica gel flash column chromatography (eluting solvent: n-hexane, ethyl acetate/n-hexane=1/20, 1/12) and then washed with cold n-hexane to obtain 377 (827 mg, 74%) as a colorless solid.

APCI-MS m/z 455[M+H]$^+$

Synthesis of THK-5166

A mixture of 377 (802 mg, 1.76 mmol) and 1M tetra-n-butylammonium fluoride/tetrahydrofuran (5.0 ml, 5.0 mmol) was stirred at room temperature for 1 hour. The solvent of the reaction solution was distilled off under reduced pressure. The residue was purified by silica gel flash column chromatography (eluting solvent: chloroform-→chloroform/methanol=50/1), purified by silica gel flash column chromatography (eluting solvent: n-hexane ethyl acetate/n-hexane=1/1, 3/2) and then washed with n-hexane to obtain THK-5166 (453 mg, 75%) as a pale yellow solid.

mp 81-84° C.

$^1$H NMR (400 MHz, DMSO-d$_6$) δ 2.86 (6H, s), 4.10-4.20 (3H, m), 4.40-4.70 (2H, m), 5.54 (1H, brs), 7.04 (1H, brd, J=7.5 Hz), 7.54-7.58 (1H, t like), 7.74-7.78 (1H, t like), 7.83 (1H, dd, J=8.5, 1.8 Hz), 7.87 (1H, d, J=1.8 Hz), 7.97 (1H, d, J=7.6 Hz), 8.05 (1H, d, J=8.5 Hz), 8.14 (1H, d, J=8.8 Hz), 8.40 (1H, d, J=8.8 Hz)

IR (Nujol) 1595, 1497, 1457, 1436 cm$^{-1}$

APCI-MS m/z 341[M+H]$^+$

Synthesis Method of THK-5167

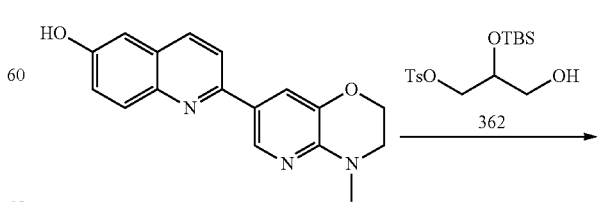

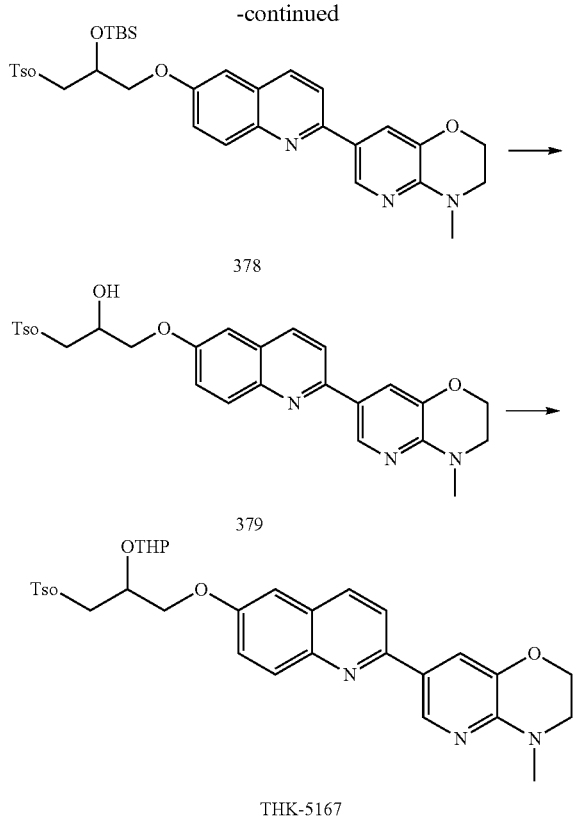

Synthesis of 378

To a mixture of 310 (452 mg, 1.54 mmol), 362 (560 mg, 1.55 mmol), triphenylphosphine (630 mg, 2.4 mmol) and tetrahydrofuran (20 ml), a tetrahydrofuran (2 ml) solution of diisopropyl azodicarboxylate (485 mg, 2.4 mmol) was added dropwise under ice cooling and stirring, followed by stirring at the same temperature for 20 minutes and further stirred at room temperature for 16 hours. To the reaction solution, 362 (250 mg, 0.69 mmol), triphenylphosphine (320 mg, 1.27 mmol) and diisopropyl azodicarboxylate (250 mg, 1.24 mmol) were added, and the solution was further stirred at room temperature for 20 hours. The reaction solution was purified by NH silica gel flash column chromatography (eluting solvent: ethyl acetate/n-hexane=1/4, 1/3, 1/2, ethyl acetate, chloroform/methanol=10/1) and then washed with n-hexane/ethyl acetate to obtain 378 (683 mg, 70%).

mp 135-138° C.

Synthesis of 379

A mixture of 378 (700 mg, 1.1 mmol), tetrahydrofuran (15 ml), water (5 ml) and trifluoroacetic acid (10 ml) was stirred at room temperature for 16 hours. The reaction solution was diluted with ethyl acetate, and the solution was washed in turn with an aqueous saturated sodium hydrogen carbonate solution and saturated saline, and dried and then the solvent was distilled off under reduced pressure. The residue was purified by silica gel flash column chromatography (eluting solvent: ethyl acetate/n-hexane=1/2, 1/1, 2/1) to obtain 379 (490 mg, 85%) as a solid.

mp 156-158° C.

APCI-MS m/z 522[M+H]$^+$

Synthesis of THK-5167

To a methylene chloride (30 ml)-tetrahydrofuran (20 ml) solution of 379 (480 mg, 0.92 mmol) and 3,4-dihydro-2H-pyran (1.55 g, 18.4 mmol), paratoluenesulfonic acid monohydrate (200 mg, 1.16 mmol) was added was added, and the mixture was stirred at room temperature for 78 hours. The reaction solution was diluted with ethyl acetate (200 ml), and the solution was washed in turn with an aqueous saturated sodium hydrogen carbonate solution and saturated saline, and dried, and then the solvent was distilled off under reduced pressure. The residue was purified by silica gel flash column chromatography (eluting solvent: ethyl acetate/n-hexane=1/2, 2/3, 1/1) and then recrystallized from ethyl acetate to obtain THK-5167 (380 mg, 68%) as a pale yellow solid.

mp 153-155° C.

$^1$H NMR (400 MHz, CDCl$_3$) δ 1.45-1.62 (4H, m), 1.66-1.84 (2H, m), 2.34, 2.35 (3H, each s), 3.21 (3H, s), 3.44-3.55 (3H, m), 3.83, 3.92 (1H, each m), 4.06-4.39 (7H, m), 4.74, 4.83 (1H, each brt), 6.98, 7.00 (1H, each d, J=2.7 Hz), 7.18, 7.19 (1H, each dd, J=9.1, 2.5 Hz), 7.227 (1H, d, J=8.2 Hz), 7.234 (1H, d, J=8.2 Hz), 7.73, 7.74 (1H, each d, J=9.4 Hz), 7.75 (1H, brd, J=8.3 Hz), 7.77 (1H, brd, J=8.3 Hz), 7.836, 7.838 (1H, each d, J=1.8 Hz), 7.95 (1H, d, J=9.4 Hz), 8.00, 8.01 (1H, each d, J=8.8 Hz), 8.486, 8.489 (1H, each d, J=1.8 Hz)

IR (Nujol) 1621, 1598 cm$^{-1}$

APCI-MS m/z 606[M+H]$^+$

Synthesis Methods of THK-5168, THK-5170, THK-5171, THK-5172, THK-5173, THK-5174, THK-5175, THK-5176, THK-5179, THK-5181 and THK-5182

Each synthesis method is the same as any one of the above-mentioned synthesis methods.

Example 2

Labeling Synthesis of [$^{18}$F] THK-5035

$^{18}$F$^-$ was synthesized by irradiating [$^{18}$O]H$_2$O having isotope purity of 95 or more with 12 MeV of proton beam accelerated by Cyclotron HM12 (manufactured by Sumitomo Heavy Industries, Ltd.). Subsequently, the solution thereof was passed through an anion-exchange resin (AG1-X8) thereby trapping $^{18}$F$^-$ on the resin, followed by elution with a 33 mM K$_2$CO$_3$ solution. After transferring this aqueous $^{18}$F$^-$-containing K$_2$CO$_3$ solution (200 µL, 3.5 GBq) in a brown vial, Kryptofix 222 (16 mg) and acetonitrile (1.5 mL) were added and a He gas was sprayed while heating in an oil bath (110° C.), and then acetonitrile was completely removed while azeotropically distilling water. Furthermore, an operation of adding acetonitrile (1 mL) and removing acetonitrile in the same manner under heating conditions was repeated, thereby turning the state inside the vial into a substantially moisture-free state. A DMSO solution (0.7 mL) containing THK-5039 (4 mg), as a label precursor, dissolved therein was added, followed by heating and stirring in the oil bath (110° C.) for 10 minutes. Thereafter, the reaction solution was diluted with distilled water (7 mL) and loaded into a Sep-Pack tC18 cartridge (manufactured by Waters) and, after washing the cartridge with distilled water, the crude product was eluted with ethanol. A portion of the ethanol solution was diluted with distilled water and subjected to semi-preparative high-performance liquid chromatography (column: YMC-Pack Pro C18 RS (10×250 mm), mobile phase: MeCN/20 mM NaH$_2$PO$_4$=60/40, flow rate: 5.0 mL/min) and then [$^{18}$F] THK-5035-derived radioactive peak (121 MBq, no decay correction), which is eluted within about 14 to 15 minutes, was dispensed. After the fraction was diluted with distilled water, [$^{18}$F] THK-5035 was subjected to solid-phase extraction using a Sep-Pak tC18 cartridge and then eluted with ethanol. In an autoradiography test, the ethanol solution was used after appropriately being diluted. In a biodistribution test, Polysorbate 80 was added to the ethanol solution and, after distilling off ethanol by an evaporator ethanol, a radioactive residue containing [$^{18}$F] THK-5035 in the flask was dissolved in physiological saline and then used as an injection in a brain migration evaluation test.

Staining Test on Compounds of the Present Invention on Brain Section of Alzheimer's Disease Patients The procedure of staining test on the compounds of the present invention on the brain section of Alzheimer's disease patients is described below:

(1) We used the brain specimens of the temporal lobe or hippocampus from patients who were definitely diagnosed as having Alzheimer's disease pathology. The specimens were obtained from Choju Medical Institute, Fukushimura Hospital, our collaborating research institute, and the consent for use for research purposes was obtained from the patients' bereaved family (Fukushimura Hospital, Ethics Committee Approval No. 20).

(2) The paraffin-embedded brain tissue was sliced to 6 or 8 μm thickness, extended on a slide glass, and dried. The paraffinized brain section was deparaffinized by washing with xylene for 10 minutes×2, 100% ethanol for 5 minutes×2, 90% ethanol for 5 minutes, and running water for 10 minutes in this order.

(3) As a pretreatment for staining with the compounds of the present invention, the treatment to remove autofluorescence with lipofuscin was performed. First, the paraffinized brain section was immersed in 0.25 $KM_nO_4$ solution for 20 minutes. It was washed with PBS for 2 minutes twice, immersed in a 0.1% $K_2S_2O_5$/oxalic acid solution for approximately 5 minutes, and further washed with PBS for 2 minutes 3 times.

(4) From 100 μM solution of the compounds of the present invention dissolved in 50% ethanol, approximately 150 μl was dropped on the section to react for 10 minutes. After being immersed in tap water 5 times, it was mounted with Flour Save Reagent (Calbiochem) and examined with a fluorescence microscope (Nikon, ECLIPSE 80i). The images were taken with a digital camera (Nikon, Dxin1200F or Photometrics, Cool SNAP ES).

The results of above mentioned staining test on the compounds of the present invention are illustrated in FIGS. 5 to 20. It was found that all of THK-5035, THK-5038, THK-5058, THK-5064, THK-5065, THK-5066, THK-5071, THK-5077, THK-5078, THK-5079, THK-5080, THK-5081, THK-5082, THK-5087, THK-5088, THK-5089, THK-5091, THK-5092, THK-5097, THK-5098, THK-5059, THK-5075, THK-5076, THK-5086, THK-5100, THK-5105, THK-5106, THK-5107, THK-5112, THK-5116, THK-5117, and THK-932 bind to neurofibrillary tangles specifically and selectively in the brain section of Alzheimer's disease patients, and that the compound of Formula (I) of the present invention has high specificity to tau (FIGS. 5 to 20).

The results of above mentioned staining test on the compounds of the present invention are illustrated in FIGS. 25 to 29. It was found that all of THK-5136, THK-5153, THK-5157, THK-5128, THK-5147, THK-5155, THK-5156, THK-5164, and THK-5154 bind to neurofibrillary tangles specifically and selectively in the brain section of Alzheimer's disease patients, and that the compound of Formula (I) of the present invention has high specificity to tau (FIGS. 25 to 29).

Autoradiography Test

After the paraffin-embedded brain section of Alzheimer's disease patients was deparaffinized, it was immersed in PBS for 10 minutes. Approximately 400 μCi/ml of [$^{18}$F] BF-227 and [$^{18}$F] THK-5035 were dropped on the section to react for 10 minutes at room temperature. It was immersed in distilled water for 2 minutes, shaken in 50% EtOH lightly for 2 minutes, immersed again in distilled water for 2 minutes, and dried in a paraffin extension device. The section was contacted on an imaging plate and settled overnight, and the next day, the images were read with a BAS5000 (Fujifilm Corporation). Furthermore, the serial section was immunostained with thioflavine-S staining and anti-tau antibody (AT8).

FIG. 21 illustrates the autoradiography images of [$^{18}$F] BF-227 and [$^{18}$F] THK-5035, the thioflavine-S (TF-S) staining images in the serial section, and the anti-tau antibody (Tau) staining. In the autoradiography images, the region where [$^{18}$F] THK-5035 was accumulated (region enclosed with rectangles) showed no accumulation of [$^{18}$F] BF-227 showing high affinity to amyloid R. In the region, abundant anti-tau antibody immunostaining positive structures were also observed. From the morphological images in the thioflavine-S staining images, which stain neurofibrillary tangles, it is strongly suggested that the structures observed in the region are neurofibrillary tangles. From the above results, it was confirmed that [$^{18}$F] THK-5035 shows higher affinity to neurofibrillary tangles (tau protein) than to amyloid 3.

Evaluation of Mouse Brain Transition of Labeled Compounds

The physiologic saline containing [$^{18}$F] THK-5035 was administered to the caudate vein of male ICR mice (6-7 week old). By considering the accumulation of radioactivity in the brain tissue and plasma tissue 2 minutes after administration, we evaluated the brain uptake of labeled compounds.

In the evaluation of radioactive accumulation, the ratio of radioactivity per unit weight of the tissue to be evaluated to all administered radioactivity (?Injected Dose/g of tissue; % ID/g) was used as index. For measurement of radioactivity, a gamma counter (1480 WIZARD, PerkinElmer, Inc.) was used. In the test, the labeled compounds were administered to the caudate vein, and 2 minutes later, cervical dislocation was performed to the mice under etherization. Then, immediately blood was collected from the heart, and the whole brain (including the cerebellum and brainstem) was extirpated. After then, the radioactivity and tissue weight of each sample were measured, and the data was used to calculate the % ID/g.

Table 3 illustrates the results of this evaluation test.

TABLE 3

| | | % ID/g or ml after 2 minutes (mean ± SD) |
|---|---|---|
| [$^{18}$F] THK-5035 | Brain | 6.01 ± 0.54 |
| | Plasma | 2.20 ± 0.26 |

The value of 0.5% ID/g or more is considered to be enough to indicate the brain trans it ion of labeled compounds for PET or SPECT targeting to the central nervous system. From that viewpoint, it was found that the [$^{18}$F] labeled compounds of the formula (I) of the present invention are [$^{18}$F] labeled compounds having extremely high brain uptake.

Synthesis of Label, [$^{18}$F] THK-5105

[$^{18}$O]—$H_2O$ with an isotope purity of 98% or higher was irradiated with a 12 MeV proton beam, which was accelerated by a cyclotron HM 12 (Sumitomo Heavy Industries, Ltd.), to produce $^{18}F^-$. Subsequently, the resulting solution was passed through an anion-exchange resin (AG 1-X8) to capture the $^{18}F^-$ on the resin, which was eluted with a 33 mM solution of $K_2CO_3$. Into an amber vial was placed 200 μL of the $^{18}F^-$-containing aqueous $K_2CO_3$ solution (3.13 GBq), and Kryptofix 222 (16 mg) and acetonitrile (2.3 mL) were added. He gas was sprayed while the vial was heated in an oil bath (110° C.), so as to remove completely the acetonitrile with azeotropic evaporation of water. Another acetonitrile (1.5 mL) was added, and the acetonitrile was removed under heating, in a similar way. These procedures were repeated twice to make the inside of the vial anhydrous. To the vial was added a DMSO solution (0.70 mL) of a label precursor THK-5121 (3.0 mg), and the mixture was heated and stirred for 10 minutes in an oil bath (110° C.). After that, hydrochloric acid (2M, 0.2 mL) was added to the reaction solution and an additional reaction was carried out at 110° C. for 3 minutes. Then, the reaction solution was diluted with a potassium acetate solution (4M, 0.1 mL) and distilled water (7.0 mL), and loaded on a Sep-Pak tC18 cartridge (Waters), which was then washed with distilled water, followed by elution of crude product with ethanol. An ethanol-eluted fraction with the highest radioactivity was diluted with distilled water and subjected to semi-preparative high performance liquid chromatography using an Inertsil ODS-4 column (10×250 mm), a mobile phase of MeCN/$NaH_2PO_4$ (20 mM) (50/50), and a flow rate of 5.0 mL/min. A radioactive peak of [$^{18}F$] THK-5105, which was eluted at about 18.5 minutes (988 MBq, decay uncorrected), was collected. Analysis of the collected sample revealed a radiochemical purity of 98% or more and a specific radioactivity of 137 GBq/μmol (on analysis).

The preparative HPLC fraction of [$^{18}F$] THK-5105, which was synthesized according to the synthesis procedure described above, was diluted with distilled water, and then subjected to solid-phase extraction using a Sep-Pak tC18 cartridge, followed by elution with ethanol or DMSO and appropriate dilution, and used in binding tests and autoradiography experiments. For experiments on its in vivo distribution (evaluation of its brain delivery), Polysorbate 80 was added to the ethanol-eluted fraction, from which the ethanol was removed using an evaporator. The [$^{18}F$] THK-5105 containing radioactive residue within the flask was dissolved in physiological saline and the solution prepared was used as a solution for injection.

Synthesis of Label, [$^{18}F$] THK-5117

[$^{18}F$] THK-5117 was synthesized according to the above-described method for synthesis of label, [$^{18}F$] THK-5105. In the synthesis of [(F] THK-5117, the synthesis was carried out using 500 μL of a $^{18}F^-$-containing aqueous $K_2CO_3$ solution (3.10 GBq), 3.0 mg of a label precursor THK-5119, and MeCN/$NaH_2PO_4$ (20 mM) (45/55) as the mobile phase in the semi-preparative high performance liquid chromatography, and was able to give 770 MBq of [$^{18}F$] THK-5117 (decay uncorrected). As in [$^{18}F$] THK-5105, a solution for injection was prepared and used in experiments for the evaluation of its brain delivery.

Synthesis of Label, [$^{18}F$] THK-5125

[$^{18}F$] THK-5125 was synthesized according to the above-described method for synthesis of label, [$^{18}F$] THK-5105. In the synthesis of [$^{18}F$] THK-5125, the synthesis was carried out using 200 μL of a $^{18}F^-$-containing aqueous $K_2CO_3$ solution (3.14 GBq), 3.3 mg of a label precursor THK-5131, and MeCN/$NaH_2PO_4$ (20 mM) (45/55) as the mobile phase in the semi-preparative high performance liquid chromatography, and was able to give 1.36 GBq of [$^{18}F$] THK-5125 (decay uncorrected). As in [$^{18}F$] THK-5105, a solution for injection was prepared and used in experiments for the evaluation of its brain delivery.

Synthesis of Label, [$^{18}F$] FDDNP

Into an amber vial was placed 300 μL of a $^{18}F^-$-containing aqueous $K_2CO_3$ solution (3.87 GBq), which was prepared in a similar way as in [$^{18}F$] THK-5105, and Kryptofix 222 (16 mg) and acetonitrile (2.3 mL) were added. He gas was sprayed while the vial was heated in an oil bath (110° C.), so as to remove completely the acetonitrile with azeotropic evaporation of water. More acetonitrile was added, and the acetonitrile was removed under heating, in a similar way. These procedures were repeated three times to make the inside of the vial anhydrous. To the vial was added an acetonitrile solution (0.70 mL) of a label precursor (2.7 mg), which has a tosyl group as a leaving group attached at the position of the fluorine in FDDNP (Jie Liu et al., Molecular Imaging and Biology (2007), vol. 9, pp. 6-16). The mixture was heated and stirred for 10 minutes in an oil bath (110° C.), in an unsealed state and with addition of 0.1 mL of acetonitrile every other minute. After that, the reaction solution was air cooled, diluted with distilled water (7.0 mL), and loaded on a Sep-Pak tC18 cartridge (Waters), which was then washed with distilled water, followed by elution of the crude product with ethanol. An ethanol-eluted fraction with the highest radioactivity was diluted with distilled water and subjected to semi-preparative high performance liquid chromatography using an Inertsil ODS-4 column (10×250 mm), a mobile phase of MeCN/$NaH_2PO_4$ (20 mM) (60/40), and a flow rate of 5.0 mL/min. A radioactive peak of [$^{18}F$] FDDNP, which was eluted at about 19.5 minutes (814 MBq, decay uncorrected), was collected. As in [$^{18}F$] THK-5105, a solution for injection was prepared and used in experiments for the evaluation of its brain delivery.

Evaluation of Brain Delivery of [$^{18}F$] THK-5105, [$^{18}F$] THK-5117, and [$^{18}F$] THK-5125 in Mice A physiological saline solution containing [$^{18}F$] THK-5105, [$^{18}F$]THK-5117, or [$^{18}F$] THK-5125 was administered into the tail vein of male ICR mice (6 to 7 weeks old), and brain delivery of these label compounds was assessed from the accumulation of radioactivity in brain and plasma tissues at two minutes post-injection.

As an index in the evaluation of radioactive accumulation, use was made of the percentage of radioactivity per unit weight of brain relative to the total radioactivity administered (% Injected Dose/g of tissue; % ID/g). For measurement of radioactivity, a gamma counter (1480 WIZARD, Perkin Elmer) was used. Experimental procedures were as follows. A label compound was administered into the tail vein of mice. Two minutes later, each mouse was subjected to cervical dislocation under ether anesthesia, and the whole brain, including the cerebellum and brain stem, was isolated immediately. The radioactivity and tissue weight of the sample were measured, and their data were used to calculate a % ID/g values for the labeled compound.

Table 4 shows % ID/g values at 2 minutes and at 60 minutes post-administration, and values of the % ID/g values at 2 minutes post-administration divided by those at 60 minutes post-administration. Labeled probes which target an intended histopathology in the brain, need to be incorporated rapidly into the brain and to be rapidly washed out from histopathologies that are not their intended histopathology. [$^{18}F$] THK-5105, [$^{18}F$] THK-5117 and [$^{18}F$] THK-5125 exhibited a sufficient intracerebral content at 2 minutes post-administration, and the quotients of their intracerebral contents at 2 minutes post-administration and 60 minutes post-administration were greater than those for [$^{18}F$] BAY94-9172 and [$^{18}F$] AV-45, which are known as amyloid imaging probes, and that for [$^{18}$F] FDDNP. Form these results, it turned out that [$^{18}$F] THK-5105, [$^{18}$F] THK-5117, and [$^{18}$F] THK-5125 were superior in being delivered to and washed out from the brain. (The data of [$^{18}$F] BAY94-9172 was taken from Zhang et al., Nuclear Medicine and Biology, 32, 799-809, 2005, and the data of [$^{18}$F] AV-45 from Choi et al., J Nucl Med, 50, 1887-1894, 2009.)

TABLE 4

| | % ID/g | | 2 minutes post-administration/ 60 minutes post-administration |
|---|---|---|---|
| | 2 minutes post-administration | 60 minutes post-administration | |
| [$^{18}$F]FDDNP | 6.23 | 2.14 | 2.91 |
| [$^{18}$F]BAY94-9172 | 7.77 | 1.61 | 4.83 |
| [$^{18}$F]AV-45 | 7.33 | 1.88 | 3.90 |
| [$^{18}$F]THK-5105 | 9.20 | 1.00 | 9.20 |
| [$^{18}$F]THK-5117 | 6.06 | 0.26 | 23.3 |
| [$^{18}$F]THK-5125 | 7.82 | 0.61 | 12.8 |

Autoradiography Experiments Using [$^{18}$F] THK-5105, [$^{18}$F] THK-5117, and [$^{18}$F] THK-5125

Paraffin-embedded sections of the brain from an Alzheimer's disease patient were deparaffinized, and then immersed in PBS for 10 minutes. Approximately 400 μCi/ml of each of [$^{18}$F] THK-5105, [$^{18}$F] THK-5117, and [$^{18}$F] THK-5125 was added dropwise to deparaffinized sections and allowed to react for 10 minutes at room temperature. After that, the sections were immersed in distilled water for 2 minutes, shaken lightly in 50% EtOH for 2 minutes, immersed again in distilled water for 2 minutes, and dried in a paraffin stretching device. The section was left overnight in contact with an imaging plate. Next day, the image was read with a BAS 5000 (Fujifilm Corporation). In addition, adjacent sections were immunostained with anti-phosphorylated tau antibody (AT8).

FIG. 22 shows an image of [$^{18}$F] THK-5105 autoradiography of a section of the hippocampus and images of unlabeled THK-5105 staining and of anti-phosphorylated tau antibody (AT8) staining of its adjacent sections. In the autoradiography image, areas where the accumulation of [$^{18}$F] THK-5105 was observed were found abundant in structures which were positive (for pTau) by immunostaining with the anti-phosphorylated tau antibody. Also in their respective higher magnification images, the [$^{18}$F] THK-5105 autoradiography image corresponded well with the image of immunostaining with the anti-phosphorylated tau antibody, and further, the image of unlabeled THK-5105 staining corresponded well with the image of immunostaining with the anti-phosphorylated tau antibody, including their morphological images.

FIG. 23 shows images of [$^{18}$F] THK-5105, [$^{18}$F] THK-5117, and [$^{18}$F] THK-5125 autoradiography of sections of the lateral temporal cortex and of the medial temporal cortex. [$^{18}$F] THK-5105, [$^{18}$F] THK-5117, and [$^{18}$F] THK-5125 were observed to be accumulated in the lateral temporal cortex and medial temporal cortex, which are known as areas where tau production occurs late in Alzheimer's disease.

From these results, it was ascertained that [$^{18}$F] THK-5105, [$^{18}$F] THK-5117, and [$^{18}$F] THK-5125 have high affinity to neurofibrillary tangles (tau protein).

Evaluation of Binding to Tau Protein Aggregates

Regarding the binding of tau imaging probes to tau protein aggregates, a binding test was carried out and evaluated using a K18-ΔK280 construct which contained a 4-repeat structure involved in the formation of beta-sheet structures in the htau40 protein. For K18-ΔK280 (Martin von Bergen et al., THE JOURNAL OF BIOLOGICAL CHEMISTRY (2001), vol. 276, pp. 48165-48174; M. Goedert et al., NEURON (1989), vol. 3, pp. 519-526), an artificial gene fragment which was prepared based on its amino acid sequence was cloned into a pET-3a vector, the resulting plasmid was used to transform *Escherichia coli* BL21 (DE3) competent cells for protein expression, and the recombinant *Escherichia coli* cell was cultured to express K18-ΔK280. The K18-ΔK280 expressed was purified according to the method described in the literature (Stefan Barghorn et al., Methods in Molecular Biology, vol. 299, pp. 35-51). In the binding test, aggregates of the purified K18-ΔK280 were made and used.

K18-ΔK280 aggregates were made by preparing 20 μM PBS (pH 7.4) and incubating the K18-ΔK280 in the PBS at 37° C. for 4 days. The state where beta-sheet structures in K18-ΔK280 aggregates were formed was ascertained by thioflavin S fluorescence binding test. The aggregates solution was diluted to 400 nM in assay buffer (PBS, 0.1% BSA) and used in the binding test.

Saturation Binding Test of THK-5105

In the binding test of [$^{18}$F] THK-5105, reaction solutions were prepared such that K18-ΔK280 aggregates was at a final concentration of 200 nM in the reaction system and [$^{18}$F] THK-5105 was at final concentrations of from 0.1 to 100 nM, and incubated at room temperature for one hour. After the incubation, [$^{18}$F] THK-5105 binding to K18-ΔK280 aggregates and THK-5105 not binding to K18-ΔK280 aggregates were separated using a MultiScreen HTS filter plate (96 wells, Millipore Corporation) and the filter was washed with assay buffer (200 μL, 3 times). The total binding of [$^{18}$F] THK-5105 to K18-ΔK280 aggregates was calculated from the radioactivity of the filter which was measured on a gamma counter (AccuFLEX γ7000, Aloka). Non-specific binding was determined by adding unlabeled THK-5105 (at a final concentration of 2 μM) to the reaction system and performing experiments in a similar way. The data of the total binding and the non-specific binding were used and analyzed using an analysis software GraphPad prism (Ver. 5), which gave a low value of dissociation constant Kd of 3.9 nM, indicating that THK-5105 displayed a high binding affinity to K18-ΔK280 aggregates.

Competitive Binding Test Using [$^{18}$F] THK-5105 as Radioactive Competitor

For tau imaging probes other than THK-5105, binding to K18-ΔK280 aggregates was evaluated with a competitive binding test using [$^{18}$F] THK-5105 as a radioactive competitor. In the binding test, [$^{18}$F] THK-5105 (at a final concentration of 1.76 nM) and a tested compound (at final concentrations of from 0.1 to 1000 nM) coexisted in the reaction system, to which K18-ΔK280 aggregates (at a final concentration of 200 nM) was then added and the mixtures were incubated at room temperature for one hour. The radioactivity of [$^{18}$F] THK-5105 binding to the aggregates was determined in a similar way as in the saturation binding test of THK-5105. The percentage of [$^{18}$F] THK-5105 bonding in the absence of each tested compound was set to be 100%, and percentages of [$^{18}$F] THK-5105 bonding at various concentrations of each of the tested compounds were determined. From these data, the inhibition constants (Kis) of the respective tested compounds were calculated using an analysis software GraphPad prism (Ver. 5). The results are shown in Table 5 and FIG. 24. Any of the tested compounds displayed a high binding affinity to K18-ΔK280 aggregates.

TABLE 5

| | Ki (nM) |
|---|---|
| THK-5116 | 36.0 |
| THK-5117 | 10.5 |
| THK-5122 | 34.9 |
| THK-5125 | 9.2 |
| THK-5129 | 21.4 |
| THK-5151 | 40.1 |
| THK-523 (reference for comparison) | 59.3 |
| FDDNP (reference for comparison) | 256 |

INDUSTRIAL APPLICABILITY

The compounds of the present invention are very useful, for example, in early detection, treatment and prevention of neurofibrillary tangles including Alzheimer's disease, and can be utilized in the fields of the production of diagnostic agents and diagnostic kits for these diseases, the fields of the production of remedies and preventatives for these diseases, studies of these diseases and the like.

What is claimed is:

1. A method of diagnosing a conformational disease in a subject, which comprises administering a labelled compound of formula (I), or a pharmaceutically acceptable salt or solvate thereof to the subject, wherein said compound of formula (I) has the following structure:

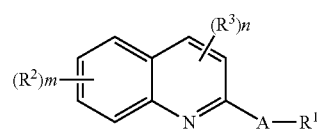

(I)

wherein
A is

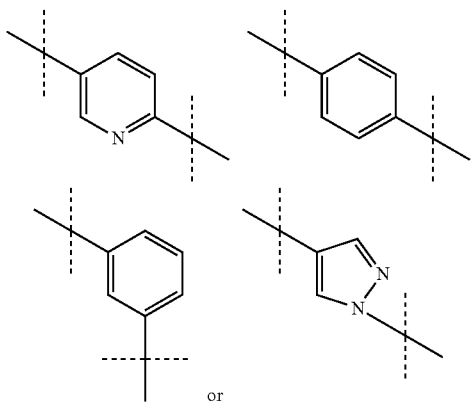

or $R^1$ is halogen, a —C(=O)-lower alkyl group (the alkyl group each independently may be substituted with one or more substituents selected from $NR^aR^b$, halogen and a hydroxy group), a lower alkyl group (the alkyl group each independently may be substituted with one or more substituents selected from halogen and a hydroxy group), a —O-lower alkyl group (the alkyl group each independently may be substituted with one or more substituents selected from halogen and a hydroxy group), or

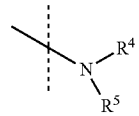

in which $R^4$ and $R^5$ each independently represents hydrogen, a lower alkyl group or a cycloalkyl group, or $R^4$, $R^5$ and the nitrogen atom to which they are attached are taken together to form a 3- to 8-membered nitrogen-containing aliphatic ring (one or more carbon atoms constituting the nitrogen-containing aliphatic ring may be substituted with a nitrogen atom, a sulfur atom or an oxygen atom, and when a carbon atom is substituted with a nitrogen atom, the nitrogen atom may be substituted with a lower alkyl group), or $R^4$ and the nitrogen atom to which it is attached are taken together with ring A to form a 8- to 16-membered nitrogen-containing fused bicyclic ring (one or more carbon atoms constituting the nitrogen-containing fused bicyclic ring may be substituted with a nitrogen atom, a sulfur atom or an oxygen atom, and when a carbon atom is substituted with a nitrogen atom, the nitrogen atom may be substituted with a lower alkyl group) and $R^5$ represents hydrogen, a lower alkyl group or a cycloalkyl group, in which the line, that the dotted line intersects, means a bond of the above general formula to the other structural moiety, $R^2$ or $R^3$ each independently represents halogen, OH, COOH, $SO_3H$, $NO_2$, SH, $NR^aR^b$, a lower alkyl group (the alkyl group each independently may be substituted with one or more substituents selected from halogen and a hydroxy group) or a —O-lower alkyl group (the alkyl group each independently may be substituted with at least two substituents selected from halogen and a hydroxy group), ring A is unsubstituted, or substituted with $R^6$ (in which $R^6$ is one or more substituents selected independently from halogen, OH, COOH, $SO_3H$, $NO_2$, SH, $NR^aR^b$, a lower alkyl group (the alkyl group each independently may be substituted with one or more substituents selected from halogen and a hydroxy group) and a —O-lower alkyl group (the alkyl group each independently may be substituted with at least two substituents selected from halogen and a hydroxy group), $R^a$ and $R^b$ each independently represents hydrogen or a lower alkyl group (the alkyl group each independently may be substituted with one or more substituents selected from halogen and a hydroxy group), m is an integer of 0 to 4, n is an integer of 0 to 4, wherein at least one of $R^2$, $R^3$ and $R^6$ is a —O-lower alkyl group substituted with one hydroxy group and one halogen, wherein said conformational disease is a tauopathy.

2. The method according to claim 1, wherein for said compound of formula (I) $R^1$ is halogen, a —C(=O)-lower alkyl group (the alkyl group each independently may be substituted with $NH_2$), a lower alkyl group (the alkyl group each independently may be substituted with a hydroxy group), —O-lower alkyl group, or

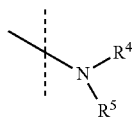

in which

R[4] and R[5] each independently represents hydrogen or a lower alkyl group.

3. The method according to claim 1, wherein for said compound of formula (I) at least one of R[2], R[3] and R[6] is represented by:

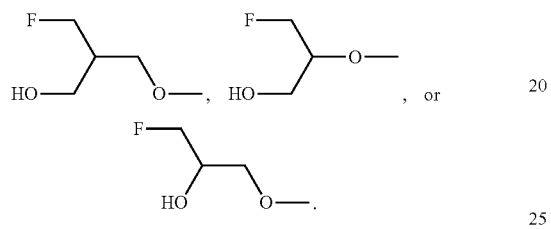

4. The method according to claim 1, wherein for said compound of formula (I) at least one of R[2], R[3] and R[6] is NR[a]R[b], and R[a] and R[b] each independently represents hydrogen or an unsubstituted lower alkyl group.

5. The method according to claim 1, wherein for said compound of formula (I) the label is a radioactive nuclide.

6. The method according to claim 5, wherein the label is a positron emitting nuclide.

7. The method according to claim 6, wherein the positron emitting nuclide is selected from the group consisting of $^{11}$C, $^{13}$N, $^{15}$O, $^{18}$F, $^{35m}$Cl, $^{76}$Br, $^{45}$Ti, $^{48}$V, $^{60}$Cu, $^{61}$Cu, $^{62}$Cu, $^{64}$Cu, $^{66}$Ga, $^{89}$Zr, $^{94m}$Tc and $^{124}$I.

8. The method according to claim 7, wherein the positron emitting nuclide is $^{11}$C or $^{18}$F.

9. The method according to claim 1, wherein said compound of formula (I) is a labeled compound of the formula (I″):

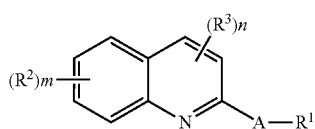

wherein
A is

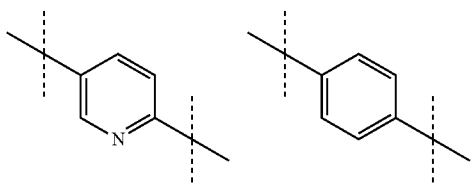

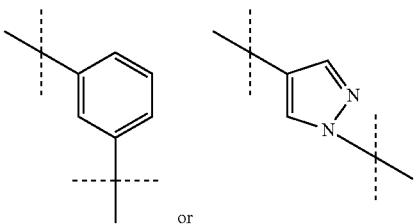

or

R[1] is

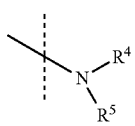

in which R[4] and R[5] each independently represents hydrogen, a lower alkyl group, R[2] or R[3] each independently represents a —O-lower alkyl group (the alkyl group each independently may be substituted with at least two substituents selected from halogen and a hydroxy group), ring A is unsubstituted, or substituted with R[6] (in which R[6] is one or more substituents selected independently from a —O-lower alkyl group (the alkyl group each independently may be substituted with at least two substituents selected from halogen and a hydroxy group)), m is an integer of 0 to 4, n is an integer of 0 to 4, wherein R[2], R[3] and R[6] each represents a —O-lower alkyl group substituted with one hydroxy group and one halogen.

10. The method according to claim 9, wherein said compound of formula I″ is selected from:

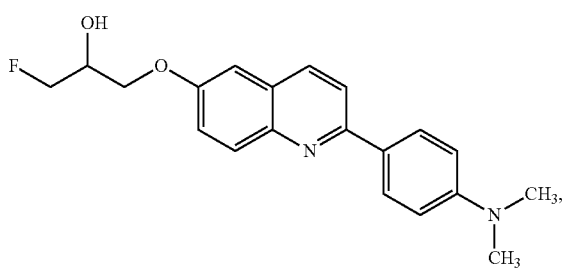

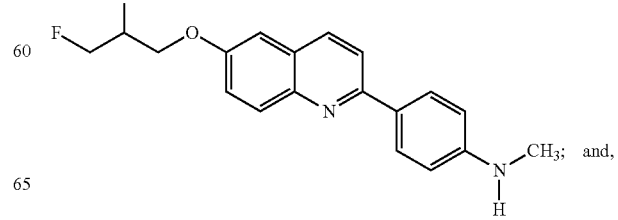

-continued

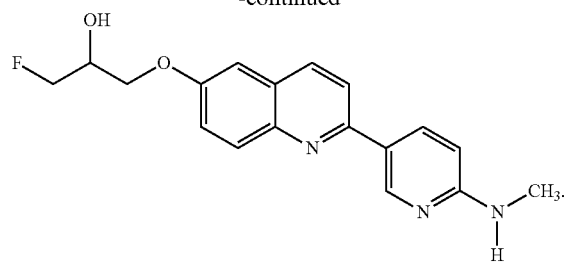

11. The method according to claim 9, wherein said compound of formula I″ is selected from:

12. The method according to claim 9, wherein for said compound of formula (I″) the label is a radioactive nuclide.

13. The method according to claim 12 wherein the label is a positron emitting nuclide.

14. The method according to claim 13, wherein the positron emitting nuclide is selected from the group consisting of $^{11}C$, $^{13}N$, $^{15}O$, $^{18}F$, $^{35m}Cl$, $^{76}Br$, $^{45}Ti$, $^{48}V$, $^{60}Cu$, $^{61}Cu$, $^{62}Cu$, $^{64}Cu$, $^{66}Ga$, $^{89}Zr$, $^{94m}Tc$ and $^{124}I$.

15. The method according to claim 14, wherein the positron emitting nuclide is $^{11}C$ or $^{18}F$.

16. The method according to claim 15, wherein said compound of formula I″ is selected from:

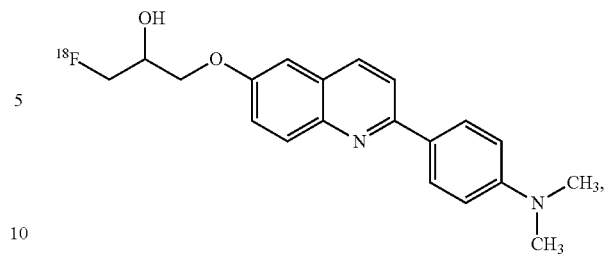

17. The method according to claim 15, wherein said compound of formula I″ is selected from:

* * * * *